US008754192B2

(12) United States Patent
Danishefsky et al.

(10) Patent No.: US 8,754,192 B2
(45) Date of Patent: Jun. 17, 2014

(54) COMPOSITIONS COMPRISING HOMOGENEOUSLY GLYCOSYLATED ERYTHROPOIETIN

(75) Inventors: Samuel J. Danishefsky, Englewood, NJ (US); J. David Warren, New York, NY (US); Jiehao Chen, Westfield, IN (US); Bin Wu, Thousand Oaks, CA (US); Gong Chen, New York, NY (US); Qian Wan, Quincy, MA (US); Zhongping Tan, New York, NY (US); Cindy Kan, New York, NY (US); Yu Yuan, New York, NY (US); Zihao Hua, Tewksbury, MA (US); Krishnakumar Ranganathan, Oak Park, CA (US); John D. Trzupek, Boston, MA (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 1157 days.

(21) Appl. No.: 12/296,608

(22) PCT Filed: Apr. 11, 2007

(86) PCT No.: PCT/US2007/008764
§ 371 (c)(1),
(2), (4) Date: Jan. 26, 2009

(87) PCT Pub. No.: WO2007/120614
PCT Pub. Date: Oct. 25, 2007

(65) Prior Publication Data
US 2010/0081786 A1   Apr. 1, 2010

Related U.S. Application Data

(60) Provisional application No. 60/841,678, filed on Aug. 31, 2006, provisional application No. 60/791,614, filed on Apr. 11, 2006.

(51) Int. Cl.
*C07K 1/00* (2006.01)
*C07K 14/00* (2006.01)
*C07K 17/00* (2006.01)
*A61K 38/00* (2006.01)

(52) U.S. Cl.
USPC ........................................ 530/350; 530/345

(58) Field of Classification Search
None
See application file for complete search history.

(56) References Cited

U.S. PATENT DOCUMENTS

| 6,660,714 B1 | 12/2003 | Danishefsky | |
|---|---|---|---|
| 2003/0153492 A1 | 8/2003 | Danishefsky et al. | |
| 2004/0208884 A1 | 10/2004 | Danishefsky et al. | |
| 2007/0173636 A1 | 7/2007 | Danishefsky et al. | |
| 2010/0081786 A1* | 4/2010 | Danishefsky et al. | ........ 530/322 |

FOREIGN PATENT DOCUMENTS

| EP | 1231278 A1 | 8/2002 |
|---|---|---|
| WO | WO/96/34878 | 11/1996 |
| WO | WO/02/19963 | 3/2002 |
| WO | WO/2004/050711 | 6/2004 |
| WO | WO/2004/060915 | 7/2004 |
| WO | WO/2005/044841 | 5/2005 |
| WO | WO-2005051327 A2 | 6/2005 |

OTHER PUBLICATIONS

Fibi MR, Hermentin P, Pauly JU, Lauffer L and Zettlmeissl G (1995) N- and O-glycosylation muteins of recombinant human erythropoietin secreted from BHK-21 cells. Blood 85: 1229-1236.*
Anisfeld et al., J. Org. Chem. 1990, 55, 5560-5562.
Arsequell et al., Tetrahedron: Asymmetry 1999, 10, 3045-3094.
Ashwell et al., Ann. Rev. Biochem. 1982, 51, 531-554.
Bang et al., Angew. Chem. 2004, 116, 2588-2592.
Bang et al., Angew. Chem. Int. Ed. 2004, 43, 2534-2538.
Bause, Biochem. J. 1983, 209, 331-336.
Bertozzi, C. R.; Kiessling, L. L. Science 2001, 291, 2357-2364.
Bezay et al., Angew. Chem. Int. Ed. 2001, 40, 2292-2295.
Blixt et al., J. Am. Chem. Soc. 2002, 124, 5739-5746.
Casadevall et al., New Engl. J. Med. 2002, 346, 469-475.
Chan et al., J. Chem. Soc., Chem. Commun., 1995, 21, 2209-2210.
Chen et al., Chem. Biol. 2005, 12, 371-383.
Chen et al., J. Am. Chem. Soc. 1998, 120, 7760-7769.
Chen et al., J. Am. Chem. Soc. 2006, 128, 7460-7462.
Chen et al., Tetrahedron Lett. 2006, 47, 1969-1972.
Chiesa et al., Eur. J. Org. Chem. 2000, 3541-3554.
Chirino et al., Drug Discov. Today 2004, 9, 82-90.
Ciommer et al., Synlett 1991, 593-595.
Cohen-Anisfeld et al., J. Am. Chem. Soc. 1993, 115, 10531-10537.
Crich et al., J. Org. Chem. 1997, 62, 1198-1199.
Crich, D.; Sun, S. Tetrahedron 1998, 54, 8321-8348.
Danishefsky et al., Angew. Chem. Int. Ed. 1996, 35, 1380-1419.
Danishefsky et al., Angew. Chem., Int. Ed. 2000, 39, 837-863.
Dawson et al., Science, 1994, 266, 776-779.
Dordal et al., Endocrinology 1985, 116, 2293-2299.
Dudkin et al., J. Am. Chem. Soc. 2004, 126, 736-738.
Dudkin et al., Tetrahedron Lett. 2003, 44, 1791-1793.
Egrie et al., Br. J. Cancer 2001, 84 (Suppl. 1), 3-10.

(Continued)

*Primary Examiner* — Robert Landsman
(74) *Attorney, Agent, or Firm* — Choate, Hall & Stewart, LLP; Brenda Herschbach Jarrell; John P. Rearick

(57) ABSTRACT

The present invention provides isolated homogeneous polyfunctionalized proteins (e.g., erythropoietin), isolated glycopeptides, and a method for preparing polyfunctionalized peptides and/or proteins via cysteine-free native chemical ligation. In certain embodiments, the invention provides an isolated homogeneous polyfunctionalized protein having the structure (I). In certain other embodiments, the invention provides an isolated glycopeptide having Formula (II). In certain other embodiments, the inventive method is a method for preparing a polyfunctionalized peptide comprising a peptidic backbone made up of four or more amino acids, wherein two or more non-adjacent amino acids are independently substituted with a moiety having the structure (III) -LH. wherein A and L1 are as defined herein.

9 Claims, 14 Drawing Sheets

(56) References Cited

OTHER PUBLICATIONS

Egrie et al., Exp. Hematol. 2003, 31, 290-299.
Elliott et al., Blood 1996, 87, 2714-2722.
Elliott et al., Nat. Biotechnol. 2003, 21, 414-421.
Fibi et al., Blood, 1995, 85, 5, 1229-1236.
Fotouhi et al., J. Org. Chem. 1989, 54, 2803-2817.
Fukuda et al., Blood 1989, 73, 84-89.
Geng et al., Angew. Chemie Int. Ed.2004, 43, 2562-2565.
Gesundheit et al., J. Biol. Chem. 1987, 262, 5197-5203.
Geyer et al., J. Biol. Chem. 1988, 263, 11760-11767.
Goldwasser et al., J. Biol. Chem. 1974, 249, 4202-4206.
Grogan et al., Annu. Rev. Biochem. 2002, 71, 593-634.
Gupta et al., J. Mol. Recognit. 2004, 17, 218-235.
Halcomb et al., J. Am. Chem. Soc. 1991, 113, 5080-5082.
Hartley et al., Proc. Natl. Acad. Sci. U. S. A. 2004, 101, 16460-16465.
Helenius, Mol. Biol. Cell 1994, 5, 253-265.
Higuchi et al., J. Biol. Chem. 1992, 267, 7703-7709.
Hojo et al., Tetrahedron Lett. 2003, 44, 14, 2961-2964.
Hokke et al., Eur. J. Biochem. 1995, 228, 981-1008.
Imai et al., J. Biochem. (Tokyo) 1990, 107, 352-359.
Imperiali et al., Biochemistry, 1991, 30, 4374-4380.
Imperiali et al., Curr. Opin. Chem. Biol. 1999, 3, 643-649.
Imperiali, B. et al., C. Pure Appl. Chem. 1999, 71, 777-787.
Inoue et al., Arch. Biochem. Biophys. 1993, 301, 375-378.
International Search Report, PCT/US2007/08764, mailed Apr. 25, 2008.
International Search Report, PCT/US2004/029047, mailed Apr. 21, 2005.
Iserloh et al., Tetrahedron Lett. 2002, 43, 7027-7030.
Jelkmann et al., Ann Hematol. 2004, 83, 673-686.
Jenkins et al., Nat. Biotechnol. 1996, 14, 975-981.
Johnson et al., J. Am. Chem. Soc. 2006, 128, 6640-6646.
Kahne et al., J. Am. Chem. Soc. 1989, 111, 6881-6882.
Kawakami et al., Org. Lett. 2001, 3, 1403-1405.
Kawakami et al., Tetrahedron Lett. 2005, 46, 8805-8807.
Kemp et al., J. Org. Chem. 1986, 51, 1821-1829.
Kemp et al., J. Org. Chem. 1981, 46, 490-498.
Kemp et al., J. Org. Chem. 1993, 58, 2216-2222.
Kemp et al., Tetrahedron Lett. 1981, 22, 181-184.
Kemp et al., Tetrahedron Lett. 1981, 22, 185-186.
Kemp et al., Tetrahedron Lett. 1987, 28, 4637-4640.
Kemp, Biopolymers 1981, 20, 1793-1804.
Klausner et al., Cell 1990, 62, 611-614.
Kochendoerfer et al., Science 2003, 299, 884-887.
Koeller et al., J. Am. Chem. Soc. 2000, 122, 4241-4242.
Kornfeld et al., Annu. Rev. Biochem. 1985, 54, 631-664.
Koury, Trends Biotechnol. 2003, 21, 462-464.
Krantz, Blood 1991, 77, 419-434.
Kuroda et al., Int. J. Pept. Protein Res. 1992, 40, 294-299.
Lai et al., J. Biol. Chem. 1986, 261, 3116-3121.
Li et al. Tetrehedron Lett. 1993, 34, 1413-1414.
Li et al., Org. Lett. 1999, 1, 91-93.
Likhosherstov et al., Carbohydr. Res. 1986, 146, C1-C5.
Lin et al., Proc. Natl. Acad. Sci. U. S. A. 1985, 82, 7580-7584.
Lis, H.; Sharon, N. Eur. J. Biochem. 1993, 218, 1-27.
Liu et al., Proc. Natl. Acad. Sci. U. S. A. 1994, 91, 6584-6588.
Macmillan et al., Chem. Biol. 2001, 8, 133-145.
Macmillan et al., Org. Lett. 2004, 6, 4659-4662.
Macmillan et al., Tetrahedron 2000, 56, 9515-9525.
Mandal et al., Angew. Chem. Int. Ed. 2004, 43, 2557-2561.
Marcaurelle et al., Glycobiology, 2002, 12, 6, 69R-77R.
Marra et al., Synlett 1990, 572-574.
Matsueda et al., Chem. Lett. 1981, 6, 737-740.
Mayeux et al., Erythropoietins and Erythropoiesis Molineux, G., Foote, M. A., Elliott, S. G., Eds. Antibodies to Endogenous and Recombinant Erythropoietin. Birkhäuser Verlag: Switzerland, 2003; pp. 229-239.

Meinjohanns et al., J. Chem. Soc.-Perkin Trans. 1 1998, 549-560.
Meinjohanns et al., Tetrahedron Lett. 1995, 36, 9205-9208.
Meutermans et al., J. Am. Chem. Soc. 1999, 121, 9790-9796.
Miller et al., Angew. Chem., Int. Ed. 2003, 42, 431-434.
Milner-White, Trends Pharmacol. Sci. 1989, 10, 70-74.
Mizuno et al., J. Am. Chem. Soc. 1999, 121, 284-290.
Muir et al., Proc. Natl. Acad. Sci. U. S. A. 1998, 95, 6705-6710.
Nilsson et al., Annu. Rev. Biophys. Biomol. Struct. 2005, 34, 91-118.
Nimtz et al., FEBS Lett. 1995, 365, 203-208.
Offer et al., J. Am. Chem. Soc. 2002, 124, 4642-4646.
Offer et al., Org. Lett. 2000, 2, 23-26.
Okada et al., Biochim. Biophys. Acta 2001, 1525, 149-160.
Parekh et al., Trends Biotechnol. 1989, 7, 117-122.
Pavlou et al., Nature Biotech. 2004, 22, 1513-1519.
Rademacher et al., Springer Semin. Immunopathol. 1988, 10, 231-249.
Rademacher et al., A. Ann. Rev. Biochem. 1988, 57, 785-838.
Ratner et al., ChemBioChem. 2004, 5, 1375-1383.
Ridley et al., J. Natl. Med. Assoc. 1994, 86, 129-135.
Roitsch et al., Eur. J. Biochem. 1989, 181, 525-529.
Roth, J. Chem. Rev. 2002, 102, 285-303.
Rudd, P. M. et al., Science 2001, 291, 2370-2376.
Ruderer et al., J. Bacteriol. 1991, 173, 3539-3546.
Rush et al., Anal. Chem. 1995, 67, 1442-1452.
Sakakibara, Biopolymers 1995, 37, 17-28.
Sasaki et al., J. Biol. Chem. 1987, 262, 12059-12076.
Schwarz et al., J. Am. Chem. Soc. 1999, 121, 2662-2673.
Shao et al., Tetrahedron Lett. 1998, 39, 3911-3914.
Shin et al., J. Am. Chem. Soc. 1999, 121, 11684-11689.
Skibeli et al., Blood 2001, 98, 3626-3634.
Spivak et al., Blood, 1989, 73, 90-99.
Syed et al., Nature 1998, 395, 511-516.
Szymkowski, Curr. Opin. Drug Discov. & Devel. 2005, 8, 590-600.
Takeuchi et al., Glycobiology, 1991, 1, 337-346.
Takeuchi et al., J. Biol. Chem. 1988, 263, 3657-3663.
Tam et al., Biopolymers, 1998, 46, 319-327.
Tam et al., Tetrahedron Lett. 1997, 38, 5599-5602.
Tolbert et al., J. Am. Chem. Soc. 2000, 122, 5421-5428.
Tsuda et al., Biochemistry 1988, 27, 5646-5654.
Tsuda et al., Eur. J. Biochem. 1990, 188, 405-411.
Unverzagt, Tetrahedron Lett. 1997, 38, 5627-5630.
van Ameijde et al., J. Chem. Soc.-Perkin Trans. 1 2002, 1042-1049.
Varki, Glycobiology 1993, 3, 97-130.
Verber et al., Trends Neurosci. 1985, 8, 392-396.
Vizzavona et al., Bioorg. Med. Lett. 2002, 12, 1963-1965.
Wang et al., Angew. Chem. Int. Ed. 2001, 40, 1728-1732.
Wang et al., Angew. Chem. Int. Ed. 2000, 39, 3652-3656.
Wang et al., J. Am. Chem. Soc. 1997, 119, 11137-11146.
Wang et al., Tetrahedron 2006, 62, 4954-4978.
Warren et al., J. Am. Chem. Soc. 2004, 126, 6576-6578.
Wilken et al., Curr. Opin. Biotech. 1998, 9, 412-426.
Witte et al., J. Am. Chem. Soc. 1997, 119, 2114-2118.
Wu et al., Angew. Chem. Int. Ed. 2006, 45, 4116-4125.
Wu et al., Tetrahedron Lett. 2006, 47, 5577-5579.
Wu et al., Tetrahedron Lett. 2006, 47, 8009-8011.
Wu et al., Tetrahedron Lett. 2006, 47, 5219-5223.
Yan et al., J. Am. Chem. Soc. 2001, 123, 526-533.
Yeo et al., Chem. Eur. J. 2004, 10, 4664-4672.
Yoon et al., Biotechnol. Prog. 2004, 20, 1293-1296.
Yuen et al., Brit. J. Haematol. 2003, 121, 511-526.
Zang et al., Neurology 2000, 55, 397-404.
Zhang et al., Carbohydr. Res. 1992, 236, 73-88.
Zhang et al., J. Am. Chem. Soc. 1997, 119, 2363-2370.
Breitling, R. et al. "Non-pathogenic trypanosomatid protozoa as a platform for protein research and production", Protein Expression and Purification, vol. 25, No. 2, 2002, pp. 209-218.
MacMillan, D. et al. "Selective in vitro glycosylation of recombinant proteins: semi-synthesis of novel homogeneous glycoforms of human erythropoietin", Chemistry and Biology, vol. 8, No. 2, 2001, pp. 133-145.

(56) References Cited

OTHER PUBLICATIONS

Wu, B. et al. "Building complex glycopeptides: development of a cysteine-free native ligation protocol", Angewandte Chemie International Edition, vol. 45, No. 25, Jun. 19, 2006, pp. 4116-4125.

Kaneshiro et al., A Convergent Synthesis of N-Glycopeptides, Angew. *Chem. Int. Ed.* 2006, 45, 1077-1081.

Quelle, F.W. et al., High-level expression and purification of a recombinant human erythropoietin produced using a baculovirus vector, Blood, 74 (2):652-657 (1989).

* cited by examiner

SEQUENCE LISTING

```
<160> NUMBER OF SEQ ID NOS: 72

<210> SEQ ID NO 1
<211> LENGTH: 166
<212> TYPE: PRT
<213> ORGANISM: artificial
<220> FEATURE:
<223> OTHER INFORMATION: Peptide fragment of human erythropoietin

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95
```

```
Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 2
<211> LENGTH: 166
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (24)..(24)
<223> OTHER INFORMATION: glycosylated
<220> FEATURE:
<221> NAME/KEY: MISC_FEATURE
<222> LOCATION: (38)..(38)
<223> OTHER INFORMATION: glycosylated
<220> FEATURE:
<221> NAME/KEY: MISC_FEATURE
<222> LOCATION: (83)..(83)
<223> OTHER INFORMATION: glycosylated
<220> FEATURE:
<221> NAME/KEY: MISC_FEATURE
<222> LOCATION: (126)..(126)
<223> OTHER INFORMATION: glycosylated

<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 3
<211> LENGTH: 28
<212> TYPE: PRT
<213> ORGANISM: artificial
<220> FEATURE:
```

```
<223> OTHER INFORMATION: Peptide fragment of human erythropoietin

<400> SEQUENCE: 3

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly
            20                  25

<210> SEQ ID NO 4
<211> LENGTH: 49
<212> TYPE: PRT
<213> ORGANISM: artificial
<220> FEATURE:
<223> OTHER INFORMATION: Peptide fragment of human erythropoietin

<400> SEQUENCE: 4

Cys Ala Glu His Cys Ser Leu Asn Glu Asn Ile Thr Val Pro Asp Thr
1               5                   10                  15

Lys Val Asn Phe Tyr Ala Trp Lys Arg Met Glu Val Gly Gln Gln Ala
            20                  25                  30

Val Glu Val Trp Gln Gly Leu Ala Leu Leu Ser Glu Ala Val Leu Arg
        35                  40                  45

Gly

<210> SEQ ID NO 5
<211> LENGTH: 36
<212> TYPE: PRT
<213> ORGANISM: artificial
<220> FEATURE:
<223> OTHER INFORMATION: Peptide fragment of human erythropoietin

<400> SEQUENCE: 5

Gln Ala Leu Leu Val Asn Ser Ser Gln Pro Trp Glu Pro Leu Gln Leu
1               5                   10                  15

His Val Asp Lys Ala Val Ser Gly Leu Arg Ser Leu Thr Thr Leu Leu
            20                  25                  30

Arg Ala Leu Gly
        35

<210> SEQ ID NO 6
<211> LENGTH: 53
<212> TYPE: PRT
<213> ORGANISM: artificial
<220> FEATURE:
<223> OTHER INFORMATION: Peptide fragment of human erythropoietin

<400> SEQUENCE: 6

Ala Gln Lys Glu Ala Ile Ser Pro Pro Asp Ala Ala Ser Ala Ala Pro
1               5                   10                  15

Leu Arg Thr Ile Thr Ala Asp Thr Phe Arg Lys Leu Phe Arg Val Tyr
            20                  25                  30

Ser Asn Phe Leu Arg Gly Lys Leu Lys Leu Tyr Thr Gly Glu Ala Cys
        35                  40                  45

Arg Thr Gly Asp Arg
    50

<210> SEQ ID NO 7
<211> LENGTH: 28
<212> TYPE: PRT
<213> ORGANISM: artificial
<220> FEATURE:
<223> OTHER INFORMATION: Peptide fragment of human erythropoietin
<220> FEATURE:
```

```
<221> NAME/KEY: MISC_FEATURE
<222> LOCATION: (24)..(24)
<223> OTHER INFORMATION: glycosylated

<400> SEQUENCE: 7

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly
            20                  25

<210> SEQ ID NO 8
<211> LENGTH: 28
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (24)..(24)
<223> OTHER INFORMATION: glycosylated

<400> SEQUENCE: 8

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly
            20                  25

<210> SEQ ID NO 9
<211> LENGTH: 49
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (10)..(10)
<223> OTHER INFORMATION: glycosylation

<400> SEQUENCE: 9

Cys Ala Glu His Cys Ser Leu Asn Glu Asn Ile Thr Val Pro Asp Thr
1               5                   10                  15

Lys Val Asn Phe Tyr Ala Trp Lys Arg Met Glu Val Gly Gln Gln Ala
            20                  25                  30

Val Glu Val Trp Gln Gly Leu Ala Leu Leu Ser Glu Ala Val Leu Arg
        35                  40                  45

Gly

<210> SEQ ID NO 10
<211> LENGTH: 63
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (23)..(23)
<223> OTHER INFORMATION: glycosylation

<400> SEQUENCE: 10

Leu Arg Ser Leu Thr Thr Leu Arg Ala Leu Gly Gln Lys Glu Ala Val
1               5                   10                  15

Ser Pro Pro Asp Ala Ala Ser Ala Ala Pro Leu Arg Thr Ile Thr Ala
            20                  25                  30

Asp Thr Phe Arg Lys Leu Phe Arg Val Tyr Ser Asn Phe Leu Arg Gly
        35                  40                  45
```

```
Lys Leu Lys Leu Tyr Thr Gly Glu Ala Cys Arg Thr Gly Asp Arg
    50                  55                  60
```

<210> SEQ ID NO 11
<211> LENGTH: 10
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (6)..(6)
<223> OTHER INFORMATION: glycosylation

<400> SEQUENCE: 11

```
Gln Ala Leu Leu Val Asn Ser Ser Gln Pro
1               5                   10
```

<210> SEQ ID NO 12
<211> LENGTH: 36
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (6)..(6)
<223> OTHER INFORMATION: glycosylation

<400> SEQUENCE: 12

```
Gln Ala Leu Leu Val Asn Ser Ser Gln Pro Trp Glu Pro Leu Gln Leu
1               5                   10                  15

His Val Asp Lys Ala Val Ser Gly Leu Arg Ser Leu Thr Thr Leu Leu
            20                  25                  30

Arg Ala Leu Gly
        35
```

<210> SEQ ID NO 13
<211> LENGTH: 79
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (39)..(39)
<223> OTHER INFORMATION: glycosylated

<400> SEQUENCE: 13

```
Trp Glu Pro Leu Gln Leu His Val Asp Lys Ala Val Ser Gly Leu Arg
1               5                   10                  15

Ser Leu Thr Thr Leu Leu Arg Ala Leu Gly Ala Gln Lys Glu Ala Ile
            20                  25                  30

Ser Pro Pro Asp Ala Ala Ser Ala Ala Pro Leu Arg Thr Ile Thr Ala
        35                  40                  45

Asp Thr Phe Arg Lys Leu Phe Arg Val Tyr Ser Asn Phe Leu Arg Gly
    50                  55                  60

Lys Leu Lys Leu Tyr Thr Gly Glu Ala Cys Arg Thr Gly Asp Arg
65                  70                  75
```

<210> SEQ ID NO 14
<211> LENGTH: 6
<212> TYPE: PRT
<213> ORGANISM: artificial
<220> FEATURE:
<223> OTHER INFORMATION: Peptide fragment of human erythropoietin

```
<400> SEQUENCE: 14

Ala Gln Asp Arg Ser Ala
1               5

<210> SEQ ID NO 15
<211> LENGTH: 6
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (3)..(3)
<223> OTHER INFORMATION: glycosylation

<400> SEQUENCE: 15

Ala Gln Asn Arg Ser Ala
1               5

<210> SEQ ID NO 16
<211> LENGTH: 6
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (3)..(3)
<223> OTHER INFORMATION: glycosylation

<400> SEQUENCE: 16

Ala Glu Asn Ile Thr Gly
1               5

<210> SEQ ID NO 17
<211> LENGTH: 12
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (3)..(3)
<223> OTHER INFORMATION: glycosylation
<220> FEATURE:
<221> NAME/KEY: MISC_FEATURE
<222> LOCATION: (9)..(9)
<223> OTHER INFORMATION: glycosylation

<400> SEQUENCE: 17

Ala Glu Asn Ile Thr Gly Ala Gln Asn Arg Ser Ala
1               5                   10

<210> SEQ ID NO 18
<211> LENGTH: 7
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (3)..(3)
<223> OTHER INFORMATION: glycosylation

<400> SEQUENCE: 18

Ala Glu Asn Leu Thr Thr Gly
1               5

<210> SEQ ID NO 19
<211> LENGTH: 8
```

```
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (6)..(6)
<223> OTHER INFORMATION: glycosylation

<400> SEQUENCE: 19

Gln Ala Leu Leu Val Asn Ser Ser
1               5

<210> SEQ ID NO 20
<211> LENGTH: 15
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (3)..(3)
<223> OTHER INFORMATION: glycosylated
<220> FEATURE:
<221> NAME/KEY: MISC_FEATURE
<222> LOCATION: (13)..(13)
<223> OTHER INFORMATION: glycosylated

<400> SEQUENCE: 20

Ala Glu Asn Leu Thr Thr Gly Gln Ala Leu Leu Val Asn Ser Ser
1               5                   10                  15

<210> SEQ ID NO 21
<211> LENGTH: 12
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (9)..(9)
<223> OTHER INFORMATION: glycosylated

<400> SEQUENCE: 21

Ala Ile Ser Pro Pro Asp Ala Ala Ser Ala Ala Pro
1               5                   10

<210> SEQ ID NO 22
<211> LENGTH: 6
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (3)..(3)
<223> OTHER INFORMATION: glycosylated

<400> SEQUENCE: 22

Arg Val Asn Ala Ser Gly
1               5

<210> SEQ ID NO 23
<211> LENGTH: 18
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (3)..(3)
<223> OTHER INFORMATION: glycosylated
```

```
<220> FEATURE:
<221> NAME/KEY: MISC_FEATURE
<222> LOCATION: (15)..(15)
<223> OTHER INFORMATION: glycosylated

<400> SEQUENCE: 23

Arg Val Asn Ala Ser Gly Ala Ile Ser Pro Pro Asp Ala Ala Ser Ala
1               5                   10                  15

Ala Pro

<210> SEQ ID NO 24
<211> LENGTH: 16
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (3)..(3)
<223> OTHER INFORMATION: glycosylated
<220> FEATURE:
<221> NAME/KEY: MISC_FEATURE
<222> LOCATION: (14)..(14)
<223> OTHER INFORMATION: glycosylated

<400> SEQUENCE: 24

Ala Glu Asn Leu Thr Thr Gly Gly Gln Ala Leu Leu Val Asn Ser Ser
1               5                   10                  15

<210> SEQ ID NO 25
<211> LENGTH: 9
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (6)..(6)
<223> OTHER INFORMATION: glycosylated

<400> SEQUENCE: 25

Cys Ala Arg Ser Leu Asn Ile Thr Gly
1               5

<210> SEQ ID NO 26
<211> LENGTH: 24
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (3)..(3)
<223> OTHER INFORMATION: glycosylated
<220> FEATURE:
<221> NAME/KEY: MISC_FEATURE
<222> LOCATION: (13)..(13)
<223> OTHER INFORMATION: glycosylated
<220> FEATURE:
<221> NAME/KEY: MISC_FEATURE
<222> LOCATION: (22)..(22)
<223> OTHER INFORMATION: glycosylated

<400> SEQUENCE: 26

Ala Glu Asn Leu Thr Thr Gly Cys Ala Arg Ser Leu Asn Ile Thr Gly
1               5                   10                  15

Gln Ala Leu Leu Val Asn Ser Ser
            20

<210> SEQ ID NO 27
```

```
<211> LENGTH: 9
<212> TYPE: PRT
<213> ORGANISM: artificial
<220> FEATURE:
<223> OTHER INFORMATION: Peptide fragment of human erythropoietin

<400> SEQUENCE: 27

Cys Ala Arg Ser Leu Asp Ile Thr Gly
1               5

<210> SEQ ID NO 28
<211> LENGTH: 8
<212> TYPE: PRT
<213> ORGANISM: artificial
<220> FEATURE:
<223> OTHER INFORMATION: Peptide fragment of human erythropoietin

<400> SEQUENCE: 28

Gln Ala Leu Leu Val Asp Ser Ser
1               5

<210> SEQ ID NO 29
<211> LENGTH: 17
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (6)..(6)
<223> OTHER INFORMATION: glycosylated
<220> FEATURE:
<221> NAME/KEY: MISC_FEATURE
<222> LOCATION: (15)..(15)
<223> OTHER INFORMATION: glycosylated

<400> SEQUENCE: 29

Cys Ala Arg Ser Leu Asn Ile Thr Gly Gln Ala Leu Leu Val Asn Ser
1               5                   10                  15

Ser

<210> SEQ ID NO 30
<211> LENGTH: 10
<212> TYPE: PRT
<213> ORGANISM: artificial
<220> FEATURE:
<223> OTHER INFORMATION: Peptide fragment of human erythropoietin

<400> SEQUENCE: 30

Ala Gln Lys Tyr Arg Asp Phe Leu Arg Gly
1               5                   10

<210> SEQ ID NO 31
<211> LENGTH: 38
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (13)..(13)
<223> OTHER INFORMATION: glycosylated

<400> SEQUENCE: 31

Ala Gln Lys Glu Ala Ile Ser Pro Pro Asp Ala Ala Ser Ala Ala Pro
1               5                   10                  15

Leu Arg Thr Ile Thr Ala Asp Thr Phe Arg Lys Leu Phe Arg Val Tyr
                20                  25                  30
```

```
Ser Asn Phe Leu Arg Gly
        35

<210> SEQ ID NO 32
<211> LENGTH: 15
<212> TYPE: PRT
<213> ORGANISM: artificial
<220> FEATURE:
<223> OTHER INFORMATION: Peptide fragment of human erythropoietin

<400> SEQUENCE: 32

Lys Leu Lys Leu Tyr Thr Gly Glu Ala Cys Arg Thr Gly Asp Arg
1               5                   10                  15

<210> SEQ ID NO 33
<211> LENGTH: 53
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (13)..(13)
<223> OTHER INFORMATION: glycosylated

<400> SEQUENCE: 33

Ala Gln Lys Glu Ala Ile Ser Pro Pro Asp Ala Ala Ser Ala Ala Pro
1               5                   10                  15

Leu Arg Thr Ile Thr Ala Asp Thr Phe Arg Lys Leu Phe Arg Val Tyr
            20                  25                  30

Ser Asn Phe Leu Arg Gly Lys Leu Lys Leu Tyr Thr Gly Glu Ala Cys
        35                  40                  45

Arg Thr Gly Asp Arg
    50

<210> SEQ ID NO 34
<211> LENGTH: 20
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (3)..(3)
<223> OTHER INFORMATION: glycosylated
<220> FEATURE:
<221> NAME/KEY: MISC_FEATURE
<222> LOCATION: (10)..(10)
<223> OTHER INFORMATION: glycosylated
<220> FEATURE:
<221> NAME/KEY: MISC_FEATURE
<222> LOCATION: (17)..(17)
<223> OTHER INFORMATION: glycosylated

<400> SEQUENCE: 34

Ala Glu Asn Ile Thr Thr Gly Cys Ala Asn Arg Ser Gly Phe Cys Ala
1               5                   10                  15

Thr Ala Ala Pro
            20

<210> SEQ ID NO 35
<211> LENGTH: 7
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (3)..(3)
```

<223> OTHER INFORMATION: glycosylated

<400> SEQUENCE: 35

Cys Ala Asn Arg Ser Gly Phe
1               5

<210> SEQ ID NO 36
<211> LENGTH: 6
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (3)..(3)
<223> OTHER INFORMATION: glycosylated

<400> SEQUENCE: 36

Cys Ala Thr Ala Ala Pro
1               5

<210> SEQ ID NO 37
<211> LENGTH: 6
<212> TYPE: PRT
<213> ORGANISM: artificial
<220> FEATURE:
<223> OTHER INFORMATION: Peptide fragment of human erythropoietin

<400> SEQUENCE: 37

Cys Ala Asp Arg Ser Gly
1               5

<210> SEQ ID NO 38
<211> LENGTH: 7
<212> TYPE: PRT
<213> ORGANISM: artificial
<220> FEATURE:
<223> OTHER INFORMATION: Peptide fragment of human erythropoietin

<400> SEQUENCE: 38

Cys Ala Asp Arg Ser Gly Phe
1               5

<210> SEQ ID NO 39
<211> LENGTH: 4
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (1)..(1)
<223> OTHER INFORMATION: glycosylated

<400> SEQUENCE: 39

Thr Ala Ala Pro
1

<210> SEQ ID NO 40
<211> LENGTH: 6
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (3)..(3)
<223> OTHER INFORMATION: glycosylated

<400> SEQUENCE: 40

```
Cys Ala Thr Ala Ala Pro
1               5

<210> SEQ ID NO 41
<211> LENGTH: 7
<212> TYPE: PRT
<213> ORGANISM: artificial
<220> FEATURE:
<223> OTHER INFORMATION: Peptide fragment of human erythropoietin

<400> SEQUENCE: 41

Ala Glu Asp Leu Thr Thr Gly
1               5

<210> SEQ ID NO 42
<211> LENGTH: 7
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (3)..(3)
<223> OTHER INFORMATION: glycosylated

<400> SEQUENCE: 42

Ala Glu Asn Leu Thr Thr Gly
1               5

<210> SEQ ID NO 43
<211> LENGTH: 36
<212> TYPE: PRT
<213> ORGANISM: artificial
<220> FEATURE:
<223> OTHER INFORMATION: Peptide fragment of human erythropoietin

<400> SEQUENCE: 43

Gln Ala Leu Leu Val Asp Ser Ser Gln Pro Trp Glu Pro Leu Gln Leu
1               5                   10                  15

His Val Asp Lys Ala Val Ser Gly Leu Arg Ser Leu Thr Thr Leu Leu
            20                  25                  30

Arg Ala Leu Gly
        35

<210> SEQ ID NO 44
<211> LENGTH: 28
<212> TYPE: PRT
<213> ORGANISM: artificial
<220> FEATURE:
<223> OTHER INFORMATION: Peptide fragment of human erythropoietin

<400> SEQUENCE: 44

Ala Pro Pro Arg Leu Ile Cys Asp Ser Arg Val Leu Glu Arg Tyr Leu
1               5                   10                  15

Leu Glu Ala Lys Glu Ala Glu Asp Ile Thr Thr Gly
            20                  25

<210> SEQ ID NO 45
<211> LENGTH: 16
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (3)..(3)
<223> OTHER INFORMATION: glycosylated
```

```
<400> SEQUENCE: 45

Ala Glu Asn Ile Thr Thr Gly Cys Ala Glu His Cys Ser Leu Asn Glu
1               5                   10                  15

<210> SEQ ID NO 46
<211> LENGTH: 7
<212> TYPE: PRT
<213> ORGANISM: artificial
<220> FEATURE:
<223> OTHER INFORMATION: Peptide fragment of human erythropoietin

<400> SEQUENCE: 46

Ala Glu Asp Ile Thr Thr Gly
1               5

<210> SEQ ID NO 47
<211> LENGTH: 7
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (3)..(3)
<223> OTHER INFORMATION: glycosylated

<400> SEQUENCE: 47

Ala Glu Asn Ile Thr Thr Gly
1               5

<210> SEQ ID NO 48
<211> LENGTH: 12
<212> TYPE: PRT
<213> ORGANISM: artificial
<220> FEATURE:
<223> OTHER INFORMATION: Peptide fragment of human erythropoietin

<400> SEQUENCE: 48

Ala Gln Lys Glu Ala Ile Ser Pro Pro Asp Ala Ala
1               5                   10

<210> SEQ ID NO 49
<211> LENGTH: 14
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (13)..(13)
<223> OTHER INFORMATION: glycosylation

<400> SEQUENCE: 49

Ala Gln Lys Glu Ala Ile Ser Pro Pro Asp Ala Ala Ser Ala
1               5                   10

<210> SEQ ID NO 50
<211> LENGTH: 39
<212> TYPE: PRT
<213> ORGANISM: artificial
<220> FEATURE:
<223> OTHER INFORMATION: Peptide fragment of human erythropoietin

<400> SEQUENCE: 50

Ala Pro Leu Arg Thr Ile Thr Ala Asp Thr Phe Arg Lys Leu Phe Arg
1               5                   10                  15
```

```
Val Tyr Ser Asn Phe Leu Arg Gly Lys Leu Lys Leu Tyr Thr Gly Glu
            20                  25                  30

Ala Cys Arg Thr Gly Asp Arg
        35

<210> SEQ ID NO 51
<211> LENGTH: 9
<212> TYPE: PRT
<213> ORGANISM: artificial
<220> FEATURE:
<223> OTHER INFORMATION: Peptide fragment of human erythropoietin

<400> SEQUENCE: 51

Lys Glu Ala Glu Asp Ile Thr Thr Gly
1               5

<210> SEQ ID NO 52
<211> LENGTH: 9
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (5)..(5)
<223> OTHER INFORMATION: glycosylation

<400> SEQUENCE: 52

Lys Glu Ala Glu Asn Ile Thr Thr Gly
1               5

<210> SEQ ID NO 53
<211> LENGTH: 18
<212> TYPE: PRT
<213> ORGANISM: artificial
<220> FEATURE:
<223> OTHER INFORMATION: Peptide fragment of human erythropoietin

<400> SEQUENCE: 53

Ala Pro Pro Arg Leu Ile Cys Asp Ser Arg Val Leu Glu Arg Tyr Leu
1               5                   10                  15

Leu Glu

<210> SEQ ID NO 54
<211> LENGTH: 19
<212> TYPE: PRT
<213> ORGANISM: artificial
<220> FEATURE:
<223> OTHER INFORMATION: Peptide fragment of human erythropoietin

<400> SEQUENCE: 54

Ala Pro Pro Arg Leu Ile Cys Asp Ser Arg Val Leu Glu Arg Tyr Leu
1               5                   10                  15

Leu Glu Ala

<210> SEQ ID NO 55
<211> LENGTH: 4
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (1)..(1)
<223> OTHER INFORMATION: glycosylation

<400> SEQUENCE: 55
```

```
Ser Ala Ala Pro
1

<210> SEQ ID NO 56
<211> LENGTH: 22
<212> TYPE: PRT
<213> ORGANISM: artificial
<220> FEATURE:
<223> OTHER INFORMATION: Peptide fragment of human erythropoietin

<400> SEQUENCE: 56

Leu Arg Ser Leu Thr Thr Leu Arg Ala Leu Gly Gln Lys Glu Ala Val
1               5                   10                  15

Ser Pro Pro Asp Ala Ala
            20

<210> SEQ ID NO 57
<211> LENGTH: 26
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (23)..(23)
<223> OTHER INFORMATION: glycosylation

<400> SEQUENCE: 57

Leu Arg Ser Leu Thr Thr Leu Arg Ala Leu Gly Gln Lys Glu Ala Val
1               5                   10                  15

Ser Pro Pro Asp Ala Ala Ser Ala Ala Pro
            20                  25

<210> SEQ ID NO 58
<211> LENGTH: 37
<212> TYPE: PRT
<213> ORGANISM: artificial
<220> FEATURE:
<223> OTHER INFORMATION: Peptide fragment of human erythropoietin

<400> SEQUENCE: 58

Leu Arg Thr Ile Thr Ala Asp Thr Phe Arg Lys Leu Phe Arg Val Tyr
1               5                   10                  15

Ser Asn Phe Leu Arg Gly Lys Leu Lys Leu Tyr Thr Gly Glu Ala Cys
            20                  25                  30

Arg Thr Gly Asp Arg
        35

<210> SEQ ID NO 59
<211> LENGTH: 13
<212> TYPE: PRT
<213> ORGANISM: artificial
<220> FEATURE:
<223> OTHER INFORMATION: Peptide fragment of human erythropoietin

<400> SEQUENCE: 59

Arg Gly Leu Ala Ile Asp Ser Thr Arg Pro Phe Gln Gly
1               5                   10

<210> SEQ ID NO 60
<211> LENGTH: 13
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
```

```
<222> LOCATION: (6)..(6)
<223> OTHER INFORMATION: glycosylation

<400> SEQUENCE: 60

Arg Gly Leu Ala Ile Asn Ser Thr Arg Pro Phe Gln Gly
1               5                   10

<210> SEQ ID NO 61
<211> LENGTH: 12
<212> TYPE: PRT
<213> ORGANISM: artificial
<220> FEATURE:
<223> OTHER INFORMATION: Peptide fragment of human erythropoietin

<400> SEQUENCE: 61

Leu Arg Thr Ile Thr Ala Asp Thr Phe Arg Lys Gly
1               5                   10

<210> SEQ ID NO 62
<211> LENGTH: 16
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (13)..(13)
<223> OTHER INFORMATION: glycosylation

<400> SEQUENCE: 62

Leu Arg Thr Ile Thr Ala Asp Thr Phe Arg Lys Gly Ser Ala Ala Pro
1               5                   10                  15

<210> SEQ ID NO 63
<211> LENGTH: 29
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (6)..(6)
<223> OTHER INFORMATION: glycosylation
<220> FEATURE:
<221> NAME/KEY: MISC_FEATURE
<222> LOCATION: (26)..(26)
<223> OTHER INFORMATION: glycosylation

<400> SEQUENCE: 63

Arg Gly Leu Ala Ile Asn Ser Thr Arg Pro Phe Gln Gly Leu Arg Thr
1               5                   10                  15

Ile Thr Ala Asp Thr Phe Arg Lys Gly Ser Ala Ala Pro
            20                  25

<210> SEQ ID NO 64
<211> LENGTH: 13
<212> TYPE: PRT
<213> ORGANISM: artificial
<220> FEATURE:
<223> OTHER INFORMATION: Peptide fragment of human erythropoietin

<400> SEQUENCE: 64

Leu Arg Val Ile Val Ala Asp Val Phe Arg Lys Gly Pro
1               5                   10

<210> SEQ ID NO 65
<211> LENGTH: 13
<212> TYPE: PRT
<213> ORGANISM: artificial
```

```
<220> FEATURE:
<223> OTHER INFORMATION: Peptide fragment of human erythropoietin

<400> SEQUENCE: 65

Ala Val Ile Val Arg Leu Pro Gly Lys Arg Phe Val Asp
1               5                   10

<210> SEQ ID NO 66
<211> LENGTH: 14
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (13)..(13)
<223> OTHER INFORMATION: glycosylation

<400> SEQUENCE: 66

Ala Gln Lys Glu Ala Ile Ser Pro Pro Asp Ala Ala Ser Ala
1               5                   10

<210> SEQ ID NO 67
<211> LENGTH: 25
<212> TYPE: PRT
<213> ORGANISM: artificial
<220> FEATURE:
<223> OTHER INFORMATION: Peptide fragment of human erythropoietin

<400> SEQUENCE: 67

Leu Arg Ser Leu Thr Thr Leu Leu Arg Ala Leu Gly Ala Gln Lys Glu
1               5                   10                  15

Ala Ile Ser Pro Pro Asp Ala Ala Pro
            20                  25

<210> SEQ ID NO 68
<211> LENGTH: 39
<212> TYPE: PRT
<213> ORGANISM: artificial
<220> FEATURE:
<223> OTHER INFORMATION: Peptide fragment of human erythropoietin

<400> SEQUENCE: 68

Ala Pro Leu Arg Thr Ile Thr Ala Asp Thr Phe Arg Lys Leu Phe Arg
1               5                   10                  15

Val Tyr Ser Asn Phe Leu Arg Gly Lys Leu Lys Leu Tyr Thr Gly Glu
            20                  25                  30

Ala Cys Arg Thr Gly Asp Arg
        35

<210> SEQ ID NO 69
<211> LENGTH: 64
<212> TYPE: PRT
<213> ORGANISM: artificial
<220> FEATURE:
<223> OTHER INFORMATION: Peptide fragment of human erythropoietin

<400> SEQUENCE: 69

Leu Arg Ser Leu Thr Thr Leu Leu Arg Ala Leu Gly Ala Gln Lys Glu
1               5                   10                  15

Ala Ile Ser Pro Pro Asp Ala Ala Pro Ala Pro Leu Arg Thr Ile Thr
            20                  25                  30

Ala Asp Thr Phe Arg Lys Leu Phe Arg Val Tyr Ser Asn Phe Leu Arg
        35                  40                  45
```

```
Gly Lys Leu Lys Leu Tyr Thr Gly Glu Ala Cys Arg Thr Gly Asp Arg
    50                  55                  60

<210> SEQ ID NO 70
<211> LENGTH: 89
<212> TYPE: PRT
<213> ORGANISM: artificial
<220> FEATURE:
<223> OTHER INFORMATION: Peptide fragment of human erythropoietin

<400> SEQUENCE: 70

Leu Arg Ser Leu Thr Thr Leu Leu Arg Ala Leu Gly Ala Gln Lys Glu
1               5                   10                  15

Ala Ile Ser Pro Pro Asp Ala Ala Pro Leu Arg Ser Leu Thr Thr Leu
            20                  25                  30

Leu Arg Ala Leu Gly Ala Gln Lys Glu Ala Ile Ser Pro Pro Asp Ala
        35                  40                  45

Ala Pro Ala Pro Leu Arg Thr Ile Thr Ala Asp Thr Phe Arg Lys Leu
    50                  55                  60

Phe Arg Val Tyr Ser Asn Phe Leu Arg Gly Lys Leu Lys Leu Tyr Thr
65                  70                  75                  80

Gly Glu Ala Cys Arg Thr Gly Asp Arg
                85

<210> SEQ ID NO 71
<211> LENGTH: 9
<212> TYPE: PRT
<213> ORGANISM: artificial
<220> FEATURE:
<223> OTHER INFORMATION: Peptide fragment of human erythropoietin

<400> SEQUENCE: 71

Cys Ala Glu His Cys Ser Leu Asn Glu
1               5

<210> SEQ ID NO 72
<211> LENGTH: 13
<212> TYPE: PRT
<213> ORGANISM: artificial
<220> FEATURE:
<223> OTHER INFORMATION: Peptide fragment of human erythropoietin
<220> FEATURE:
<221> NAME/KEY: MISC_FEATURE
<222> LOCATION: (3)..(3)
<223> OTHER INFORMATION: glycosylated
<220> FEATURE:
<221> NAME/KEY: MISC_FEATURE
<222> LOCATION: (10)..(10)
<223> OTHER INFORMATION: glycosylated

<400> SEQUENCE: 72

Cys Ala Asn Arg Ser Gly Phe Cys Ala Thr Ala Ala Pro
1               5                   10
```

COMPOSITIONS COMPRISING HOMOGENEOUSLY GLYCOSYLATED ERYTHROPOIETIN

GOVERNMENT SUPPORT

The invention was supported in part by New York State Department of Health and Grant Nos.: CA103823a and CA62948 from the National Institutes of Health. The U.S. government may have certain rights in this invention.

RELATED APPLICATIONS

The present application claims priority under 35 U.S.C. §119(e) to U.S. provisional applications, U.S. Ser. No. 60/841,678, filed Aug. 31, 2006, and U.S. Ser. No. 60/791,614, filed Apr. 11, 2006, each of which is incorporated herein by reference. This application is also related to U.S. patent application Ser. No. 10/570,556, filed on Mar. 3, 2006 (US National Phase of PCT/US2004/29047); International Application No.: PCT/US2004/29047, filed on Sep. 3, 2004; and U.S. provisional application Ser. No. 60/500,708, filed on Sep. 5, 2003; and U.S. Ser. No. 60/560,147, filed on Apr. 7, 2004; each of which is incorporated herein by reference.

BACKGROUND OF THE INVENTION

Glycoproteins are important biomacromolecules that are biosynthesized through posttranslational glycosylation of newly fashioned proteins emerging from the ribosome. Interest in glycoproteins arises at many levels. A long-term goal of the growing field of chemistry-based glycobiology is the delineation of the consequences of glycosylation on critical properties such as protein folding, proteolytic stability, and cell adhesion (Imperiali, B.; O'Connor, S. E.; Hendrickson, T.; Kellenberger, C. *Pure Appl. Chem.* 1999, 71, 777-787; Lis, H.; Sharon, N. *Eur. J. Biochem.* 1993, 218, 1-27; Rudd, P. M.; Elliott, T.; Cresswell, P.; Wilson, I. A.; Dwek, R. A. *Science* 2001, 291, 2370-2376; Bertozzi, C. R.; Kiessling, L. L. *Science* 2001, 291, 2357-2364; each of which is incorporated herein by reference). Such insights could explain why nature bothers to glycosylate otherwise functional proteins. Moreover, glycoproteins have potentially important clinical roles in the context of vaccines, diagnostics, and therapeutics. Indeed, erythropoietin, albeit a heterogeneous glycoprotein (Rush, R. S.; Derby, P. L.; Smith, D. M.; Merry, C.; Rogers, G.; Rohde, M. F.; Katta, V. *Anal. Chem.* 1995, 67, 1442-1452), is clinically valuable as a treatment for anemia, among other indications (Ridley, D. M.; Dawkins, F.; Perlin, E. *J. Natl. Med. Assoc.* 1994, 86, 129-135).

Many naturally occurring, medicinally important glycoproteins (cf., for example, erythropoietin [Ridley, D. M.; Dawkins, F.; Perlin, E. *J. Natl. Med. Assoc.* 1994, 86, 129-135] and gp120 [Geyer, H.; Holschbach, C.; Hunsmann, G.; Schneider, J. *J. Biol. Chem.* 1988, 263, 11760-11767]) display multiple glycosylation sites containing large oligosaccharide domains. However, given the complexity and variability of biological glycosylation pathways (Kornfeld, R.; Kornfeld, S. *Annu. Rev. Biochem.* 1985, 54, 631-664; Roth, J. *Chem. Rev.* 2002, 102, 285-303; each of which is incorporated herein by reference), the isolation of homogeneous glycoproteins from natural sources in significant quantity is extremely difficult.

Numerous methods exist for the production of glycopeptides by chemical synthesis. For example, glycans have been introduced into peptides via amino acid "cassettes" with pendant protected saccharides (Chen et al., *J. Am. Chem. Soc.* 1998, 120, 7760-7769; Bezay et al., *Angew. Chem. Int. Ed.* 2001, 40, 2292-2295; van Ameijde et al., *J. Chem. Soc.-Perkin Trans.* 1 2002, 1042-1049; Ciommer et al., *Synlett* 1991, 593-595; Chiesa et al., *Eur. J. Org. Chem.* 2000, 3541-3554; Meinjohanns et al., *Tetrahedron Lett.* 1995, 36, 9205-9208; each of which is incorporated herein by reference), through enzymatic manipulations of glycopeptides (Unverzagt, *Tetrahedron Lett.* 1997, 38, 5627-5630; Witte et al., *J. Am. Chem. Soc.* 1997, 119, 2114-2118; Wang et al., *J. Am. Chem. Soc.* 1997, 119, 11137-11146; Arsequell et al., *Tetrahedron: Asymmetry* 1999, 10, 3045-3094; Mizuno et al., *J. Am. Chem. Soc.* 1999, 121, 284-290; Koeller et al., *J. Am. Chem. Soc.* 2000, 122, 4241-4242; Blixt et al., *J. Am. Chem. Soc.* 2002, 124, 5739-5746; each of which is incorporated herein by reference), or by conjugation of fully elaborated, complex saccharides to short synthetic peptides (Anisfeld et al., *J. Org. Chem.* 1990, 55, 5560-5562; Cohen-Anisfeld et al., *J. Am. Chem. Soc.* 1993, 115, 10531-10537; Meinjohanns et al., *J. Chem. Soc.-Perkin Trans.* 1 1998, 549-560; each of which is incorporated herein by reference). Larger O-linked glycopeptides have been synthesized using ligation techniques (Dawson et al., *Science* 1994, 266, 776-779; Liu et al., *Proc. Natl. Acad. Sci. U.S.A.* 1994, 91, 6584-6588; each of which is incorporated herein by reference) such as expressed protein ligation (Muir et al., *Proc. Natl. Acad. Sci. U.S.A.* 1998, 95, 6705-6710; Macmillan et al., *Tetrahedron* 2000, 56, 9515-9525; Tolbert et al., *J. Am. Chem. Soc.* 2000, 122, 5421-5428; each of which is incorporated herein by reference). Bertozzi and coworkers extended the scope of the "cassette" approach by applying native chemical ligation to the synthesis of a biologically active glycoprotein with two single-residue O-linked glycans (Shin et al., *J. Am. Chem. Soc.* 1999, 121, 11684-11689; incorporated herein by reference). Tolbert and Wong described the ligation of a 392-residue intein-generated peptide thioester and a dipeptide functionalized with a single N-acetylglucosamine residue. However, none of these approaches has allowed the assembly of complex glypeptides or glycoproteins multiply functionalized (e.g., multiply glycosylated) at designated sites.

Accordingly, there remains a need for novel synthetic methods for the preparation of homogeneous glycosylated, or otherwise post-translationally modified, peptides and proteins. Specifically, convergent, stereoselective, versatile methods for preparing such glycopeptides and/or glycoproteins are needed.

SUMMARY OF THE INVENTION

The present invention provides novel chemistry and compounds (e.g., peptides, glycopeptides, proteins, glycoproteins, auxillary groups, intermediates, reagents) for the synthesis of peptides and proteins, particularly glycosylated petides or proteins, or other post-translationally modified peptides and proteins. The inventive chemistry has been developed to prepare compositions of homogeneously glycosylated proteins such as erythropoietin, wherein all the molecules of the composition have the same, identical glycosylation pattern. Purifying erythropoietin from living organisms or cells leads to heterogeneous mixtures of various glycosylated forms of erythropoietin; therefore, to date, a homogeneous composition of erythropoietin has not been achieved. As would be appreciated by one of skill in the art, the inventive chemistry may be applied to other proteins and peptides, besides erythropoietin, allowing for the preparation of homogenous compositions of glycosylated or other post-translationally modified proteins and peptides never before prepared. The invention provides novel ligation methods as well as methods, strategies, and intermediates for building larger glycosylated proteins and peptides, including linear and cyclic proteins and petides. The methods are amenable to the solution phase as well as the solid phase. The proteins and peptides may include other post-translational modifications besides glycosylation such as phosphorylation, acylation, farnesylation, hydroxylation, lipidation, etc. The methodology includes ligation methods that do not include the use of an auxillary group, thereby avoiding the synthesis, installation, and removal of the auxillary group. Methods have also been developed that covert a cysteine or seleno-cysteine amino acid in a peptide or protein to an alanine. Such methods are particularly useful when native chemical ligation (NCL) methods are used to synthesize a peptide or protein.

In one aspect, the invention provides a composition of purified homogeneously glycosylated erythropoietin or a purified homogeneously glycosylated fragment of erythropoietin. The primary amino acid sequence of erythropoietin is as follows:

Ala-Pro-Pro-Arg-Leu-Ile-Cys-Asp-Ser-Arg-Val-Leu-Glu-Arg-Tyr-Leu-Leu-Glu-Ala- Lys-Glu-Ala-Glu-Asn-Ile-Thr-Thr-Gly-Cys-Ala-Glu-His-Cys-Ser-Leu-Asn-Glu-Asn- Ile-Thr-Val-Pro-Asp-Thr-Lys-Val-Asn-Phe-Tyr-Ala-Trp-Lys-Arg-Met-Glu-Val-Gly- Gln-Gln-Ala-Glu-Val-Trp-Gln-Gly-Leu-Ala-Leu-Leu-Ser-Glu-Ala-Val-Leu-Arg- Gly-Gln-Ala-Leu-Leu-Val-Asn-Ser-Ser-Gln-Pro-Trp-Glu-Pro-Leu-Gln-Leu-His-Val- Asp-Lys-Ala-Val-Ser-Gly-Leu-Arg-Ser-Leu-Thr-Thr-Leu-Leu-Arg-Ala-Leu-Gly- Ala-Gln-Lys-Glu-Ala-Ile-Ser-Pro-Pro-Asp-Ala-Ala-Ser-Ala-Ala-Pro-Leu-Arg-Thr-Ile-Thr-Ala-Asp-Thr-Phe-Arg-Lys-Leu-Phe-Arg-Val-Tyr-Ser-Asn-Phe-Leu-Arg-Gly- Lys-Leu-Lys-Leu-Tyr-Thr-Gly-Glu-Ala-Cys-Arg-Thr-Gly-Asp-Arg (SEQ ID NO: XX).

Erythropoietin is known to be glycosylated at Asn24, Asn38, Asn83, and Ser126. One form of glycosylated erythropoietin is of the formula:

Ala-Pro-Pro-Arg-Leu-Ile-Cys-Asp-Ser-Arg-Val-Leu-Glu-Arg-Tyr-Leu-Leu-Glu-Ala-Lys-

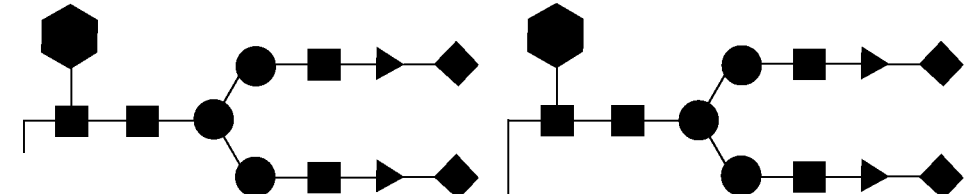

Glu-Ala-Glu-Asn$^{24}$-Ile-Thr-Thr-Gly-Cys-Ala-Glu-His-Cys-Ser-Leu-Asn-Glu-Asn$^{38}$-Ile-
Thr-Val-Pro-Asp-Thr-Lys-Val-Asn-Phe-Tyr-Ala-Trp-Lys-Arg-Met-Glu-Val-Gly-Gln-Gln-
Ala-Glu-Val-Trp-Gln-Gly-Leu-Ala-Leu-Leu-Ser-Glu-Ala-Val-Leu-Arg-Gly-Gln-Ala-Leu-

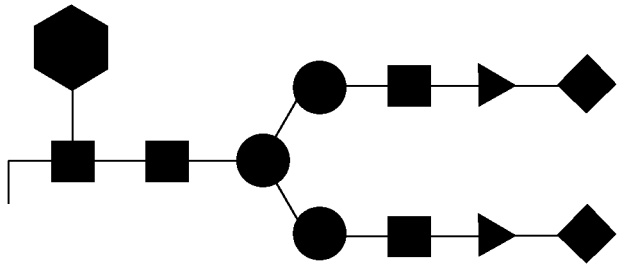

Leu-Val-Asn$^{83}$-Ser-Ser-Gln-Pro-Trp-Glu-Pro-Leu-Gln-Leu-His-Val-Asp-Lys-Ala-Val-
Ser-Gly-Leu-Arg-Ser-Leu-Thr-Thr-Leu-Leu-Arg-Ala-Leu-Gly-Ala-Gln-Lys-Glu-Ala-Ile-

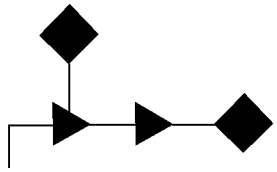

Ser-Pro-Pro-Asp-Ala-Ala-Ser$^{126}$-Ala-Ala-Pro-Leu-Arg-Thr-Ile-Thr-Ala-Asp-Thr-Phe-Arg-
Lys-Leu-Phe-Arg-Val-Tyr-Ser-Asn-Phe-Leu-Arg-Gly-Lys-Leu-Lys-Leu-Tyr-Thr-Gly-Glu-
Ala-Cys-Arg-Thr-Gly-Asp-Arg

◆ Sialic acid

▶ Galactose   ⬢ Fucose

● Mannose   ■ Glucosamine.

In certain embodiments, the homogeneous composition comprises erythropoietin of the above structure. The invention also provide fragments of erythropoietin. Such fragment may be useful in the synthesis of erythropoietin. Examplary fragments include the primary sequence:

Ala-ProPro-Arg-Leu-Ile-Cys-Asp-Ser-Arg-Val-Leu-Glu-Arg-Tyr-Leu-Leu-Glu-Ala-Lys- Glu-Ala-Glu-Asn-Ile-Thr-Thr-Gly (Amino acids 1-28; SEQ ID NO: XX);

Cys-Ala-Glu-His-Cys-Ser-Leu-Asn-Glu-Asn-Ile-Thr-Val-Pro-Asp-Thr-Lys-Val-Asn-Phe- Tyr-Ala-Trp-Lys-Arg-Met-Glu-Val-Gly-Gln-Gln-Ala-Glu-Val-Trp-Gln-Gly-Leu-Ala-Leu- Leu-Ser-Glu-Ala-Val-Leu-Arg-Gly (Amino acids 29-77; SEQ ID NO: XX);

Gln-Ala-Leu-Leu-Val-Asn-Ser-Ser-Gln-Pro-Trp-Glu-Pro-Leu-Gln-Leu-His-Val-Asp-Lys- Ala-Val-Ser-Gly-Leu-Arg-Ser-Leu-Thr-Thr-Leu-Leu-Arg-Ala-Leu-Gly (Amino acids 78-113; SEQ ID NO: XX);

Ala-Gln-Lys-Glu-Ala-Ile-Ser-Pro-Pro-Asp-Ala-Ala-Ser-Ala-Ala-Pro-Leu-Arg-Thr-Ile-Thr- Ala-Asp-Thr-Phe-Arg-Lys-Leu-Phe-Arg-Val-Tyr-Ser-Asn-Phe-Leu-Arg-Gly-Lys-Leu-Lys- Leu-Tyr-Thr-Gly-Glu-Ala-Cys-Arg-Thr-Gly-Asp-Arg (amino acids 114-166; SEQ ID NO: XX); or combinations of the above fragments. The primary sequence of the fragements may be modified. The sequence may include 1, 2, 3, 4, 5, 6, 7, 8, 9, or 10 amino acid substitutions, additions, and/or deletions. For example, an asparagine residue may be replace with an aspartate residue (e.g., at positions 24, 38, or 83). The fragments may also be glycosylated and/or the termini of the fragments may be modified. Examples of some synthetically useful fragments include:

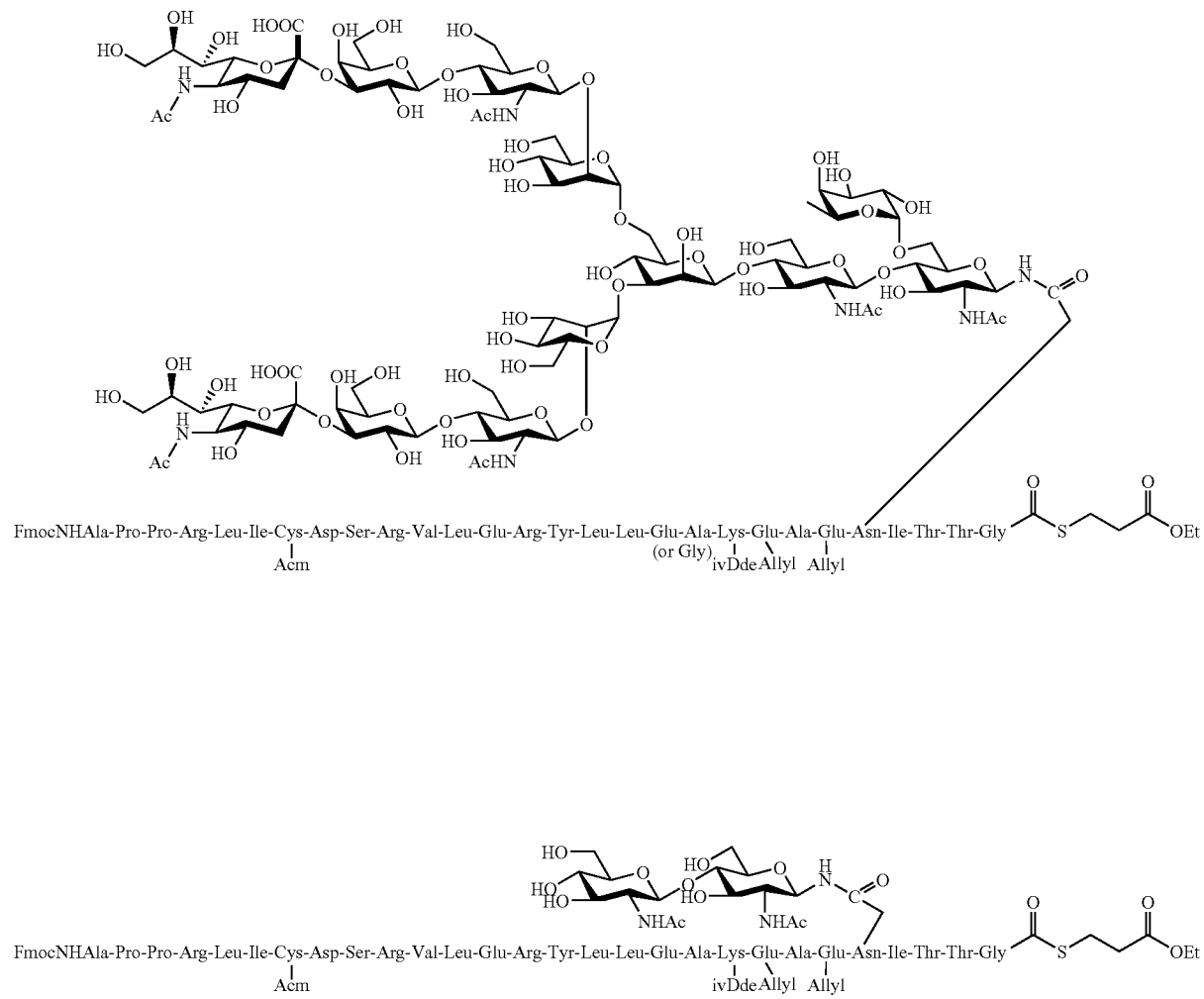

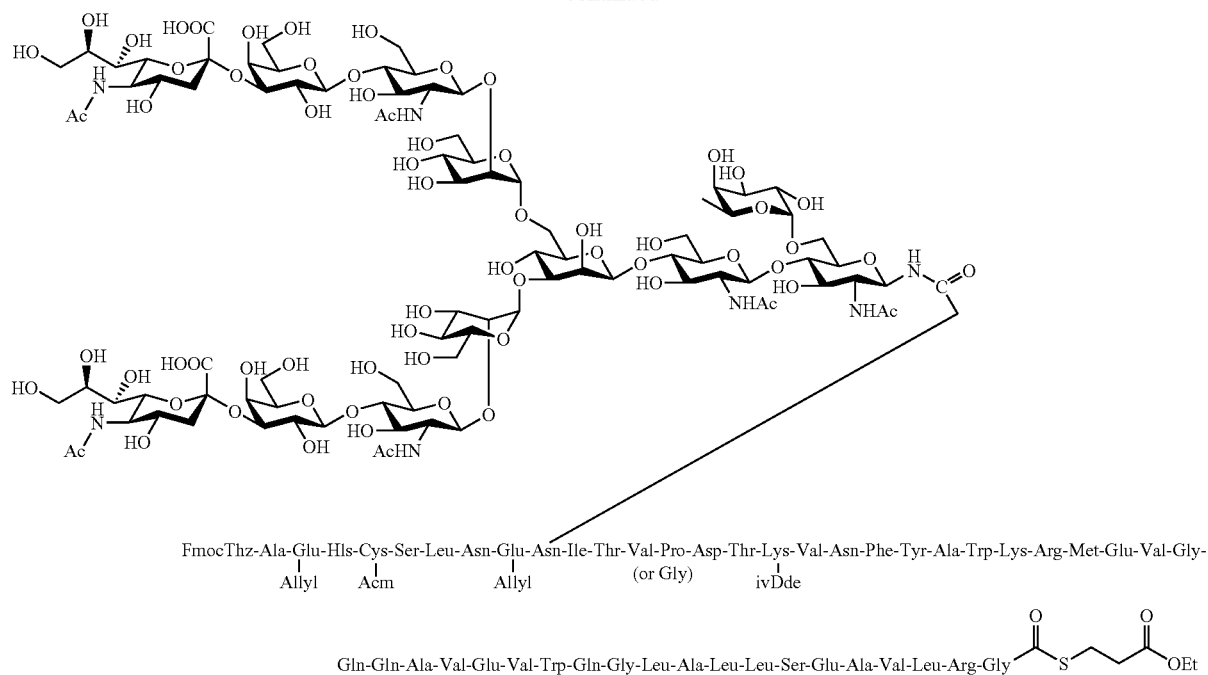
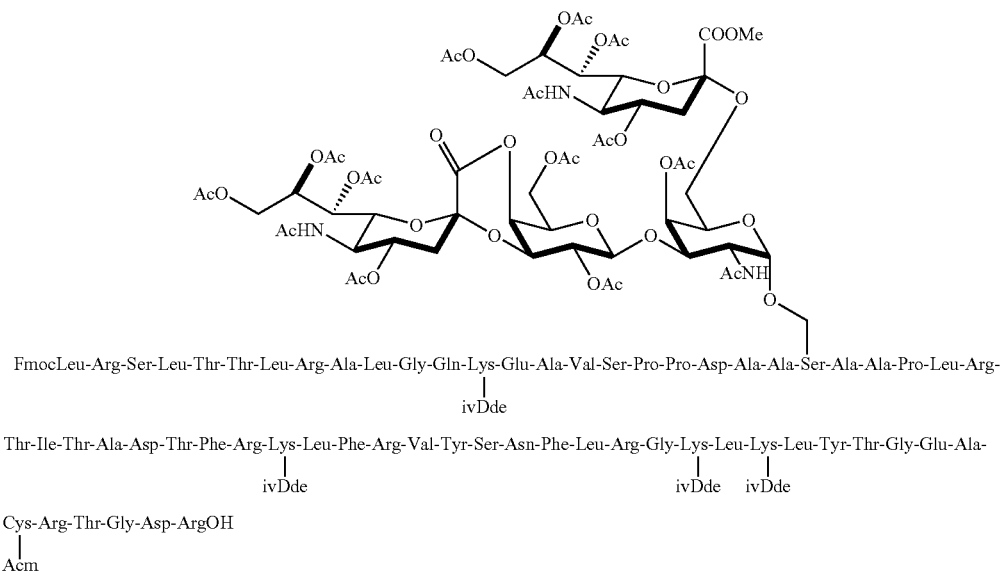
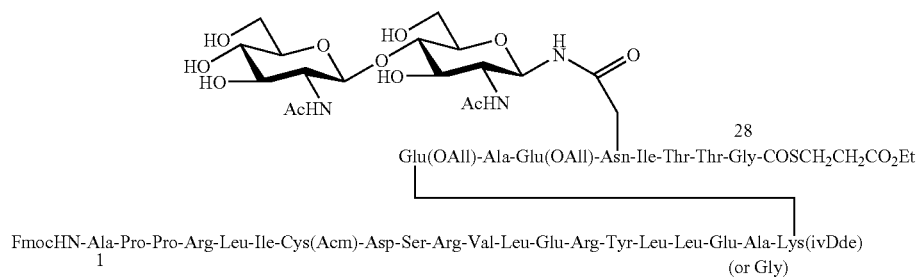

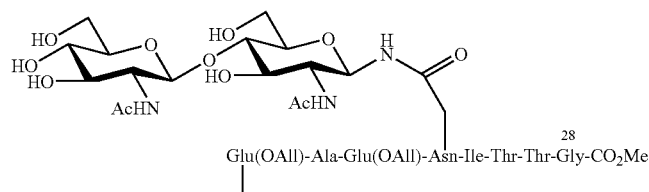
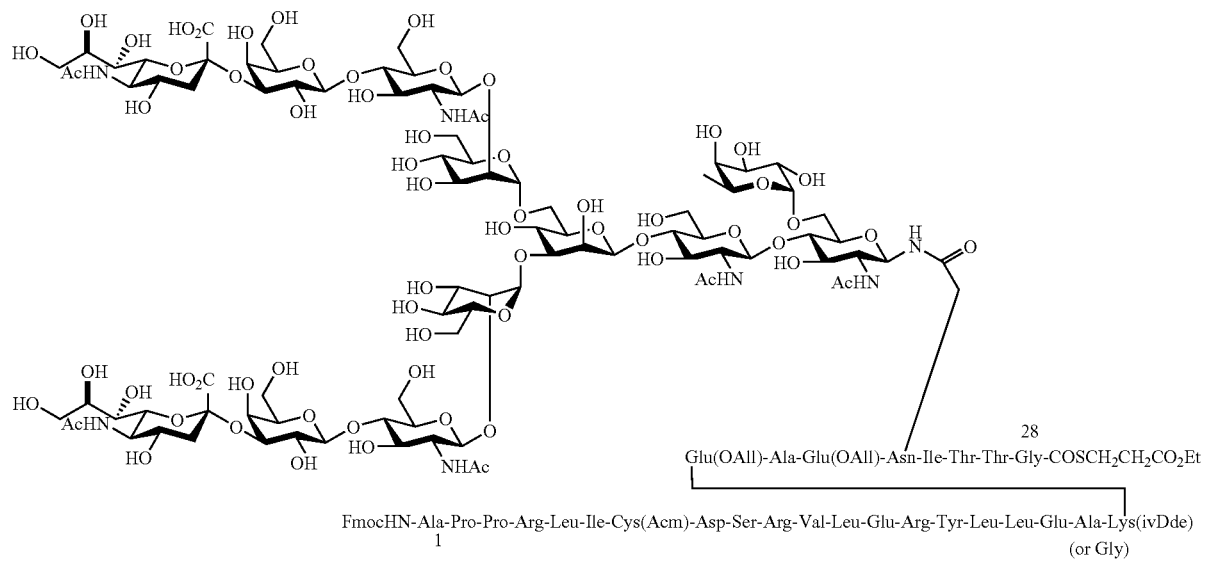
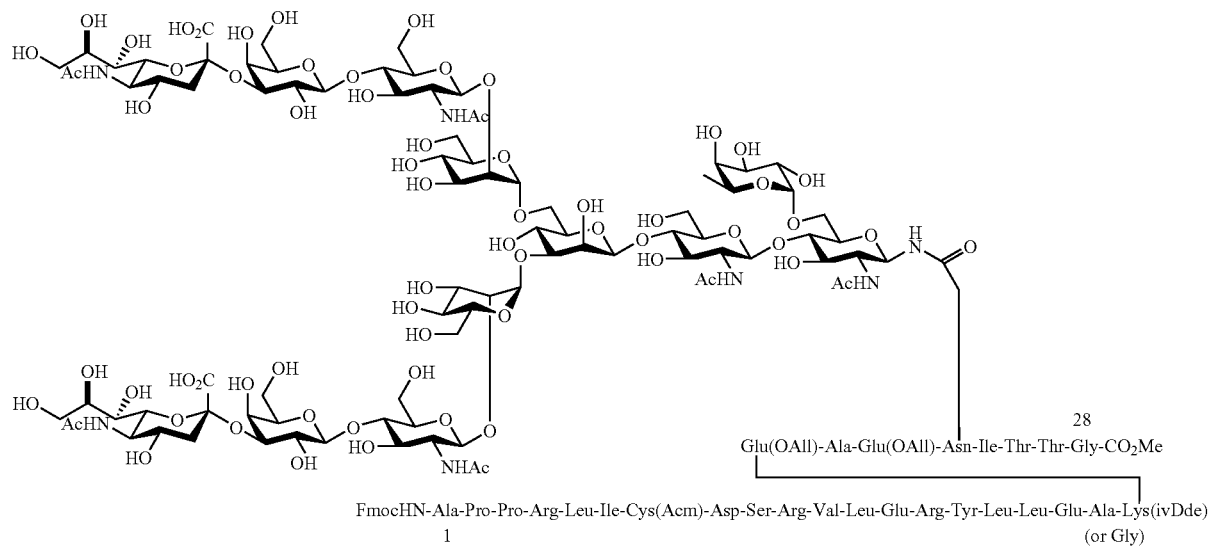

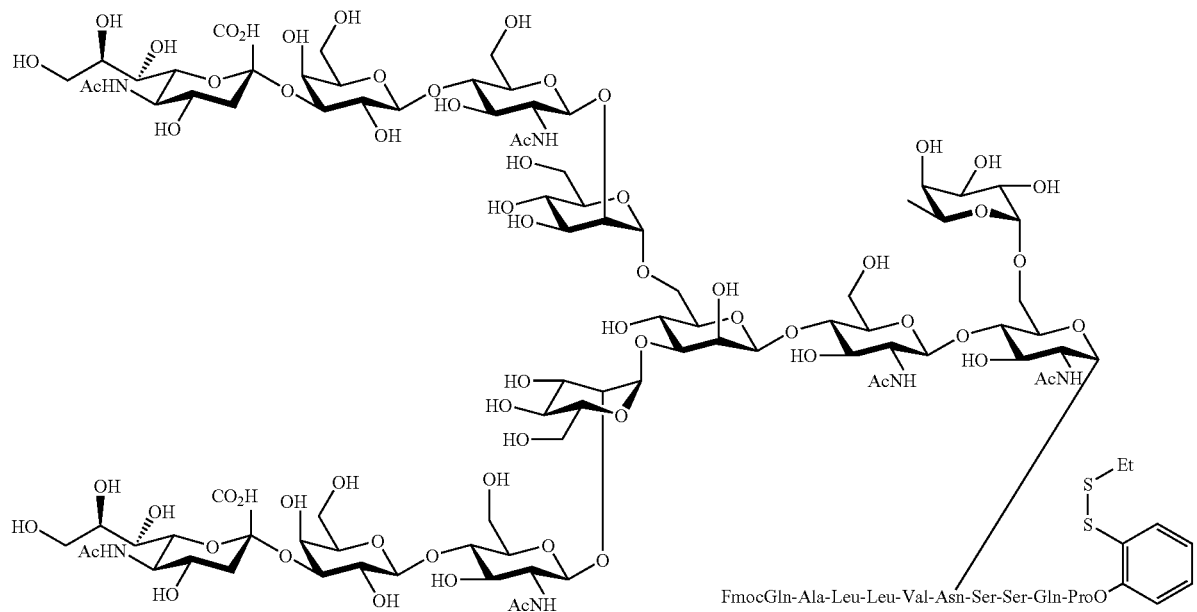
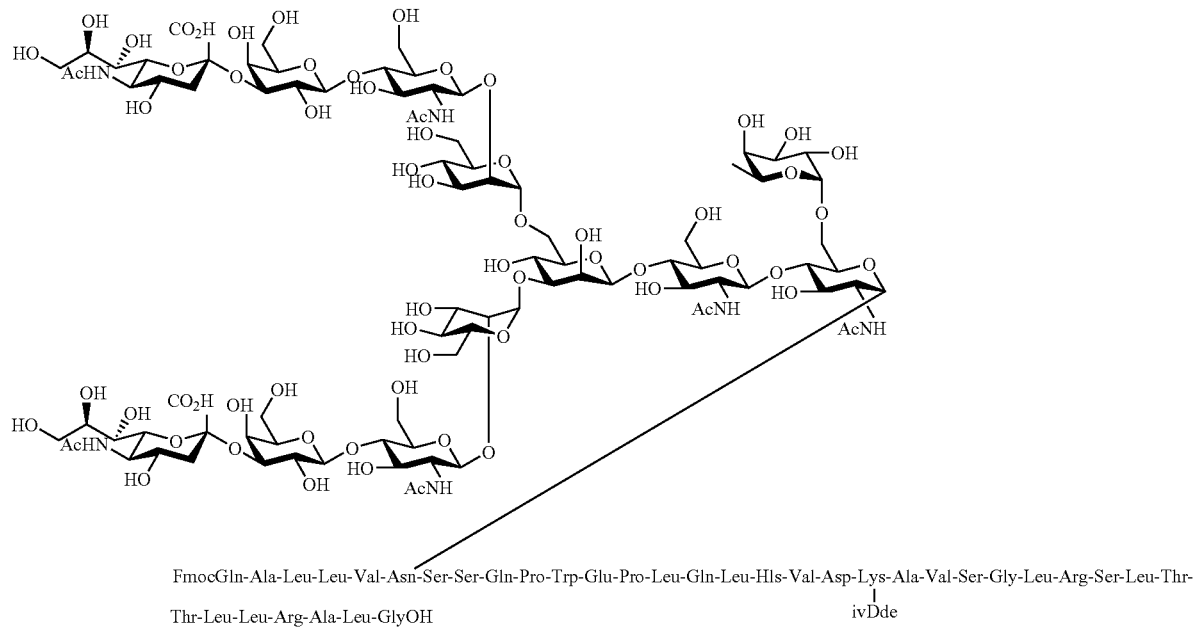

-continued

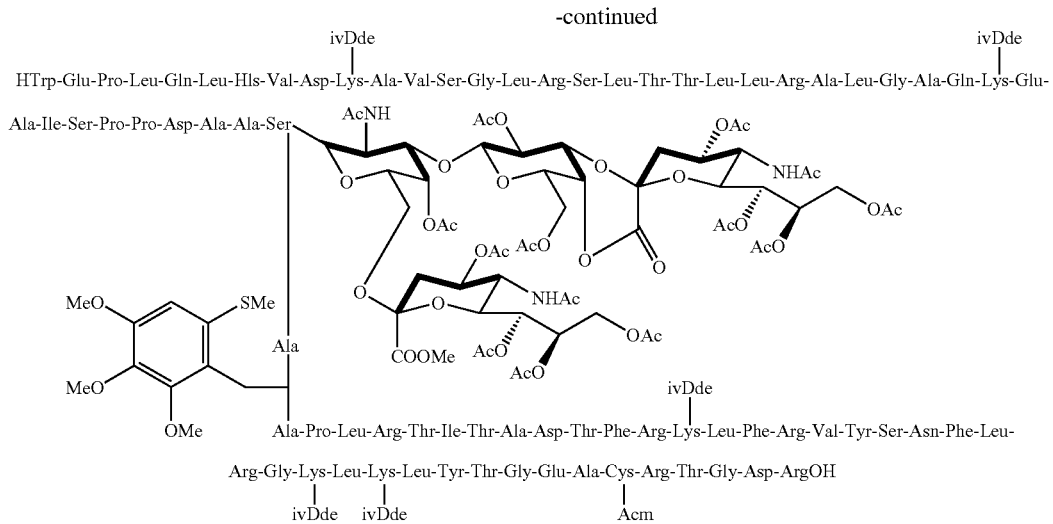

EQUIVALENTS

The present invention also provides strategies for preparing erythropoietin or fragments of erythropoietin. In one embodiments, erythropoietin (EPO) is synthesized by ligating together a fragment containing amino acids 1-28 of EPO, a fragment containing amino acids 29-77 of EPO, a fragment containing amino acids 78-113 of EPO; and a fragment containing amino acids 114-166. The fragments may be ligated together using any methods known in the art including those described herein (e.g., native chemical ligation or non-native chemical ligation). In certain embodiments, one or more of the fragments is glycosylated prior to ligation. In other embodiments, one or more of the fragments is glycosylated after ligation. The glycosylation of an aspartate residue may be achieved by the Kochetkov-Lansbury amination-aspartylation protocol, thereby forming an N-linked glycosylated asparagine. In certain embodiments, a fragment (e.g., amino acids 78-113 of EPO) is prepared by solid phase peptide synthesis using single amino acids in combination with dipeptides. For example, dipeptides Leu105-Thr106, Val99-Ser100, Asp96-Lys97, and Asp83-Ser84. The peptide fragments may optionally include protecting groups and/or auxillary groups. As would be appreciated by one of skill in the art, the above four fragments may in turn be synthesized by ligating smaller fragments. For example, the fragment of EPO containing amino acids 78-113 may be prepared by ligating a fragment containing amino acids 78-87 to a fragment containing amino acids 88-113; or by by ligating a fragment containing amino acids 78-90 to a fragment containing amino acids 91-113. To give but one other example, the fragment of EPO containing amino acids 1-28 may be prepared by ligating a fragment containing amino acids 1-19 to a fragment containing amino acids 20-28. The fragment of EPO containing amino acids 29-77 may be prepared by ligating a fragment containing amino acids 29-42 to a fragment containing amino acids 43-77. The fragment of EPO containing amino acids 78-166 may be prepared by ligating a fragment containing amino acids 88-113 to a fragment containing amino acids 114-166, and then ligating amino acids 78-87 onto the resulting fragment. All of the gyclosylated or unglycosylated, protected or unprotected fragments are also considered to be within the scope of the invention.

In one aspect, the invention provides an isolated homogeneous polyfunctionalized protein having the structure:

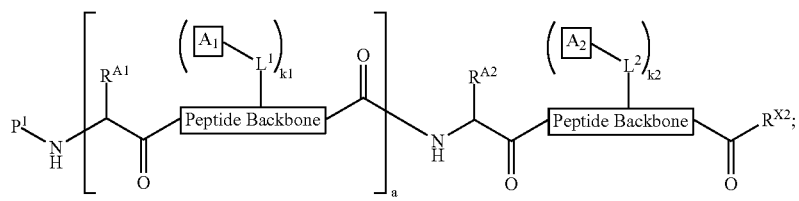

wherein each occurrence of the "peptide backbone" has an amino acid sequence that is either identical to or closely related to that of a naturally occurring protein near a functionalized site, or a truncated, elongated or derivatized version thereof; wherein any one or more of the amino acid residues may bear one or more protecting groups;

$P^1$ is hydrogen or a nitrogen protecting group;

a is an integer between 1 and about 20;

each occurrence of $R^{A1}$ and $R^{A2}$ is independently a natural or non-natural amino acid side chain;

each occurrence of k1 and k2 is independently an integer between 1 and about 20;

each occurrence of $A_1$ and $A_2$ is independently an aliphatic, heteroaliphatic, aromatic, heteroaromatic, aryl, heteroaryl, carbohydrate, or a pharmaceutically useful group or entity;

each occurrence of $L^1$ is independently a substituted or unsubstituted, linear or branched, cyclic or acyclic, saturated or unsaturated aliphatic or heteroaliphatic moiety or a natural or non-natural amino acid side chain; and $R^{X2}$ is $-OR^{X2a}$ or $-NR^{X2b}R^{X2c}$, wherein $R^{X2a}$ is hydrogen, alkyl, aromatic, heteroaromatic, aryl, heteroaryl, -alkyl (aryl), -alkyl(heteroaryl), a carboxylic acid protecting group, an amino acid or a protected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid or a protected amino acid.

In another aspect, the invention provides an isolated glycopeptide having formula:

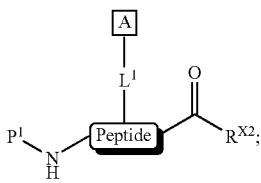

wherein the peptide has an amino acid sequence that is either identical to or closely related to that of a naturally occurring glycoprotein near a glycosylation site, or a truncated, elongated or derivatized version thereof; wherein any one or more of the amino acid residues may bear one or more protecting groups; each occurrence of $L^1$ is independently a substituted or unsubstituted, linear or branched, cyclic or acyclic, saturated or unsaturated aliphatic or heteroaliphatic moiety or a natural or non-natural amino acid side chain; and $R^{X2}$ is $-OR^{X0}$, $-OR^{X2a}$ or $-NR^{X2b}R^{X2c}$, wherein $R^{X2a}$ is hydrogen, alkyl, aromatic, heteroaromatic, aryl, heteroaryl, -alkyl(aryl), -alkyl(heteroaryl), a carboxylic acid protecting group, an amino acid or a protected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid or a protected amino acid;

$R^{X0}$ is a group such that the moiety $-C(=O)$ $OR^{X0}$ can be made to undergo ligation with a peptide acyl acceptor, $P^1$ is hydrogen, a nitrogen protecting group, or a moiety having the structure:

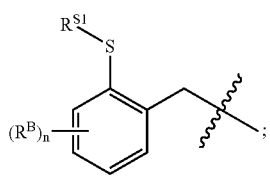

wherein n is 2 or 3; $R^{S1}$ is hydrogen or a sulfide protecting group; each occurrence of $R^B$ is independently alkoxy, hydroxy or silyloxy; and A is a carbohydrate determinant. In certain embodiments, A is of the structure:

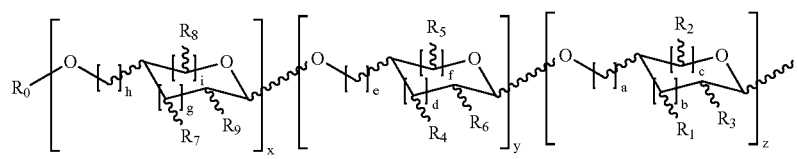

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, $COOR^{ii}$, or a substituted or unsubstituted linear or branched chain alkyl, acyl, arylalkyl or aryl group or a saccharide moiety having the structure:

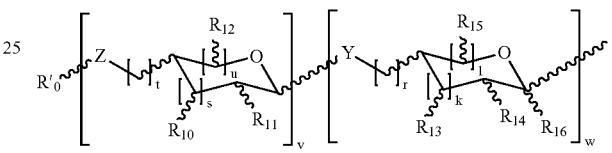

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein $R^{ii}$ and $R^{iv}$ are each independently H, or a substituted or unsubstituted linear or branched chain alkyl, arylalkyl or aryl group. In certain embodiments, A is selected from the group consisting of:

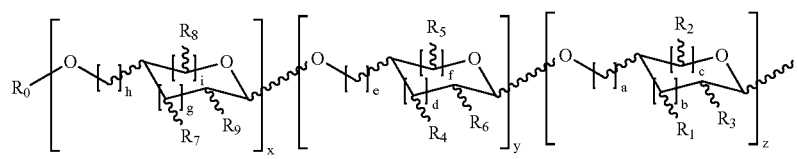

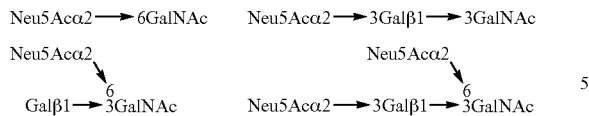
when A is O-linked; and
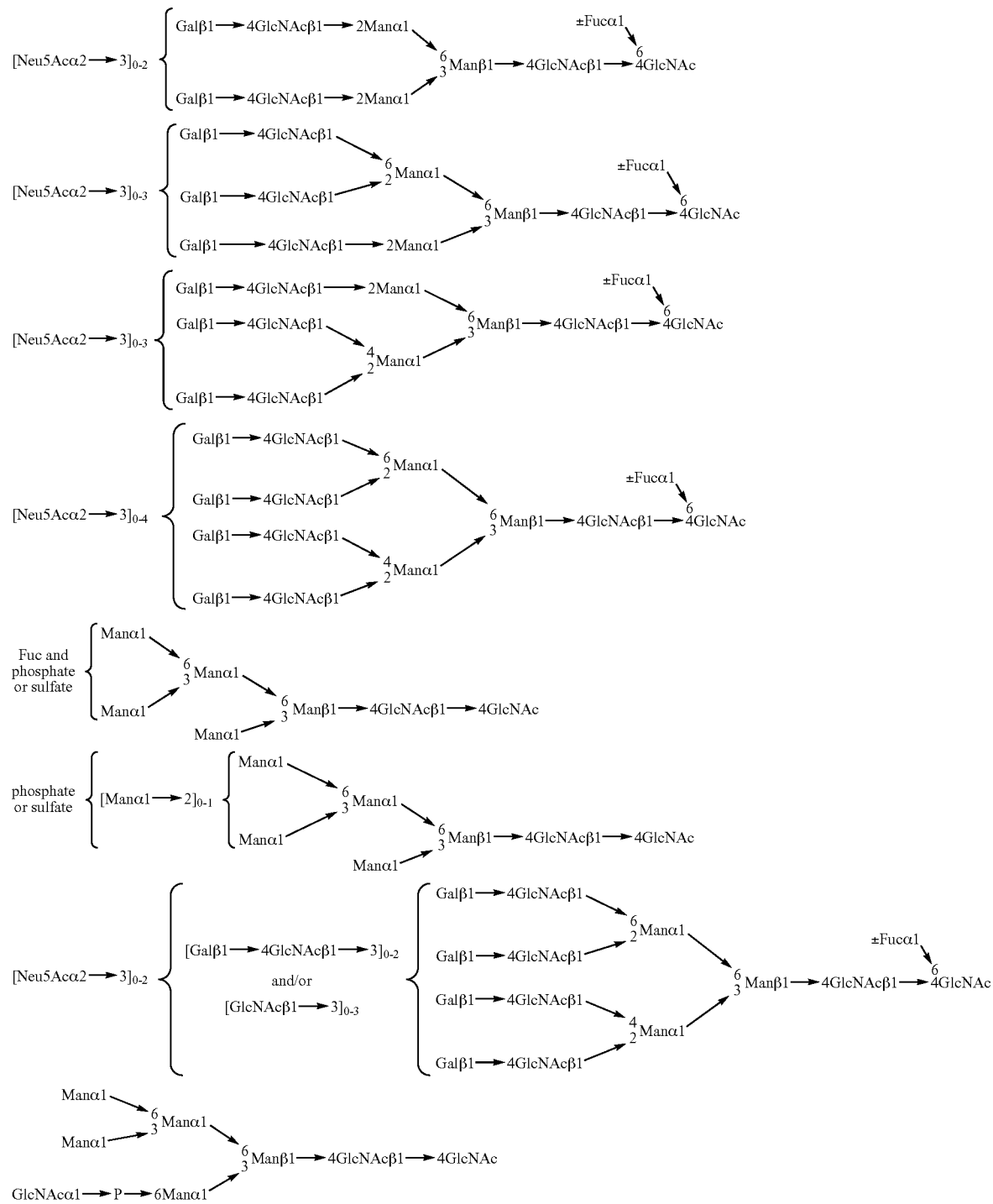

when A is N-linked. In certain embodiments, the glycopeptide is not a naturally occurring glycopeptide.

In another aspect, the invention provides an isolated intermediate having the structure:

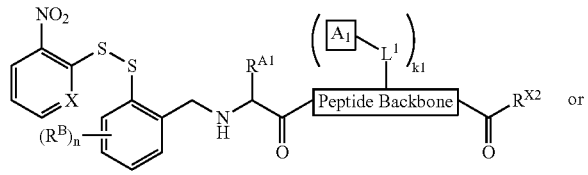

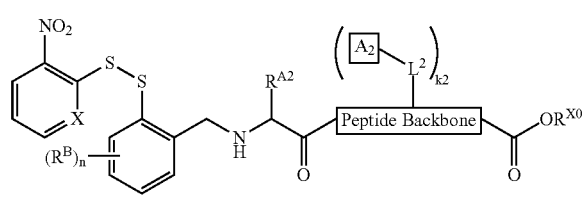

wherein
Peptide Backbone comprise two or more amino acids;
X is N or CH;
n is 2 or 3;

$R^{A1}$ and $R^{A2}$ are independently natural or non-natural amino acid side chains; each occurrence of $R^B$ is independently alkoxy, hydroxy, or silyloxy;

k1 and k2 are independently integers between 1 and about 20;

each occurrence of $A_1$ and $A_2$ is independently an aliphatic, heteroaliphatic, aromatic, heteroaromatic, aryl, heteroaryl, carbohydrate, or a pharmaceutically useful group or entity;

$R^{X0}$ is a group such that the moiety —C(=O)$OR^{X0}$ can be made to undergo ligation with a peptide acyl acceptor, each occurrence of $L^1$ is independently a substituted or unsubstituted, linear or branched, cyclic or acyclic, saturated or unsaturated aliphatic or heteroaliphatic moiety, or a natural or non-natural amino acid side chain; and $R^{X2}$ is —$OR^{X2a}$ or —$NR^{X2b}R^{X2c}$, wherein $R^{X2a}$ is hydrogen, alkyl, aromatic, heteroaromatic, aryl, heteroaryl, -alkyl(aryl), -alkyl(heteroaryl), a carboxylic acid protecting group, an amino acid or a protected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid or a protected amino acid. In certain embodiments, $A_1$ or $A_2$ is a carbohydrate moiety or nothing. $A_1$ and $A_2$ may also be hydroxyl groups, farnesyl moieties, phosphates, lipids, or other groups that result from the post-translational modification of a peptide or protein. Exemplary structures include peptide of formula:

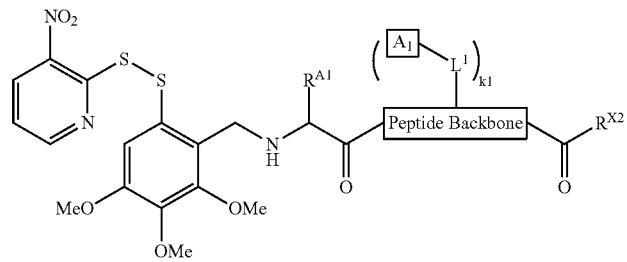

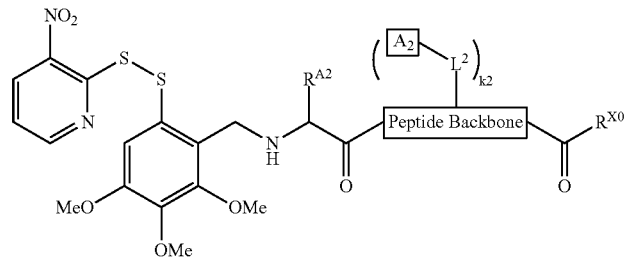

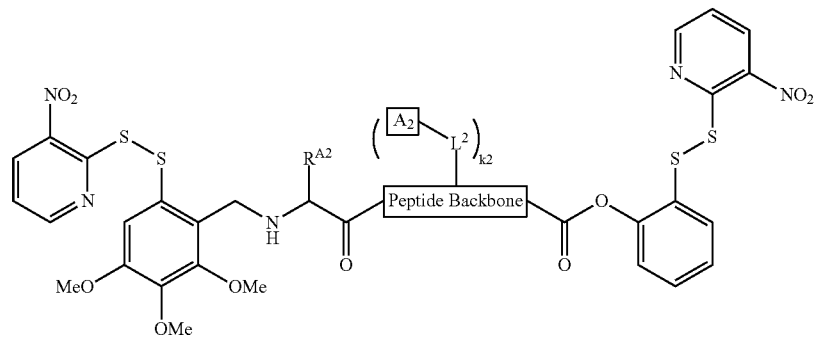

-continued
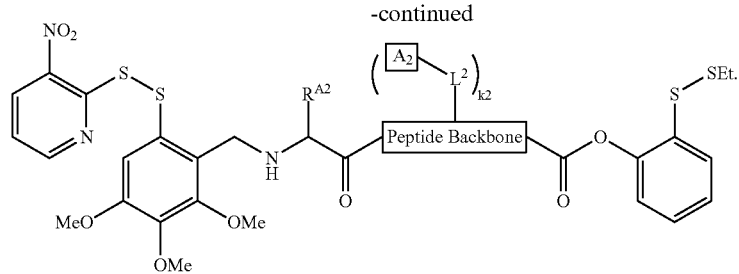
In certain embodiments, each occurrence of $A_1$ or $A_2$ is independently selected from the group consisting of:
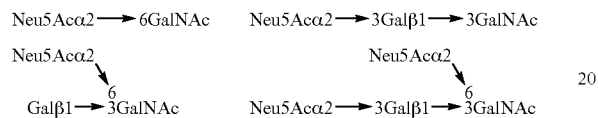
when $A_1$ or $A_2$ is O-linked; and
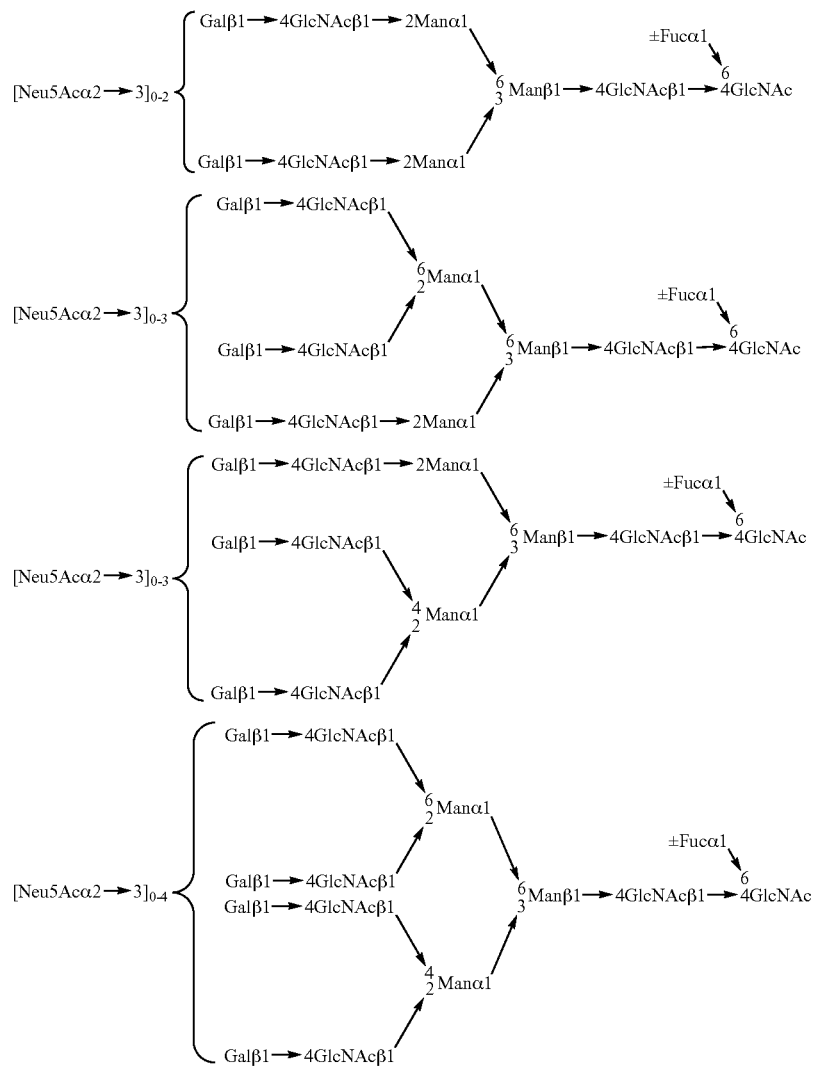

-continued

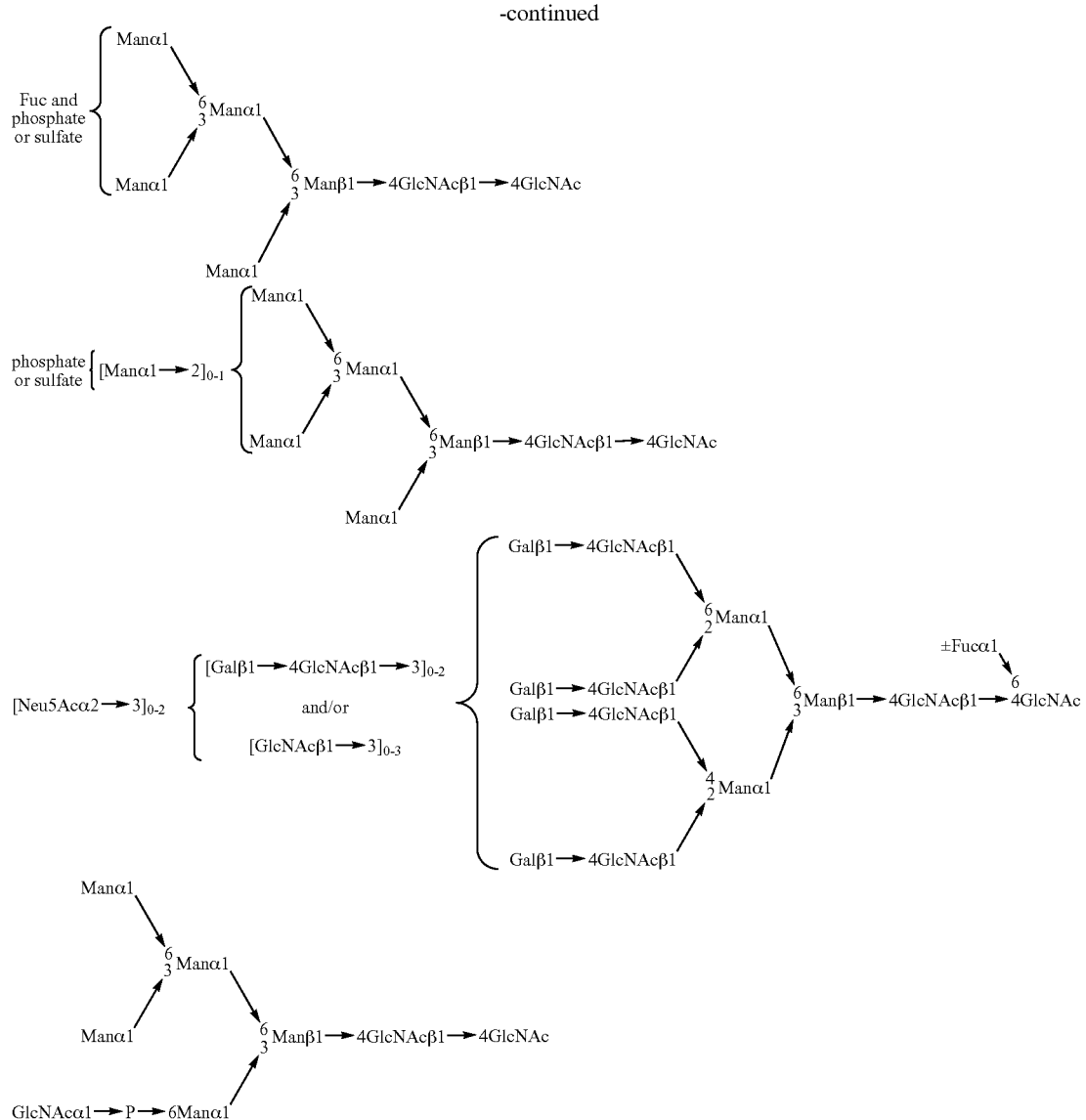

when $A_1$, or $A_2$ is N-linked.

In yet another aspect, the invention provides a peptide with a modified C-terminus of formula:

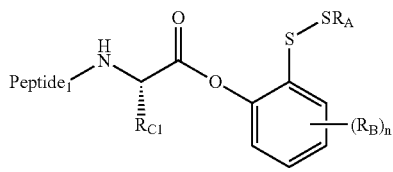

wherein

Peptide1 is a peptide comprising two or more natural or unnatural amino acids, wherein the peptide is protected, partially protected, or unprotected, and the peptide is optionally glycosylated or includes another type of post-translational modification;

n is 0, 1, 2, 3, or 4;

$R_A$ is hydrogen; a substituted or unsubstituted, linear or branched, cyclic or acyclic saturated or unsaturated aliphatic; a substituted or unsubstituted, linear or branched, cyclic or acyclic saturated or unsaturated heteroaliphatic; substituted or unsubstituted aryl; or substituted or unsubstituted heteroaryl;

each occurrence of $R_B$ is independently hydrogen; halogen; alkoxy; —CN; —NO$_2$; substituted or unsubstituted acyl; a substituted or unsubstituted, linear or branched, cyclic or acyclic saturated or unsaturated aliphatic, or a substituted or unsubstituted, linear or branched, cyclic or acyclic saturated or unsaturated heteroaliphatic; and $R_{C1}$ is a side chain of a natural or unnatural amino acid.

In another aspect, the invention also provides a or protein of formula:

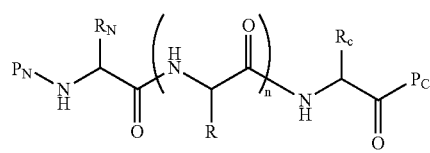

wherein each occurrence of $R_N$, $R_C$, and R is independently the side chain of a natural or unnatural amino acid, optionally glycosylated;

$P_C$ is —$OR^{X2a}$, —$SR^{X2a}$, or $NR^{X2b}R^{X2c}$, wherein $R^{X2a}$ is hydrogen, alkyl, aromatic, heteroaromatic, substituted or unsubstituted aryl, substituted or unsubstituted heteroaryl, -alkyl(aryl), -alkyl(heteroaryl), a carboxylic acid protecting group, an amino acid, or a protected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid or a protected amino acid;

$P_N$ is hydrogen, a nitrogen protecting group, or a moiety having the structure:

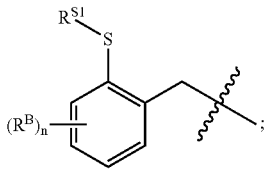

wherein n is 1, 2, 3, or 4; $R^{S1}$ is hydrogen; substituted or unsubstituted aryl; substituted or unsubstituted heteroaryl; or a sulfide protecting group; each occurrence of $R^B$ is independently alkoxy, hydroxy, or silyloxy.

In another aspect, the invention provides a method of ligating two peptides, each peptide comprising a peptidic backbone made up of two or more amino acids wherein one or more amino acids are optionally independently substituted with a moiety having the structure:

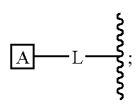

wherein the method comprises a step of:

coupling a peptide acyl donor comprising a peptidic backbone made up of two or more amino acids wherein said peptide acyl donor has the structure:

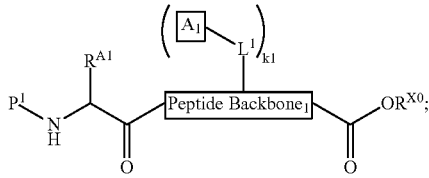

with a peptide acyl acceptor comprising a peptidic backbone made up of two or more amino acids wherein said peptide acyl acceptor has the structure:

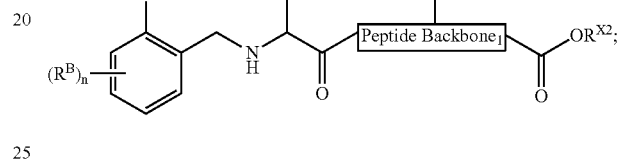

under suitable conditions to effect ligation and form the following adduct:

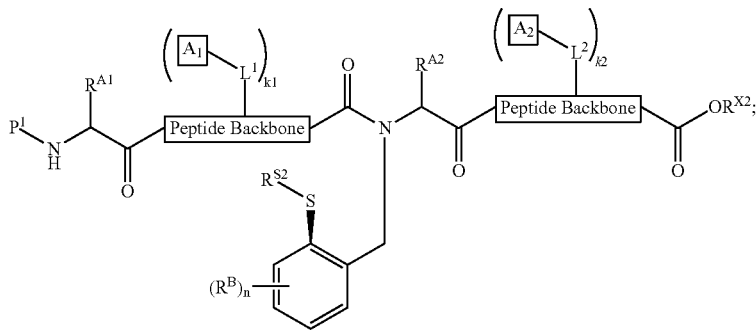

wherein n is 2 or 3;

$R^{A1}$ and $R^{A2}$ are independently natural or non-natural amino acid side chains;

each occurrence of $R^B$ is independently alkoxy, hydroxy or silyloxy;

k1 and k2 are independently integers between 1 and about 20;

each occurrence of A, $A_1$ and $A_2$ is independently an aliphatic, heteroaliphatic, aromatic, heteroaromatic, aryl, heteroaryl, carbohydrate, or a pharmaceutically useful group or entity;

$R^{S1}$ is hydrogen or a sulfide protecting group;

$R^{X0}$ is a group such that the moiety —C(=O)$OR^{X0}$ can be made to undergo ligation with the peptide acyl acceptor, each occurrence of $L^1$ is independently a substituted or unsubstituted, linear or branched, cyclic or acyclic, saturated or unsaturated aliphatic or heteroaliphatic moiety or a natural or non-natural amino acid side chain; and $R^{X2}$ is —$OR^{X2a}$ or —$NR^{X2b}R^{X2c}$, wherein $R^{X2a}$ is hydrogen, alkyl, aromatic, heteroaromatic, aryl, heteroaryl, -alkyl(aryl), -alkyl(heteroaryl), a carboxylic acid protecting group, an amino acid or a protected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid or a protected amino acid. In certain embodiments, $A_1$ or $A_2$ is a carbohydrate moiety or nothing. $A_1$ and $A_2$ may also be hydroxyl groups, farnesyl moieties, phosphates, lipids, or other groups that result from the post-translational modification of a peptide or protein. The auxiliary group may be subsequently removed under suitable conditions to leave an amide linkage.

In another aspect, there is provided a method for preparing a peptide/protein comprising a peptidic backbone made up of four or more amino acids wherein two or more non-adjacent amino acids are optionally independently substituted with a moiety having the structure:

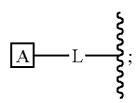

wherein the method comprises steps of:

(a) coupling a peptide acyl donor comprising a peptidic backbone made up of two or more amino acids wherein said peptide acyl donor has the structure:

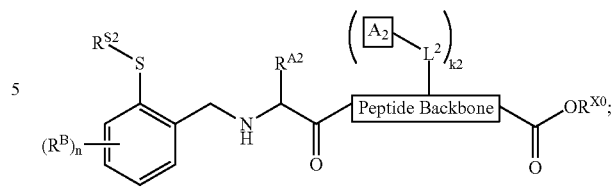

with a starting peptide acyl acceptor comprising a peptidic backbone made up of two or more amino acids wherein said peptide acyl acceptor has the structure:

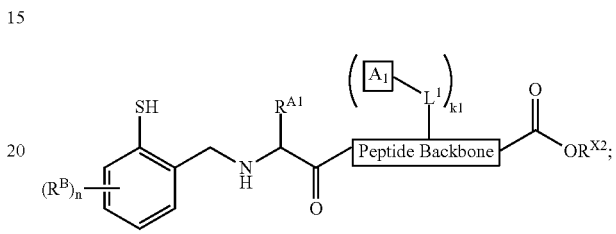

under suitable conditions to effect ligation and form a resulting peptide acyl acceptor having the structure:

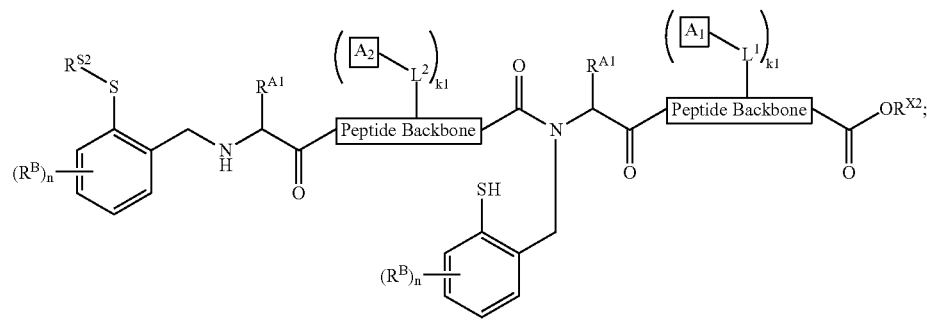

(b) repeating step (a) using the resulting peptide acyl acceptor of step (a) as starting peptide acyl acceptor to give a polyfunctionalized peptide/protein having the structure:

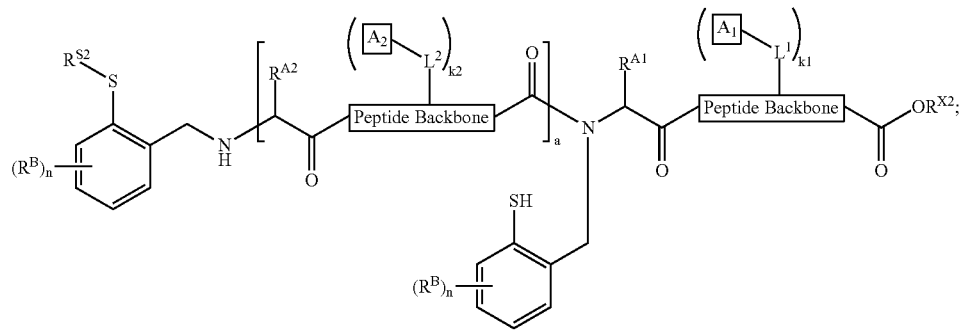

wherein $P^1$ is hydrogen or a nitrogen protecting group;

(c) deprotecting the polyfunctionalized peptide/protein of step (b) to give a polyfunctionalized peptide/protein having the structure:

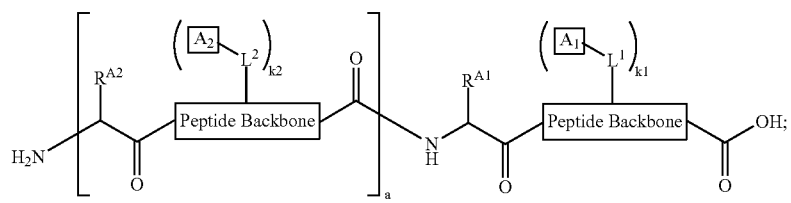

or salt form thereof;

wherein a is an integer between 1 and about 20;

each occurrence of n is independently 2 or 3;

each occurrence of $RA^1$ and $R^{A2}$ is independently a natural or non-natural amino acid side chain;

each occurrence of $R^B$ is independently alkoxy, hydroxy or silyloxy;

each occurrence of k1 and k2 is independently an integer between 1 and about 20;

each occurrence of A, $A_1$ and $A_2$ is independently an aliphatic, heteroaliphatic, aromatic, heteroaromatic, aryl, heteroaryl or a pharmaceutically useful group or entity;

$R^{S1}$ is hydrogen or a sulfide protecting group;

$R^{X0}$ is a group such that the moiety —C(=O)O$R^{X0}$ can be made to undergo ligation with the peptide acyl acceptor, each occurrence of $L^1$ is independently a substituted or unsubstituted, linear or branched, cyclic or acyclic, saturated or unsaturated aliphatic or heteroaliphatic moiety or a natural or non-natural amino acid side chain; and $R^{X2}$ is —O$R^{X2a}$ or —N$R^{X2b}R^{X2c}$, wherein $R^{X2a}$ is hydrogen, alkyl, aromatic, heteroaromatic, aryl, heteroaryl, -alkyl(aryl), -alkyl(heteroaryl), a carboxylic acid protecting group, an amino acid or a protected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid or a protected amino acid.

In another aspect, the provides a method of ligating two peptides to form a peptide of formula:

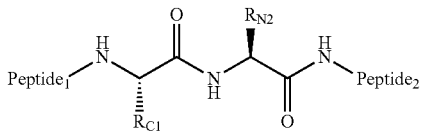

wherein

Peptide1 is a peptide comprising two or more natural or unnatural amino acids, wherein the peptide is protected, partially protected, or unprotected, and the peptide is optionally glycosylated or otherwise post-translationally modified;

Peptide2 is a peptide comprising two or more natural or unnatural amino acids, wherein the peptide is protected, partially protected, or unprotected, and the peptide is optionally glycosylated or otherwise post-translationally modified;

$R_{C1}$ is a side chain of a natural or unnatural amino acid, wherein the side chain is protected or unprotected; and $R_{N2}$ is a side chain of a natural or unnatural amino acid, wherein the side chain is protected or unprotected;

the method comprising steps of:

ligating a peptide of formula:

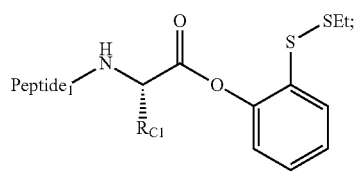

to a peptide of formula:

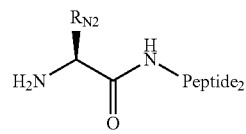

under suitable conditions to form a peptide of formula:

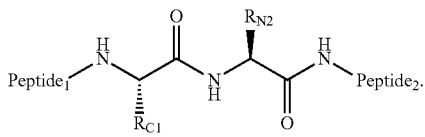

The ligation reaction may be effected by an Ag+1 salt such as AgCl, AgBr, AgI, AgNO3, AgOAc, and AgBF4. The ligation may also be effected using tris(2-carobxyethyl)phosphine hydrochloride (TCEP-HCl). The ligation reaction is typically done in the presence of an activator (e.g., 3,4-dihydro-3-hydroxy-4-oxo-1,2,3-benzotriazine (HOOBt), 1-hydroxy-benzotriazole (HOBt), 1-hydroxy-7-azabenzotriazole (HOAt), and N-hydroxysuccinimide (HOSu)) and a base (e.g., sodium bicarbonate (NaHCO3), N,N-diisopropylethylamine (DIEA), 2,6-di-tert-butyl-4-(dimethylamino)pyridine (DBDMAP)). Exemplary reaction conditions include AgCl or TCEP-HCl; HOOBt; and N,N-diisopropylethylamine (DIEA).

In another, the invention a method of ligating two peptides to form a peptide of formula:

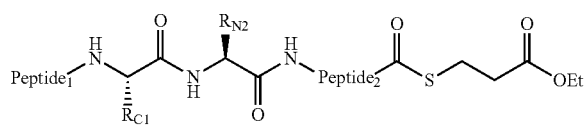

wherein

Peptide1 is a peptide comprising two or more natural or unnatural amino acids, wherein the peptide is protected, partially protected, or unprotected, and the peptide is optionally glycosylated or otherwise post-translationally modified;

Peptide2 is a peptide comprising two two or more natural or unnatural amino acids, wherein the peptide is protected, partially protected, or unprotected, and the peptide is optionally glycosylated or otherwise post-translationally modified;

$R_{C1}$ is a side chain of a natural or unnatural amino acid, wherein the side chain is protected or unprotected; and $R_{N2}$ is a side chain of a natural or unnatural amino acid, wherein the side chain is protected or unprotected;

the method comprising steps of:

ligating a peptide of formula:

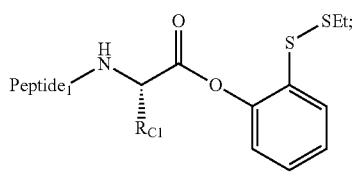

to a peptide of formula:

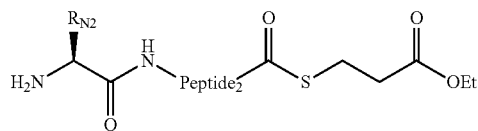

under suitable conditions to form a peptide of formula:

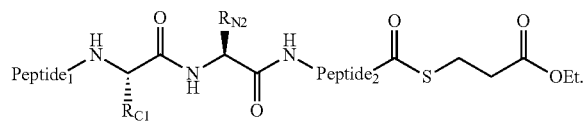

The ligation may be effected using tris(2-carobxyethyl)phosphine hydrochloride (TCEP-HCl). The ligation reaction is typically done in the presence of an activator (e.g., 3,4-dihydro-3-hydroxy-4-oxo-1,2,3-benzotriazine (HOOBt), 1-hydroxybenzotriazole (HOBt), 1-hydroxy-7-azabenzotriazole (HOAt), and N-hydroxysuccinimide (HOSu)) and a base (e.g., sodium bicarbonate (NaHCO3), N,N-diisopropylethylamine (DIEA), 2,6-di-tert-butyl-4-(dimethylamino)pyridine (DBDMAP)). Exemplary reaction conditions include TCEP-HCl; HOOBt; and N,N-diisopropylethylamine (DIEA).

In another aspect, the invention provides a method for preparing a cyclic peptide having the structure:

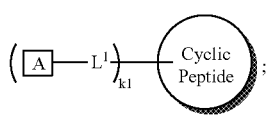

the method comprising a step of:

subjecting a peptide having the structure:

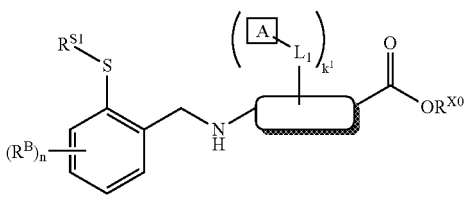

to suitable conditions to effect ligation;

wherein the peptide comprises at least four amino acid residues;

n is 2 or 3;

each occurrence of $R^B$ is independently alkoxy, hydroxy, or silyloxy;

k1 is an integer between 0 and about 20;

each occurrence of A is independently an aliphatic, heteroaliphatic, aromatic, heteroaromatic, aryl, heteroaryl, carbohydrate, or a pharmaceutically useful group or entity;

$R^{S1}$ is hydrogen or a sulfide protecting group;

$R^{X0}$ is a group such that the moiety —C(=O)OR$^{X0}$ can be made to undergo ligation with the N-terminal peptide acyl acceptor; and each occurrence of $L^1$ is independently a substituted or unsubstituted, linear or branched, cyclic or acyclic, saturated or unsaturated aliphatic or heteroaliphatic moiety or a natural or non-natural amino acid side chain.

Any of the ligation methods described herein may be used to in succession to synthesize a peptide or protein. The methods may also be used in solid phase peptide synthesis. In certain embodiments, the method comprises the steps of:

(a) ligating a first peptide fragment of formula:

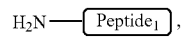

to a second peptide fragment of formula:

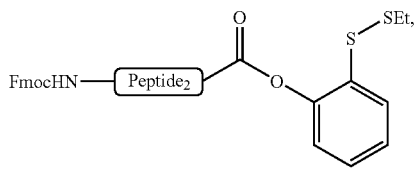

under suitable conditions to form a first ligated peptide of formula:

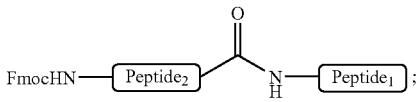

(b) deprotecting the first ligated peptide;

(c) ligating a third peptide fragment of formula:

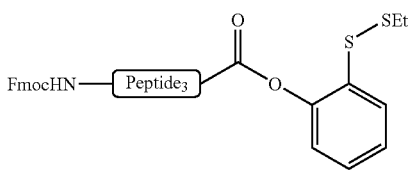

to the first ligated peptide under suitable conditions to form a peptide of formula:

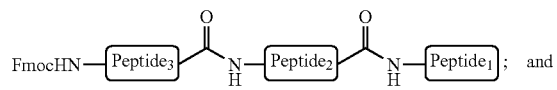

(d) optionally, repeating the steps (b) and (c);

wherein Peptide1, Peptide2, and Peptide3 are each independently a peptide comprising two or more natural or unnatural amino acids, wherein the peptide is protected, partially protected, or unprotected, and the peptide is optionally glycosylated or otherwise post-translationally modified. A solid phase synthetic method comprises the steps of:

(a) ligating a first peptide fragment of formula:

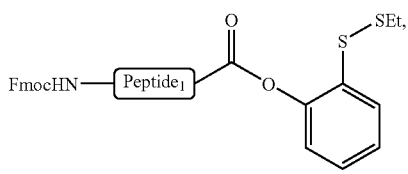

to a solid support of formula:

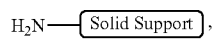

under suitable conditions to form a first ligated peptide of formula:

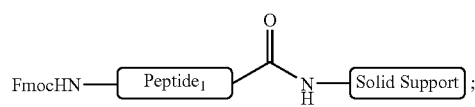

(b) deprotecting the first peptide attached to the solid support;

(c) ligating a second peptide fragment of formula:

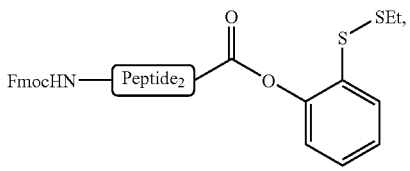

to the first peptide attached to the solid support under suitable conditions to form a peptide on a solid support of formula:

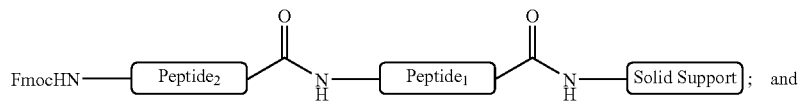; and (d) optionally, repeating the steps (b) and (c) to add onto the N-terminus of the growing peptide;

wherein Peptide1 and Peptide2 are each independently a peptide comprising two or more natural or unnatural amino acids, wherein the peptide is protected, partially protected, or unprotected, and the peptide is optionally glycosylated or otherwise post-translationally modified. As would be appreciated by one of skill in the art, the growing peptide chain can be continued until the desired peptide or protein is created following which the peptide or protein is optionally deprotected and/or purified.

The invention also provides another of forming a cyclic peptide of formula:

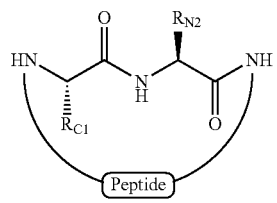

wherein

Peptide is a peptide comprising two or more natural or unnatural amino acids, wherein the peptide is protected, partially protected, or unprotected, and the peptide is optionally glycosylated; and $R_{N2}$ is a side chain of a natural or unnatural amino acid, wherein the side chain is protected or unprotected;

the method comprising steps of:

cyclizing a peptide of formula:

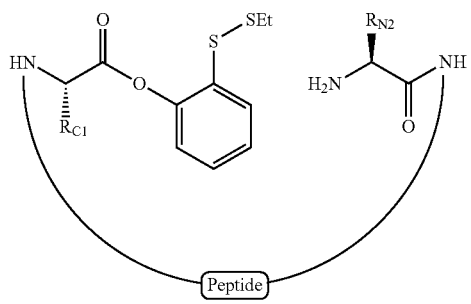

under suitable conditions to form a cyclic peptide of formula:

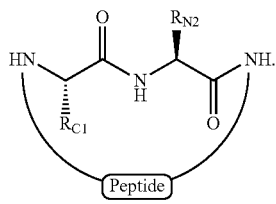

The ligation reaction may be effected by an Ag+1 salt such as AgCl, AgBr, AgI, AgNO$_3$, AgOAc, and AgBF$_4$. The ligation may also be effected using tris(2-carobxyethyl)phosphine hydrochloride (TCEP-HCl). The ligation reaction is typically done in the presence of an activator (e.g., 3,4-dihydro-3-hydroxy-4-oxo-1,2,3-benzotriazine (HOOBt), 1-hydroxybenzotriazole (HOBt), 1-hydroxy-7-azabenzotriazole (HOAt), and N-hydroxysuccinimide (HOSu)) and a base (e.g., sodium bicarbonate (NaHCO3), N,N-diisopropylethylamine (DIEA), 2,6-di-tert-butyl-4-(dimethylamino)pyridine (DBDMAP)). Exemplary reaction conditions include AgCl or TCEP-HCl; HOOBt; and N,N-diisopropylethylamine (DIEA).

In another aspect, the invention provide a method of desulfurizing or deselenizing a peptide or protein containing a cysteine or seleno-cysteine moiety to form an alanine residue. Such residues are found in protein after native chemical ligation, and it is useful in some instances to convert them into alanine residues. Such a method allows for ligating peptides at a position which includes alanine. The method of desulfurizing a peptide, the method comprising steps of: desulfurizing or deselenizing a peptide of formula:

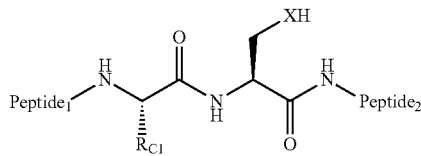

wherein

Peptide$_1$ is a peptide comprising two or more natural or unnatural amino acids, wherein the peptide is protected, partially protected, or unprotected, and the peptide is optionally glycosylated;

Peptide$_2$ is a peptide comprising two or more natural or unnatural amino acids, wherein the peptide is protected, partially protected, or unprotected, and the peptide is optionally glycosylated;

X is Se or S;

R$_{C1}$ is a side chain of a natural or unnatural amino acid, wherein the side chain is protected or unprotected, and the side chain is optionally glycosylated; under suitable conditions to form a peptide of formula:

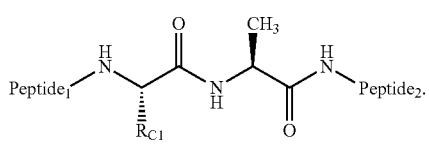

The suitable conditions include a phospine or phosphite; a thiol-containing reagent (e.g., alkyl thiol, aryl thiol); and a free radical initiator (e.g., AIBN, peroxides, VA-044) in an aqueous medium.

DEFINITIONS

As used herein, the singular forms "a", "an", and "the" include the plural reference unless the context clearly indicates otherwise. Thus, for example, a reference to "a peptide" includes a plurality of such peptides.

The abbreviations as used herein corresponding to units of measure include: "g" means gram(s), "mg" means milligram(s), "ng" means nanogram(s), "kDa" means kilodalton(s), "° C." means degree(s) Celsius, "min" means minute(s), "h" means hour(s), "l" means liter(s), "ml" means milliliter(s), "μl" means microliter(s), "M" means molar, "mM" means millimolar, "mmole" means millimole(s), and "RT" means room temperature. The abbreviations for chemical terms as used herein have the following definitions: "A" means alanine; "Ac" means acetyl; "AIBN" means 2,2'-azobis(2-methylpropionitrile); "Ala" means alanine; "Arg" means arginine; "Asn" means asparagine; "Asp" means aspartic acid; "Bn" means benzyl; "Boc" means tert-butyloxycarbonyl; "Bu" means butyl; "Bz" means benzoyl; "CAN" means ceric ammonium nitrate; "C-terminus" means carboxy terminus of a peptide or protein; "Cys" means cysteine'"D" means aspartic acid; "DIEA" means N,N-diisopropylethylamine; "DMAP" means N,N-dimethylaminopyridine; "DMF" means dimethyl formamide; "DMSO" means dimethyl sulfoxide; "DTBMP" means di-tert-butylmethylpyridine; "DTBP" means di-tert-butylpyridine; "Et" means ethyl; "Fmoc" means 9-fluorenylmethyloxycarbonyl; "Fuc" means L-Fucose; "G" means glycine; "Gal" means D-galactose; "GalNAc" means N-acetyl-D-galactosamine; "Glc" means D-glucose; "GlcNAc" means N-acetyl-D-glucosamine; "Gln" means glutamine; "Glu" means glutamic acid; "Gly" means glycine; "H" means histidine; "HATU" means 7-azahydroxybenzotriazolyl tetramethyluronium hexafluorophosphate; "His" means histidine; "Ile" means isoleucine; "K" means lysine; "KLH" means keyhole limpet hemocyanin; "L" means leucine; "Leu:" means leucine; "Lys" means lysine; "Man" means D-mannose; "MES-Na" means 2-mercaptoethanesulfonic acid, sodium salt; "N" means asparagine; "NAc" means N-acetyl; "NCL" means native chemical ligation; "Neu5Ac" means N-acetylneuraminic acid; "N-terminus" means amino-terminus of a peptide or protein; "O-linked" means linked through an ethereal oxygen; "PamCys" or "Pam3Cys" means tripalmitoyl-5-glycerylcysteinylserine; "PBS" means phosphate-buffered saline; "Ph" means phenyl; "PMB" means p-methoxybenzyl; "Pro" means proline; "PSA" means prostate specific antigen; "Py" means pyridine; "QS21" means a glycosteroidal immunoadjuvant; "R" means arginine; "S" means serine; "sat. aq." means saturated aqueous; "Ser" means serine; "T" means threonine; "TBAF" means tetra-n-butylammonium fluoride; "TBS" means tert-butyldimethylsilyl; "tBu" means tert-butyl; "TCEP" means tricarboxyethylphosphine; "Tf" means trifluoromethanesulfonate; "TFA" means trifluoroacetic acid; "THF" means tetrahydrofuran; "Thr" means threonine; "Trp" means tryptophan; "V" means valine; "Val" means valine; and "W" means tryptophan.

Certain specific functional groups defined in the inventive method are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic, carbon and heteroatom substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment and prevention, for example of disorders, as described generally above. Examples of substituents include, but are not limited to aliphatic; heteroaliphatic; alicyclic; heteroalicyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br, I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$;— or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The term "stable", as used herein, preferably refers to compounds which possess stability sufficient to allow manufacture and which maintain the integrity of the compound for a sufficient period of time to be useful for the purposes detailed herein.

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having about 1-6 carbon atoms.

In certain embodiments, the alkyl, alkenyl and alkynyl groups employed in the invention contain about 1-20 aliphatic carbon atoms. In certain other embodiments, the alkyl, alkenyl, and alkynyl groups employed in the invention contain about 1-10 aliphatic carbon atoms. In yet other embodiments, the alkyl, alkenyl, and alkynyl groups employed in the invention contain about 1-8 aliphatic carbon atoms. In still other embodiments, the alkyl, alkenyl, and alkynyl groups employed in the invention contain about 1-6 aliphatic carbon atoms. In yet other embodiments, the alkyl, alkenyl, and alkynyl groups employed in the invention contain about 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl-n, cyclohexyl, —CH$_2$-cyclohexyl, cyclohexenylethyl, cyclohexanylethyl, norborbyl moieties and the like, which again, may bear one or more substituents.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted. An analogous convention applies to other generic terms such as "cycloalkenyl", "cycloalkynyl" and the like.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be branched or linear unbranched. In certain embodiments, heteroaliphatic moieties are substituted by independent replacement of one or more of the hydrogen atoms thereon with one or more moieties including, but not limited to aliphatic; heteroaliphatic; alicyclic; heteroalicyclic; aromatic, heteroaromatic; aryl; heteroaryl; alkylheteroaryl; alkoxy; aryloxy; heteroalkoxy; heteroaryloxy; alkylthio; arylthio; heteroalkylthio; heteroarylthio; F; Cl; Br, I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$;— or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The term "heteroalicyclic", "heterocycloalkyl" or "heterocyclic", as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups, as defined herein. In certain embodiments, the term "heterocyclic" refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 2 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; alicyclic; heteroalicyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; C; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$;— or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples or generally applicable substituents are illustrated by the specific embodiments shown in the Examples, which are described herein.

Additionally, it will be appreciated that any of the alicyclic or heteroalicyclic moieties described above and herein may comprise an aryl or heteroaryl moiety fused thereto. Additional examples of generally applicable substituents are illustrated by the specific embodiments shown in the Examples that are described herein.

In general, the term "aromatic moiety", as used herein, refers to stable substituted or unsubstituted unsaturated mono- or polycyclic hydrocarbon moieties having preferably 3-14 carbon atoms, comprising at least one ring satisfying the Huckel rule for aromaticity. Examples of aromatic moieties include, but are not limited to, phenyl, indanyl, indenyl, naphthyl, phenanthryl and anthracyl.

In general, the term "heteroaromatic moiety", as used herein, refers to stable substituted or unsubstituted unsaturated mono-heterocyclic or polyheterocyclic moieties having preferably 3-14 carbon atoms, comprising at least one ring satisfying the Huckel rule for aromaticity. Examples of heteroaromatic moieties include, but are not limited to, pyridyl, quinolinyl, dihydroquinolinyl, isoquinolinyl, quinazolinyl, dihydroquinazolyl, and tetrahydroquinazolyl.

It will also be appreciated that aromatic and heteroaromatic moieties, as defined herein, may be attached via an aliphatic (e.g., alkyl) or heteroaliphatic (e.g., heteroalkyl) moiety and thus also include moieties such as -(aliphatic)aromatic, -(heteroaliphatic)aromatic, -(aliphatic)heteroaromatic, -(heteroaliphatic)heteroaromatic, -(alkyl)aromatic, -(heteroalkyl)aromatic, -(alkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

In general, the term "aryl" refers to aromatic moieties, as described above, excluding those attached via an aliphatic (e.g., alkyl) or heteroaliphatic (e.g., heteroalkyl) moiety. In certain embodiments of the present invention, "aryl" refers to a mono- or bicyclic carbocyclic ring system having one or two rings satisfying the Huckel rule for aromaticity, including, but not limited to, phenyl, naphthyl, tetrahydronaphthyl, indanyl, indenyl and the like.

Similarly, the term "heteroaryl" refers to heteroaromatic moieties, as described above, excluding those attached via an aliphatic (e.g., alkyl) or heteroaliphatic (e.g., heteroalkyl) moiety. In certain embodiments of the present invention, the term "heteroaryl", as used herein, refers to a cyclic unsaturated radical having from about five to about ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

Substituents for aryl and heteroaryl moieties include, but are not limited to, any of the previously mentioned substitutents, i.e., the substituents recited for aliphatic moieties, or for other moieties as disclosed herein, resulting in the formation of a stable compound. For example, aryl and heteroaryl groups (including bicyclic aryl groups) can be unsubstituted or substituted, wherein substitution includes replacement of one, two or three of the hydrogen atoms thereon independently with any one or more of the following moieties including, but not limited to: aliphatic; heteroaliphatic; alicyclic;

heteroalicyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br, I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$;— or -GR$^{G1}$ wherein G is —O—, —S—, —NR$^{G2}$—, —C(=O)—, —S(=O)—, —SO$_2$—, —C(=O)O—, —C(O)NR$^{G2}$—, —OC(O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The terms "alkoxy" (or "alkyloxy"), and "thioalkyl" as used herein refers to an alkyl group, as previously defined, attached to the parent molecular moiety through an oxygen atom ("alkoxy") or through a sulfur atom ("thioalkyl"). In certain embodiments, the alkyl group contains about 1-20 aliphatic carbon atoms. In certain other embodiments, the alkyl group contains about 1-10 aliphatic carbon atoms. In yet other embodiments, the alkyl group contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkoxy groups, include but are not limited to, methoxy, ethoxy, propoxy, isopropoxy, n-butoxy, tert-butoxy, neopentoxy and n-hexoxy. Examples of thioalkyl groups include, but are not limited to, methylthio, ethylthio, propylthio, isopropylthio, n-butylthio, and the like.

The term "amine" refers to a group having the structure —N(R)$_2$ wherein each occurrence of R is independently hydrogen, or an aliphatic, heteroaliphatic, aromatic or heteroaromatic moiety, or the R groups, taken together, may form a heterocyclic moiety.

The term "alkylamino" refers to a group having the structure —NHR' wherein R' is alkyl, as defined herein. The term "aminoalkyl" refers to a group having the structure NH$_2$R'—, wherein R' is alkyl, as defined herein. In certain embodiments, the alkyl group contains about 1-20 aliphatic carbon atoms. In certain other embodiments, the alkyl group contains about 1-10 aliphatic carbon atoms. In yet other embodiments, the alkyl, alkenyl, and alkynyl groups employed in the invention contain about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkylamino include, but are not limited to, methylamino, ethylamino, iso-propylamino and the like.

The terms "halo" and "halogen" as used herein refer to an atom selected from fluorine, chlorine, bromine and iodine.

The term "acyloxy", as used herein, does not substantially differ from the common meaning of this term in the art, and refers to a moiety of structure —OC(O)R$_X$, wherein R$_X$ is a substituted or unsubstituted aliphatic, alicyclic, heteroaliphatic, heteroalicyclic, aryl or heteroaryl moiety.

The term "acyl", as used herein, does not substantially differ from the common meaning of this term in the art, and refers to a moiety of structure —C(O)R$_X$, wherein R$_X$ is a substituted or unsubstituted, aliphatic, alicyclic, heteroaliphatic, heteroalicyclic, aryl or heteroaryl moiety.

The term "imine", as used herein, does not substantially differ from the common meaning of this term in the art, and refers to a moiety of structure —C(=NR$_X$)R$_Y$, wherein R$_X$ is hydrogen or an optionally substituted aliphatic, alicyclic, heteroaliphatic, heteroalicyclic, aryl or heteroaryl moiety; and R$_Y$ is an optionally substituted aliphatic, alicyclic, heteroaliphatic, heteroalicyclic, aryl or heteroaryl moiety.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heteroalicyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aryl", "heteroaryl" and the like encompass both substituted and unsubstituted groups.

It will be appreciated that additional examples of generally applicable substitutents are illustrated by the specific embodiments shown in the Examples which are described herein, but are not limited to these Examples.

By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P.G., Eds., John Wiley & Sons, New York: 1999, the entire contents of which are hereby incorporated by reference.

The term "natural amino acid side chain" as used herein refers to the side chain of any one of the common, naturally occurring L-amino acids found in naturally occurring proteins: glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys) and methionine (Met).

The term "unnatural amino acid side chain" as used herein refers to the side chain of all amino acids which are not natural amino acids. This includes, for example, α-, β-, D-, L-amino acid residues, and compounds of the general formula

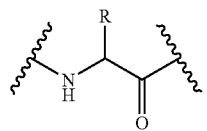

wherein the side chain R is other than the amino acid side chains occurring in nature.

More generally, the term "amino acid side chain", as used herein, encompasses natural amino acid and unnatural amino acid side chains.

As used herein, the term "pharmaceutically useful group or entity" refers to a compound or fragment thereof, or an organic moiety which, when covalently attached to a peptide or protein, can exert some biological or diagnostic function or activity when administered to a subject, or enhance the therapeutic, diagnostic or preventive properties of the parent peptide and/or protein in biomedical applications, or improve safety, alter biodegradation or excretion, or is detectable. Examples of suitable pharmaceutically useful groups or entities include hydrophilicity/hydrophobicity modifiers, pharmacokinetic modifiers, biologically active modifiers, detectable modifiers. A modifier can have one or more pharmaceutical functions, e.g., biological activity and/or pharmacokinetics modification. Pharmacokinetics modifiers can include, for example, antibodies, antigens, receptor ligands, hydrophilic, hydrophobic or charged groups. Biologically active modifiers include, for example, therapeutic drugs and prodrugs, antigens, immunomodulators. Detectable modifiers include diagnostic labels, such as radioactive, fluorescent, paramagnetic, superparamagnetic, ferromagnetic, X-ray modulating, X-ray-opaque, ultrosound-reflective, and other substances detectable by one of available clinical or laboratory methods, e.g., scintigraphy, NMR spectroscopy, MRI, X-ray tomography, sonotomography, photoimaging, radioimmunoassay. Modifiers can be small molecules or macromolecules, and can belong to any chemical or pharmaceutical class, e.g., nucleotides, chemotherapeutic agents, antibacterial agents, antiviral agents, immunomodulators, hormones or analogs thereof, enzymes, inhibitors, alkaloids and therapeutic radionuclides. Viral and non-viral gene vectors are considered to be a pharmaceutically useful entity or group.

The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) which belong to classes of chemical compounds, whether naturally-occurring or artificially created (e.g., by synthetic or recombinant methods), that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

As used herein, the term "small molecule" refers to molecules, whether naturally-occurring or artificially created (e.g., via chemical synthesis) that have a relatively low molecular weight. Preferred small molecules are biologically active in that they produce a local or systemic effect in animals, preferably mammals, more preferably humans. Typically, small molecules have a molecular weight of less than about 1500 g/mol. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, incorporated herein by reference, are all considered suitable for use with the present hydrophilic polymers.

Classes of small molecule drugs that can be used in the practice of the present invention include, but are not limited to, vitamins, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, imaging agents. Many large molecules are also drugs.

A more complete, although not exhaustive, listing of classes and specific drugs suitable for practicing the present invention may be found in "Pharmaceutical Substances: Syntheses, Patents, Applications" by Axel Kleemann and Jurgen Engel, Thieme Medical Publishing, 1999 and the "Merck Index: An Encyclopedia of Chemicals, Drugs, and Biologicals", Edited by Susan Budavari et al., CRC Press, 1996, both of which are incorporated herein by reference.

As used herein, the term "macromolecules" refers to molecules, whether naturally-occurring or artificially created (e.g., via chemical synthesis) that have a relatively high molecular weight, e.g., generally above 1500 g/mole. Preferred macromolecules are biologically active in that they exert a biological function in animals, preferably mammals, more preferably humans. Examples of macromolecules include proteins, enzymes, growth factors, cytokines, peptides, polypeptides, polylysine, proteins, lipids, polyelectrolytes, immunoglobulins, DNA, RNA, ribozymes, plasmids, and lectins. For the purpose of this invention, supramolecular constructs such as viruses and protein associates (e.g., dimers) are considered to be macromolecules. When covalently attached to a peptide or protein, a macromolecule may be chemically modified prior to being covalently attached to said peptide or protein.

As used herein, the term "diagnostic label" refers to an atom, group of atoms, moiety or functional group, a nanocrystal, or other discrete element of a composition of matter, that can be detected in vivo or ex vivo using analytical methods known in the art. When covalently attached to a peptide or protein, such diagnostic labels permit the monitoring of the peptide or protein in vivo. On the other hand, constructs and compositions that include diagnostic labels can be used to monitor biological functions or structures. Examples of diagnostic labels include, without limitations, labels that can be used in medical diagnostic procedures, such as, radiopharmaceutical or radioactive isotopes for gamma scintigraphy and Positron Emission Tomography (PET), contrast agent for Magnetic Resonance Imaging (MRI) (for example paramagnetic atoms and superparamagnetic nanocrystals), contrast agent for computed tomography, contrast agent for X-ray imaging method, agent for ultrasound diagnostic method, agent for neutron activation, and moiety which can reflect, scatter or affect X-rays, ultrasounds, radiowaves and microwaves, fluorophores in various optical procedures, etc.

DETAILED DESCRIPTION OF CERTAIN PREFERRED EMBODIMENTS OF THE INVENTION

Figure 1:
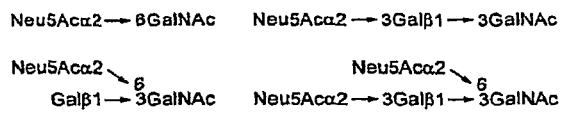
FIG. 1 depicts O- and N-linked sugar chains of human erythropoietins.

The present invention provides novel methodologies for the synthesis of peptides and proteins, particularly those functionalized at two or more amino acids (e.g., glycosylated amino acids or other post-translationally modified amino acids). In certain embodiments, the invention provides a system for the synthesis of polypeptides and proteins bearing at least one carbohydrate moiety covalently attached to an amino acid residue of the polypeptide/protein chain. In certain embodiments, in the context of synthetic studies developed for the total synthesis of glycosylated erythropoietin and fragments of erythropoietin, generalized methodologies were developed for the improved synthesis of glycosylated peptides and proteins. This general synthetic method encompasses the realization that cysteine-free native chemical ligation (cysteine-free NCL) is a glycan-compatible process that may be used for assembling large glycosylated polypeptides from glycopeptide building blocks. In yet another aspect, the present invention also provides the recognition that chemoselective reaction of a glycopeptide containing a C-terminal aromatic disulfide auxiliary with a glycopeptide thioester may be achieved to form the corresponding glycosylated peptide adduct. In yet another aspect, the present invention also provides the recognition that cysteine-free native chemical ligation (cysteine-free NCL) provides a versatile and viable method for preparing cyclic peptides.

Specific examples, particularly with respect to the synthesis of glycopeptides, are described in more detail below and in the Examples herein, along with certain general methodologies developed during the course of these syntheses. It will be appreciated by one of ordinary skill in the art that these examples are not intended to be limiting; rather all equivalents are intended to be incorporated into the scope of the present invention. In particular, the inventive method may be generally adapted to the preparation of polyfunctionalized peptides and proteins, as well as cyclic peptides.

Compositions

The synthetic methodolgy described herein allows one to prepare homogeneous compositions of peptides or proteins, wherein the peptide or protein is post-translationally modified (e.g., glycosylated). That is, all the peptides or proteins in the composition have the same chemical structure. In the case of glycopeptides or glycoproteins, all the glycopeptides or glycoproteins have the same glycosylation pattern. This is, in contrast, to what is typically found in nature where a heterogeneous pattern of glycosylation if found on many peptides and proteins. Therefore, isolating such peptides or proteins from natural sources such as living organisms or cells leads to heterogeneous mixtures. The present invention provides synthetic methodology for the preparation of homogenous mixture of such pepties and proteins.

An example of a glycosylated peptide found in nature for which a homogeneous composition has not been achieved is erythropoietin, a biologically active glycopeptide that is used clinically to treat anemia. Erythropoietin is produced by purifying the glycopeptide from natural sources or from overexpressing cell lines leading to mixtures of various glycosylated forms of erythropoietin. The present invention focuses on the total synthesis of erythropoietin. Such a total synthesis would provide a homogenous composition of erythropoietin wherein all the molecules of erythropoietin have the same glycosylation pattern. Such a composition would be incredibly useful in determining the biological activity of different glycosylated forms of erythropoietin. A feat which has not been achieved to date.

In certain embodiments, the invention provides a composition of purified homogeneously glycosylated erythropoietin. The primary amino acid sequence of human erythropoietin is as follows:

Ala-Pro-Pro-Arg-Leu-Ile-Cys-Asp-Ser-Arg-Val-Leu-Glu-Arg-Tyr-Leu-Leu-Glu-Ala-Lys-Glu-Ala-Glu-Asn-Ile-Thr-Thr-Gly-Cys-Ala-Glu-His-Cys-Ser-Leu-Asn-Glu-Asn-Ile-Thr-Val-Pro-Asp-Thr-Lys-Val-Asn-Phe-Tyr-Ala-Trp-Lys-Arg-Met-Glu-Val-Gly-Gln-Gln-Ala-Glu-Val-Trp-Gln-Gly-Leu-Ala-Leu-Leu-Ser-Glu-Ala-Val-Leu-Arg-Gly-Gln-Ala-Leu-Leu-Val-Asn-Ser-Ser-Gln-Pro-Trp-Glu-Pro-Leu-Gln-Leu-His-Val-Asp-Lys-Ala-Val-Ser-Gly-Leu-Arg-Ser-Leu-Thr-Thr-Leu-Leu-Arg-Ala-Leu-Gly-Ala-Gln-Lys-Glu-Ala-Ile-Ser-Pro-Pro-Asp-Ala-Ala-Ser-Ala-Ala-Pro-Leu-Arg-Thr-Ile-Thr-Ala-Asp-Thr-Phe-Arg-Lys-Leu-Phe-Arg-Val-Tyr-Ser-Asn-Phe-Leu-Arg-Gly-Lys-Leu-Lys-Leu-Tyr-Thr-Gly-Glu-Ala-Cys-Arg-Thr-Gly-Asp-Arg (SEQ ID NO: XX).

Human erythropoietin is known to be glycosylated at one or more of the following sites: Asn24, Asn38, Asn83, and Ser126. The carbohydrates attached to Asn24, Asn38, and Asn83 are N-linked. The carbohydrate attached to Ser126 are O-linked. In certain embodiments, the carbohydrate moiety attached to Ser126 is glycophorin.

One form of glycosylated is of the formula:

Ala-Pro-Pro-Arg-Leu-Ile-Cys-Asp-Ser-Arg-Val-Leu-Glu-Arg-Tyr-Leu-Leu-Glu-Ala-Lys-

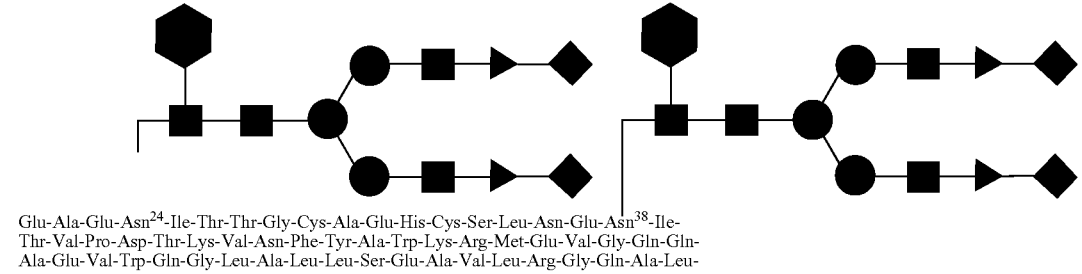

Glu-Ala-Glu-Asn[24]-Ile-Thr-Thr-Gly-Cys-Ala-Glu-His-Cys-Ser-Leu-Asn-Glu-Asn[38]-Ile-Thr-Val-Pro-Asp-Thr-Lys-Val-Asn-Phe-Tyr-Ala-Trp-Lys-Arg-Met-Glu-Val-Gly-Gln-Gln-Ala-Glu-Val-Trp-Gln-Gly-Leu-Ala-Leu-Leu-Ser-Glu-Ala-Val-Leu-Arg-Gly-Gln-Ala-Leu-

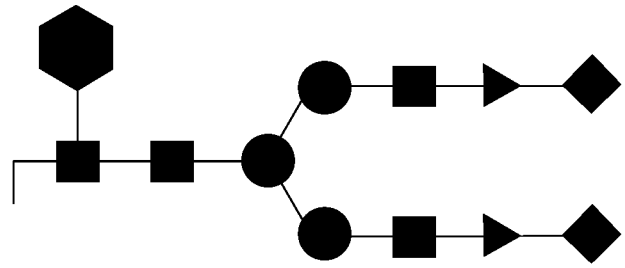

Leu-Val-Asn[83]-Ser-Ser-Gln-Pro-Trp-Glu-Pro-Leu-Gln-Leu-His-Val-Asp-Lys-Ala-Val-Ser-Gly-Leu-Arg-Ser-Leu-Thr-Thr-Leu-Leu-Arg-Ala-Leu-Gly-Ala-Gln-Lys-Glu-Ala-Ile-

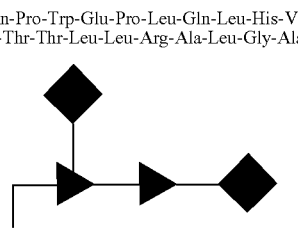

Ser-Pro-Pro-Asp-Ala-Ala-Ser[126]-Ala-Ala-Pro-Leu-Arg-Thr-Ile-Thr-Ala-Asp-Thr-Phe-Arg-Lys-Leu-Phe-Arg-Val-Tyr-Ser-Asn-Phe-Leu-Arg-Gly-Lys-Leu-Lys-Leu-Tyr-Thr-Gly-Glu-Ala-Cys-Arg-Thr-Gly-Asp-Arg

♦ Sialic acid
▶ Galactose
⬢ Fucose
● Mannose
■ Glucosamine.

In certain embodiments, the homogeneous composition comprises only erythropoietin molecules of the above structure. In other embodiments, the invention provides homogeneous compositions of other glycosylated forms of erythropoietin. For example, the erythropoietin may be glycosylated at only 1, 2, or 3 of the four available sites for glycosylation, or the erythropoietin may be glycosylated at additional sites besides the ones listed above. In certain embodiments, the erthropoietin may be glycosylated at the four sites, Asn24, Asn38, Asn83, and Ser126, but the carbohydrate moiety may be different from the one shown in the structure above. The carbohydrate moiety may be smaller or larger and may contain different sugar units and/or different linkages between the sugar units. Such homogeneous compositions are useful for both research and therapeutic purposes.

In certain embodiments, invention provides particular mixtures of glycosylated forms of erythropoietin. The present invention allows for the preparation of such mixtures with specific ratios of gycosylated forms as compared to compositions of erythropoietin purified from natural sources where one has to be content with what is produced by cellular machinery. Such novel mixtures are particularly useful in studying the biological role of erythropoietin, particularly the biological role of different glycosylated forms. The mixtures may also be used a therapeutic compositions. For example, the mixtures may be used to treat anemia.

In certain embodiments, the invention provides fragments of erythropoietin. Any fragment of erythropoietin may be prepared using synthetic methodolgy known in the art combined with the teachings herein. In certain embodiments, the fragment is glycosylated. For example, the fragment may contain residue Asn24, Asn38, Asn83, and Ser126 with a pendant carbohydrate moiety. Such fragments may be useful in the synthesis of erythropoietin. In certain embodiments, the fragment is biologically active. Exemplary fragments that include the primary sequence:
Ala-Pro-Pro-Arg-Leu-Ile-Cys-Asp-Ser-Arg-Val-Leu-Glu-Arg-Tyr-Leu-Leu-Glu-Ala-Lys-Glu-Ala-Glu-Asn-Ile-Thr-Thr-Gly (Amino acids 1-28; SEQ ID NO: XX);
Cys-Ala-Glu-His-Cys-Ser-Leu-Asn-Glu-Asn-Ile-Thr-Val-Pro-Asp-Thr-Lys-Val-Asn-Phe-Tyr-Ala-Trp-Lys-Arg-Met-Glu-Val-Gly-Gln-Gln-Ala-Glu-Val-Trp-Gln-Gly-Leu-Ala-Leu-Leu-Ser-Glu-Ala-Val-Leu-Arg-Gly (Amino acids 29-77; SEQ ID NO: XX);
Gln-Ala-Leu-Leu-Val-Asn-Ser-Ser-Gln-Pro-Trp-Glu-Pro-Leu-Gln-Leu-His-Val-Asp-Lys-Ala-Val-Ser-Gly-Leu-Arg-Ser-Leu-Thr-Thr-Leu-Leu-Arg-Ala-Leu-Gly (Amino acids 78-113; SEQ ID NO: XX); or
Ala-Gln-Lys-Glu-Ala-Ile-Ser-Pro-Pro-Asp-Ala-Ala-Ser-Ala-Ala-Pro-Leu-Arg-Thr-Ile-Thr-Ala-Asp-Thr-Phe-Arg-Lys-Leu-Phe-Arg-Val-Tyr-Ser-Asn-Phe-Leu-Arg-Gly-Lys-Leu-Lys-Leu-Tyr-Thr-Gly-Glu-Ala-Cys-Arg-Thr-Gly-Asp-Arg (Amino acids 114-166; SEQ ID NO: XX). The exemplary fragments may be combined to yield larger fragments of erythropoietin such as amino acids 1-77, amino acids 1-113, amino acids 29-113, amino acids 29-166, or amino acids 78-166 of erythropoietin. The primary sequence of the fragement may be modified. In certain embodiments, the fragment includes a deletion, addition, and/or substitution as compared to the wild type human erythropoietin sequence. In certain embodiments, the fragment includes 1, 2, 3, 4, 5, 6, 7, 8, 9, or 10 deletion, additions, and/or substitutions. For example, an asparagine residue may be replaced with an aspartate residue (e.g., at positions 24, 38, or 83). The fragment may also be glycosylated and/or the termini of the fragment may be modified. The fragment may also include protecting groups, for example, side chain protecting groups, C-terminus protecting group, and/or N-terminus protecting groups.

Particular examples of some synthetically useful fragments include:

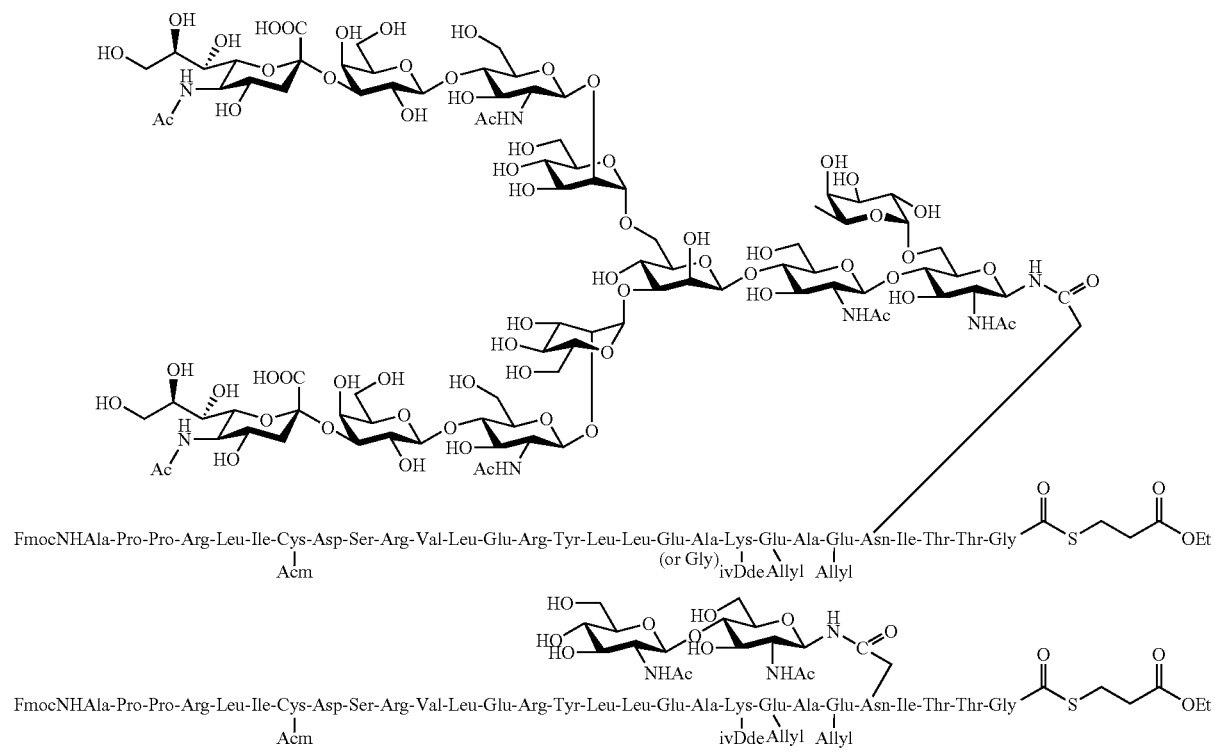

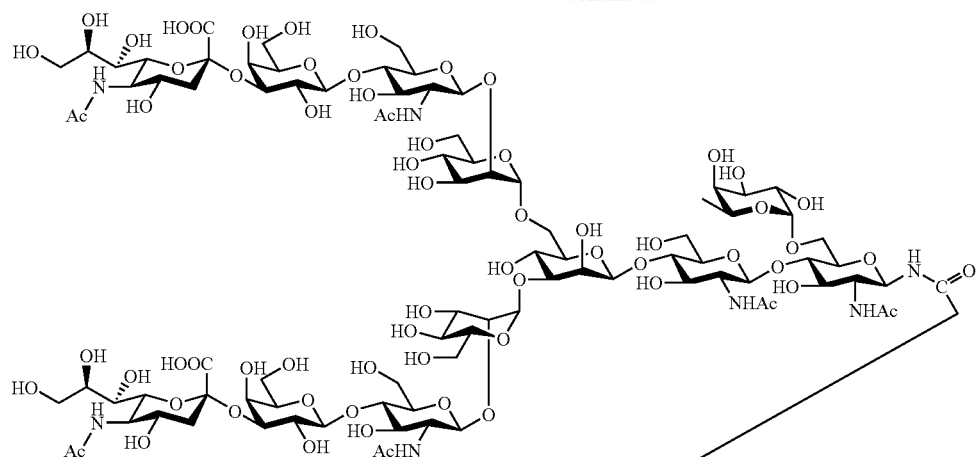
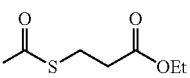
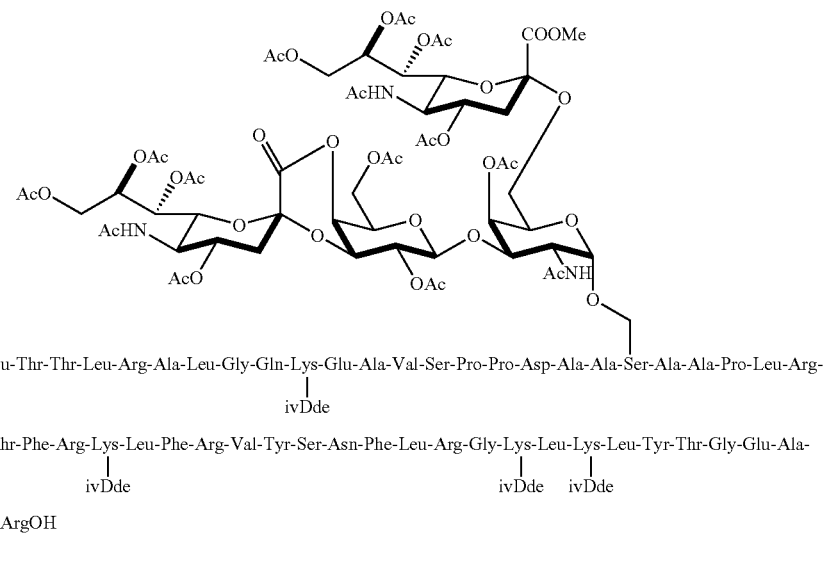
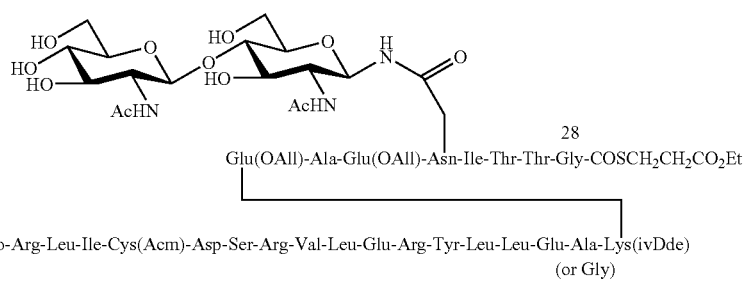

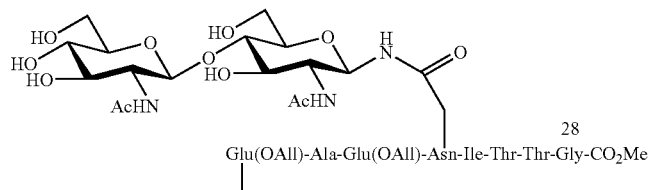
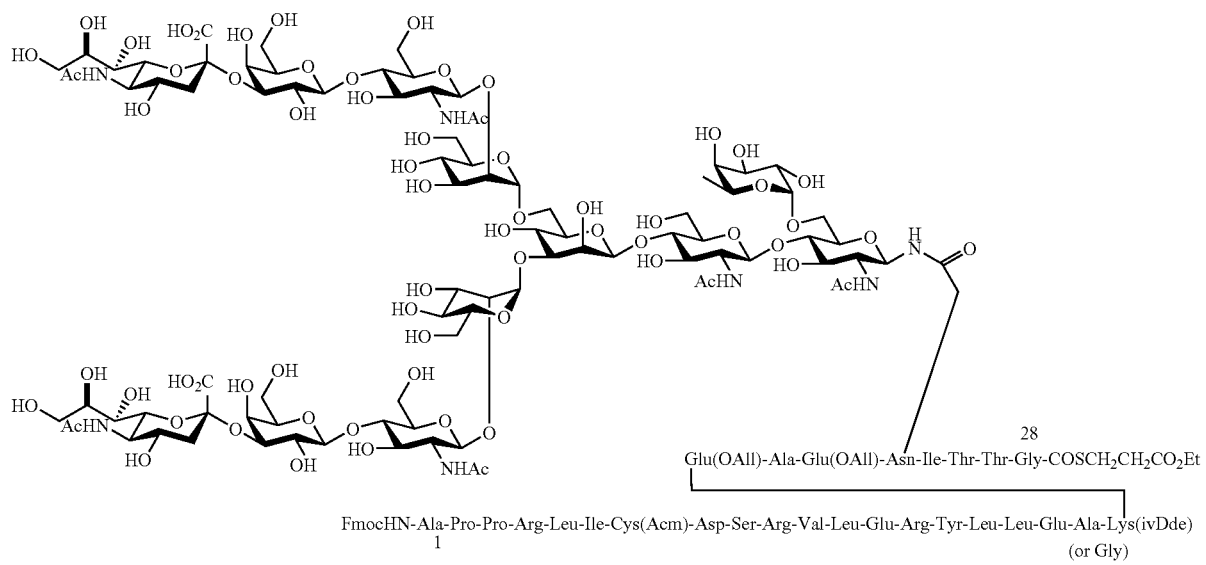
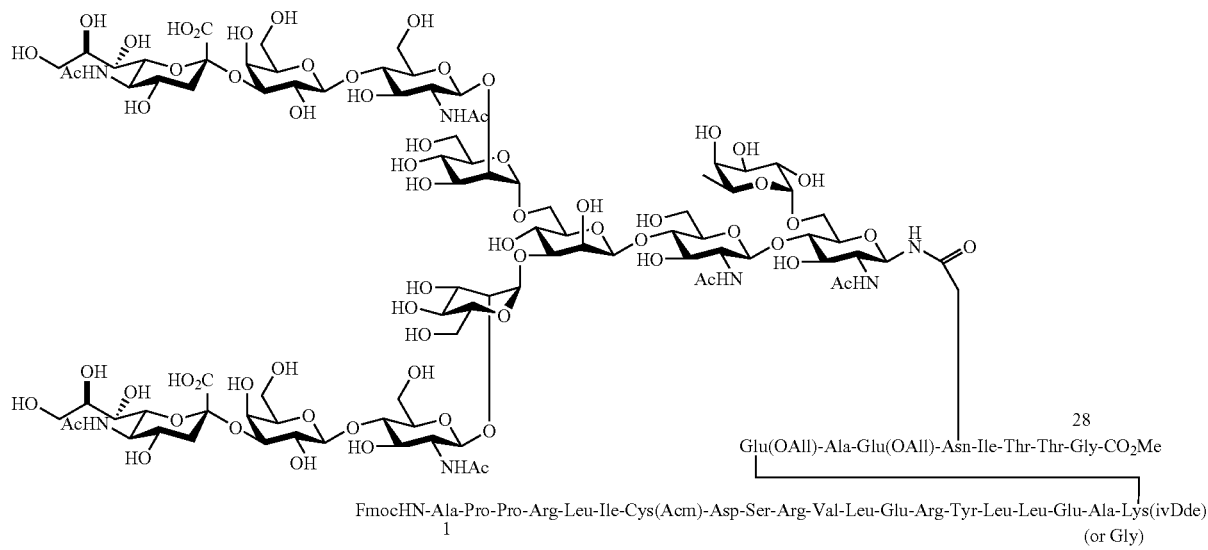

-continued
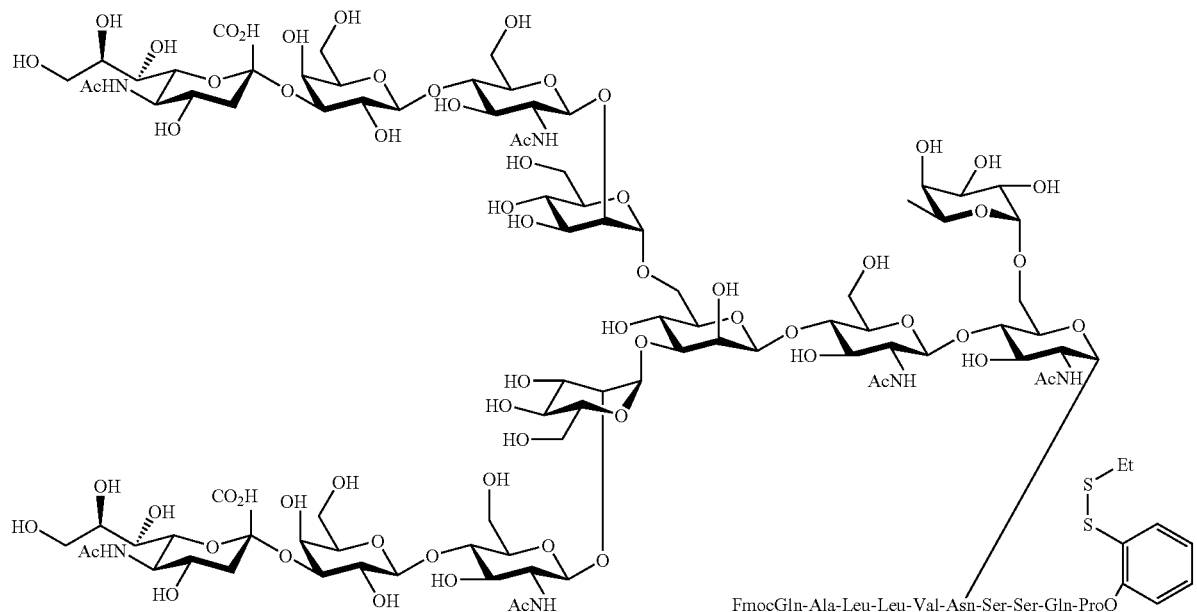
FmocGln-Ala-Leu-Leu-Val-Asn-Ser-Ser-Gln-ProO
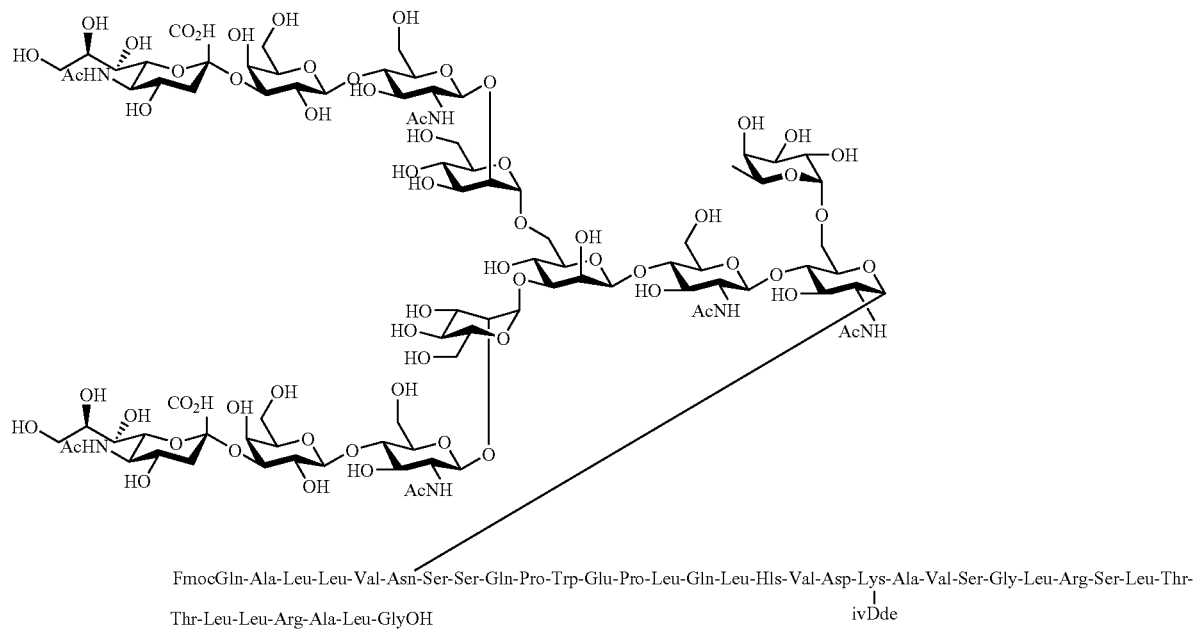
FmocGln-Ala-Leu-Leu-Val-Asn-Ser-Ser-Gln-Pro-Trp-Glu-Pro-Leu-Gln-Leu-His-Val-Asp-Lys-Ala-Val-Ser-Gly-Leu-Arg-Ser-Leu-Thr-
Thr-Leu-Leu-Arg-Ala-Leu-GlyOH
|
ivDde -continued

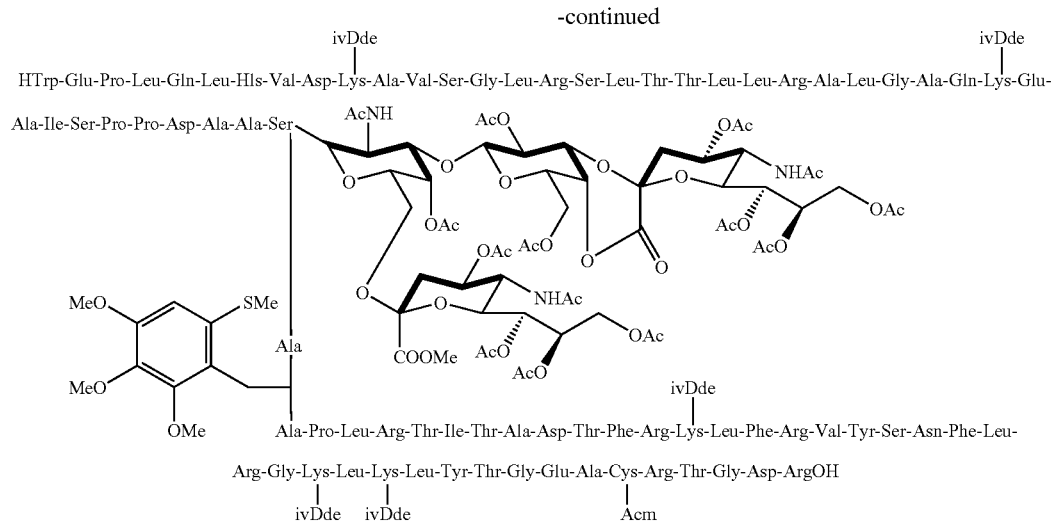

The methodology described herein may also be used to prepare homogeneous compositions of other glycosylated peptides or proteins. Examples of other glycopeptides or glycoproteins that may be synthesized using the inventive methodology include gp120 or vaccine antigens. Other modified peptides and proteins may also be synthesized using the inventive methodology. For example, proteins and peptides that are typically post-translationally modified may be prepared. In certain examples, phosphorylated, hydroxylated, lipidated, acylated, farnesylated, isoprenylated, methylated, palmitoylated, geranylgeranylated, carboxylated, sulfated, carbamylated, myristoylated, formylated, acetylated, or ubiquitinated. The synthesize peptide or protein can then be used to prepare homogeneous composition wherein all the molecules in the composition have the same structure. In certain embodiments, homogeneous compositions have never been prepared before. In certain embodiments, as described above for erythropoietin, particular compositions with particular forms of the peptide or protein may be prepared from synthesized peptides and proteins.

Synthetic Strategies for Preparing Erythropoietin

The present invention also provides methodology for synthesizing erythropoietin or fragments thereof described herein. In certain embodiments, the erythropoietin is human erythropoietin.

In one aspect, erthropoietin is constructed by condensation of smaller peptide fragments. In certain embodiments, erythropoietin is synthesized by condensing four glycopeptide fragments, EPO (114-166), EPO(78-113), EPO(29-77), and EPO(1-28). Each of these fragments ends with a glycine residue to facilitate the coupling.

In certain embodiments, the glycopeptide fragments containing N-linked glycans are generated by appending the desired oligosaccharide unit onto the peptide fragment using a Kochetkov-Lansbury amination-aspartylation protocol. In this embodiments, the Asn residue of the glycopeptide fragment is substituted for an Asp residue to allow for the amination-aspartylation protocol. The peptide fragment may include a C-terminal phenolic ester as described herein and/or a N-terminal auxillary group as described herein. For example, the fully protected EPO(78-113) is synthesized using Fmoc (9-fluorenylmethyloxycarbonyl) chemistry. In certain embodiments, the protected EPO(78-113) is of the formula:

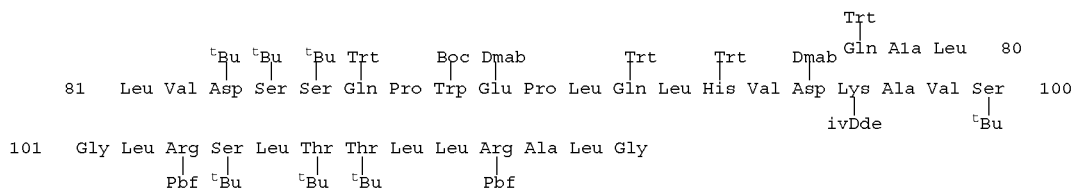

The amino acid residues are typically protected using standard protecting groups such as those most commonly used in Fmoc chemistry. In certain embodiments, the glutamic acid and aspartic acid residues are protected with Dmab [1-(4,4-dimethyl-2,6-dioxocyclohexylidene)-3-methylbutyl)amino benzyl)] and the lysine residue is protected with ivDde [1-(4,4-dimethyl-2,6-dioxocyclohex-1-ylidene)-3-methylbutyl]. The use of the Dmab and ivDde protecting groups allows for the selective appendage of the desired oligosaccharide moietyto the aspartic acid residue and the auxillary to the N-terminus fragment.

In certain embodiments, the peptide fragment useful in the synthesis of erythropoietin are prepared from condensing single amino acids and dipeptides. In certain embodiments, one of more of the dipeptides Asp83-Ser84, Asp96-Lys97, Val99-Ser100, and Leu105-Thr106 are used in in the synthesis of the EPO(78-113) fragment. In certain embodiments, all four dipeptides are used as shown below.

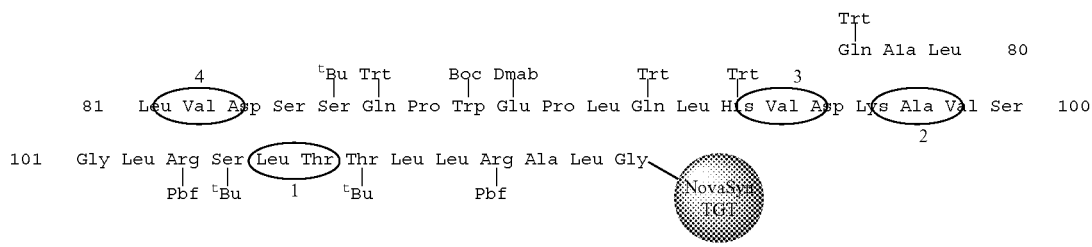

In certain other embodiments, dipeptides are used in the synthesis of the EPO(29-77) fragment. One or more of the four dipeptides Cys33-Ser34, Asp43-Thr44, Tyr49-Ala50, and Leu70-Ser71 are used. In certain embodiments, the commercially available protected glycine, Dmb-Gly, is used in the synthesis of EPO(29-77). A schematic of the synthesis of EPO(29-77) is shown below:

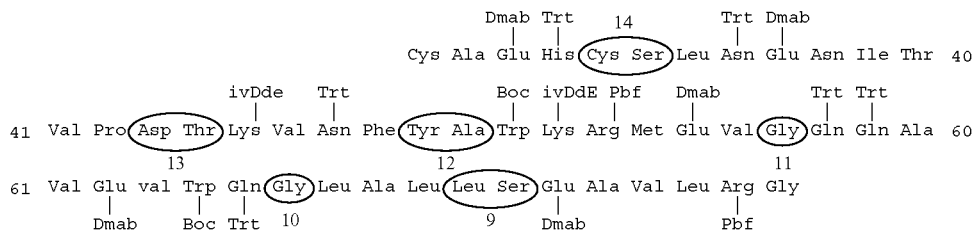

Such dipeptides may be used in the same manner as single amino acid activated with HATU. The use of dipeptides increases the overall yield of the peptide fragment. In addition, a solid phase resin such as NovaSyn® TGT resin pre-loaded with an amino acid may be used.

After synthesis of the amino acid portion of the fragment, the termini of the fragment may be modified. For example, protecting groups may be installed or removed; auxillary groups may be installed; or other modification may be made. In certain embodiments, an auxillary group such as one of those described herein is added to the N-terminus of the fragment. In certain embodiments, the C-terminus is modified with a phenolic ester moiety (e.g., 2-(ethyldithio)-phenol). As exemplary modification of EPO(78-113) is shown below:

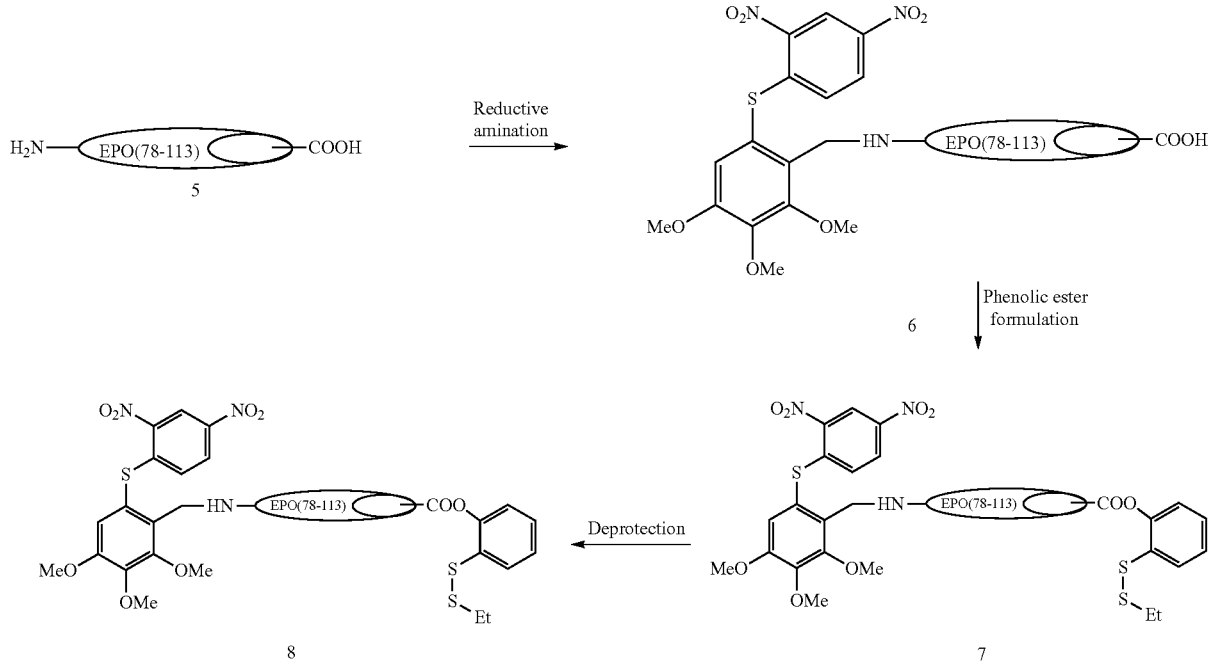

As would be appreciated by one of skill in the art, the peptide fragment may be purified after any step.

The carbohydrate moiety is then installed on the peptide fragment. In certain embodiments, the carbohydrate moiety is installed on an aspartic acid using the Kochetkov-Lansbury amination-aspartylation as shown below:

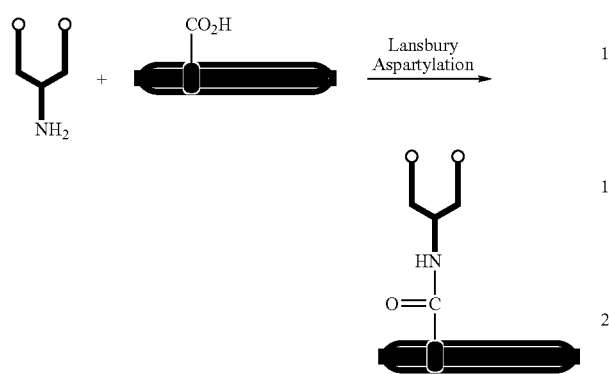

In certain embodiments, a carbohydrate moiety is installed on Asp83 of the EPO(78-113) fragment. In certain embodiments, a carbohydrate moiety is installed on Asp38 of the EPO(29-77) fragment.

In certain embodiments, the EPO(78-113) fragment is prepared by condensing the glycosylated EPO(78-87) fragment to the EPO(88-113) fragment. In certain embodiments, the EPO(78-113) fragment is prepared by condensing the glycosylated EPO(78-90) fragment to the EPO(91-113) fragment. In certain embodiments, the four fragments, EPO(78-87), EPO(88-113), EPO(78-90), and EPO(91-113), are prepared using the dipeptide approach as outlined above. Both of these retrosynthetic disconnection occur at a proline residue (i.e., Pro87-Trp88; Pro90-Leu91). The smaller fragments may be ligated using silver chloride catalyzed conditions. In certain embodiments, the C-terminus at the junction is equipped with a phenolic ester (e.g., 2-(ethyldithio)-phenol).

In certain embodiments, the glycopeptide EPO(78-87) is joined to peptide EPO(88-113) using silver chloride catalyzed conditions. In certain embodiments, the conditions include 3.3 eq. AgCl, 33 eq. HOOBt, and 22 eq. DIEA.

In certain embodiments, the EPO(1-28) fragment is prepared by condensing the EPO(1-19) fragment to the glycopeptide EPO(20-28) fragment. The retrosynthetic disconnection occurs at an alanine residue (i.e., Ala19-Lys20). In certain embodiments, the C-terminus at the junction is equipped with a phenolic ester (e.g., 2-(ethyldithio)-phenol). In certain embodiments, the fragments are ligated using silver chloride catalyzed conditions.

In certain embodiments, the EPO(29-77) fragment is prepared by condensing the glycosylated EPO(29-42) fragment to the EPO(43-77) fragment. The retrosynthetic disconnection occurs at a proline residue (i.e., Pro42-Asp43). In certain embodiments, the C-terminus at the junction is equipped with a phenolic ester (e.g., 2-(ethyldithio)-phenol). In certain embodiments, the fragments are ligated using silver chloride catalyzed conditions.

In certain embodiments, the EPO(88-166) fragment is prepared by condensing the EPO(88-113) fragment to the EPO(114-166) fragment. In certain embodiments, the silver chloride catalyzed conditions are used.

In certain embodiments, the EPO(78-166) fragment is prepared by condensing the EPO(78-87) fragment to the EPO(88-166) fragment. In certain embodiments, the silver chloride catalyzed conditions are used. In certain embodiments, one or both of EPO(78-87) fragment and EPO(88-166) fragment are glycosylated. The synthetic plan is shown below:

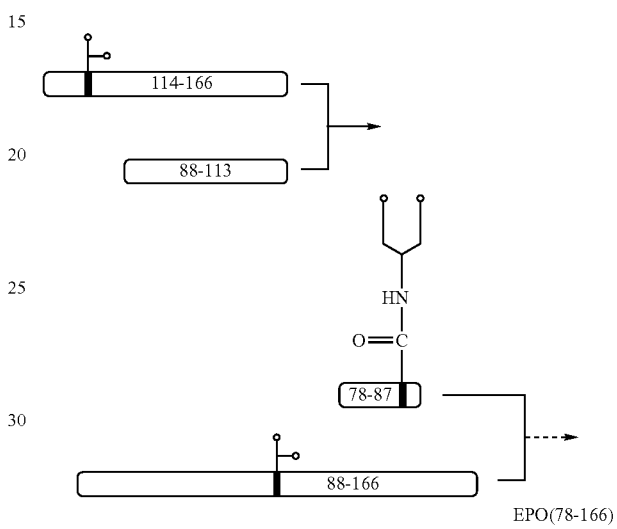

EPO(78-166)

Synthetic Methods

The present invention also provides synthetic methodology useful in the synthesis of peptides and proteins, particularly glycosylated peptides and proteins. In certain embodiments, the invention provides methods of ligating two peptide or protein fragments

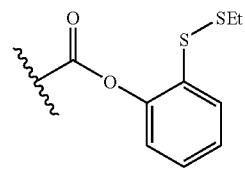

using a phenolic ester such as
at the C-terminus of the acyl donor. The invention also provides intermediates such as peptide fragments that are useful in the inventive methods. Such peptide fragments for ligation may be protected, partially protected, or unprotected.

In one aspect, the invention provides an isolated homogeneous polyfunctionalized protein having the structure:

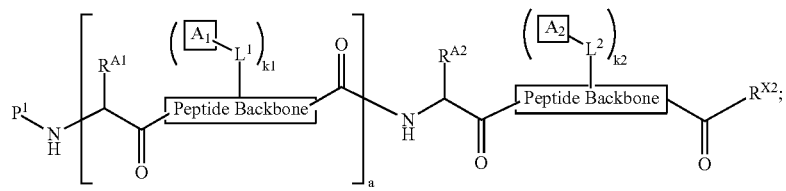

wherein each occurrence of the "peptide backbone" has an amino acid sequence that is either identical to or closely related to that of a naturally occurring protein near a functionalized site, or a truncated, elongated or derivatized version thereof; wherein any one or more of the amino acid residues may bear one or more protecting groups;

$P^1$ is hydrogen or a nitrogen protecting group;

a is an integer between 1 and about 20, inclusive;

each occurrence of $R^{A1}$ and $R^{A2}$ is independently a natural or non-natural amino acid side chain; each occurrence of k1 and k2 is independently an integer between 1 and about 20;

each occurrence of $A_1$ and $A_2$ is independently an aliphatic, heteroaliphatic, aromatic, heteroaromatic, aryl, heteroaryl, carbohydrate, or a pharmaceutically useful group or entity;

each occurrence of $L^1$ is independently a substituted or unsubstituted, linear or branched, cyclic or acyclic, saturated or unsaturated aliphatic or heteroaliphatic moiety or a natural or non-natural amino acid side chain; and $R^{X2}$ is —$OR^{X2}$ or —$NR^{X2b}R^{X2c}$, wherein $R^{X2a}$ is hydrogen, alkyl, aromatic, heteroaromatic, aryl, heteroaryl, -alkyl(aryl), -alkyl(heteroaryl), a carboxylic acid protecting group, an amino acid or a protected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid or a protected amino acid. In certain embodiments, $P^1$ is a hydrogen. In certain embodiments, $P^1$ is a nitrogen-protecting group. In certain embodiments, $P^1$ is an Fmoc nitrogen-protecting group. In certain embodiments, $P^1$ is a Boc nitrogen-protecting group. In certain embodiments, $P^1$ is acetyl. In certain embodiments, $R^{X2}$ is —$OR^{X2a}$. In certain embodiments, $R^{X2}$ is —OH. In certain embodiments, $R^{X2}$ is —$OR^{X2a}$, wherein $R^{X2a}$ is $C_1$-$C_6$ alkyl. In certain embodiments, $R^{X2}$ is —$OR^{X2a}$, wherein $R^{X2a}$ is a carboxylic acid protecting group. In certain embodiments, $R^{X2}$ is —$OR^{X2a}$, wherein $R^{X2a}$ is a substituted or unsubstituted aryl moiety. In certain embodiments, $R^{X2}$ is —$OR^{X2a}$, wherein $R^{X2a}$ is a substituted or unsubstituted phenyl moiety. In certain embodiments, $R^{X2}$ is —$OR^{X2a}$, wherein $R^{X2a}$ is

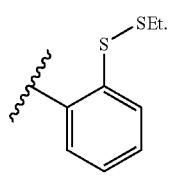

In certain embodiments, $R^{X2}$ is —$NR^{X2b}R^{X2c}$. In certain embodiments, $R^{X2}$ is —$SR^{X2a}$. In certain embodiments, $R^{X2}$ is —SH. In certain embodiments, $R^{X2}$ is —$SR^{X2a}$, wherein $R^{X2a}$ is $C_1$-$C_6$ alkyl. In certain embodiments, $R^{X2}$ is —$SR^{X2a}$, wherein $R^{X2a}$ is

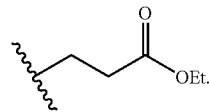 [SMILES: *CCC(=O)OCC]

In certain embodiments, one or both of $R^{A1}$ and $R^{A2}$ are hydrogen, methyl, of —$CH_2$—$SR^S$, wherein $R^S$ is hydrogen or a sulfur-protecting group. In certain embodiments, $R^{A2}$ is hydrogen, methyl, of —$CH_2$—$SR^S$, wherein $R^S$ is hydrogen or a sulfur-protecting group. In certain embodiments, $R^{A1}$ is hydrogen, methyl, of —$CH_2$—$SR^S$, wherein $R^S$ is hydrogen or a sulfur-protecting group. In certain embodiments, each occurrence of $A_1$ or $A_2$ is a carbohydrate moiety or absent. In certain embodiments, $A_1$ is a carbohydrate moiety. In certain embodiments, $A_2$ is a carbohydrate moiety. In certain embodiments, each occurrence of $L^1$ and $L^2$ is the side chain of a natural or unnatural amino acid. In certain embodiments, each occurrence of $L^1$ and $L^2$ is the side chain of a natural amino acid. In certain embodiments, a is an integer between 1 and 10, inclusive. In certain embodiments, each occurrence of $A_1$ and $A_2$ is independently selected is independently selected from the group consisting of:

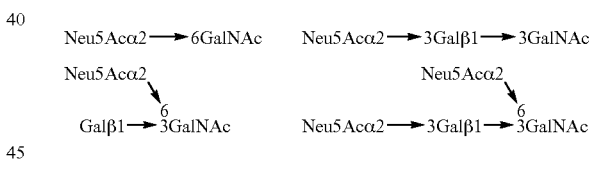

when $A_1$ or $A_2$ is O-linked; and

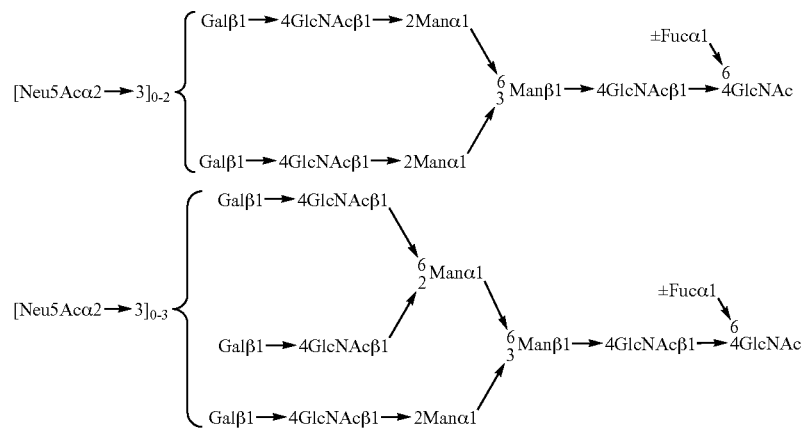

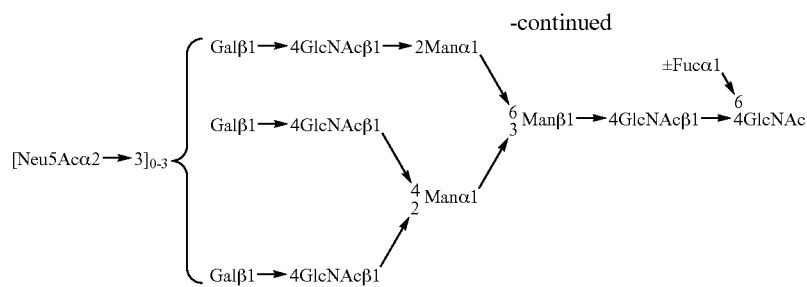
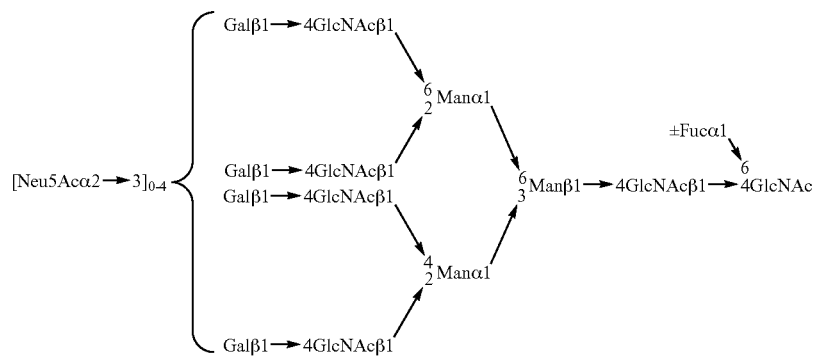
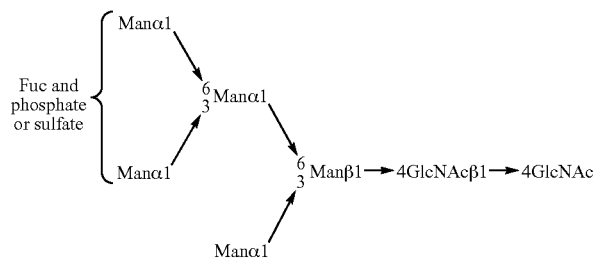
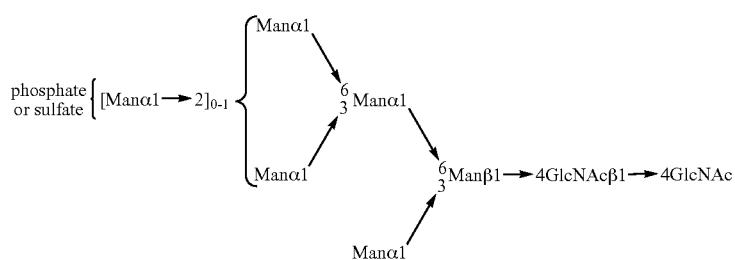
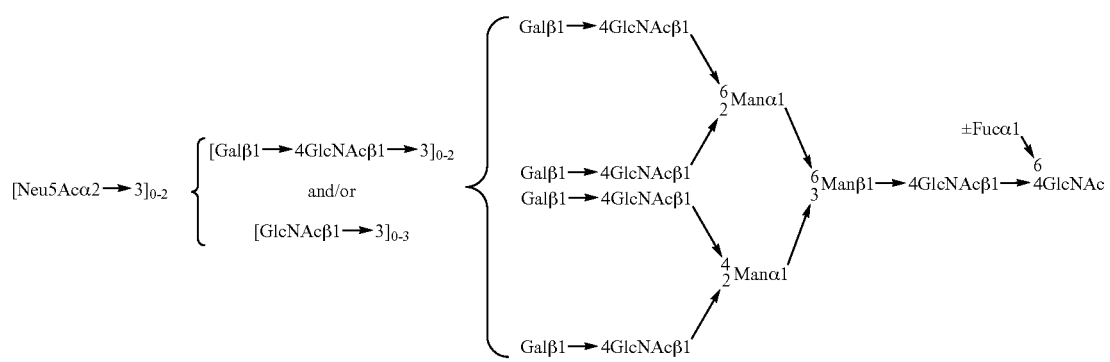

-continued

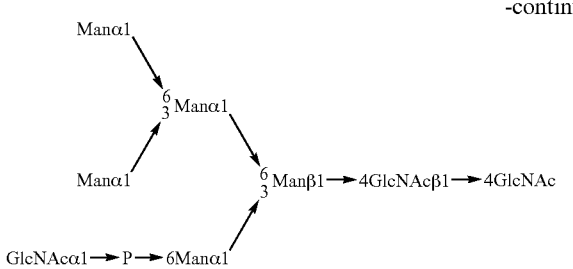

when $A_1$, or $A_2$ is N-linked.

In another aspect, the invention provides an isolated having formula:

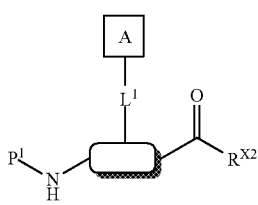

wherein the peptide has an amino acid sequence that is either identical to or closely related to that of a naturally occurring glycoprotein near a glycosylation site, or a truncated, elongated or derivatized version thereof; wherein any one or more of the amino acid residues may bear one or more protecting groups;

each occurrence of $L^1$ is independently a substituted or unsubstituted, linear or branched, cyclic or acyclic, saturated or unsaturated aliphatic or heteroaliphatic moiety or a natural or non-natural amino acid side chain; and $R^{X2}$ is —$OR^{X0}$, —$OR^{X2a}$ or —$NR^{X2b}R^{X2c}$, wherein $R^{X2a}$ is hydrogen, alkyl, aromatic, heteroaromatic, aryl, heteroaryl, -alkyl(aryl), -alkyl(heteroaryl), a carboxylic acid protecting group, an amino acid or a protected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid or a protected amino acid;

$R^{X0}$ is a group such that the moiety —C(=O)$OR^{X0}$ can be made to undergo ligation with a peptide acyl acceptor;

$P^1$ is hydrogen, a nitrogen protecting group, or a moiety having the structure:

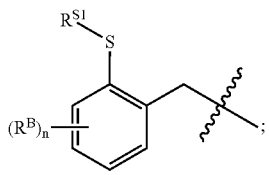

wherein n is 2 or 3; $R^{S1}$ is hydrogen or a sulfide protecting group; each occurrence of $R^B$ is independently alkoxy, hydroxy or silyloxy; and A is a carbohydrate moiety. In certain embodiments, A is selected from the group consisting of:

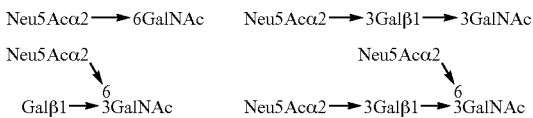

when A is O-linked; and

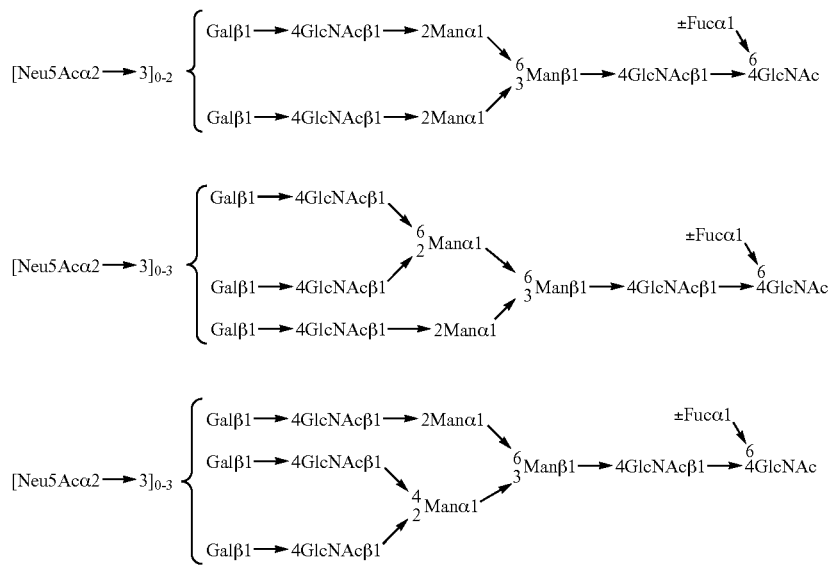

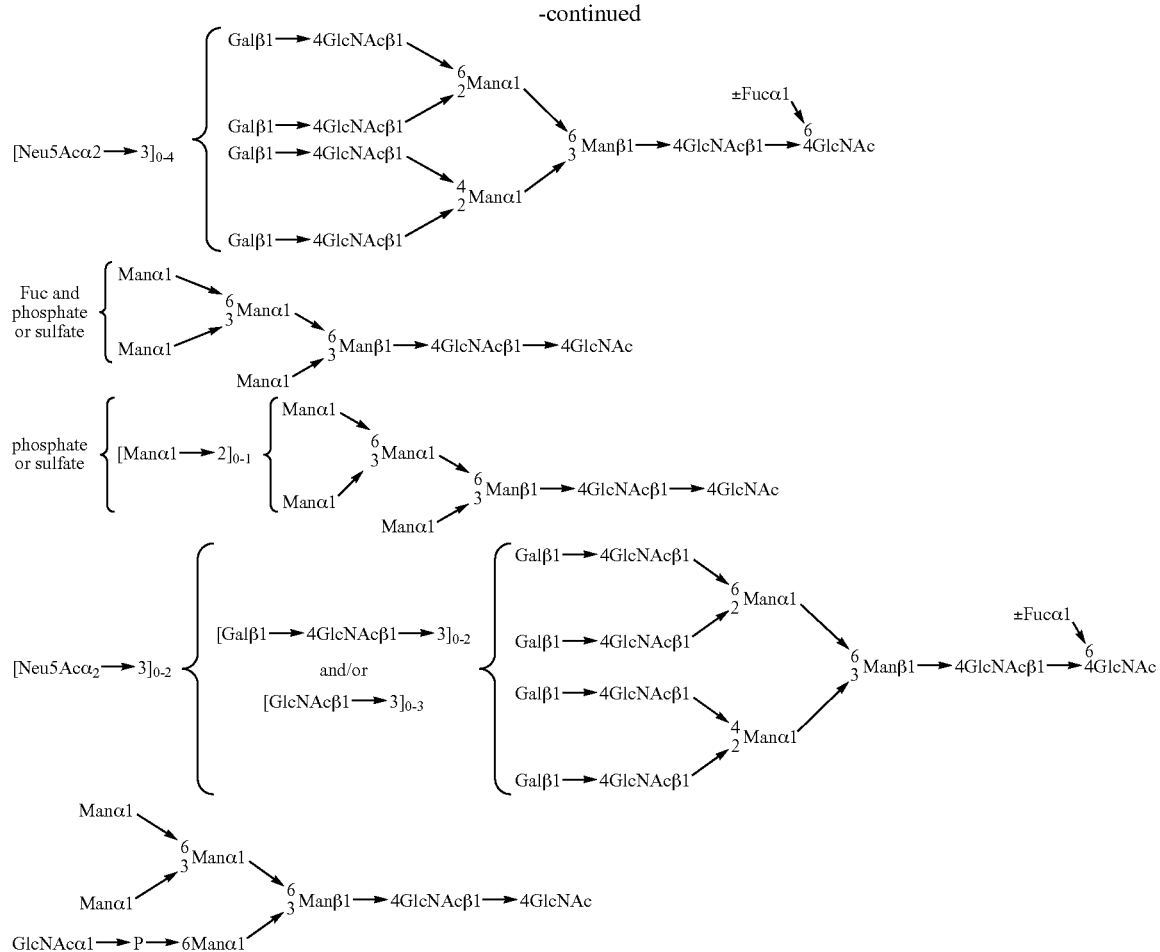

when A is N-linked. In certain embodiments, A is of the structure:

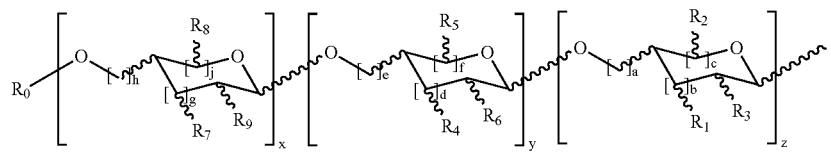

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, $COOR^{ii}$, or a substituted or unsubstituted linear or branched chain alkyl, acyl, arylalkyl or aryl group or a saccharide moiety having the structure:

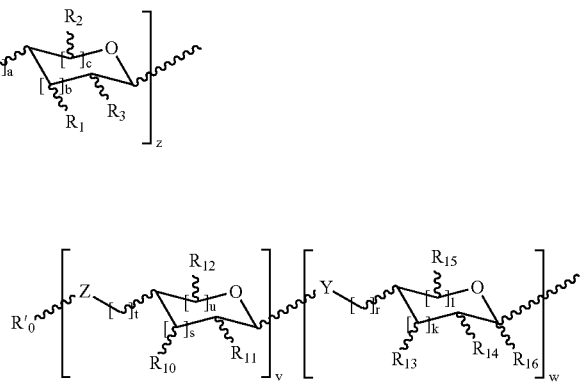

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, CH₂OH, CH₂OR^{iii}, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, COOR^{ii}, CONHR^{ii}, a substituted or unsubstituted linear or branched chain alkyl or aryl group; wherein each occurrence of R^{iii} is hydrogen, CHO, COOR^{iv}, or a substituted or unsubstituted linear or branched chain alkyl, acyl, arylalkyl or aryl group; and wherein each occurrence of R^{ii} and R^{iv} are each independently H, or a substituted or unsubstituted linear or branched chain alkyl, arylalkyl or aryl group. In certain embodiments, the glycopeptide is not a naturally occurring glycopeptide. In certain embodiments, $P^1$ is a hydrogen. In certain embodiments, $P^1$ is a nitrogen-protecting group. In certain embodiments, $P^1$ is an Fmoc nitrogen-protecting group. In certain embodiments, $P^1$ is

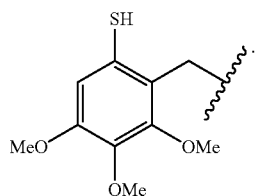

In certain embodiments, $R^{X2}$ is —OR^{X2a}. In certain embodiments, $R^{X2}$ is —OH. In certain embodiments, $R^{X2}$ is —OR^{X2a}, wherein $R^{X2a}$ is $C_1$-$C_6$ alkyl. In certain embodiments, $R^{X2}$ is —OR^{X2a}, wherein $R^{X2a}$ is a carboxylic acid protecting group. In certain embodiments, $R^{X2}$ is —OR^{X2a}, wherein $R^{X2a}$ is a substituted or unsubstituted aryl moiety. In certain embodiments, $R^{X2}$ is —OR^{X2a}, wherein $R^{X2a}$ is a substituted or unsubstituted phenyl moiety. In certain embodiments, $R^{X2}$ is —OR^{X2a}, wherein $R^{X2a}$ is

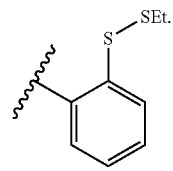

In certain embodiments, $R^{X2}$ is —NR^{X2b}R^{X2c}. In certain embodiments, $R^{X2}$ is —SR^{X2a}. In certain embodiments, $R^{X2}$ is —SH. In certain embodiments, $R^{X2}$ is —SR^{X2a}, wherein $R^{X2a}$ is $C_1$-$C_6$ alkyl. In certain embodiments, $R^{X2}$ is —SR^{X2a}, wherein $R^{X2a}$ is

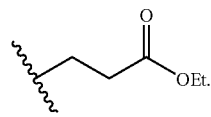 [SMILES: *CCC(=O)OCC]

In certain embodiments, A is absent.

In certain embodiments, the glycopeptide has the structure:

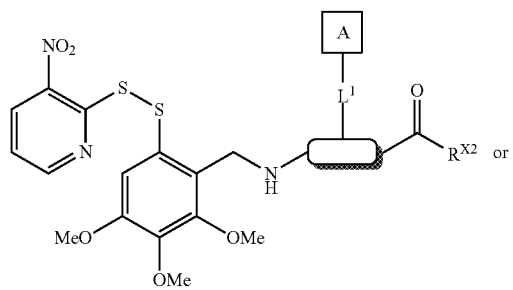

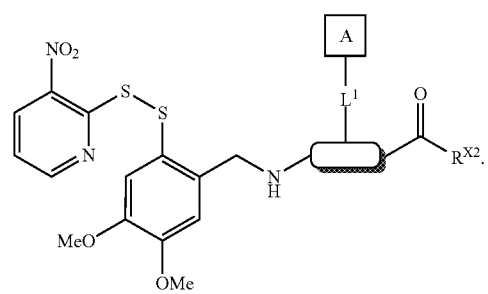

In certain embodiments, the glycopeptide has the structure:

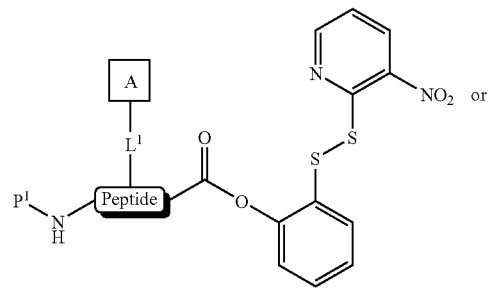

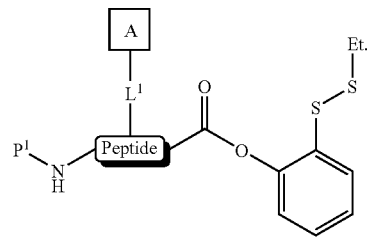

In certain embodiments, the glycopeptide has the structure:

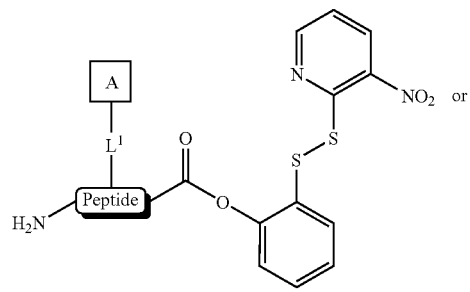

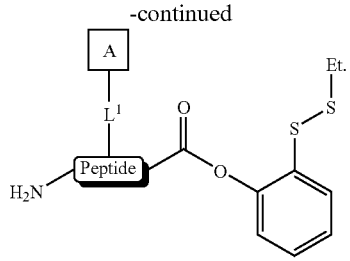

In certain embodiments, the glycopeptide has the structure:

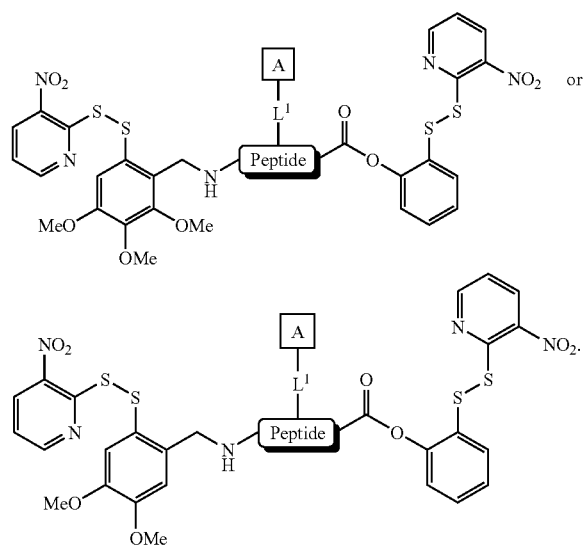

In certain embodiments, $R^{X2}$ is $-OR^{X0}$, and/or P is a moiety having the structure:

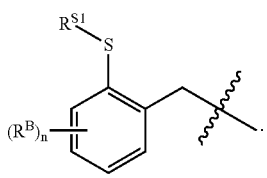

In certain exemplary embodiments, n is 2. In certain other exemplary embodiments, n is 3.

In certain exemplary embodiments, each occurrence of $R^B$ is independently $C_{1-6}$ alkoxy, hydroxy, or silyloxy. In certain other exemplary embodiments, each occurrence of $R^B$ is $C_1$-$C_6$ alkoxy. In certain other exemplary embodiments, each occurrence of $R^B$ is methoxy.

In certain embodiments, n is 2 and each occurrence of $R^B$ is methoxy. In certain other embodiments, n is 3 and each occurrence of $R^B$ is methoxy.

In certain embodiments, $L^1$ may comprise any functional moiety that is compatible with native chemical ligation reaction conditions (either cysteine-free or cysteine-dependent native chemical ligation). In certain embodiments, $L^1$ may comprise any functional moiety that is compatible with aqueous conditions. In certain embodiments, a compatible functionality is one that is stable, unreactive and/or minimally interferes with the reaction. A thiol group is considered a compatible functionality, even though a thiol group may slow down the reaction. Examples of suitable functionalities include, but are not limited to, hydrocarbons, amines, amides, imines, hydroxyls, ethers, carboxylic esters, aldehydes, thiols, olefins, alkynes, aryls and heteroaryls. In certain exemplary embodiments, $L^1$ does not comprise a thiol group. In certain embodiments, each occurrence of $L^1$ is the side chain of a natural or unnatural amino acid. In certain embodiments, each occurrence of $L^1$ is the side chain of a natural amino acid.

In certain embodiments, $L^1$ is $-O-(CH_2)_n-$, wherein n is 0-9, or a glycoside-containing moiety (e.g., mono- or polysaccharide).

In certain other embodiments, A is a carbohydrate moiety, and $L^1$ is either α- or β-linked to an amino acid residue of the peptide backbone. It will be appreciated that polyfunctionalized peptides made according to the method of the present invention are not limited to those where each occurrence of $L^1$ comprises n-alkyl where n is greater than or equal to 1; rather each occurrence of A can be independently linked via the traditional direct linkage (n=0), via n-alkyl (such as pentyl), via a monosaccharide moiety or any combination thereof. In certain embodiments, A is selected from the group consisting of Globo-H, fucosyl GM1, GM2, KH-1, glycophorin, STN, (2,3)ST, Le$^y$, Le$^x$, N3, Tn, 2,6-STn, Gb3 and TF, or protected form thereof. In certain embodiments, A is O-linked to $L^1$ and A has one of the following structures:

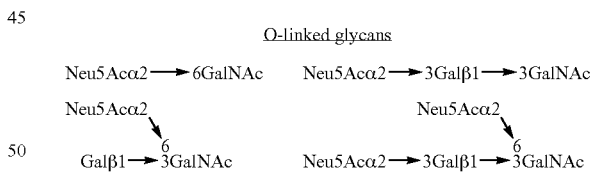

or a protected form thereof.

In certain embodiments, A is N-linked to $L^1$ and A has one of the following structures:

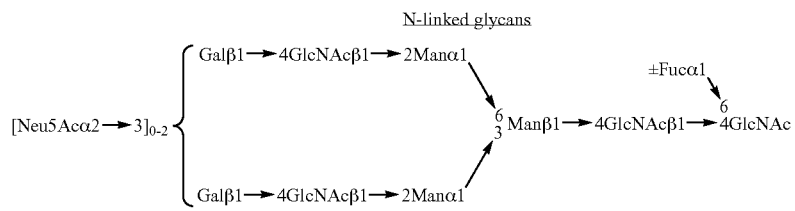

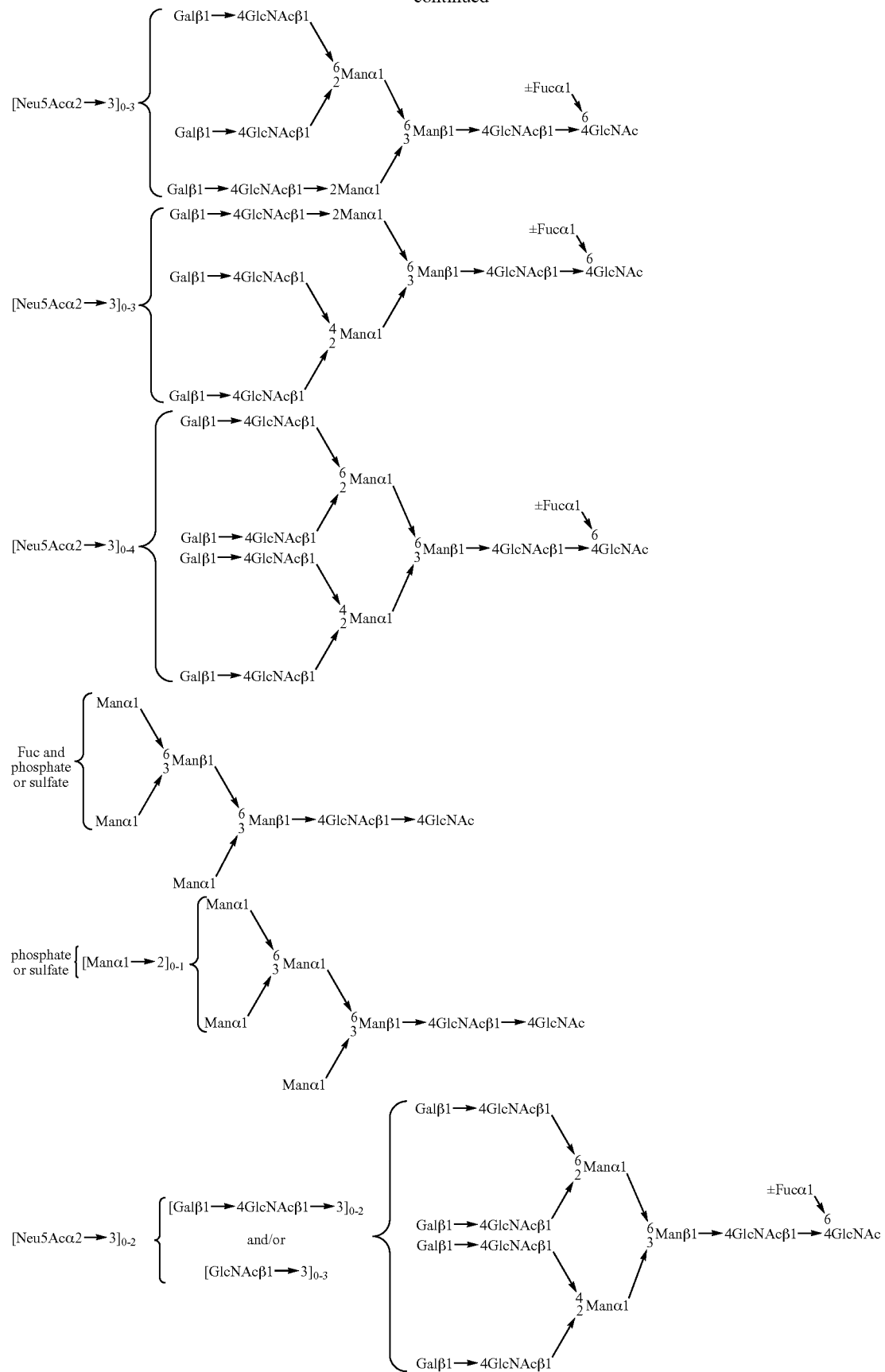

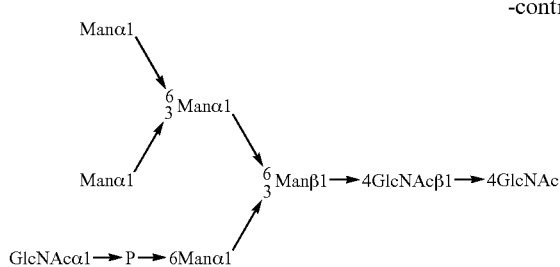

or a protected form thereof.

In certain other embodiments, $P^1$ is hydrogen, Boc, Fmoc, or Ac. In certain embodiments, $P^1$ is a moiety having the structure:

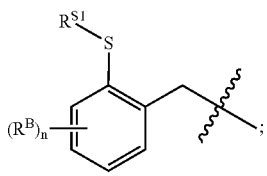

and n is 2. In certain embodiments, $P^1$ is a moiety having the structure:

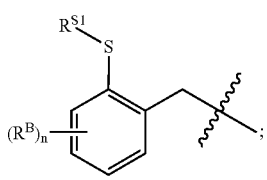

and n is 3. In certain embodiments, all $R^B$ are $C_1$-$C_6$alkoxy. In certain embodiments, $P^1$ is of formula:

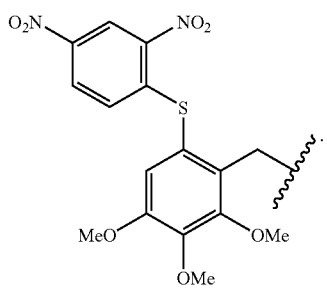

In certain embodiments, $P^1$ is of formula:

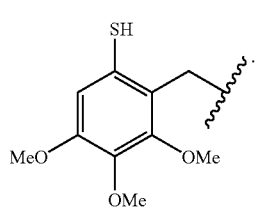

In certain other embodiments, $R^{X2}$ is $NH_2$.

In certain other embodiments, $R^{X0}$ is a sulfur-substituted aryl moiety. In certain embodiments, $R^{X0}$ is a disulfide-substituted aryl moiety. In certain embodiments, $R^{X0}$ has the structure:

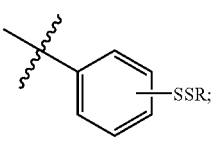

wherein R is an aliphatic, heteroaliphatic, aromatic or heteroaromatic moiety. In certain exemplary embodiments, $R^{X0}$ has the structure:

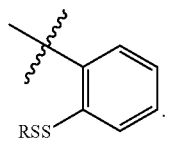

In certain embodiments, R is lower alkyl. In certain exemplary embodiments, R is methyl. In certain exemplary embodiments, R is ethyl. In certain embodiments, $R^{X0}$ has the structure:

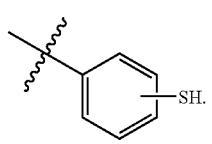

In certain embodiments, $R^{X0}$ has the structure:

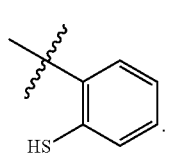 [SMILES: *c1ccccc1S ; "."]

In certain other embodiments, $R^{S1}$ is —S-PMB.

In certain other embodiments, $R^{S1}$ is an aromatic disulfide radical. In certain other embodiments, $R^{S1}$ is an aromatic disulfide radical having the structure:

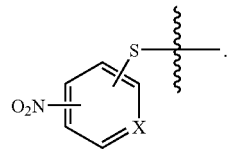

wherein X is N or CH.

In certain other embodiments, $R^{S1}$ is an aromatic disulfide radical having the structure:

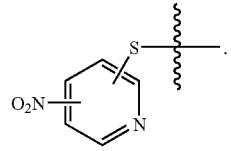

In certain other embodiments, $R^{S1}$ is an aromatic disulfide radical having the structure:

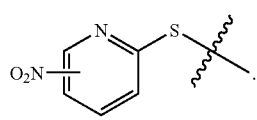

In certain other embodiments, $R^{S1}$ is an aromatic disulfide radical having the structure:

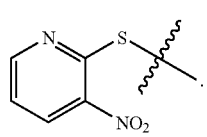 [SMILES: *Sc1ncccc1[N+](=O)[O-] ; "."]

In another aspect of the present invention, there is provided a method for effecting ligation of two (poly)functionalized peptides, each peptide comprising a peptidic backbone made up of two or more amino acids wherein one or more amino acids are independently substituted with a moiety having the structure:

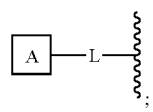

wherein the method comprises a step of:

coupling a peptide acyl donor comprising a peptidic backbone made up of two or more amino acids wherein said peptide acyl donor has the structure:

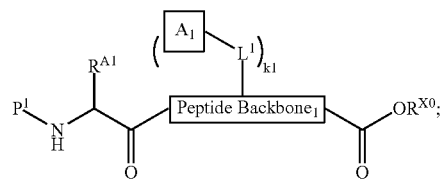

with a peptide acyl acceptor comprising a peptidic backbone made up of two or more amino acids wherein said peptide acyl acceptor has the structure:

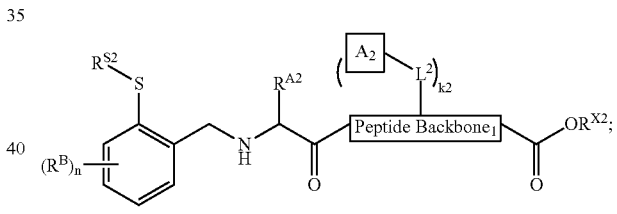

under suitable conditions to effect ligation and form the following adduct:

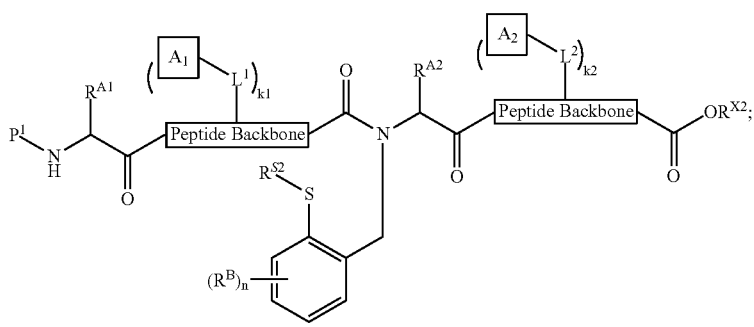

wherein n is 2 or 3;

$R^{A1}$ and $R^{A2}$ are independently natural or non-natural amino acid side chains;

each occurrence of $R^B$ is independently alkoxy, hydroxy or silyloxy;

k1 and k2 are independently integers between 1 and about 20;

each occurrence of $A_1$ and $A_2$ is independently an aliphatic, heteroaliphatic, aromatic, heteroaromatic, aryl, heteroaryl or a pharmaceutically useful group or entity;

$R^{S1}$ is hydrogen or a sulfide protecting group;

$R^{X0}$ is a group such that the moiety —C(=O)OR$^{X0}$ can be made to undergo ligation with the peptide acyl acceptor, each occurrence of $L^1$ is independently a substituted or unsubstituted, linear or branched, cyclic or acyclic, saturated or unsaturated aliphatic or heteroaliphatic moiety or a natural or non-natural amino acid side chain; and $R^{X2}$ is —OR$^{X2a}$ or —NR$^{X2b}$R$^{X2c}$, wherein $R^{X2a}$ is hydrogen, alkyl, aromatic, heteroaromatic, aryl, heteroaryl, -alkyl(aryl), -alkyl(heteroaryl), a carboxylic acid protecting group, an amino acid or a protected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid or a protected amino acid. In certain embodiments, n is 2. In other embodiments, n is 3. In certain embodiments, all $R_B$ are alkoxy. In certain embodiments, all $R_B$ are methoxy. In certain embodiments, $R^{S2}$ is hydrogen.

The auxiliary may optionally be removed by methylating the adduct of formula:

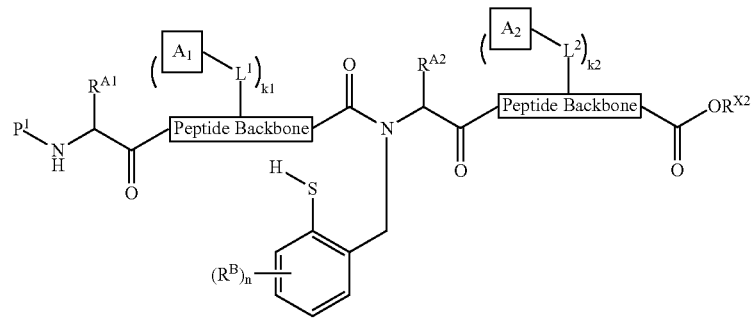

under suitable conditions to form a methylated adduct of formula:

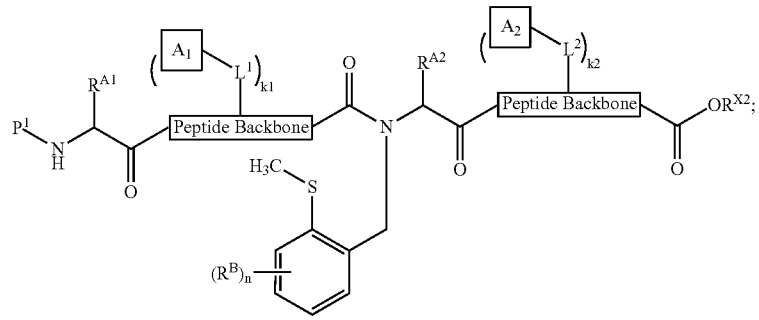

removing the auxillary under suitable conditions to form the product with a native amide linkage of formula:

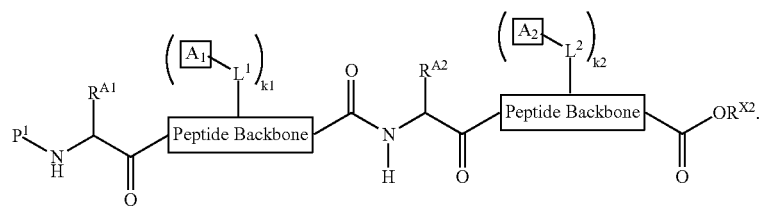

In another aspect of the present invention, there is provided a method for preparing a polyfunctionalized peptide/protein comprising a peptidic backbone made up of four or more amino acids wherein at least two amino acids are independently substituted with a moiety having the structure:

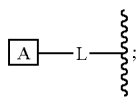

wherein the method comprises steps of:

(a) coupling a peptide acyl donor comprising a peptidic backbone made up of two or more amino acids wherein said peptide acyl donor has the structure:

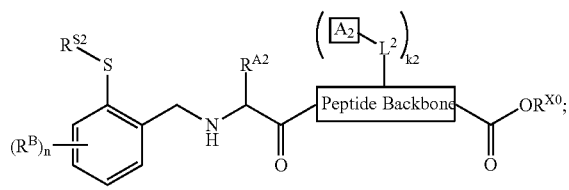

with a starting peptide acyl acceptor comprising a peptidic backbone made up of two or more amino acids wherein said peptide acyl acceptor has the structure:

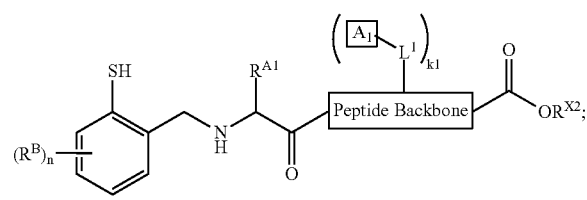

under suitable conditions to effect ligation and form a resulting peptide acyl acceptor having the structure:

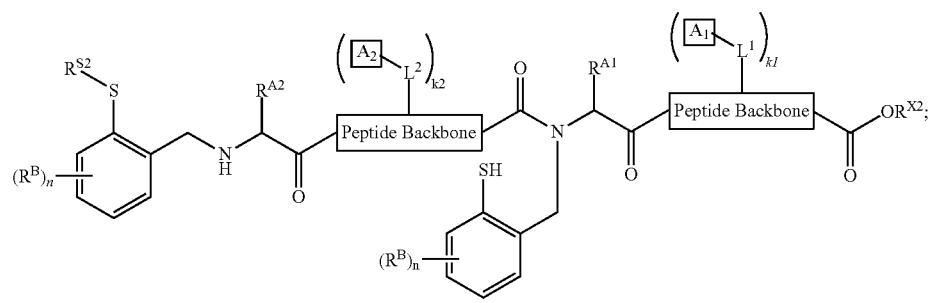

(b) repeating step (a) using the resulting peptide acyl acceptor of step (a) as starting peptide acyl acceptor to give a polyfunctionalized peptide/protein having the structure:

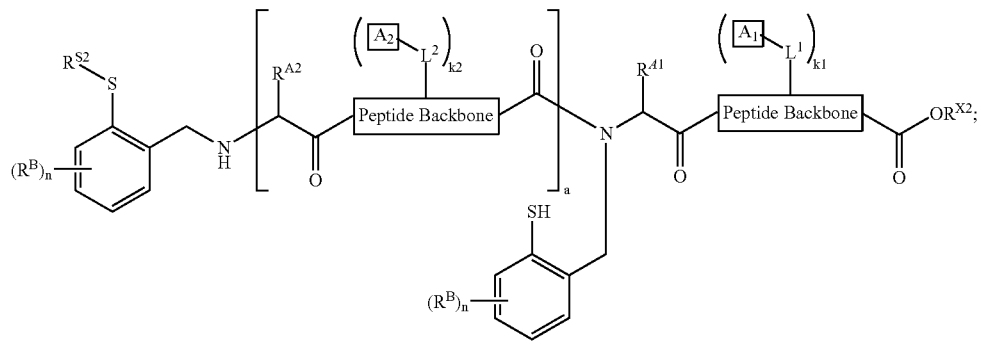

(c) deprotecting the polyfunctionalized peptide/protein of step (b) to give a polyfunctionalized peptide/protein having the structure:

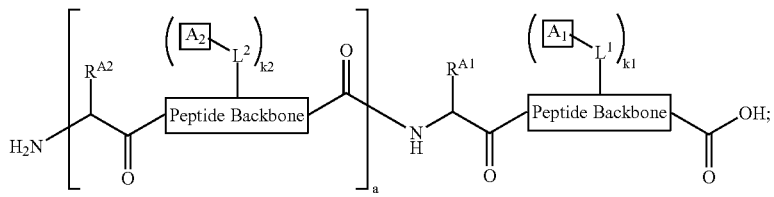

or salt forms thereof;

wherein a is an integer between 1 and about 20;

each occurrence of n is independently 2 or 3;

each occurrence of $R^{A1}$ and $R^{A2}$ is independently a natural or non-natural amino acid side chain;

each occurrence of $R^B$ is independently alkoxy, hydroxy, or silyloxy;

each occurrence of k1 and k2 is independently an integer between 1 and about 20;

each occurrence of $A_1$ and $A_2$ is independently an aliphatic, heteroaliphatic, aromatic, heteroaromatic, aryl, heteroaryl, carbohydrate, or a pharmaceutically useful group or entity;

$R^{S1}$ is hydrogen or a sulfide protecting group;

$R^{X0}$ is a group such that the moiety —C(=O)O$R^{X0}$ can be made to undergo ligation with the peptide acyl acceptor, each occurrence of $L^1$ and $L^2$ is independently a substituted or unsubstituted, linear or branched, cyclic or acyclic, saturated or unsaturated aliphatic or heteroaliphatic moiety or a natural or non-natural amino acid side chain; and $R^{X2}$ is —O$R^{X2a}$ or —N$R^{X2b}R^{X2c}$, wherein $R^{X2a}$ is hydrogen, alkyl, aromatic, heteroaromatic, aryl, heteroaryl, -alkyl(aryl), -alkyl(heteroaryl), a carboxylic acid protecting group, an amino acid or a protected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid, or a protected amino acid. In certain embodiments, n is 2. In other embodiments, n is 3. In certain embodiments, all $R_B$ are alkoxy. In certain embodiments, all $R_B$ are methoxy. In certain embodiments, the substituted amino acids are not adjacent.

In certain embodiments, the peptide acyl acceptor having the structure:

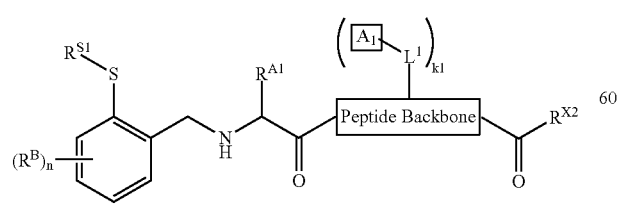

is prepared by a method comprising steps of:
(a) coupling a peptide acyl acceptor having the structure:

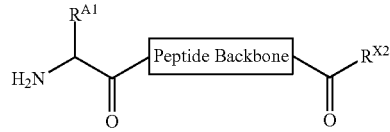

with an aldehyde having the structure:

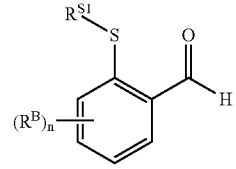

under suitable reductive amination conditions to form an adduct having the structure:

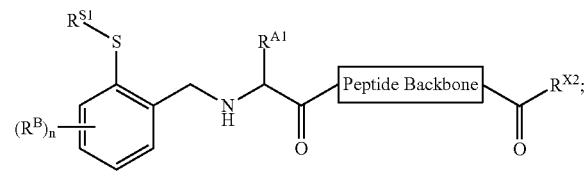

(b) functionalizing the adduct of step (a) to form the peptide acyl acceptor having the structure:

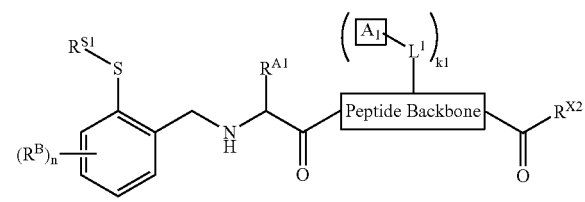

wherein n is independently 2 or 3;
$R^{A1}$ is a natural or non-natural amino acid side chain;
each occurrence of $R^B$ is independently alkoxy, hydroxy or silyloxy;
k1 is an integer between 1 and about 20;
each occurrence of $A_1$ is independently an aliphatic, heteroaliphatic, aromatic, heteroaromatic, aryl, heteroaryl, carbohydrate, or a pharmaceutically useful group or entity;

$R^{S1}$ is hydrogen or a sulfide protecting group;

each occurrence of $L^1$ is independently a substituted or unsubstituted, linear or branched, cyclic or acyclic, saturated or unsaturated aliphatic or heteroaliphatic moiety or a natural or non-natural amino acid side chain; and $R^{X2}$ is —$OR^{X2a}$ or —$NR^{X2b}R^{X2c}$, wherein $R^{X2a}$ is hydrogen, alkyl, aromatic, heteroaromatic, aryl, heteroaryl, -alkyl(aryl), -alkyl(heteroaryl), a carboxylic acid protecting group, an amino acid or a protected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid or a protected amino acid.

In certain embodiments, the invention also provides intermediates useful in the inventive ligation methods. In certain embodiments, the intermediate is of the formula:

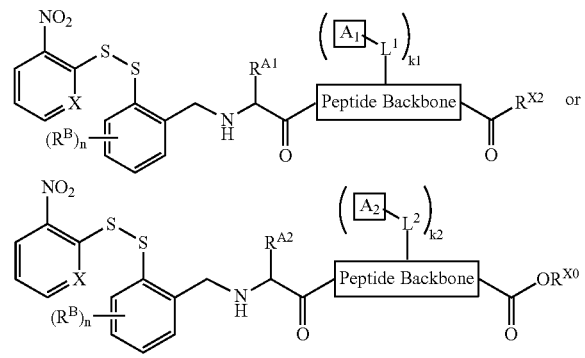

wherein
the peptide backbone comprises two or more amino acids;
X is N or CH;
n is 2 or 3;
$R^{A1}$ and $R^{A2}$ are independently natural or non-natural amino acid side chains;
each occurrence of $R^B$ is independently alkoxy, hydroxy or silyloxy;
k1 and k2 are independently integers between 1 and about 20;
each occurrence of $A_1$ and $A_2$ is independently an aliphatic, heteroaliphatic, aromatic, heteroaromatic, aryl, heteroaryl, carbohydrate, or a pharmaceutically useful group or entity;
$R^{X0}$ is a group such that the moiety —C(=O)$OR^{X0}$ can be made to undergo ligation with a peptide acyl acceptor,
each occurrence of $L^1$ is independently a substituted or unsubstituted, linear or branched, cyclic or acyclic, saturated or unsaturated, aliphatic or heteroaliphatic moiety or a natural or non-natural amino acid side chain; and
$R^{X2}$ is —$OR^{X2a}$, —$SR^{X2a}$, or —$NR^{X2b}R^{X2c}$, wherein $R^{X2a}$ is hydrogen, alkyl, aromatic, heteroaromatic, aryl, heteroaryl, -alkyl(aryl), -alkyl(heteroaryl), a carboxylic acid protecting group, an amino acid or a protected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid, or a protected amino acid.

In certain other embodiments, $R^{X2a}$ is —$OR^{X2a}$, wherein $R^{X2a}$ is a sulfur-substituted aryl moiety. In certain embodiments, $R^{X2a}$ is —$OR^{X2a}$, wherein $R^{X2a}$ is a disulfide-substituted aryl moiety. In certain embodiments, $R^{X2a}$ has the structure:

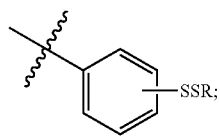

wherein R is an aliphatic, heteroaliphatic, aromatic or heteroaromatic moiety. In certain exemplary embodiments, $R^{X2a}$ has the structure:

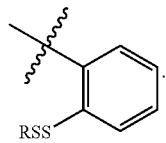

In certain embodiments, R is lower alkyl. In certain exemplary embodiments, R is methyl. In certain exemplary embodiments, R is ethyl. In certain embodiments, $R^{X2a}$ has the structure:

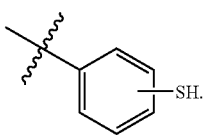

In certain embodiments, $R^{X2a}$ has the structure:

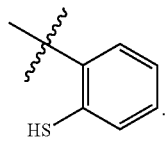

In certain embodiments, $R^{X2}$ is —OH. In certain embodiments, $R^{X2}$ is —$SR^{S2a}$. Examplary intermediates include:

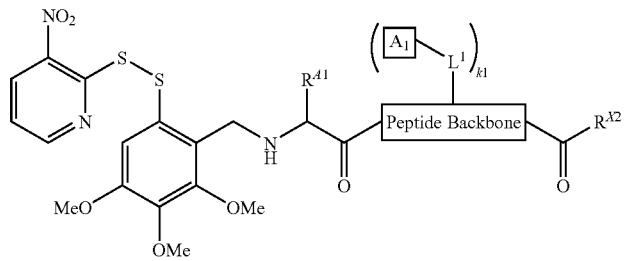

-continued
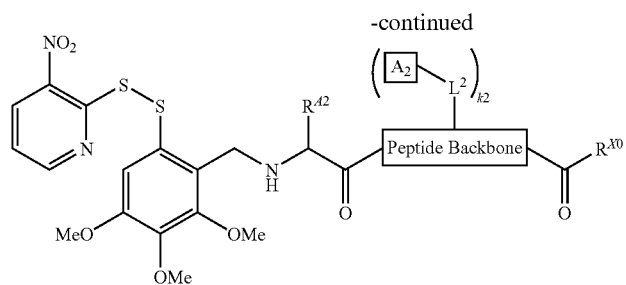
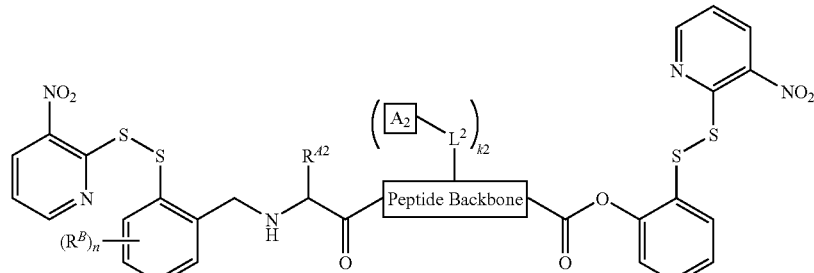
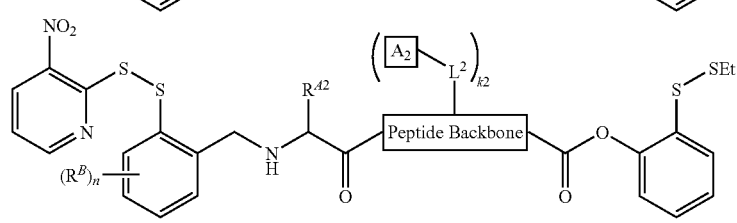
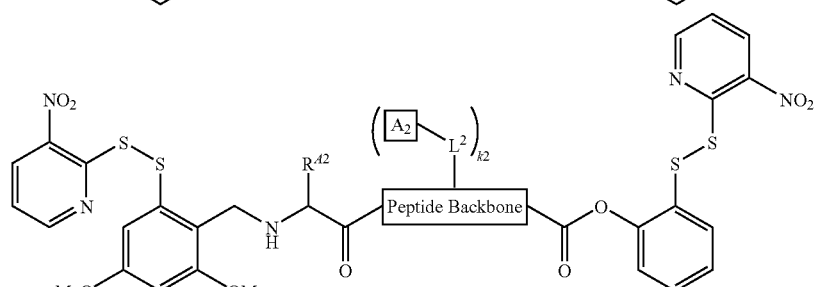
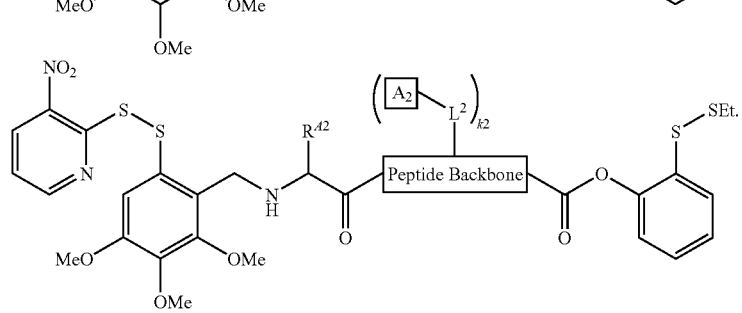
In certain embodiments, the intermediate is of formula:
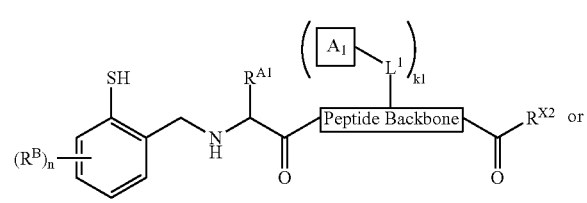
-continued
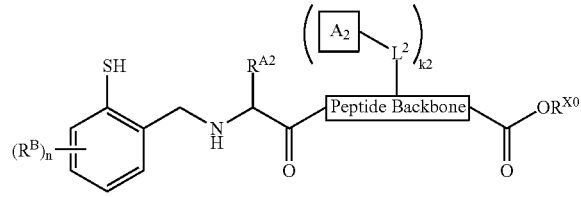
wherein
peptide backbone comprises two or more amino acids;
X is N or CH;

n is 2 or 3;

$R^{A1}$ and $R^{A2}$ are independently natural or non-natural amino acid side chains;

each occurrence of $R^B$ is independently alkoxy, hydroxy, or silyloxy;

k1 and k2 are independently integers between 1 and about 20;

each occurrence of $A_1$ and $A_2$ is independently an aliphatic, heteroaliphatic, aromatic, heteroaromatic, aryl, heteroaryl, carbohydrate, or a pharmaceutically useful group or entity;

$R^{X0}$ is a group such that the moiety —C(=O)O$R^{X0}$ can be made to undergo ligation with a peptide acyl acceptor;

each occurrence of $L^1$ is independently a substituted or unsubstituted, linear or branched, cyclic or acyclic, saturated or unsaturated aliphatic or heteroaliphatic moiety, or a natural or non-natural amino acid side chain; and $R^{X2}$ is —O$R^{X2a}$ or —N$R^{X2b}R^{X2c}$, wherein $R^{X2a}$ is hydrogen, alkyl, aromatic, heteroaromatic, aryl, heteroaryl, -alkyl(aryl), -alkyl(heteroaryl), a carboxylic acid protecting group, an amino acid or a protected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid or a protected amino acid. In certain embodiments, the intermediate is of formula:

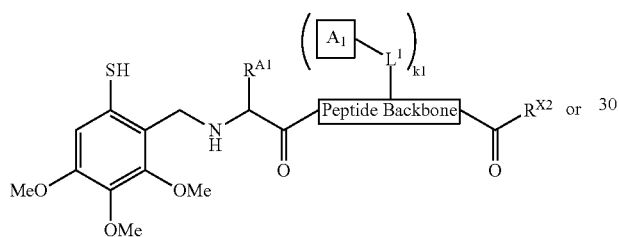

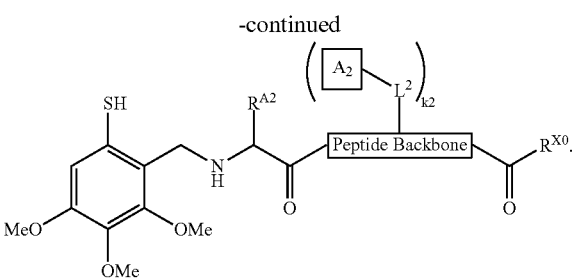

In certain embodiments, A, $A^1$, or $A^2$ is selected from the group consisting of Globo-H, fucosyl GM1, GM2, KH-1, glycophorin, STN, (2,3)ST, Le$^y$, Le$^x$, N3, Tn, 2,6-STn, Gb3 and TF, or protected form thereof. In certain embodiments, A, $A^1$, or $A^2$ is O-linked to $L^1$, and A, $A^1$, or $A^2$ has one of the following structures:

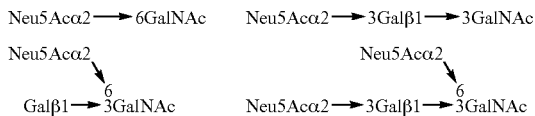

or a protected form thereof.

In certain embodiments, A, $A^1$, or 2 is N-linked to $L^1$, and A, $A^1$, or $A^2$ has one of the following structures:

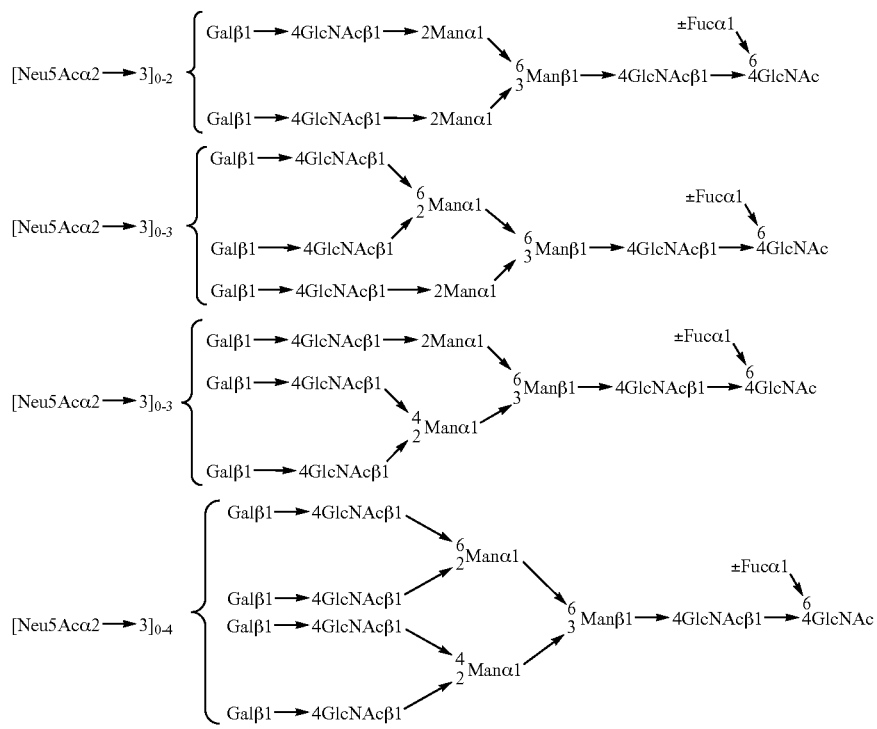

or a protected form thereof.

In certain, the peptide or glycopeptide is of formula:

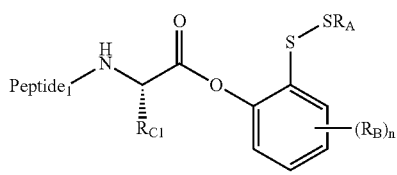

wherein

Peptide1 is a peptide comprising two or more natural or unnatural amino acids, wherein the peptide is protected, partially protected, or unprotected, and the peptide is optionally glycosylated;

n is 0, 1, 2, 3, or 4;

$R_A$ is hydrogen; a substituted or unsubstituted, linear or branched, cyclic or acyclic saturated or unsaturated aliphatic; a substituted or unsubstituted, linear or branched, cyclic or acyclic saturated or unsaturated heteroaliphatic; substituted or unsubstituted aryl; or substituted or unsubstituted heteroaryl;

each occurrence of $R_B$ is independently hydrogen; halogen; alkoxy; —CN; —NO$_2$; substituted or unsubstituted acyl; a substituted or unsubstituted, linear or branched, cyclic or acyclic saturated or unsaturated aliphatic, or a substituted or unsubstituted, linear or branched, cyclic or acyclic saturated or unsaturated heteroaliphatic; and $R_{C1}$ is a side chain of a natural or unnatural amino acid. In certain embodiments, the peptide has at least one post-translational modification. In certain embodiments, the peptide is glycosylated. In certain embodiments, $R_{C1}$, is a side chain of a natural amino acid. In certain embodiments, the peptide has an unprotected N-terminus. In other embodiments, the peptide has a protected N-terminus. In certain embodiments, the peptide has an Fmoc-protected N-terminus.

In certain embodiments, the present invention provides a method for preparing a cyclic peptide having the structure:

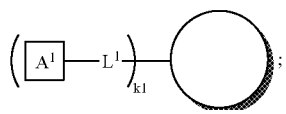

said method comprising a step of subjecting a peptide having the structure:

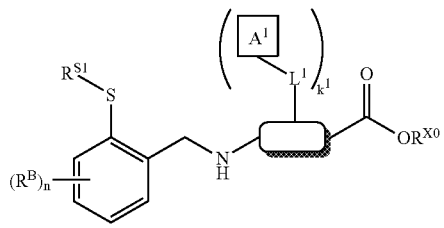

to suitable conditions to effect cyclization;

wherein the peptide comprises at least four amino acid residues;

n is 2 or 3;

each occurrence of $R^B$ is independently alkoxy, hydroxy, or silyloxy;

k1 is an integer between 0 and about 20;

each occurrence of $A^1$ is independently an aliphatic, heteroaliphatic, aromatic, heteroaromatic, aryl, heteroaryl, carbohydrate, or a pharmaceutically useful group or entity;

$R^{S1}$ is hydrogen or a sulfide protecting group;

$R^{X0}$ is a group such that the moiety $-C(=O)OR^{X0}$ can be made to undergo ligation with the N-terminal peptide acyl acceptor; and each occurrence of $L^1$ is independently a substituted or unsubstituted, linear or branched, cyclic or acyclic, saturated or unsaturated aliphatic or heteroaliphatic moiety or a natural or non-natural amino acid side chain.

In certain exemplary embodiments, the stereochemistry of the carbon atom bearing $R^{A1}$ is unchanged.

In certain exemplary embodiments, n is 2. In certain other exemplary embodiments, n is 3.

In certain exemplary embodiments, each occurrence of $R^B$ is independently $C_{1-6}$alkoxy, hydroxy or silyloxy. In certain other exemplary embodiments, each occurrence of $R^B$ is methoxy.

In certain exemplary embodiments, n is 2 and each occurrence of $R^B$ is methoxy. In certain other exemplary embodiments, n is 3 and each occurrence of $R^B$ is methoxy.

In certain embodiments, each occurrence of A is independently a pharmaceutically useful group or entity. In certain embodiments, each occurrence of A is independently a biomolecule, a small molecule, a macromolecule or a diagnostic label.

In certain exemplary embodiments, each occurrence of A is independently a carbohydrate determinant having the structure:

CHO, $COOR^{ii}$, or a substituted or unsubstituted linear or branched chain alkyl, acyl, arylalkyl or aryl group or a saccharide moiety having the structure:

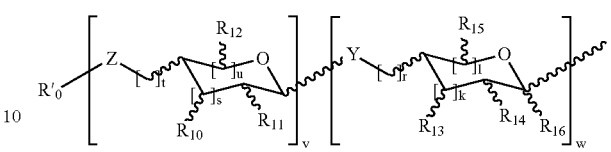

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group.

In certain embodiments, A is selected from the group consisting of Globo-H, fucosyl GM1, GM2, KH-1, glycophorin, STN, (2,3)ST, $Le^y$, $Le^x$, N3, Tn, 2,6-STn, Gb3 and TF, or

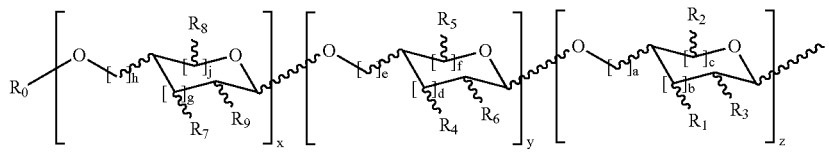

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, protected form thereof. In certain embodiments, A is O-linked to $L^1$, and A has one of the following structures:

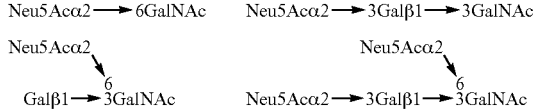

or a protected form thereof.

In certain embodiments, A is N-linked to $L^1$, and A has one of the following structures:

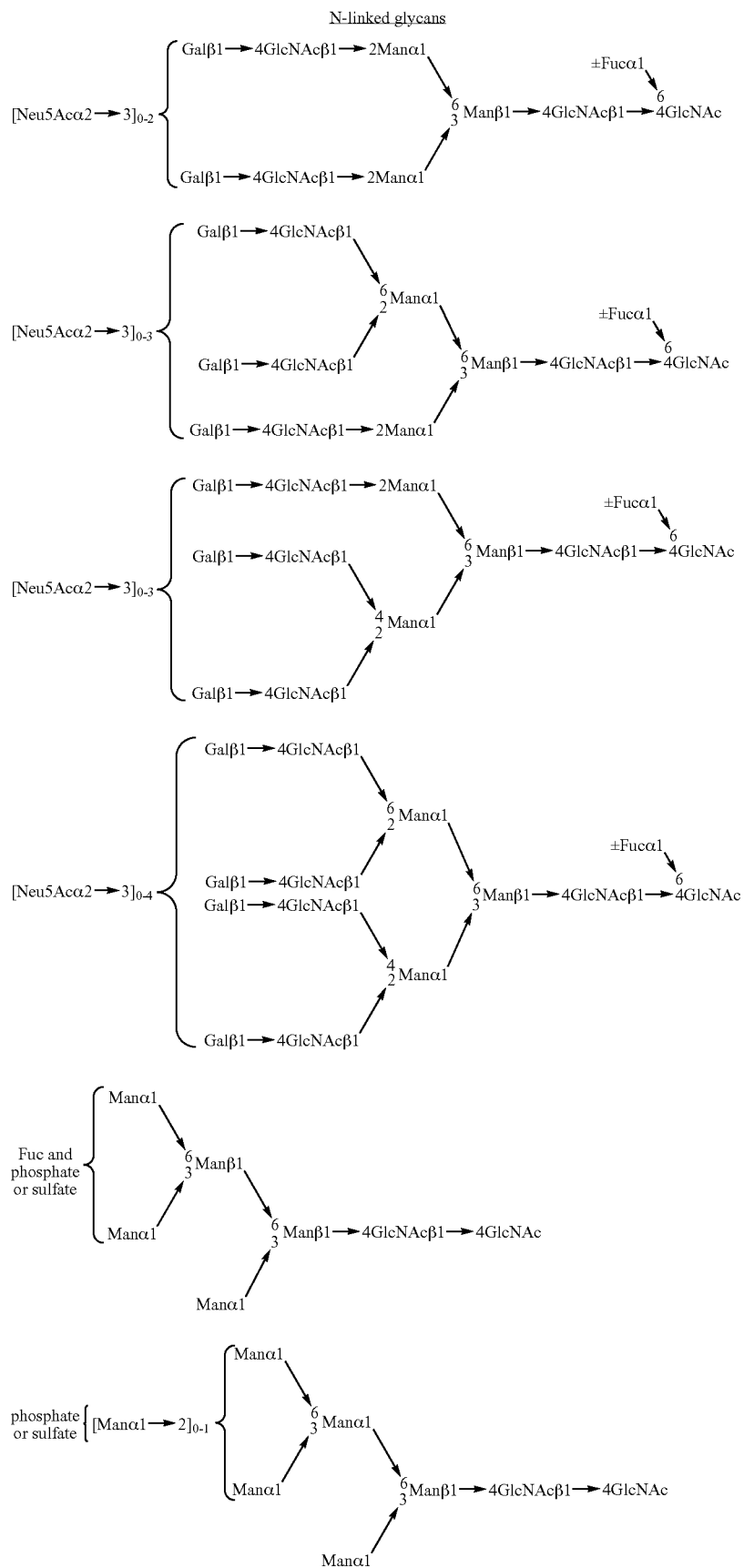

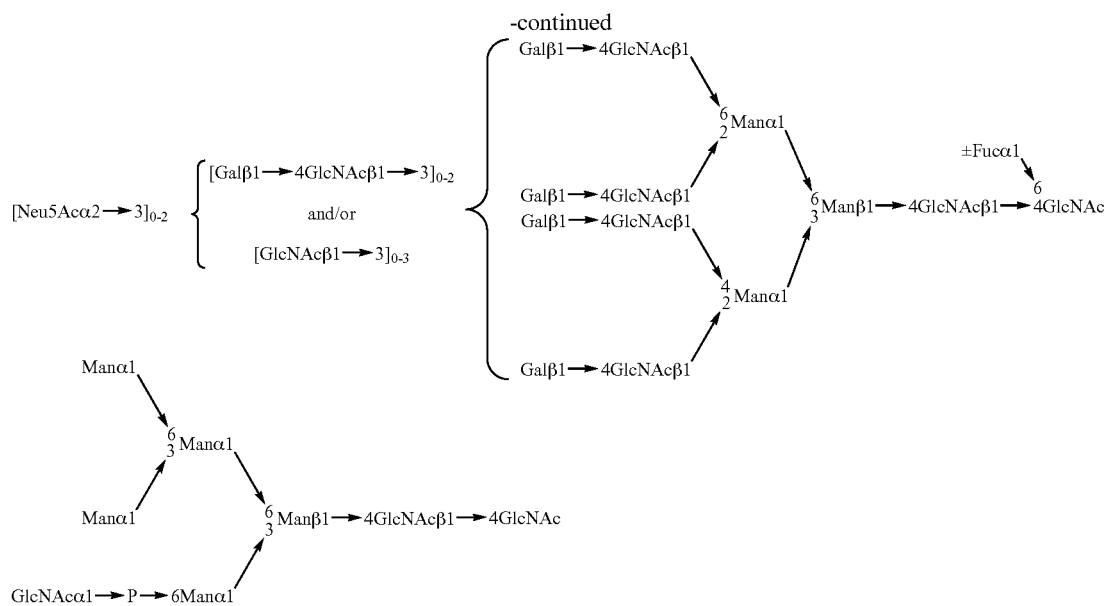

or a protected form thereof.

In certain embodiments, the present invention provides a method for preparing a polyfunctionalized peptide having the structure:

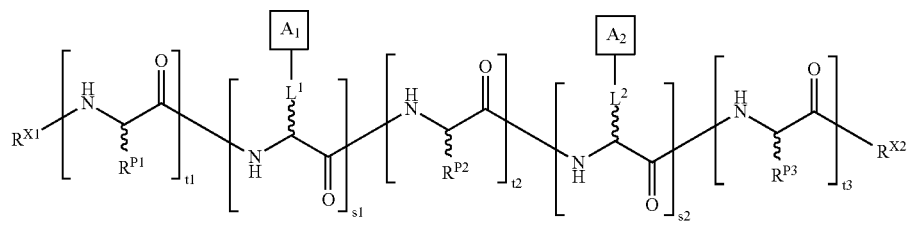

s1 and s2 are independently an integer from 1 to about 20; t1, t2, and t3 are each independently an integer;

$R^{X1}$ is hydrogen, alkyl, acyl, aromatic, heteroaromatic, aryl, heteroaryl, -alkyl(aryl), -alkyl(heteroaryl), a nitrogen protecting group, an amino acid or a protected amino acid;

$R^{X2}$ is —$OR^{X2a}$ or —$NR^{X2b}R^{X2c}$, wherein $R^{X2a}$ is hydrogen, alkyl, aromatic, heteroaromatic, aryl, heteroaryl, -alkyl(aryl), -alkyl(heteroaryl), a carboxylic acid protecting group, an amino acid or a protected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid, or a protected amino acid;

$R^{P1}$, $R^{P2}$, and $R^{P3}$ are independently H, alkyl, heteroalkyl, aromatic, heteroaromatic, aryl, heteroaryl, -alkyl(aryl), -alkyl(heteroaryl), or a natural or non-natural amino acid side chain; each occurrence of $L^1$ and $L^2$ is independently a substituted or unsubstituted aliphatic or heteroaliphatic moiety or a natural or non-natural amino acid side chain;

$A_1$ and $A_2$ are each independently an aliphatic, heteroaliphatic, aromatic, heteroaromatic, aryl, heteroaryl, carbohydrate, or a pharmaceutically useful group or entity; and wherein the method comprises a step of:

reacting a peptide acyl donor having the structure:

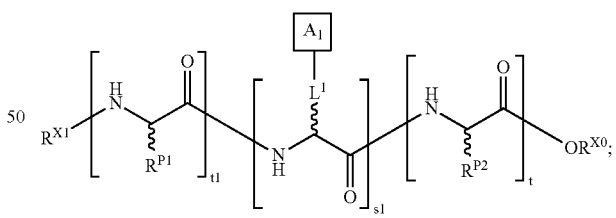

with a peptide acyl acceptor having the structure:

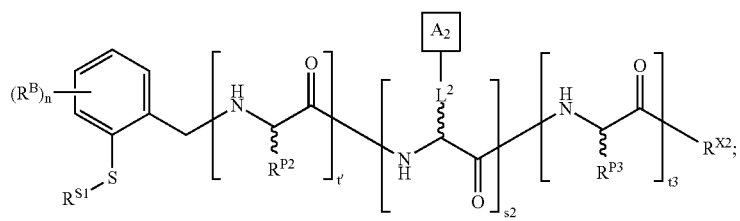

under suitable conditions to effect ligation;
wherein n is 2 or 3;
each occurrence of $R^B$ is independently alkoxy, hydroxy, or silyloxy;
the sum t+t' equals t2; $R^{S1}$ is hydrogen or a sulfide protecting group; and $R^{X0}$ is a group such that the moiety —C(=O) $OR^{X0}$ can be made to undergo ligation with the glycopeptide acyl acceptor.

In certain exemplary, $A_1$ and $A_2$ are each independently a carbohydrate domain having the structure:

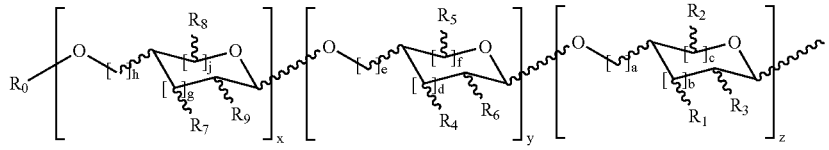

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, $COOR^{ii}$, or a substituted or unsubstituted linear or branched chain alkyl, acyl, arylalkyl or aryl group or a saccharide moiety having the structure:

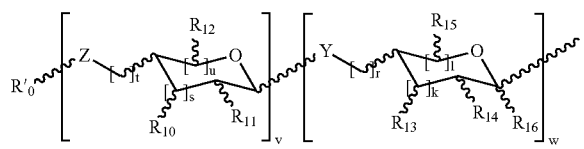

wherein Y and Z are independently NH or O; wherein k, l, r, s, t, u, v, and w are each independently 0, 1, or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$, and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group; and wherein each glycosidic moiety is either α- or β-linked to an amino acid.

In certain embodiments, the step may be carried out once, or repeated a desired number of times, to prepare a polyfunctionalized peptide having the structure:

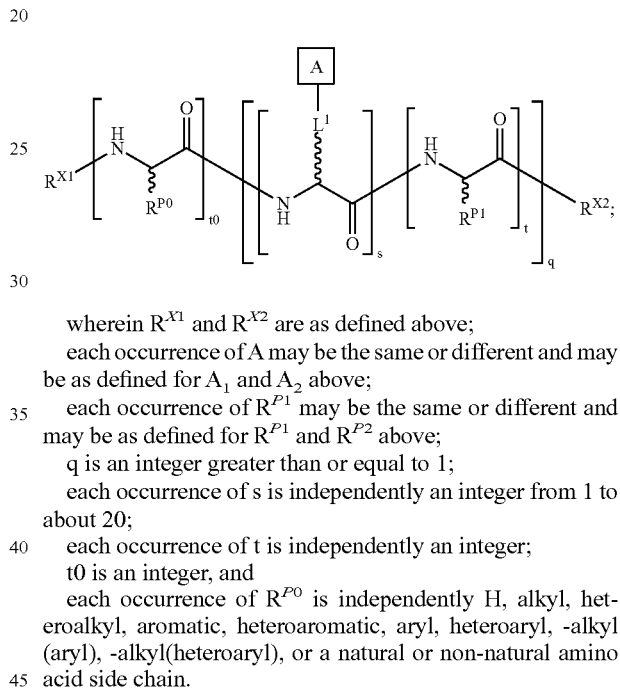

wherein $R^{X1}$ and $R^{X2}$ are as defined above;
each occurrence of A may be the same or different and may be as defined for $A_1$ and $A_2$ above;
each occurrence of $R^{P1}$ may be the same or different and may be as defined for $R^{P1}$ and $R^{P2}$ above;
q is an integer greater than or equal to 1;
each occurrence of s is independently an integer from 1 to about 20;
each occurrence of t is independently an integer;
t0 is an integer, and
each occurrence of $R^{P0}$ is independently H, alkyl, heteroalkyl, aromatic, heteroaromatic, aryl, heteroaryl, -alkyl(aryl), -alkyl(heteroaryl), or a natural or non-natural amino acid side chain.

In certain embodiments, q is an integer between 2 and about 5. In certain embodiments, q is an integer between 2 and about 10. In certain embodiments, q is an integer between 2 and about 15. In certain embodiments, q is an integer between 2 and about 20. In certain embodiments, q is an integer between 2 and about 25. In certain embodiments, q is an integer between 2 and about 30. In certain embodiments, q is an integer greater than 30. In certain embodiments, q is 2.

In certain embodiments, the sum s+t is between about 2 and about 6. In certain embodiments, the sum s+t is between about 2 and about 10. In certain embodiments, the sum s+t is between about 2 and about 15. In certain embodiments, the sum s+t is between about 2 and about 20. In certain embodiments, the sum s+t is between about 2 and about 50. In certain embodiments, the sum s+t is between about 2 and about 100. In certain embodiments, the sum s+t is between about 2 and about 150. In certain embodiments, the sum s+t is between about 2 and about 200. In certain embodiments, the sum s+t may be greater than 200.

In certain embodiments, t0 is an integer from 0 to about 2. In certain embodiments, t0 is an integer from 0 to about 5. In certain embodiments, t0 is an integer from 0 to about 10. In certain embodiments, t0 is an integer from 0 to about 15. In certain embodiments, t0 is an integer from 0 to about 20. In certain embodiments, t0 is an integer from 0 to about 25. In certain embodiments, t0 is an integer from 0 to about 30. In certain embodiments, t0 is an integer from 0 to about 50. In certain embodiments, t0 is an integer from 0 to about 100. In certain embodiments, t0 is an integer from 0 to about 150. In certain embodiments, t0 is an integer from 0 to about 200. In certain embodiments, t0 is an integer greater than 200.

In certain other embodiments, $R^{X1}$ is hydrogen, Boc, Fmoc, or Ac.

In certain other embodiments, $R^{X2}$ is $NH_2$.

In certain other embodiments, $R^{X0}$ is a sulfur-substituted aryl moiety. In certain embodiments, $R^{X0}$ is a disulfide-substituted aryl moiety. In certain embodiments, $R^{X0}$ has the structure:

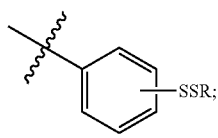

wherein R is an aliphatic, heteroaliphatic, aromatic or heteroaromatic moiety. In certain exemplary embodiments, $R^{X0}$ has the structure:

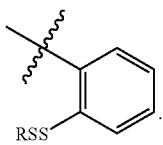

In certain embodiments, R is lower alkyl. In certain exemplary embodiments, R is ethyl. In certain exemplary embodiments, R is o-nitro-2-pyridyl. In certain embodiments, $R^{X0}$ has the structure:

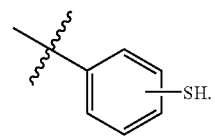

In certain exemplary embodiments, $R^{X0}$ has the structure:

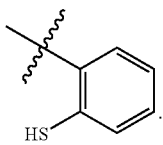 [SMILES: *c1ccccc1S ; "."]

In certain other embodiments, $R^{S1}$ is —S-PMB. In certain other embodiments, $R^{S2}$ is —S-PMB. In certain other embodiments, $R^{S1}$ and $R^{S2}$ are each —S-PMB.

In certain other embodiments, $R^{S1}$ and $R^{S2}$ are independently an aromatic disulfide radical. In certain other embodiments, $R^{S1}$ and $R^{S2}$ are independently an aromatic disulfide radical having the structure:

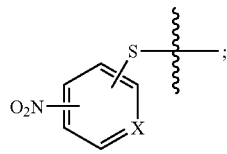

wherein X is N or CH.

In certain other embodiments, $R^{S1}$ and $R^{S2}$ are independently an aromatic disulfide radical having the structure:

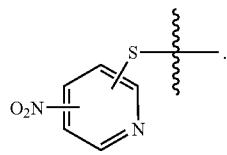

In certain other embodiments, $R^{S1}$ and $R^{S2}$ are independently an aromatic disulfide radical having the structure:

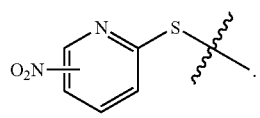

In certain other embodiments, $R^{S1}$ and $R^{S2}$ are independently an aromatic disulfide radical having the structure:

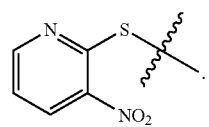

In certain exemplary embodiments, $R^{S1}$ is an aromatic disulfide radical and the peptide acyl acceptor has the structure:

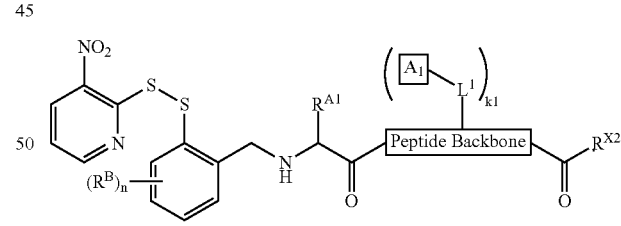

In certain exemplary embodiments, $R^{S2}$ is an aromatic disulfide radical and the peptide acyl donor has the structure:

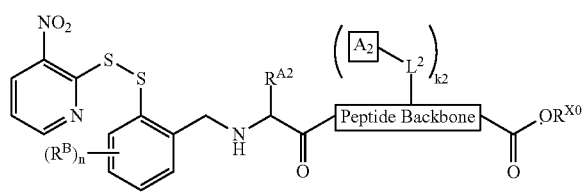

In certain exemplary embodiments, the peptide acyl donor having the structure:

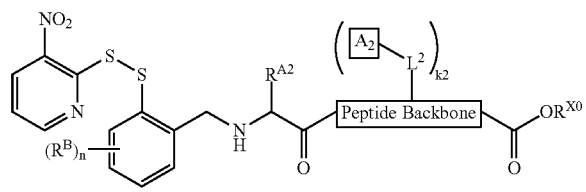

is prepared by reacting:

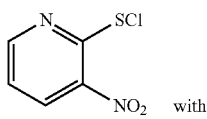

with

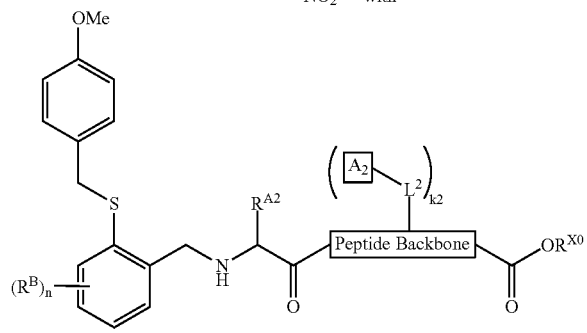

under suitable conditions.

In certain exemplary embodiments, the peptide acyl acceptor having the structure:

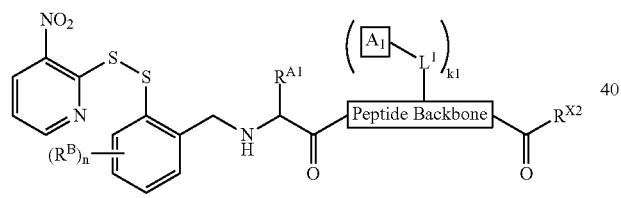

is prepared by reacting:

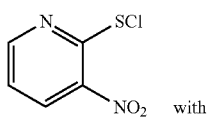

with

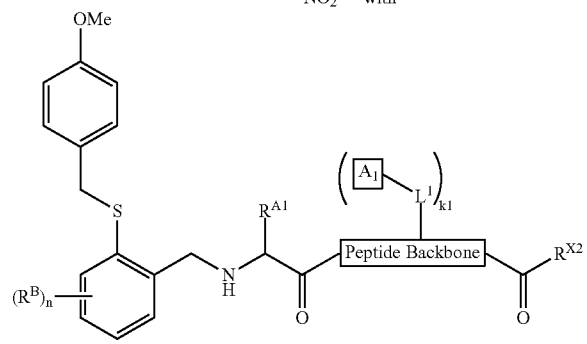

under suitable conditions.

In certain exemplary embodiments, the peptide acyl acceptor has the structure:

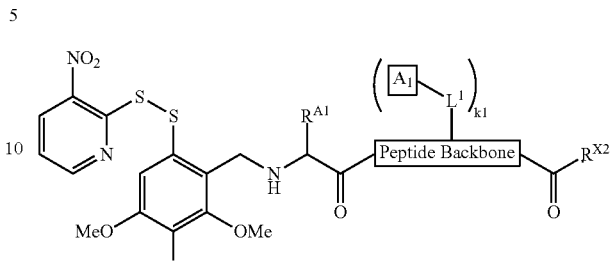

In certain exemplary embodiments, the peptide acyl acceptor has the structure:

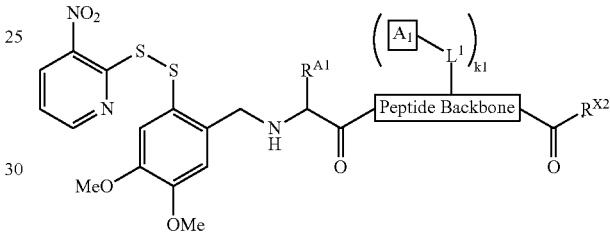

In certain exemplary embodiments, the peptide acyl donor has the structure:

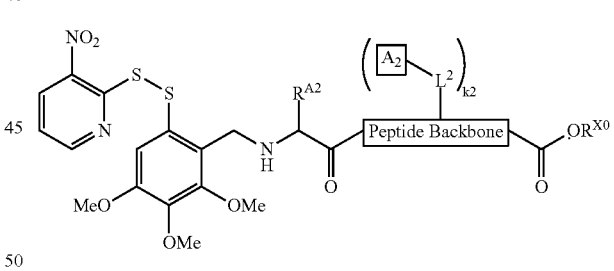

In certain exemplary embodiments, the peptide acyl donor has the structure:

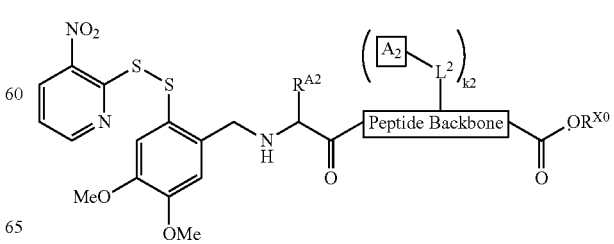

In certain exemplary embodiments, the peptide acyl donor has the structure:
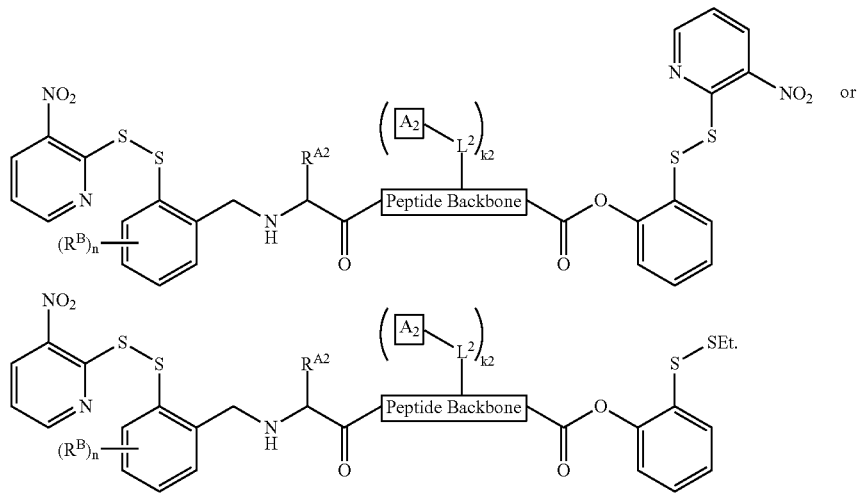
In certain exemplary embodiments, the peptide acyl donor has the structure:
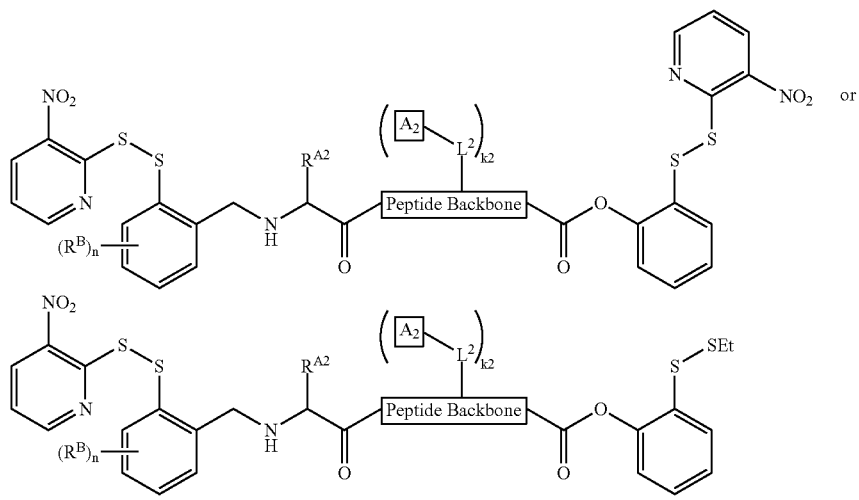
is prepared by reacting:
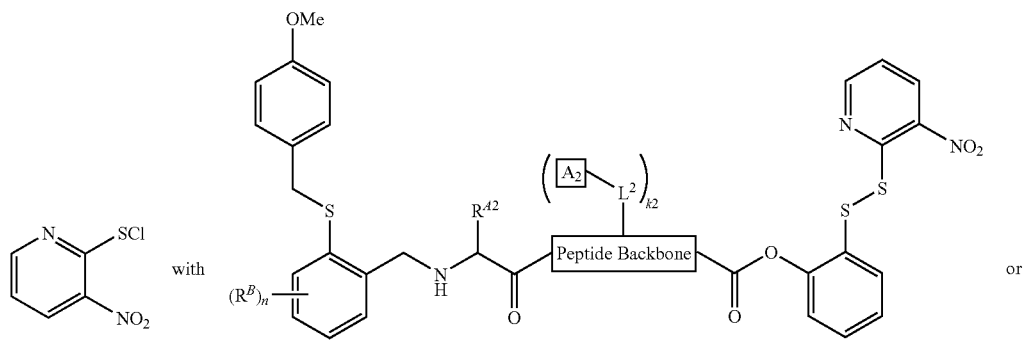

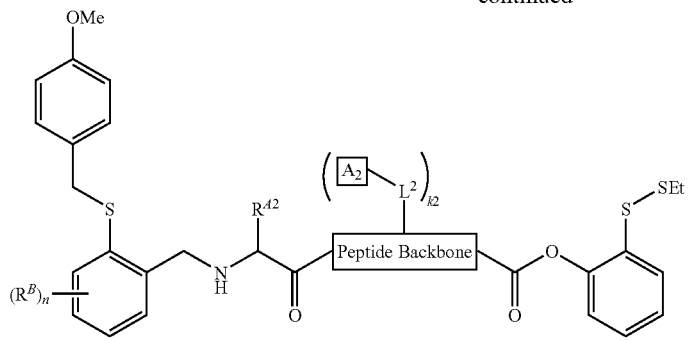

under suitable conditions.

In certain exemplary embodiments, the peptide acyl donor has the structure:

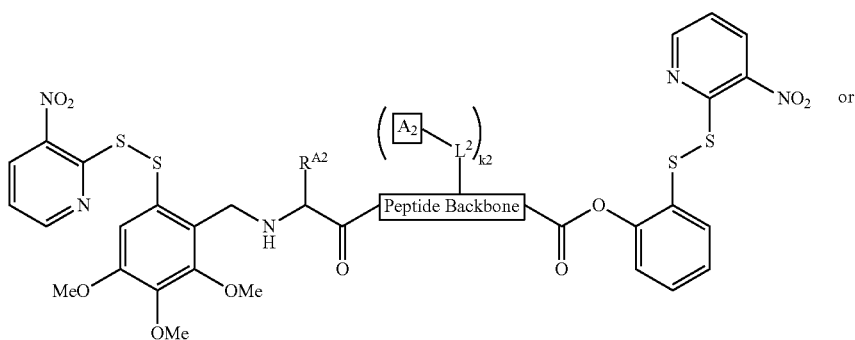

In certain exemplary embodiments, in the step of reacting the peptide acyl donor having the structure:

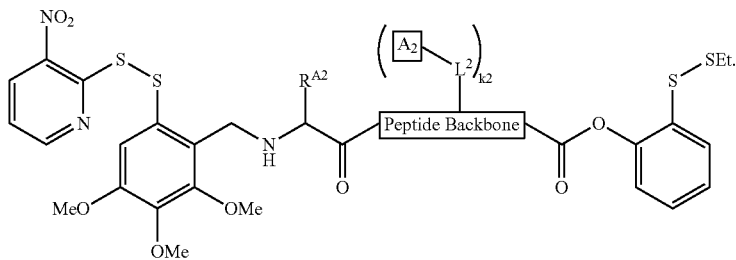

with the peptide acyl acceptor under suitable conditions to effect ligation, an intermediate having the following structure is formed in situ:

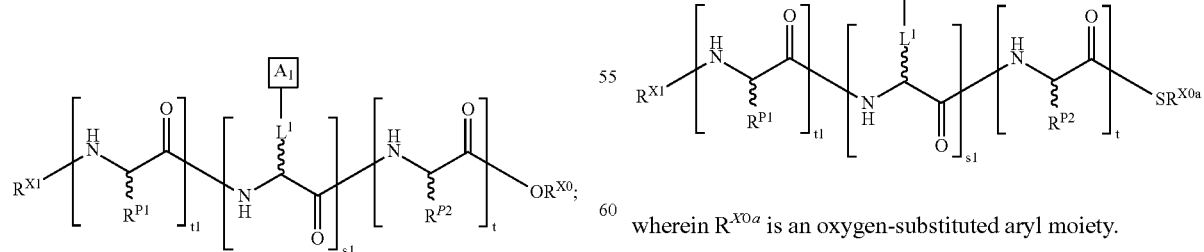

wherein $R^{X0a}$ is an oxygen-substituted aryl moiety.

In certain embodiments, the suitable conditions to effect ligation comprise disulfide reducing agents such as TCEP and MES-Na.

In certain exemplary embodiments, in the peptide acyl donor having the structure:

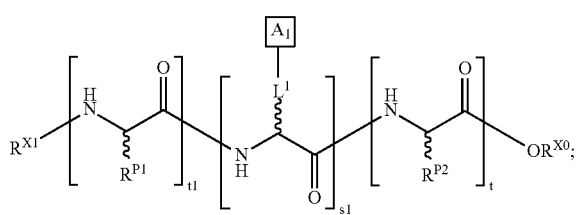

the amino acyl residue directly attached to —OR$^{X0}$ is glycine, phenylalanine, alanine or histidine.

In certain exemplary embodiments, in the peptide acyl acceptor having the structure:

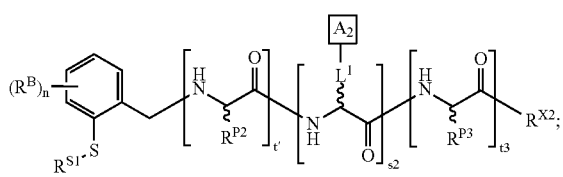

the amino acyl residue directly attached to the phenyl group is glycine, alanine, glutamine, or lysine.

In certain embodiments, L$^1$ may comprise any functional moiety that is compatible with native chemical ligation reaction conditions (either cysteine-free or cysteine-dependent native chemical ligation). In certain embodiments, L$^1$ may comprise any functional moiety that is compatible with aqueous conditions. In certain embodiments, a compatible functionality is one that is stable, unreactive and/or minimally interferes with the reaction. A thiol group is considered a compatible functionality, even though a thiol group may slow down the reaction. Examples of suitable functionalities include, but are not limited to, hydrocarbons, amines, amides, imines, hydroxyls, ethers, carboxylic esters, aldehydes, thiols, olefins, alkynes, aryls and heteroaryls. In certain exemplary embodiments, L$^1$ does not comprise a thiol group.

In certain other embodiments, each occurrence of L$^1$ is independently a natural amino acid side chain. In certain embodiments, each occurrence of L$^1$ is independently an unnatural amino acid side chain. In certain embodiments, each occurrence of L$^1$ is independently —O(CHR$^{aa}$)$_n$— or —NHC(=O)(CHR$^{aa}$)$_n$— wherein each occurrence of n is independently an integer from 1-10; and each occurrence of R$^{aa}$ is hydrogen, lower alkyl, aryl, heteroaryl, -alkyl(aryl) or -alkyl(heteroaryl). In certain exemplary embodiments, each occurrence of n is 1 and each occurrence of R$^{aa}$ is hydrogen or methyl. In certain embodiments, at least one occurrence of L$^1$ is a moiety having the structure —O(CH$_2$)$_n$— wherein n is an integer from 1-10 and each occurrence of A is O-linked to the construct backbone. In certain embodiments, at least one occurrence of L$^1$ is a moiety having the structure —NHC(=O)(CH$_2$)$_n$— wherein n is an integer from 1-10 and each occurrence of A is N-linked to the construct backbone. In certain embodiments, each occurrence of L$^1$ is independently a moiety having the structure —O(CH$_2$)$_n$— wherein n is an integer from 1-10 and each occurrence of A is O-linked to the construct backbone. In certain embodiments, each occurrence of L$^1$ is independently a moiety having the structure —NHC(=OX)(CH$_2$)$_n$— wherein n is an integer from 1-10 and each occurrence of A is N-linked to the construct backbone.

In certain embodiments, occurrences of A may be the same or different.

In certain other embodiments, certain occurrences of A are clustered. For example, in certain embodiments, the polyfunctionalized peptide or protein comprises at least two adjacent functionalized amino acids (i.e., clustered functionalized amino acids). In certain embodiments, the polyfunctionalized peptide or protein comprises at least two adjacent functionalized amino acids (i.e., clustered functionalized amino acids), separated from another functionalized site by a peptide amino acid sequence comprising at least one cysteine residue. In certain other embodiments, the polyfunctionalized peptide or protein comprises at least two adjacent functionalized amino acids (i.e., clustered functionalized amino acids), separated from another functionalized site by a peptide amino acid sequence that does not comprise a cysteine residue.

In certain other embodiments, certain occurrences of A are clustered glycosides. For example, in certain embodiments, the multiglycosylated peptide or protein comprises at least two adjacent glycosylated amino acids (i.e., clustered glycosylated amino acids). In certain embodiments, the polyglycosylated peptide or protein comprises at least two adjacent functionalized amino acids (i.e., clustered glycosylated amino acids), separated from another glycosylated site by a peptide amino acid sequence comprising at least one cysteine residue. In certain other embodiments, the polyglycosylated peptide or protein comprises at least two adjacent glycosylated amino acids (i.e., clustered glycosylated amino acids), separated from another glycosylated site by a peptide amino acid sequence that does not comprise a cysteine residue.

For the purpose of the invention, a peptide or "peptide backbone" having an amino acid sequence that is "closely related to that of a naturally occurring protein near a functionalized site" designates a peptide fragment of the naturally occurring protein, or truncated, elongated or derivatized version thereof, comprising ≤about 60 amino acid residues, wherein one amino acid residue bears a functionalized site, and at least one amino acid residue has been added, deleted and/or substituted with a natural or non-natural amino acid residue, so that the resulting peptide fragment has a sequence identity greater or equal to about 70% with the original naturally occurring peptide fragment. In certain embodiments, the peptide or "peptide backbone" comprises ≤about 55 amino acid residues. In certain embodiments, the peptide or "peptide backbone" comprises ≤about 50 amino acid residues. In certain embodiments, the peptide or "peptide backbone" comprises ≤about 45 amino acid residues. In certain embodiments, the peptide or "peptide backbone" comprises ≤about 40 amino acid residues. In certain embodiments, the peptide or "peptide backbone" comprises ≤about 35 amino acid residues. In certain embodiments, the peptide or "peptide backbone" comprises ≤about 30 amino acid residues. In certain embodiments, the peptide or "peptide backbone" comprises ≤about 25 amino acid residues. In certain embodiments, the peptide or "peptide backbone" comprises ≤about 20 amino acid residues. In certain embodiments, the peptide or "peptide backbone" has a sequence identity greater or equal to about 75% with the original naturally occurring protein fragment. In certain other embodiments, the peptide or "peptide backbone" has a sequence identity greater or equal to about 80% with the original naturally occurring protein fragment. In certain other embodiments, the peptide or "peptide backbone" has a sequence identity greater or equal to about 85% with the original naturally occurring protein fragment. In certain other embodiments, the peptide or "peptide backbone" has a sequence identity greater or equal to about 90% with the original naturally occurring protein fragment. In certain other embodiments, the peptide or "peptide backbone" has a sequence identity greater or equal to about 95% with the original naturally occurring protein fragment.

A peptide or "peptide backbone" having an amino acid sequence that is "identical to that of a naturally occurring protein near a functionalized site" designates a peptide fragment of the naturally occurring protein, comprising ≤about 60 amino acid residues, wherein one amino acid residue bears a functionalized site. In certain embodiments, the peptide or "peptide backbone" comprises ≤about 55 amino acid residues. In certain embodiments, the peptide or "peptide backbone" comprises ≤about 50 amino acid residues. In certain embodiments, the peptide or "peptide backbone" comprises ≤about 45 amino acid residues. In certain embodiments, the peptide or "peptide backbone" comprises ≤about 40 amino acid residues. In certain embodiments, the peptide or "peptide backbone" comprises ≤about 35 amino acid residues. In certain embodiments, the peptide or "peptide backbone" comprises ≤about 30 amino acid residues. In certain embodiments, the peptide or "peptide backbone" comprises ≤about 25 amino acid residues. In certain embodiments, the peptide or "peptide backbone" comprises ≤about 20 amino acid residues.

In certain embodiments, at least one functionalized site is a glycosylation site. In certain embodiments, the naturally occurring functionalized protein is a glycoprotein, and the functionalised sites are glycosylated sites. In certain embodiments, at least one glycosylated site is an O-glycosylated site. In certain embodiments, at least one glycosylated site is an N-glycosylated site.

In certain embodiments, the naturally occurring functionalized protein is a homogeneous Human Erythropoietin (HuEPO). In certain embodiments, the naturally occurring functionalized protein is a homogeneous Human Erythropoietin (HuEPO) and the functionalized sites are glycosylated sites wherein the glycan is O- or N-linked and is selected from:

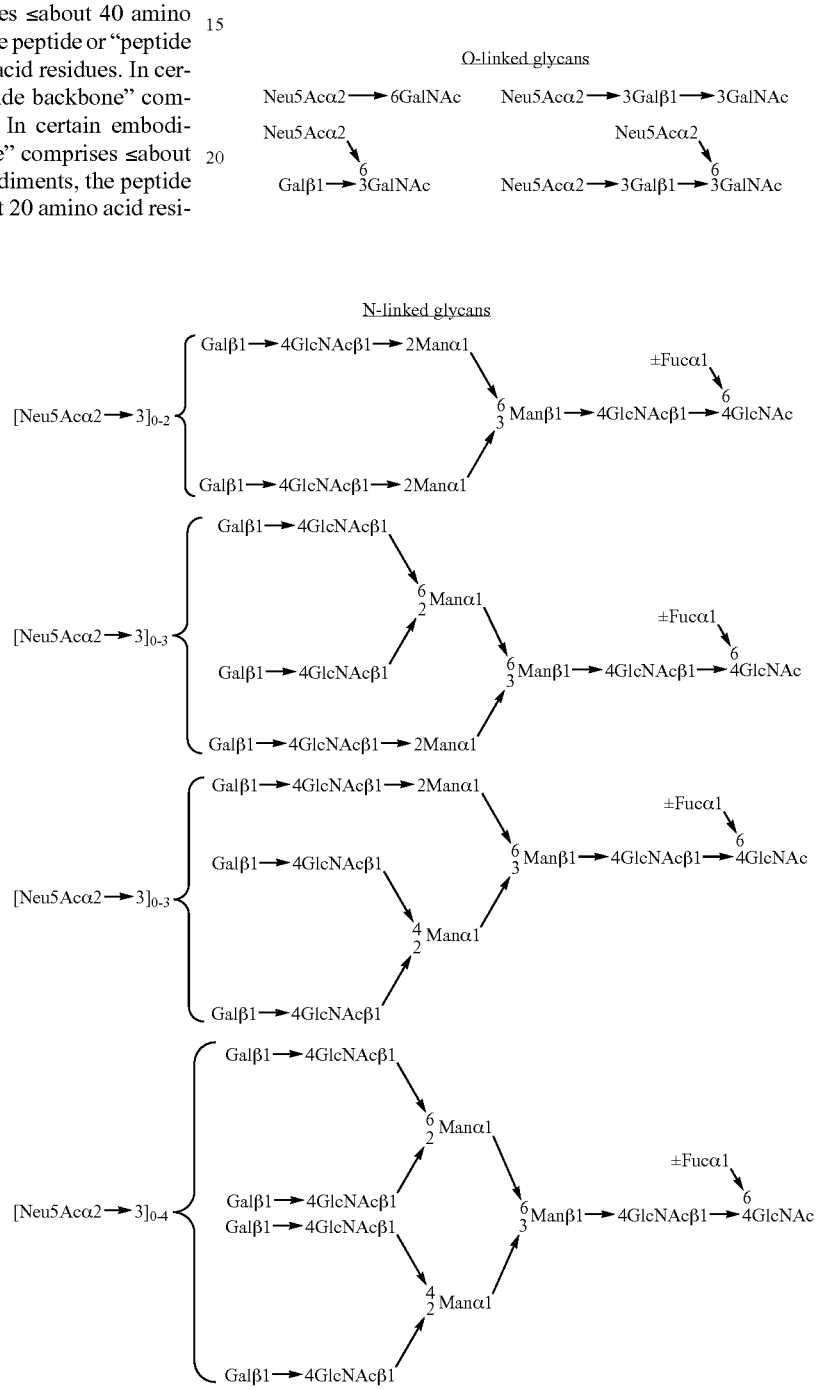

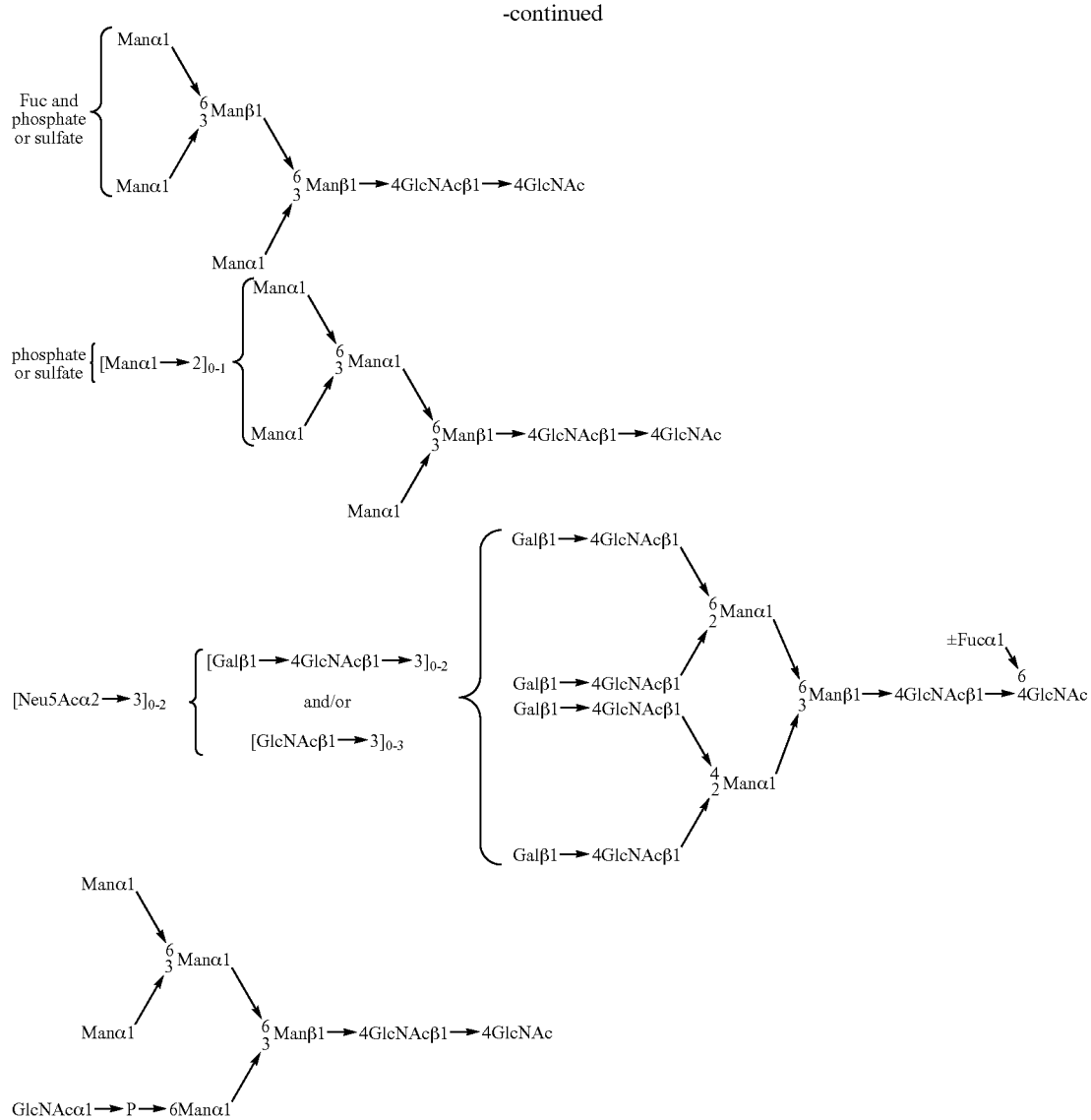

-continued or protected forms thereof.

In certain embodiments, the peptide has an amino acid sequence that is either identical to or closely related to that of a naturally occurring human erythropoietin near a glycosylation site, or a truncated, elongated or derivatized version thereof; wherein any one or more of the amino acid residues may bear one or more protecting groups. In certain embodiments, the peptide has an amino acid sequence that is either identical to or closely related to that of a naturally occurring Human erythropoietin EPO 2-27 near a glycosylation site, or a truncated, elongated or derivatized version thereof; wherein any one or more of the amino acid residues may bear one or more protecting groups. In certain embodiments, the peptide has an amino acid sequence that is either identical to or closely related to that of a naturally occurring Human erythropoietin EPO 30-76 near a glycosylation site, or a truncated, elongated or derivatized version thereof; wherein any one or more of the amino acid residues may bear one or more protecting groups. In certain embodiments, the peptide has an amino acid sequence that is either identical to or closely related to that of a naturally occurring Human erythropoietin EPO 79-112 near a glycosylation site, or a truncated, elongated or derivatized version thereof; wherein any one or more of the amino acid residues may bear one or more protecting groups. In certain embodiments, the peptide has an amino acid sequence that is either identical to or closely related to that of a naturally occurring Human erythropoietin EPO 115-165 near a glycosylation site, or a truncated, elongated or derivatized version thereof; wherein any one or more of the amino acid residues may bear one or more protecting groups.

In certain embodiments, the naturally occurring functionalized protein is a homogeneous tumor-associated glycoprotein. In certain embodiments, the naturally occurring functionalized protein is a homogeneous tumor-associated glycoprotein and the functionalized sites are selected from the group consisting of Globo-H, fucosyl GM1, GM2, KH-1, glycophorin, STN, (2,3)ST, Le$^y$, Le$^x$, N3, Tn, 2,6-STn, Gb3 and TF or protected form thereof.

In certain embodiments, the naturally occurring functionalized protein is homogeneous form of gp120.

In certain embodiments, the naturally occurring functionalized protein is homogeneous form of prostate specific antigen (PSA).

For purposes of the invention, "truncated", refers to a peptide fragment comprising no fewer than about 6 amino acid residues; "elongated", refers to a peptide comprising no more than about 60 amino acid residues; and "derivatized" refers to a peptide in which at least one, but not more than about 2 out of every 10, amino acid residues have been added and/or deleted; and/or in which at least one amino acid residue has been substituted with a natural or non-natural amino acid residue so that the resulting peptide has a sequence identity equal or greater to about 70% with the original peptide.

In certain embodiments, A may comprise any functional moiety that is compatible with native chemical ligation reaction conditions. In certain embodiments, A may comprise any functional moiety that is compatible with aqueous conditions. In certain embodiments, a compatible functionality is one that is stable, unreactive and/or minimally interferes with the reaction. A thiol group is considered a compatible functionality, even though a thiol group may slow down the reaction. Examples of suitable functionalities include, but are not limited to, hydrocarbons, amines, amides, imines, hydroxyls, ethers, carboxylic esters, aldehydes, thiols, olefins, alkynes, aryls and heteroaryls. In certain exemplary embodiments, A does not comprise a thiol group.

In certain embodiments, when at least one occurrence of A (or $A_1$ and/or $A_2$, as further defined for A) is a carbohydrate domain, some or all of carbohydrate domains are O-linked to the peptide backbone. In certain other embodiments, when at least one occurrence of A (or $A_1$ and/or $A_2$, as further defined for A) is a carbohydrate domain, some or all of carbohydrate domains are N-linked to the peptide backbone. In certain other embodiments, when at least one occurrence of A (or $A_1$ and/or $A_2$, as further defined for A) is a carbohydrate domain, the inventive method may be practiced while the carbohydrate domain is partially or fully deprotected (i.e., comprises exposed OH groups). In certain embodiments, the peptide sequence between each point of attachment of the A moieties comprises a cysteine residue. In certain embodiments, the polyfunctionalized construct (i.e., construct bearing more than one A moiety) is prepared by the inventive method (i.e., cysteine-free Native Chemical Ligation). In certain embodiments, the polyfunctionalized construct (i.e., construct bearing more than one A moiety) is prepared by a combination of the inventive method (i.e., cysteine-free Native Chemical Ligation) and cysteine-dependent Native Chemical Ligation. Guidance regarding the cysteine-dependent Native Chemical Ligation methodology and its applications can be found in published PCT application No. WO 2005/044841 which is hereby incorporated herein by reference in its entirety. In certain embodiments, the polyfunctionalized peptides obtained by the inventive method are symmetrical (functionalized peptide building blocks to be ligated have the same peptide sequence (safe for N- and/or C-terminals) and bear the same functionalization pattern), nonsymmetrical (functionalized peptide building blocks to be ligated differ in peptide sequence (excluding N- and C-terminals) and/or functionalization pattern). In certain embodiments, the inventive method allows the preparation of multiglycosylated peptides designed to approximate the spatial position(s) of carbohydrate(s) in glycoprotein/glycopeptides of interest (e.g., naturally occurring glycoproteins such as gp120 and erythropoietin).

In certain embodiments, the method further comprises a step of conjugating the polyfunctionalized peptide to an immunogenic carrier. In certain exemplary embodiments, the carrier is a protein, a peptide or a lipid. In certain other exemplary embodiments, the carrier is Bovine Serum Albumin (BSA), Keyhole Limpet Hemocyanin (KLH), or polylysine. In certain other embodiments, the carrier is a lipid carrier having the structure:

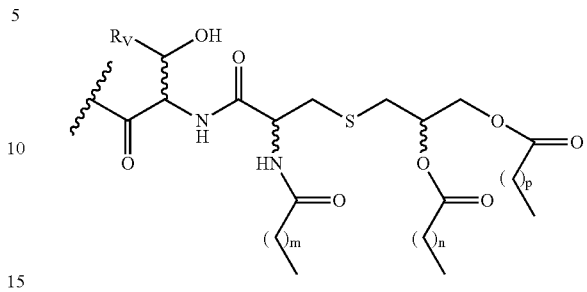

wherein m, n and p are each independently integers between about 8 and 20; and $R_V$ is hydrogen, substituted or unsubstituted linear or branched chain lower alkyl or substituted or unsubstituted phenyl. In certain exemplary embodiments, m', n' and p' are each 14 and the lipid is tripalmitoyl-S-glycerylcysteinylserine (i.e., PamCys).

It will be appreciated that the carrier can be linked to the polyfunctionalized peptide either directly or through a crosslinker, and thus the peptide may be attached to a protein, peptids, or lipid, as well as a (crosslinker-protein), (crosslinker-peptide), and (crosslinker-lipid) moiety.

Crosslinkers suited to the invention are widely known in the art (see, for example, 1994 Pierce Technical Handbook: cross-linking (Appendix A), which is available at http://www.piercenet.com/resources/browse.cfm?fldID=184), including bromoacetic NHS ester, 6-(iodoacetamido)caproic acid NHS ester, maleimidoacetic acid NHS ester, maleimidobenzoic acide NHS ester, etc. In certain preferred embodiments, the crosslinker is MMCCH (4-(maleimidomethyl)cyclohexane-1-carboxyl hydrazide). In certain other preferred embodiments, the crosslinker is MBS (m-maleimidobenzoyl acid N-Hydroxysuccinimidyl ester). In certain embodiments, the crosslinker is a fragment having the structure:

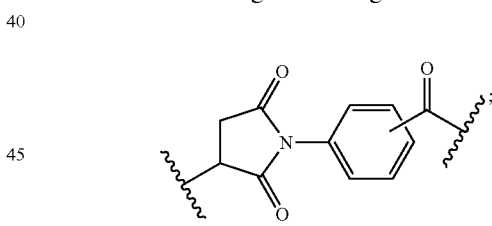

whereby said structure is generated upon conjugation of a maleimidobenzoic acid N-hydroxy succinimide ester with a suitable functionality on the polyfunctionalized peptide.

In certain embodiments, the present invention provides a method of ligating two peptides to form a peptide of formula:

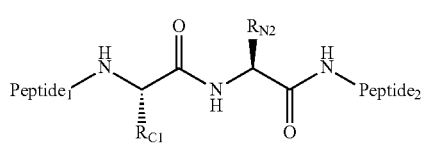

wherein

Peptide1 is a peptide comprising two or more natural or unnatural amino acids, wherein the peptide is protected, partially protected, or unprotected, and the peptide is optionally glycosylated;

Peptide2 is a peptide comprising two or more natural or unnatural amino acids, wherein the peptide is protected, partially protected, or unprotected, and the peptide is optionally glycosylated;

$R_{C1}$ is a side chain of a natural or unnatural amino acid, wherein the side chain is protected or unprotected; and $R_{N2}$ is a side chain of a natural or unnatural amino acid, wherein the side chain is protected or unprotected;

the method comprising steps of:

ligating a peptide of formula:

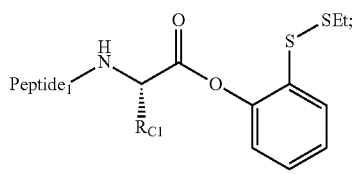

to a peptide of formula:

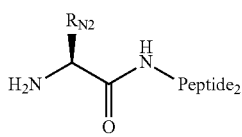

under suitable conditions to form a peptide of formula:

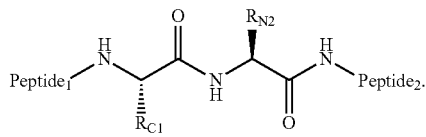

In certain embodiments, the invention provides a method of ligating two peptides to form a peptide of formula:

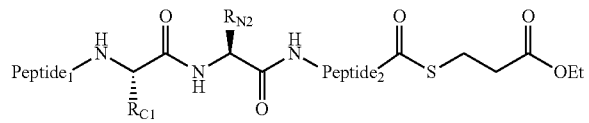

wherein

Peptide1 is a peptide comprising two or more natural or unnatural amino acids, wherein the peptide is protected, partially protected, or unprotected, and the peptide is optionally glycosylated;

Peptide2 is a peptide comprising two two or more natural or unnatural amino acids, wherein the peptide is protected, partially protected, or unprotected, and the peptide is optionally glycosylated;

$R_{C1}$ is a side chain of a natural or unnatural amino acid, wherein the side chain is protected or unprotected; and $R_{N2}$ is a side chain of a natural or unnatural amino acid, wherein the side chain is protected or unprotected;

the method comprising steps of:

ligating a peptide of formula:

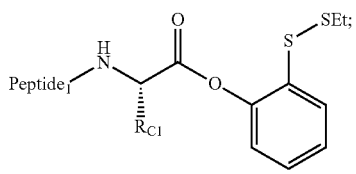

to a peptide of formula:

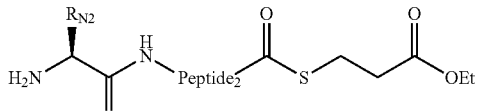

under suitable conditions to form a peptide of formula:

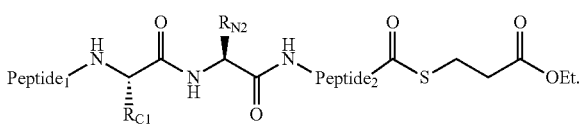

The peptides being ligated together may be glycosylated or otherwise post-translationally modified. In certain embodiments, at least one of Peptide 1 and Peptide2 is glycosylated. In certain embodiments, both Peptide1 and Peptide2 are glycosylated. In certain embodiments, Peptide1 and/or Peptide2 include various protecting groups. The N-terminus, C-terminus, and/or the amino acid side chains are optionally protected with suitable protecting groups. In certain embodiments, Peptide1 is Fmoc-protected at the N-terminus. In certain embodiments, the ligation reaction is done in the presence $Ag^{+1}$. In certain embodiments, the $Ag^{+1}$ ion is provided as AgCl, AgBr, AgI, AgNO$_3$, AgOAc, and AgBF$_4$. In certain embodiments, $Ag^{+1}$ is provided as AgCl. The ligation reaction is typically done in the presence of an activator (e.g., 3,4-dihydro-3-hydroxy-4-oxo-1,2,3-benzotriazine (HOOBt), 1-hydroxybenzotriazole (HOBt), 1-hydroxy-7-azabenzotriazole (HOAt), and N-hydroxysuccinimide (HOSu)) and a base (e.g., sodium bicarbonate (NaHCO3), N,N-diisopropylethylamine (DIEA), 2,6-di-tert-butyl-4-(dimethylamino)pyridine (DBDMAP)). In certain embodiments, the conditions include AgCl, HOOBt, and (N,N-diisopropylethylamine (DIEA). In certain embodiments, DMSO is used as the solvent. In certain embodiments, DMF is used as the solvent. In certain embodiments, the ligation reaction is done in the presence of tri(2-carboxyethyl)phosphine hydrochloride (TCEP-HCl). In certain embodiments, the contions include TCEP-HCl, HOOBt, N,N-diisopropylethylamine (DIEA). The inventive methods may be used repeated to create a longer peptide or protein. The inventive methods are also amenable to solid phase synthesis. In certain embodiments, the method comprises the steps of:

(a) ligating a first peptide fragment of formula:

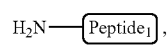

to a second peptide fragment of formula:

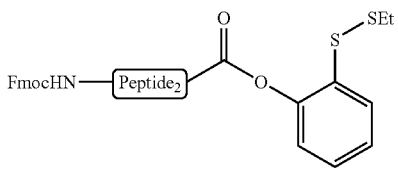

under suitable conditions to form a first ligated peptide of formula:

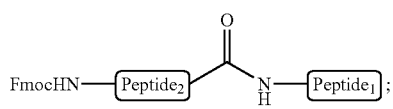

(b) deprotecting the first ligated peptide;
(c) ligating a third peptide fragment of formula:

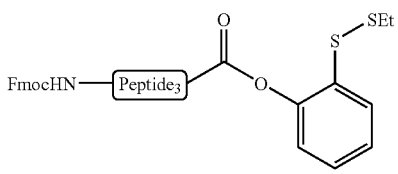

to the first ligated peptide under suitable conditions to form a peptide of formula:

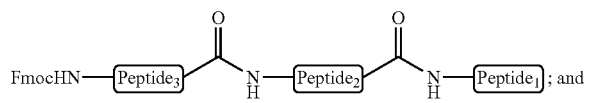

(d) optionally, repeating the steps (b) and (c);
wherein Peptide1, Peptide2, and Peptide3 are each independently a peptide comprising two or more natural or unnatural amino acids, wherein the peptide is protected, partially protected, or unprotected, and the peptide is optionally glycosylated.

In certain embodiments, the method is performed on the solid phase comprising the steps of:
(a) ligating a first peptide fragment of formula:

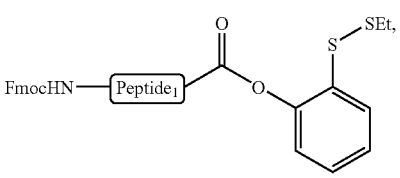

to a solid support of formula:

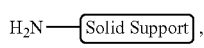

under suitable conditions to form a first ligated peptide of formula:

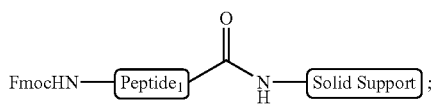

(b) deprotecting the first peptide attached to the solid support;
(c) ligating a second peptide fragment of formula:

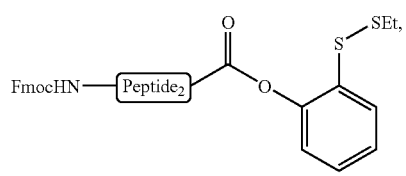

to the first peptide attached to the solid support under suitable conditions to form a peptide on a solid support of formula:

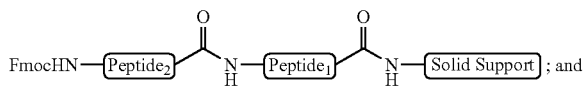

(d) optionally, repeating the steps (b) and (c) to add onto the N-terminus of the growing peptide;
wherein Peptide1 and Peptide2 are each independently a peptide comprising two or more natural or unnatural amino acids, wherein the peptide is protected, partially protected, or unprotected, and the peptide is optionally glycosylated.

In certain embodiments, the inventive methods are used for cyclizing a peptide. In certain embodiments, the invention provides a method of forming a cyclic peptide of formula:

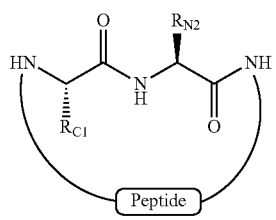

wherein

Peptide is a peptide comprising two or more natural or unnatural amino acids, wherein the peptide is protected, partially protected, or unprotected, and the peptide is optionally glycosylated; and $R_{N2}$ is a side chain of a natural or unnatural amino acid, wherein the side chain is protected or unprotected;

the method comprising steps of:
cyclizing a peptide of formula:

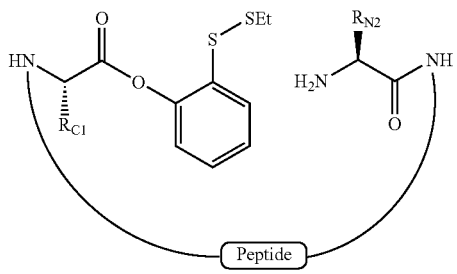

under suitable conditions to form a cyclic peptide of formula:

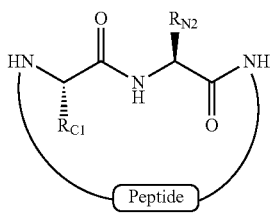

In certain embodiments, the ligation reaction is done in the presence $Ag^{+1}$. In certain embodiments, the $Ag^{+1}$ ion is provided as AgCl, $AgNO_3$, AgOAc, $AgBF_4$, AgBr, and AgI. In certain embodiments, $Ag^{+1}$ is provided as AgCl. The ligation reaction is typically done in the presence of an activator (e.g., 3,4-dihydro-3-hydroxy-4-oxo-1,2,3-benzotriazine (HOOBt), 1-hydroxybenzotriazole (HOBt), 1-hydroxy-7-azabenzotriazole (HOAt), and N-hydroxysuccinimide (HOSu)) and a base (e.g., sodium bicarbonate ($NaHCO3$), N,N-diisopropylethylamine (DIEA), 2,6-di-tert-butyl-4-(dimethylamino)pyridine (DBDMAP)). In certain embodiments, the conditions include AgCl, HOOBt, and N,N-diisopropylethylamine (DIEA). In certain embodiments, DMSO is used as the solvent. In certain embodiments, DMF is used as the solvent. In certain embodiments, the ligation reaction is done in the presence of tri(2-carboxyethyl)phosphine hydrochloride (TCEP-HCl). In certain embodiments, the contions include TCEP-HCl, HOOBt, N,N-diisopropylethylamine (DIEA).

The present invention also provides methods of desulfuring or deselenizing a peptide or protein. The method thereby converts a cystein residue or seleno-cysteine residue to an alanine residue. In certain embodiments, the method of desulfurizing or deselenizing comprises the steps of:
desulfurizing or deselenizing a peptide of formula:

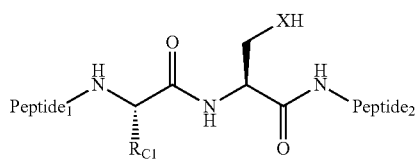

wherein
Peptide$_1$ is a peptide comprising two or more natural or unnatural amino acids, wherein the peptide is protected, partially protected, or unprotected, and the peptide is optionally glycosylated;

Peptide$_2$ is a peptide comprising two or more natural or unnatural amino acids,
wherein the peptide is protected, partially protected, or unprotected, and the peptide is optionally glycosylated;
X is Se or S;
$R_{C1}$ is a side chain of a natural or unnatural amino acid, wherein the side chain is protected or unprotected, and the side chain is optionall glycosylated; under suitable conditions to form a peptide of formula:

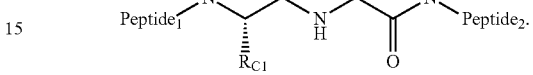

In certain embodiments, X is sulfur. In other embodiments, X is selenium. In certain embodiments, the suitable conditions include a phosphine, a thiol-containing reagent, and a free radical initiator. In certain embodiments, the suitable conditions include a phosphite, a thiol-containing reagent, and a free radical initiator. In certain embodiments, the suitable conditions include an isocyanide, a thiol-containing reagent, and a free radical initiator. The phosphine or phosphite is preferably water soluble. Exemplary phosphines that may be used in the reaction include TCEP-HCl, [2-(di-tert-butyl phosphanyl)ethyl]trimethyl ammonium iodide; 1,3,5-triaza-7-phosphaadamantane (PTA); 2-(di-tert-butylphosphino) ethyltrimethylammonium chloride (t-Bu-Amphos), 4-(di-tert-butylphosphino)-N,N-dimethylpiperidinium chloride (t-Bu-Pip-phos), and 4-(dicyclohexylphosphino)-N,N-dimethylpiperidinium chloride (Cy-Pip-phos). Any thiol-containing reagent may be used (e.g., methyl thiol, ethyl thiol, propyl thiol, iso-propyl thiol, 2-methyl-2-propyl thiol. tert-butyl thiol. phenyl thiol, and benzyl thiol). Exemplary free radical initiator include, but are not limited to, AIBN, $Et_3B$, peroxides, V-70, VA-044, VA-50, VA-061, VA-057, VA-086, and VA-041. The reaction is typically done under aqueous conditions. Suitable solvents include water, alcohols, THF, DMF, DMSO, acetonitrile, or mixtures thereof.

In certain embodiments, the present invention provides a peptide of formula:

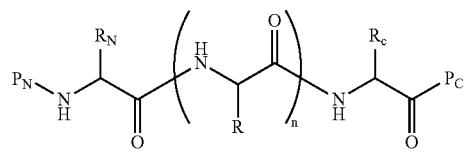

wherein
each occurrence of $R_N$, $R_C$, and R is independently the side chain of a natural or unnatural amino acid, optionally glycosylated;
$P_C$ is —$OR^{X2a}$, —$SR^{X2a}$, or $NR^{X2b}R^{X2c}$, wherein $R^{X2a}$ is hydrogen, alkyl, aromatic, heteroaromatic, substituted or unsubstituted aryl, substituted or unsubstituted heteroaryl, -alkyl(aryl), -alkyl(heteroaryl), a carboxylic acid protecting group, an amino acid, or a protected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid or a protected amino acid;

$P_N$ is hydrogen, a nitrogen protecting group, or a moiety having the structure:

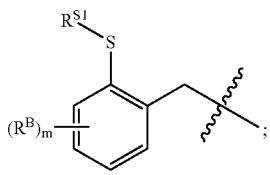

wherein m is 1, 2, 3, or 4; $R^{S1}$ is hydrogen; substituted or unsubstituted aryl; substituted or unsubstituted heteroaryl; or a sulfide protecting group; each occurrence of $R^B$ is independently alkoxy, hydroxy, or silyloxy. In certain embodiments, m is 1. In certain embodiments, m is 2. In certain embodiments, m is 3. In certain embodiments, m is 4. In certain embodiments, $P_N$ is a nitrogen protecting group. In certain embodiments, $P_N$ is an Fmoc nitrogen protecting group. In certain embodiments, $P_N$ is a Boc nitrogen protecting group. In certain embodiments, $P_N$ is acetyl. In certain embodiments, $P_N$ is hydrogen. In certain embodiments, $P_N$ is

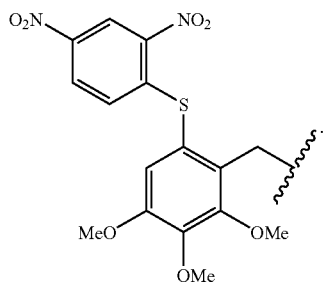 [SMILES: *Cc1c(Sc2ccc([N+](=O)[O-])cc2[N+](=O)[O-])cc(OC)c(OC)c1OC]

In certain embodiments, $P_N$ is

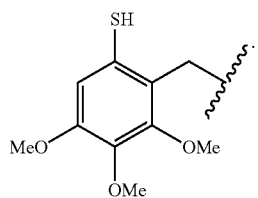

In certain embodiments, $P_N$ is

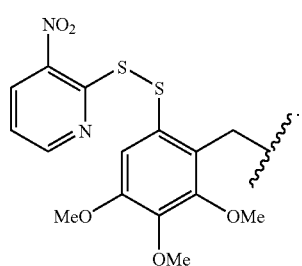 [SMILES: *Cc1c(SSc2ncccc2[N+](=O)[O-])cc(OC)c(OC)c1OC]

In certain embodiments, $P_C$ is —$OR^{X2a}$, wherein $R^{X2a}$ is

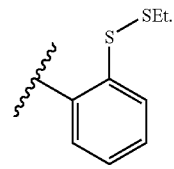

In certain embodiments, $P_C$ is —$OR^{X2a}$, wherein $R^{X2a}$ is

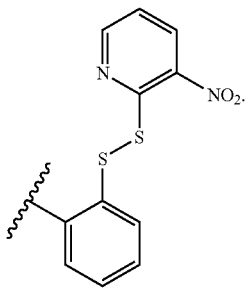 [SMILES: *c1ccccc1SSc1ncccc1[N+](=O)[O-]]

In certain embodiments, $P_C$ is —$OR^{X2a}$, wherein $R^{X2a}$ is $C_1$-$C_6$ alkyl. In certain embodiments, $P_C$ is —$OR^{X2a}$, wherein $R^{X2a}$ is a carboxylic acid protecting group. In certain embodiments, $P_C$ is —OH. In certain embodiments, $P_C$ is —$SR^{X2a}$. In certain embodiments, at least one of $R_C$, $R_N$, and R is side chain of a natural or unnatural amino acid, wherein the side chain is glycosylated or otherwise post-translationally modified. In certain embodiments, $R_C$, $R_N$, and R are selected from the group consisting of:

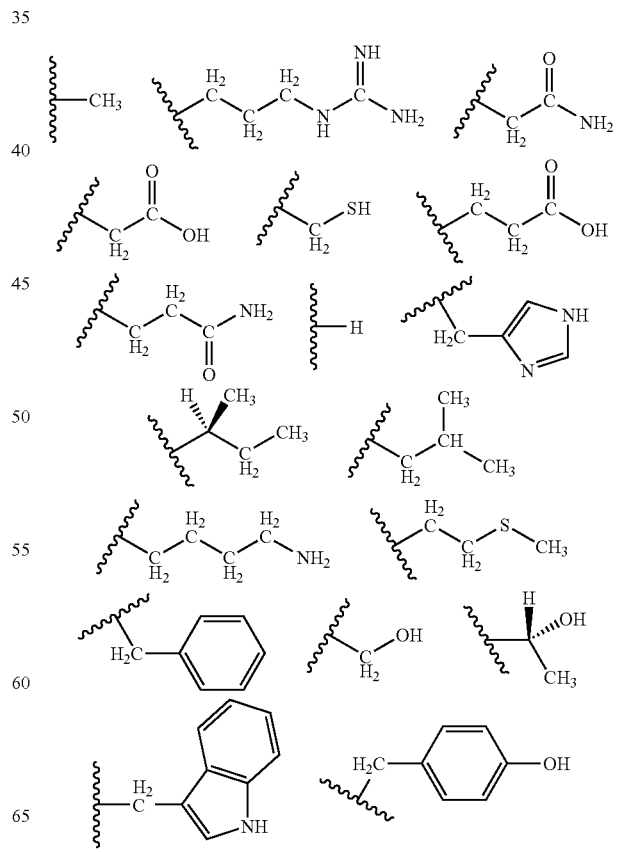

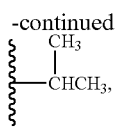

wherein the above formula may be optionally glycosylated.

Exemplary Synthetic Methodology

Glycosylation is the most common form of covalent modification that newly synthesized proteins undergo in living organisms; it is also the most diverse. Not only are several different amino acids modified, but also the attached carbohydrate can assume many structures. Such diversity is the result of both chemical as well as biological factors. Chemically, monosaccharides have the ability to combine with each other to form larger structures that can vary in chain length and sequence as well as anomery (α or β), linkage position and branching points. Each individual monomer can then be further modified by the attachment of sulfate, phosphate, acetate or methyl groups. Therefore, an immense assortment of glycans can be generated from a relatively small number of monosaccharides. Biological diversity arises from the fact that glycans are secondary gene products (i.e., their synthesis is not under direct genetic control as is the case with proteins). As a result, glycosylation patterns are typically determined by the structure of the protein itself and can be species- and even cell-specific, meaning that the protein glycosylation is dependent on the cell or tissue in which it is produced.

In a given glycoprotein, more than one carbohydrate unit is often present and can be attached by an N-linkage, an O-linkage or both. For instance, the pleiotropic cytokine erythropoietin contains four distinct carbohydrate domains, three N-linked and one O-linked. Each of these domains can accommodate many different glycans (Rush et al., Anal. Chem. 1995, 67, 1442-1452). This occurrence, known as site heterogeneity, results in an overall microheterogeneous complex. In glycoproteins as a class, each discrete glycoform can have completely different physical and biochemical properties, often leading to functional diversity even though each complex shares an identical peptidic backbone.

The use of glycoproteins in the clinic has increased tremendously in the past two decades. Driven by advances in genetic engineering, glycoproteins can now be produced in heterologous systems on large scale (Rademacher et al., A. Ann. Rev. Biochem. 1988, 57, 785-838). Typically this is accomplished with recombinant DNA technology, the gene encoding the desired glycoprotein is cloned and then expressed in cell culture. Glycosylation events under these conditions are highly sensitive processes, and can be influenced by a number of factors, including choice of expression system (E. coli, yeast, insect cells, tobacco cells, or mammalian cells) and cell culture conditions (pH, temperature, ammonia or glucose concentration, enzymatic activity and bioreactor configuration) (Rademacher et al., A. Ann. Rev. Biochem. 1988, 57, 785-838; Parekh et al., Trends Biotechnol. 1989, 7, 117-122; Jenkins et al., Nat. Biotechnol. 1996, 14, 975-981)). The glycoform heterogeneity obtained during in vitro glycoprotein production coupled with the influence of non-native glycans on their therapeutic properties has necessitated the development of strict guidelines for glycan profiling and selective purification strategies. Consequently, the determination of a "homogeneous lot" of a particular biopharmaceutical glycoprotein, with a known glycan profile, is the result of cumulative input from highly optimized production, purification and glycan analysis (Gupta et al., J. Mol. Recognit. 2004, 17, 218-235).

If a glycoprotein therapeutic exhibits microheterogeneity, it is generally necessary to establish the therapeutic and technological consequences of such modulation. The native and recombinant forms of a protein will invariably differ in their N-glycosylation patterns, either in the types of oligosaccharide present or in their relative distribution. For example, in human erythropoietin (HuEPO), detailed comparisons of the native and recombinant (rHuEPO) forms have determined that the recombinant forms were never N-glycosylated in the same manner as the native form ((a) Tsuda et al., Biochemistry 1988, 27, 5646-5654. (b) Takeuchi et al., J. Biol. Chem. 1988, 263, 3657-3663). When obtained from baby hamster kidney (BHK) cells, rHuEPO contained oligosaccharides not found on human urinary EPO, ((a) Tsuda et al., Biochemistry 1988, 27, 5646-5654) while in Chinese hamster ovary (CHO) cells, the oligosaccharides were similar, but the relative amounts were different ((b) Takeuchi et al., J. Biol. Chem. 1988, 263, 3657-3663). Adding to the complexity is that the "native" form of any given glycoprotein is often difficult to define. Alterations in N-glycosylation patterns can occur naturally as a physical response to changing physiological conditions, leading to natural variants with differing biological activity (Gesundheit et al., J. Biol. Chem. 1987, 262, 5197-5203; Yoon et al., Biotechnol. Prog. 2004, 20, 1293-1296). In fact, isoform production of rHuEPO can differ not only between different cell lines, but also between different batches of product within the same cell line (Yuen et al., Brit. J. Haematol. 2003, 121, 511-526).

Not only do oligosaccharides influence the biological activity of a glycoprotein, they can also impact its bio-distribution, molecular stability, solubility, immunogenicity, and circulatory lifetime (Rademacher et al., A. Ann. Rev. Biochem. 1988, 57, 785-838; Ashwell et al., Ann. Rev. Biochem. 1982, 51, 531-554). In recombinant glycoproteins, perhaps the most concerning of these is the potential immunogenicity of the administered therapeutic, as antibodies raised to protein therapeutics can have deleterious consequences, including neutralization. There have been increasing reports of patients developing antibodies to administered rHuEPO that recognize and neutralize endogenous HuEPO resulting in the development of antibody mediated pure red cell aplasia (PRCA) (Casadevall et al., New Engl. J. Med. 2002, 346, 469-475). The incidence of PRCA before 1998 was extremely rare (only three cases reported), however by 2003 over 160 patients worldwide had been diagnosed with antibody-positive PRCA after treatment with rHuEPO (Mayeux et al., In Erythropoietins and Erythropoiesis; Molineux, G., Foote, M. A., Elliott, S. G., Eds. Antibodies to Endogenous and Recombinant Erythropoietin. Birkhäuser Verlag: Switzerland, 2003; pp 229-239). It has been suggested that since millions of patients had been treated with rHuEPO prior to 1998, the increase in reported cases of PRCA might be due to changes in manufacturing procedures and/or formulation (Casadevall et al., New Engl. J. Med. 2002, 346, 469-475). While the absolute cause of the increased antigenicity remains speculative, (Chirino et al. Drug Discov. Today 2004, 9, 82-90) it is likely that the oligosaccharide portion of the molecule plays a significant role, either in direct immunogenicity (While this has not necessarily been seen in rHuEPO, it has been observed in other protein therapeutics. For an example, see: Zang et al., Neurology 2000, 55, 391-404) or by virtue of the fact that the carbohydrate can occupy a significant volume surrounding the protein thereby reducing the available surface area to immune surveillance (Imperiali et al., Curr. Opin. Chem. Biol. 1999, 3, 643-649; Elliott et al. Blood 1996, 87, 2714-2722).

Since glycan synthesis is not under direct genetic control, it is primarily the cellular atmosphere in which the glycoprotein is produced that determines the type and extent of protein glycosylation. A recombinant glycoprotein produced in a transgenic cell line would then intrinsically contain non-physiological N-glycosylation. Although the carbohydrates themselves might be the same, their relative incidence would not necessarily coincide, potentially leading to a product with different biological properties (Rademacher et al., A. *Ann. Rev. Biochem.* 1988, 57, 785-838; Rademacher et al., *Springer Semin. Immunopathol.* 1988, 10, 231-249). In that respect, fully synthetic glycoproteins might be superior. It has been suggested that a single natural glycoform of a glycoform may, in some cases, be more efficacious than either the endogenous or recombinant glycoforms that are produced as heterogenous mixtures (Parekh et al., *Trends Biotechnol.* 1989, 7, 117-122). Furthermore, synthesis allows for the generation of proteins and glycoproteins that may not be available via biological processes, for example those containing unnatural oligosaccharides or amino acids (Macmillan et al., *Chem. Biol.* 2001, 8, 133-145; Kochendoerfer et al., *Science* 2003, 299, 884-887; Hartley et al., *Proc. Natl. Acad. Sci. U.S.A.* 2004, 101, 16460-16465; Chen et al., *Chem. Biol.* 2005, 12, 371-383). Having absolute control over the synthesis allows for the generation of therapeutics with enhanced bioactivity, specific cellular targeting and increased circulatory lifetime.

Exemplary Synthetic Target: Erythropoietin

The glycoprotein hormone erythropoietin (EPO) is synthesized in humans by the fetal liver and adult kidney. Upon maturation, EPO's main function is to modulate the production of erythrocytes via a classical feedback mechanism whereby the concentration of serum oxygen determines whether the hormone is up- or downregulated. Low oxygen levels signal higher EPO expression while high oxygen levels signal decreased EPO expression (Lin et al., *Proc. Natl. Acad. Sci. U.S.A.* 1985, 82, 7580-7584; Krantz, *Blood* 1991, 77, 419-434; Syed et al., *Nature* 1998, 395, 511-516). During chronic renal failure, the kidneys are no longer able to contend with the corporal demands of EPO production, leading to anemia. Advances in the biopharmaceutical industry have lead to the development of recombinant erythropoietin therapeutics. When administered intravenously, rHuEPO is able to stimulate erythrocyte formation, allowing the patient to avoid regular blood transfusions.

HuEPO exists as a heterogeneous mixture of glycoforms, with as many as 58 different N-linked oligosaccharides associated with a single sample (Rush et al., *Anal. Chem.* 1995, 67, 1442-1452; Hokke et al., *Eur. J. Biochem.* 1995, 228, 981-1008). Clearly, glycosylation of the peptide backbone is exceedingly important for proper biological function. HuEPO contains 4 sites of glycosylation, one O-linked (Ser$^{126}$) and three N-linked (Asn$^{24}$, Asn$^{38}$ and Asn$^{83}$) (Lai et al., *J. Biol. Chem.* 1986, 261, 3116-3121). The carbohydrates themselves constitute approximately 40% of the molecular weight of the glycoprotein and likely cover the molecular surface of the protein (For example, a single sialylated triantennary complex carbohydrate occupies approximately 2542 Å$^3$, see: Imperiali et al., *Curr. Opin. Chem. Biol.* 1999, 3, 643-649).

Given the importance of the carbohydrates, it is not surprising that their structural details have been extensively investigated (Takeuchi et al., *Glycobiology,* 1991, 1, 337-346). In the case of the Asn-linked carbohydrates, the major structure has been identified as being a complex tetraantennary type, however tri- and biantennary structures also exist. All of the sugar chains are sialylated to some degree, with the sialic acid linked mainly by α2→3 linkages and periodically via α2→6 linkages (Warren et al., *J. Am. Chem. Soc.* 2004, 126, 6576-6578). While the O→S acyl transfer method which we have developed and its application to complex glycopeptide synthesis had not been reported, the general concept of chemical ligation of polypeptides through (i) an organizing preliminary attachment, (ii) acyl transfer, (iii) de-convolution with emergence of a peptide bond establishing the ligation has a distinguished intellectual history. For an early paper that can be so classified, see: Brenner et al., *Helv. Chim. Acta.* 1957, 40, 1497-1517. The key seminal advance was incubated in a series of papers by Kemp: Kemp et al., *Tetrahedron Lett.* 1981, 22, 181-184; Kemp et al., *Tetrahedron Lett.* 1981, 22, 185-186; Kemp et al., *J. Org. Chem.* 1981, 46, 490-498; Kemp, *Biopolymers* 1981, 20, 1793-1804; Kemp et al., *J. Org. Chem.* 1986, 51, 1821-1829; Kemp et al., *Tetrahedron Lett.* 1987, 28, 4637-4640; Fotouhi et al., *J. Org. Chem.* 1989, 54, 2803-2817; Kemp et al., *J. Org. Chem.* 1993, 58, 2216-2222; Sasaki et al., *J. Biol. Chem.* 1987, 262, 12059-12076. Repeating N-acetyllactosamine structures are often found in the terminal chain portion and the reducing terminal GlcNAc frequently contains a fucose residue linked α1→6. The mucin-type sugar chain structure, located at Ser$^{126}$ does not have as many variants as found in the Asn-linked carbohydrates. They were found to contain a Galβ1→3GalNAc core structure with one or two Neu5Acs (Tsuda et al., *Eur. J. Biochem.* 1990, 188, 405-411; Inoue et al., *Arch. Biochem. Biophys.* 1993, 301, 375-378).

The role of the individual carbohydrate moieties has also been intensely studied; it has been shown that the branching pattern of the N-linked oligosaccharides and presence or absence of terminal sialic acids on the branches impacts the biological activity both in vitro and in vivo (Fukuda et al. *Blood* 1989, 73, 84-89; Imai et al., *J. Biochem.* (Tokyo) 1990, 107, 352-359; Higuchi et al., *J. Biol. Chem.* 1992, 267, 7703-7709). Due to differences in branching and terminal monosaccharides, the number of sialic acids present in any single glycoform of rHuEPO can vary, with a maximum of 14. Endogenous HuEPO typically has a lower sialic acid content than the recombinant variety (Skibeli et al., *Blood* 2001, 98, 3626-3634). Several reports have indicated that removal of the sialic acid residues increases in vitro activity, but decreases in vivo activity (Goldwasser et al., *J. Biol. Chem.* 1974, 249, 4202-4206; Dordal et al., *Endocrinology* 1985, 116, 2293-2299; Spivak et al., *Blood,* 1989, 73, 90-99). Such studies have shown that the in vivo terminal half-life is directly correlated to the sialic content of the glycoforms, while affinity for the EPO receptor (EPO-R), measured in vitro, was shown to be inversely related. Thus, despite the decrease in affinity for its receptor, sialylation of the N-linked carbohydrates on HuEPO increases its in vivo activity by minimizing its metabolic clearance, presumably by protecting the penultimate galactose residue from the asialoglycoprotein receptor (Ashwell et al., *Ann. Rev. Biochem.* 1982, 51, 531-554).

The intrinsic ability of sialylated N-linked carbohydrates to reduce metabolic clearance has led to the development of longer-acting rHuEPO derivatives (Egrie et al., *Br. J. Cancer* 2001, 84 (*Suppl.* 1), 3-10; Egrie et al., *Exp. Hematol.* 2003, 31, 290-299; Koury, *Trends Biotechnol.* 2003, 21, 462-464). Using site directed mutagenesis, several glycosylation analogs of rHuEPO have been created by adding additional consensus N-linked glycosylation sites (This consensus sequence is Asn-X-Ser/Thr, where X is any amino acid other than proline. See: Bause, *Biochem. J.* 1983, 209, 331-336; Roitsch et al., *Eur. J. Biochem.* 1989, 181, 525-529; Imperiali et al., *Biochemistry,* 1991, 30, 4374-4380) in regions of the protein that were unlikely to alter stability or EPO-R binding (Elliott et al., *Nat. Biotechnol.* 2003, 21, 414-421). One of these analogs, containing an additional two N-linked carbohydrates, has been advanced through the clinic and is currently on the market as ARANESP™ (darbepoetin alfa). Due to the additional N-linked carbohydrate moieties, the maximal total number of sialic acid residues increases to 22. In vitro assays of darbepoetin alfa indicate that its affinity for the EPO-R was diminished by approximately one-fourth, compared to rHuEPO. However, its activity in vivo remained the same, suggesting that the extended half-life plays a larger role in its activity than receptor affinity (Egrie et al., *Exp. Hematol.* 2003, 31, 290-299).

Exemplary Synthesis of EPO Carbohydrates

A significant part in the development of a wholly synthetic EPO is the ability to readily obtain any of the carbohydrates found on the periphery of the protein. Endogenous HuEPO contains one O-linked and three N-linked glycosylation sites. The degree of heterogeneity is certainly greater at the N-linked sites. Typical carbohydrates found at these sites are displayed in FIG. 1.

Figure 2:
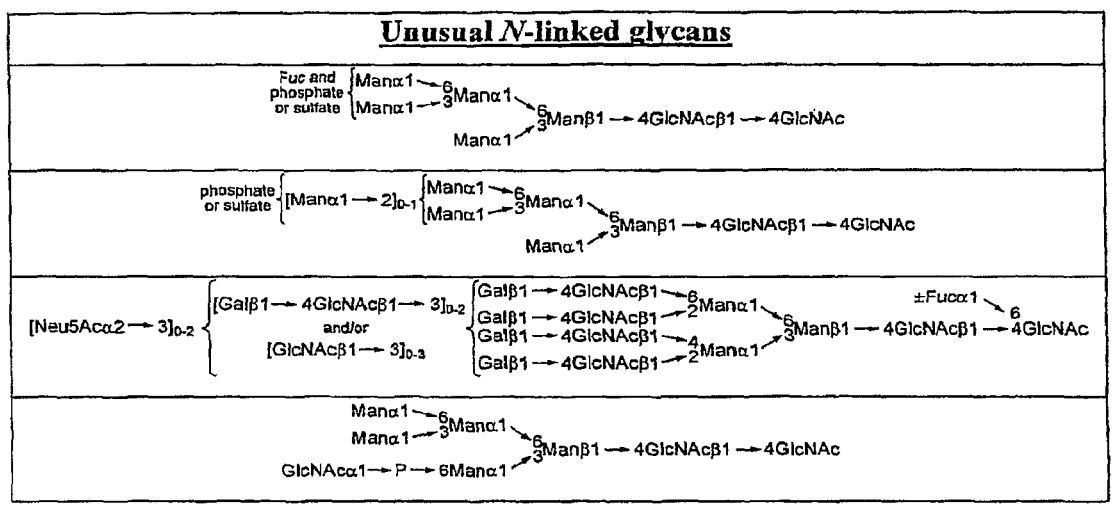
FIG. 2 depicts unusual N-linked glycans that have been observed in recombinant cell lines.

In addition to these "standard" carbohydrates, a number of unusual N-linked glycans have been identified (FIG. 2). These consist of three acidic oligomannose units having molecular masses consistent with fucosylated and non-fucosylated oligomannose 5 structures, an oligomannose 6 structure, and structures with additional N-acetyllactosamine extensions (Yuen et al., *Brit. J. Haematol.* 2003, 121, 511-526). In the case of the oligomannose structures, an additional mass of 80 was typically observed, indicating the presence of either a phosphate or sulfate residue. In addition, an oligomannose 6 structure has been reported that contains a phosphodiester-bridged N-acetylglucosamine (Nimtz et al., *FEBS Lett.* 1995, 365, 203-208) as well as N-glycans with incomplete outer chains terminated by a N-acetylglucosamine residue (Yuen et al., *Brit. J. Haematol.* 2003, 121, 511-526).

Exemplary O-Linked Glycan Synthesis

The synthesis of the major O-linked carbohydrates follows precedent from the Danishefsky laboratory, utilizing the cassette method for glycopeptide synthesis (Schwarz et al., *J. Am. Chem. Soc.* 1999, 122, 2662-2673). This methodology is summarized in Scheme 1. Utilizing this method, each individual carbohydrate is synthesized pre-linked to either serine or threonine. The "cassette" can then be used in standard solid phase peptide synthesis (SPPS) to yield the desired glycopeptide. While not maximally convergent, this method allows for the rapid buildup of glycopeptide fragments containing any of the O-linked glycans found naturally on HuEPO. In addition, the natural linkage to Ser[126] can be modified to threonine or even to another, unnatural residue.

Scheme 1. The cassette method for the synthesis of complex, sialylated, α-O-linked carbohydrates.

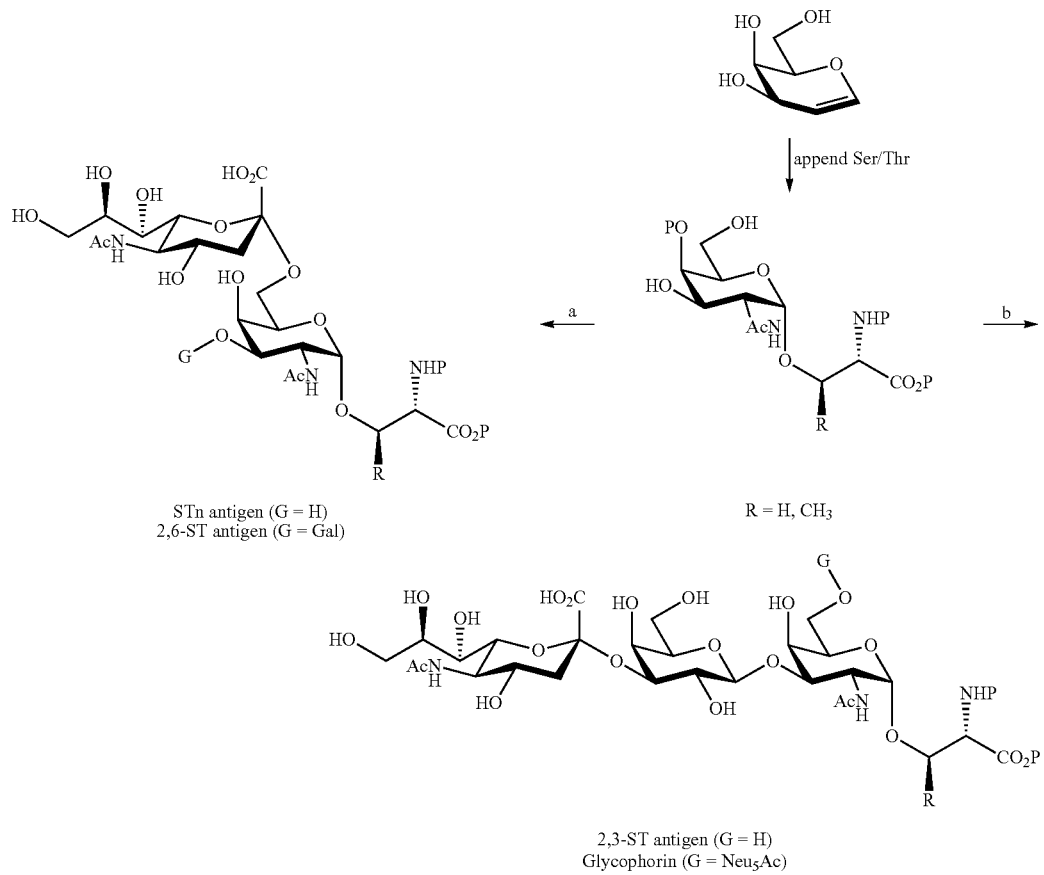

STn antigen (G = H)
2,6-ST antigen (G = Gal)

R = H, CH₃

2,3-ST antigen (G = H)
Glycophorin (G = Neu5Ac)

a) append sialic acid and galactose to the cassette, b) append sialic and sialyllactose to the cassette Exemplary N-Linked Glycan Synthesis Since the greatest amount of heterogeneity is found in the N-linked carbohydrates, and the fully assembled glycan can be attached to an intact peptide fragment, it seems important to devise a synthesis that is ultimately convergent. Given the multitude of structures observed for HuEPO, such a convergent synthesis should allow for the rapid buildup of any of the more common moieties (i.e. those found in FIG. 1). Using existing methodology, the non-fucosylated trisaccharide can be generated (Scheme 2) (Dudkin et al., *Tetrahedron Lett.* 2003, 44, 1791-1793) with the 3 and 6 positions of the β-mannoside suitably protected in such a way as to allow for access to any of the branched glycans by glycosylation with one (or more) of the branch-differentiating monosaccharide donors (Scheme 3) (Dudkin et al., *J. Am. Chem. Soc.* 2003, 126, 736-738; Mandal et al., *Angew. Chem. Int. Ed.* 2004, 43, 2557-2561; Geng et al., *Angew. Chem. Int. Ed.* 2004, 43, 2562-2565).

Scheme 2.
Exemplary synthesis of the "core" tri- or tetrasaccharides that allow for the maximally divergent synthesis of any N-linked carbohydrates found in HuEPO.

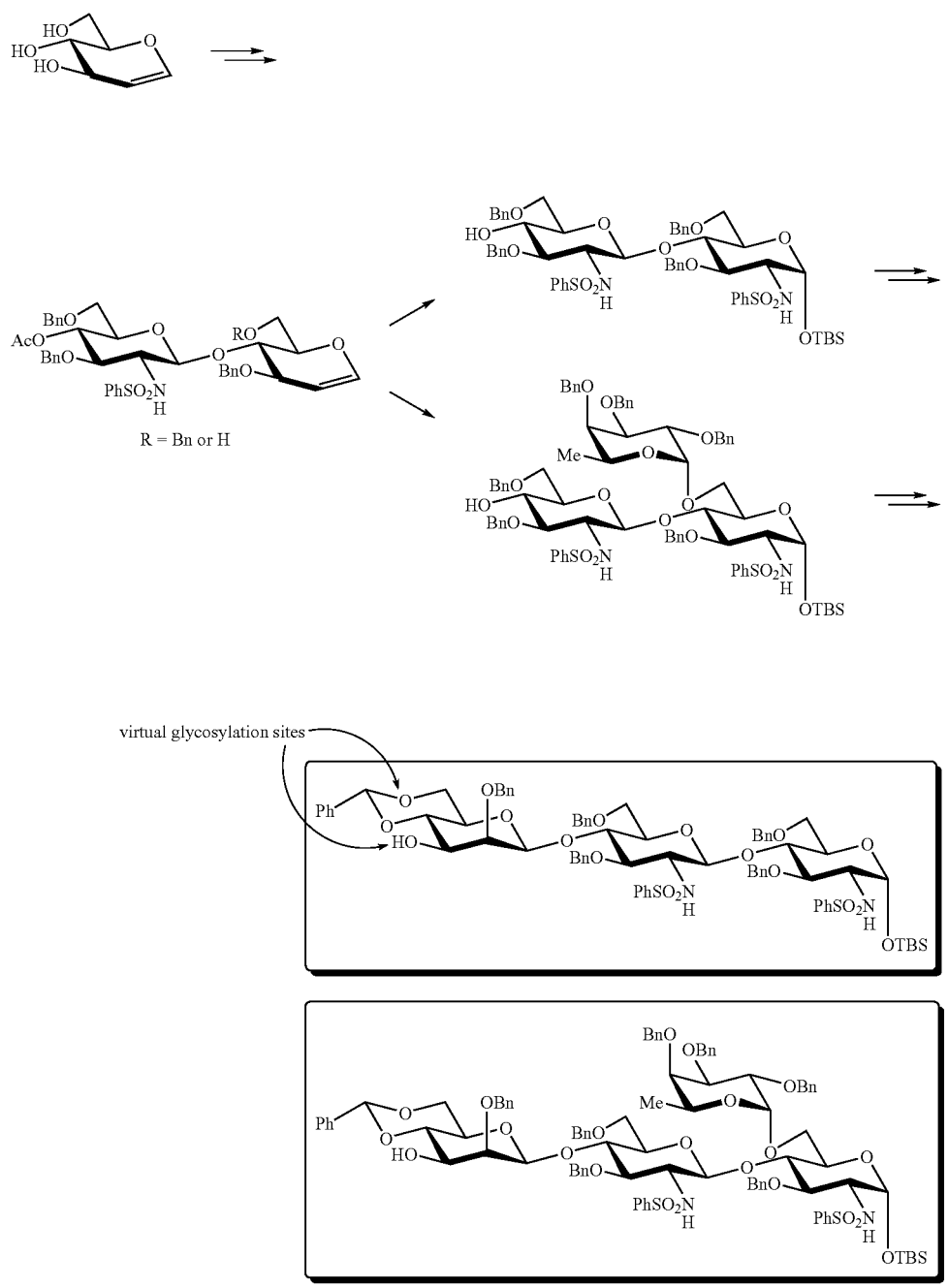

Scheme 3.
Exemplary synthesis of the "core" penta- and hexasaccharides that allow for the generation of the di-, tri- or tetraantennary N-linked glycans found in HuEPO. The degree of branching depends on the monosaccharide donor used in the initial gylcosylation.

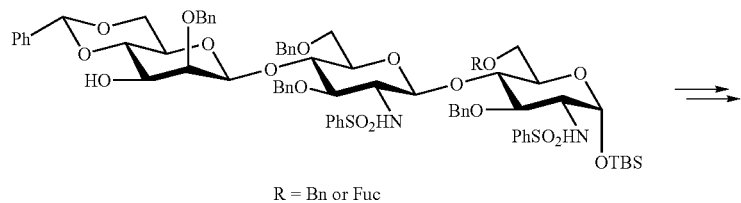

R = Bn or Fuc

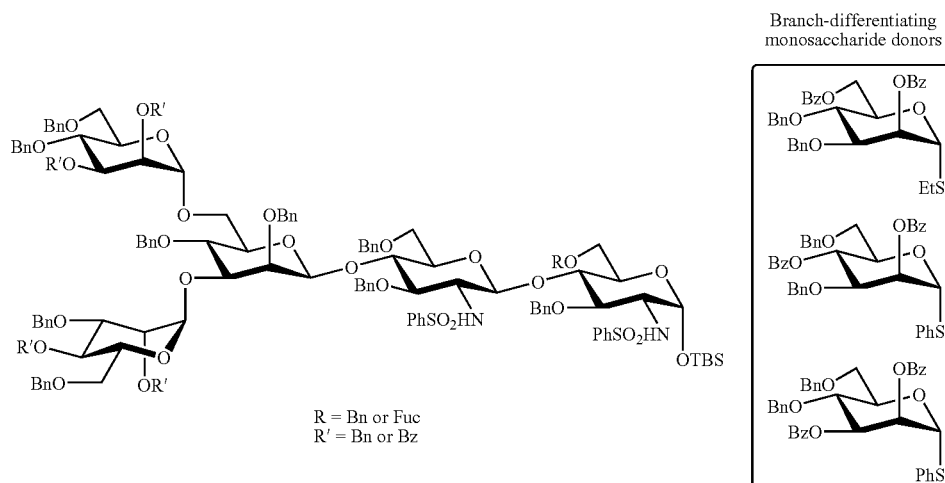

R = Bn or Fuc
R' = Bn or Bz

Branch-differentiating monosaccharide donors

The sialic acid-containing trisaccharide donor can be assembled utilizing the monosaccharides shown in Scheme 4. Application of this sequence permits the rapid generation of the trisaccharide in such a way as to allow for modification at any step to include any of the more unusual branching units.

Scheme 4.
Synthesis of the "wing" trisaccharide donor.

Representative monosaccharides used in the synthesis of the wing trisaccharide

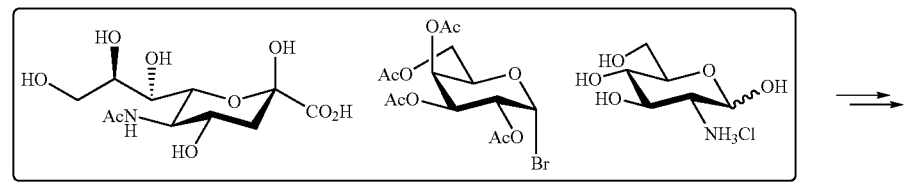

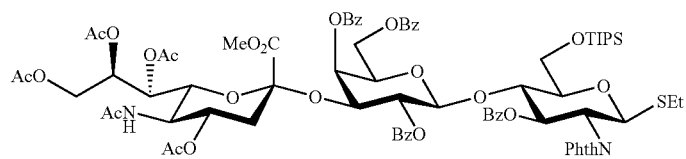

In the final steps of the synthesis, the trisaccharide is combined with either the pentasaccharide or (fucose-containing) hexasaccharide to generate the desired di-, tri- or tetraantennary glycan as a glycosylamine (Scheme 5). By using this convergent strategy, extension of the synthesis to include any of the "unusual" N-linked glycans should easily be accomplished.

bohydrate, synthesis will be accomplished via the cassette method (Danishefsky et al., *Angew. Chem. Int. Ed.* 2000, 39, 836-863). Using the "cassettes" shown in Scheme 1, the glycopeptide is generated using standard solid phase peptide synthesis (SPPS). For fragments containing a N-linked carbohydrate, a much more convergent route can be taken. Each

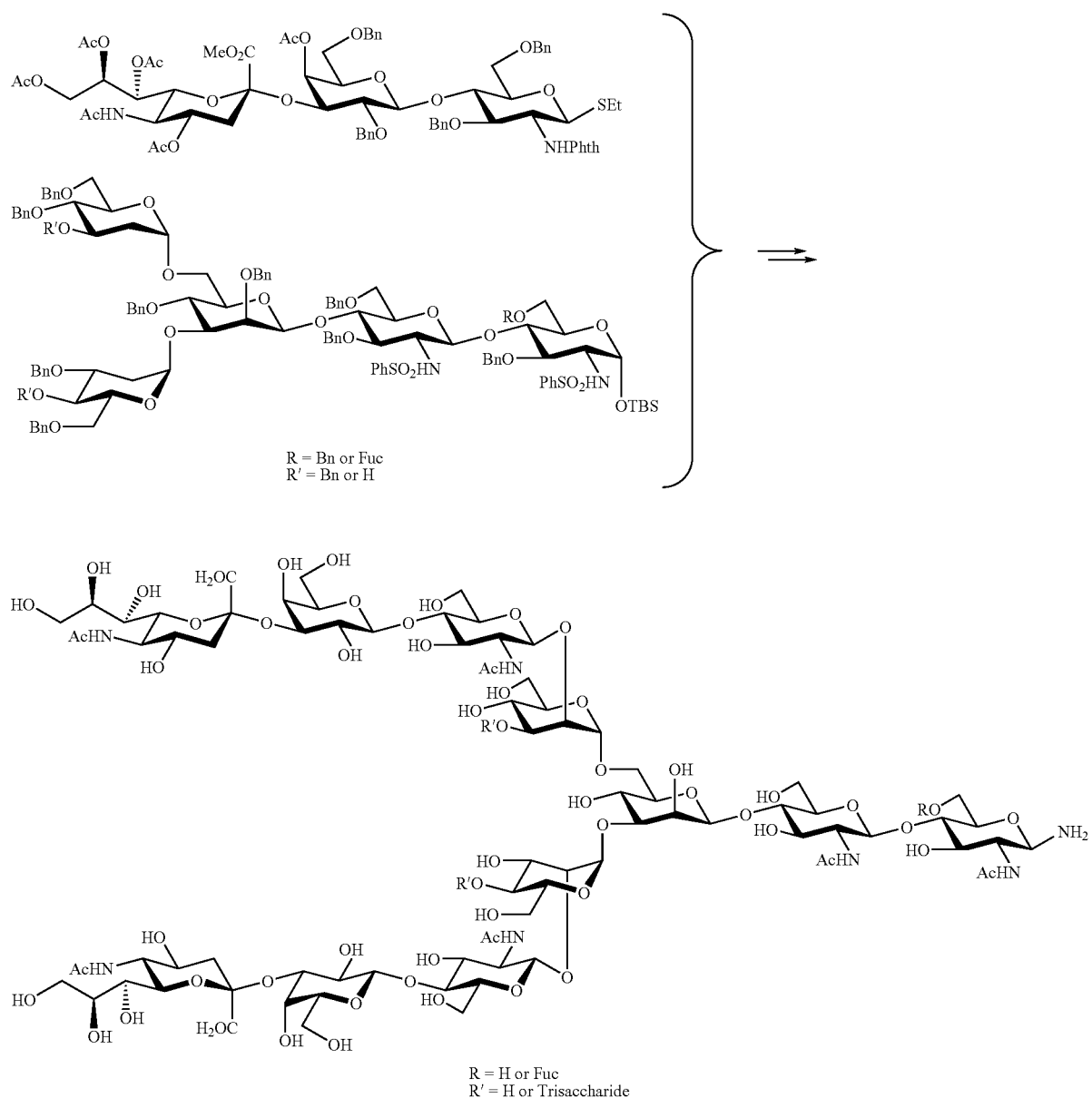

Assembly of the Glycopeptide Fragments

In order to maintain ultimate convergence, and to allow for individual glycans to be freely substituted, small peptide fragments will be generated, each one potentially containing a carbohydrate. For the fragment containing an O-linked carbohydrate, individual carbohydrate is synthesized as a glycosylamine and then linked to a pre-made peptide chain using conditions set out by Kochetkov (Likhosherstov et al., *Carbohydr. Res.* 1986, 146, C1-C5) and Lansbury (Cohen-Anisfeld et al., *J. Am. Chem. Soc.* 1993, 115, 10531-10537) (Scheme 6).

Scheme 6. Synthesis of glycopeptide fragments containing O- and N- linked glycans.

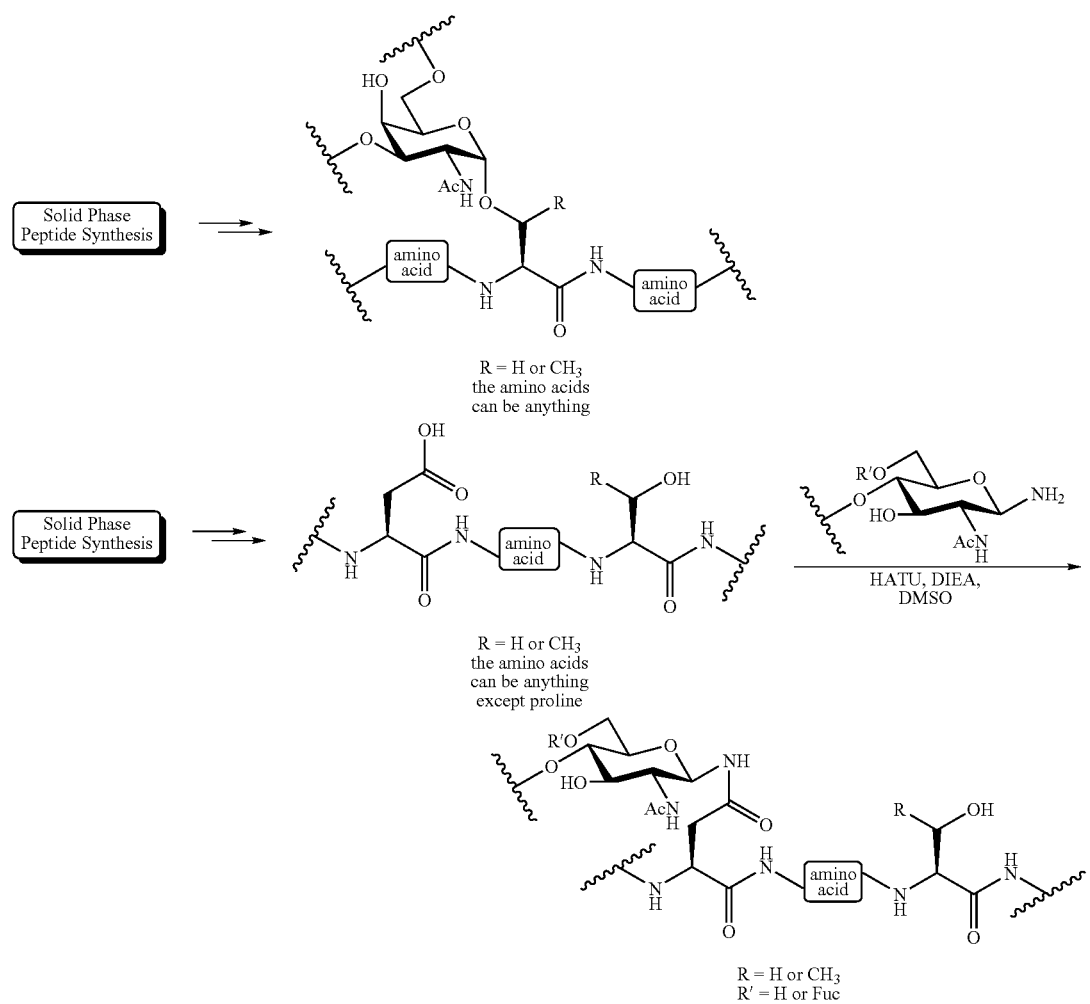

Figure 3:
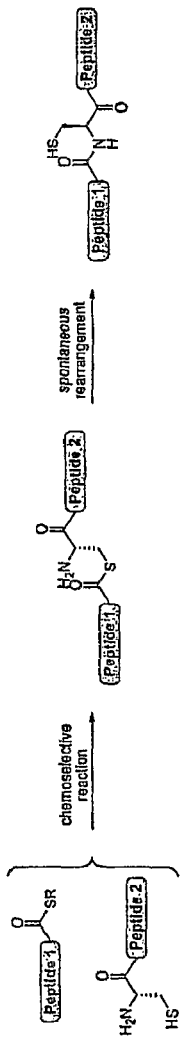
FIG. 3 depicts Native Chemical Ligation.

Assembly of the fully intact glycoprotein can be accomplished by coupling the various glycopeptide fragments using Native Chemical Ligation (NCL) (Warren et al., *J. Am. Chem. Soc.* 2004, 126, 6576-6578). In NCL, reaction between a N-terminal peptide thioester and C-terminal cysteine-containing peptide results in the formation of a native amide bond at the reaction site (FIG. 3)—"cysteine-dependent NCL". This methodology has already been extended to include the use of glycopeptides on the cysteine-containing reaction partner (peptide 2, FIG. 3) (Dudkin et al., *J. Am. Chem. Soc.* 2003, 126, 736-738).

Figure 4:
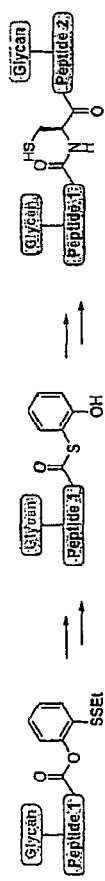
FIG. 4 depicts a In situ generation of the thioester requisite for Native Chemical Ligation.

One of the limitations in using NCL as that it was initially described is the necessity of peptide thioesters as one of the coupling partners. Given the expected difficulty in synthesizing glycopeptide thioesters, it was clear that the ultimate success of the erythropoietin project would initially rely on the ability to resolve this issue. We recently disclosed a novel method for accomplishing NCL using "virtual" glycopeptide thioesters (Offer et al., *J. Am. Chem. Soc.* 2002, 124, 4642-4646). This method relies on the use of a phenolic ester equipped with an ortho disulfide moiety to replace the thioester (FIG. 4). Under the reaction conditions the disulfide is cleaved, generating a thiolate and setting the stage for an in situ elaboration into a thioester, putatively via an intermolecular O→S acyl migration. Upon generation of the thioester in situ, the reaction is able to intersect the normal machinery of NCL.

Figure 5:
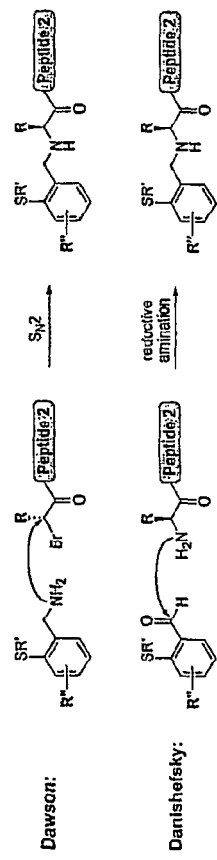
FIG. 5 depicts a comparison of two approaches to a cysteine surrogate for NCL.

A second limitation in using existing NCL methodology is that the reaction requires a cysteine as one of the coupling partners, severely impacting the choices for individual fragment coupling. One promising strategy to avoid the use of cysteine has been reported by Dawson (Offer et al., *J. Am. Chem. Soc.* 2002, 124, 4642-4646). In this case, a sulfur-containing auxilliary is attached to the N-terminal coupling partner that effectively mimics cysteine, and can be reacted with a peptide thioester following standard NCL conditions. One potential drawback of this methodology is how the auxilliary is attached to the peptide; another is the way it is removed. Dawson reports the synthesis via an $S_N2$ route, displacing an α-bromo amide with a benzylic amine. This methodology is expected to be limited to either glycine or alanine, as complete inversion of the α-center might become an issue. In addition, the Dawson methodology has not been tested with functionalized peptides as coupling partners, such as glycopeptides. The present invention establishes that the same auxiliary can be reached via reductive amination of a benzaldehyde derivative. Thus, in constrast to the Dawson methodology, potentially any amino acid can be used to bear the sulfur-containing auxiliary (FIG. 5).

Figure 6:
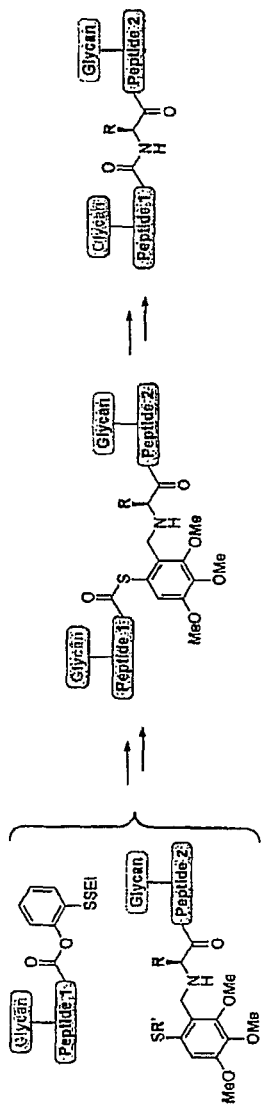
FIG. 6 depicts a cysteine-free Native Chemical Ligation.
Figure 7:
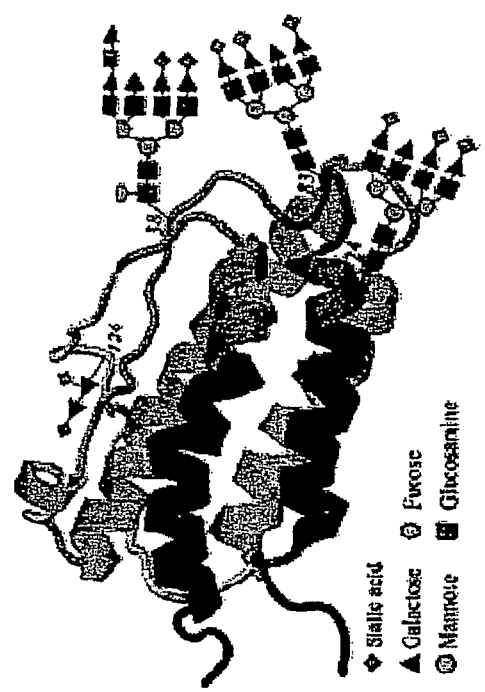
FIG. 7 depicts a structure of Erythropoietin.
Figure 8:
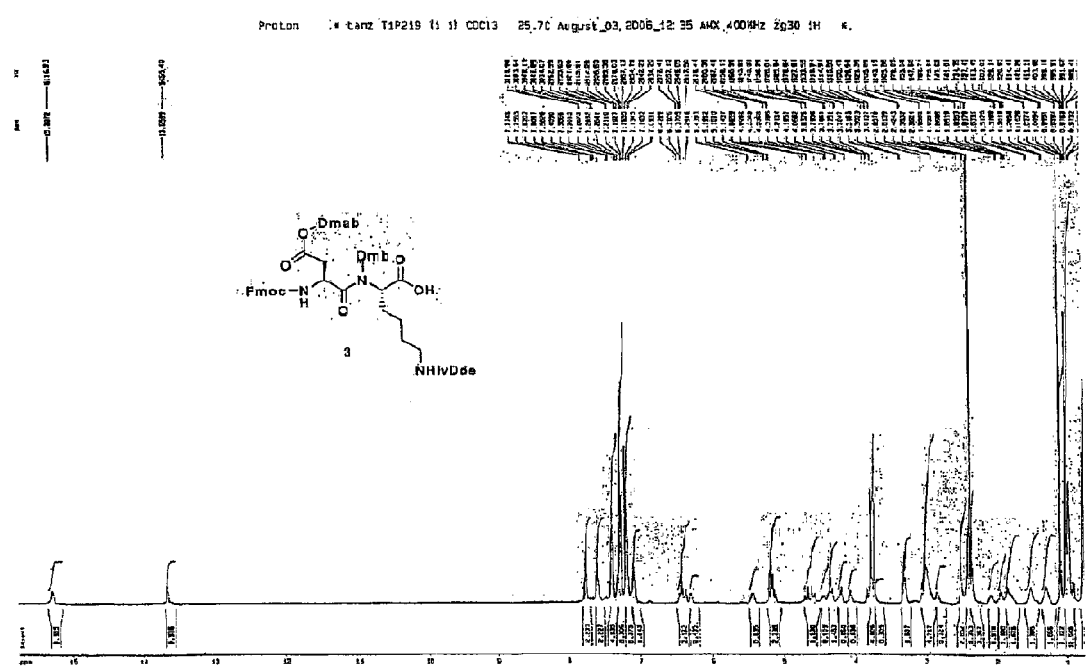
FIG. 8 depicts an $^1$H NMR spectrum of compound 3 (Example 1).
Figure 9:
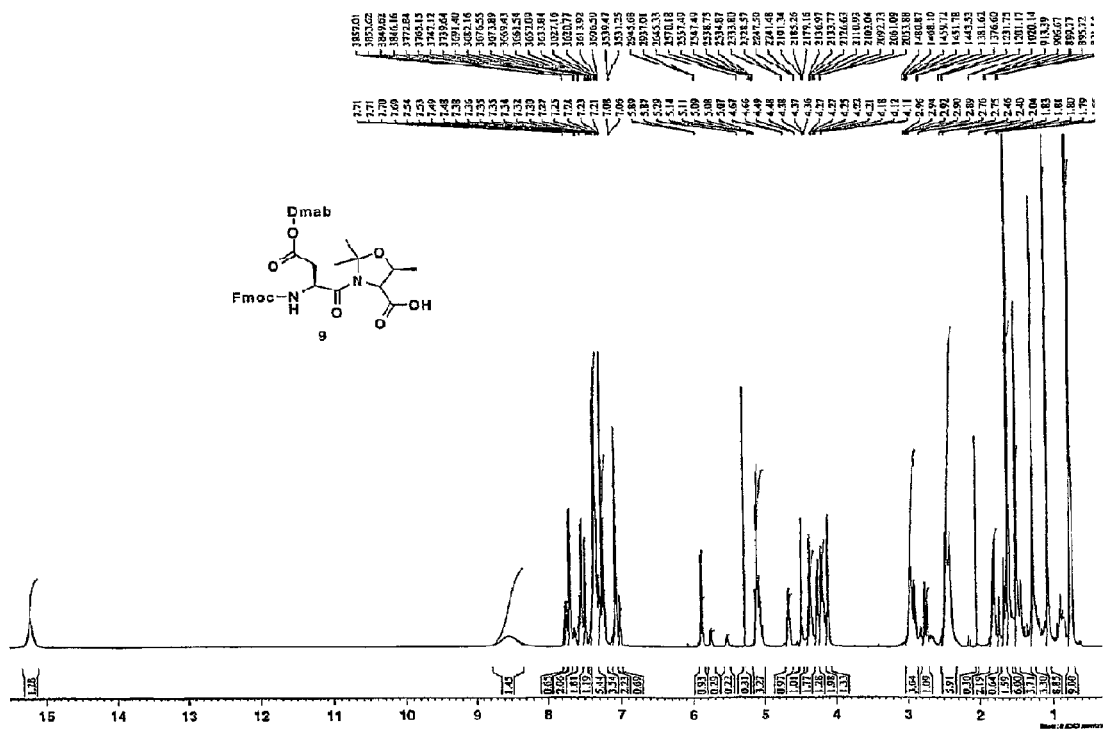
FIG. 9 depicts an $^1$H NMR spectrum of compound 9 (Example 1).
Figure 10:
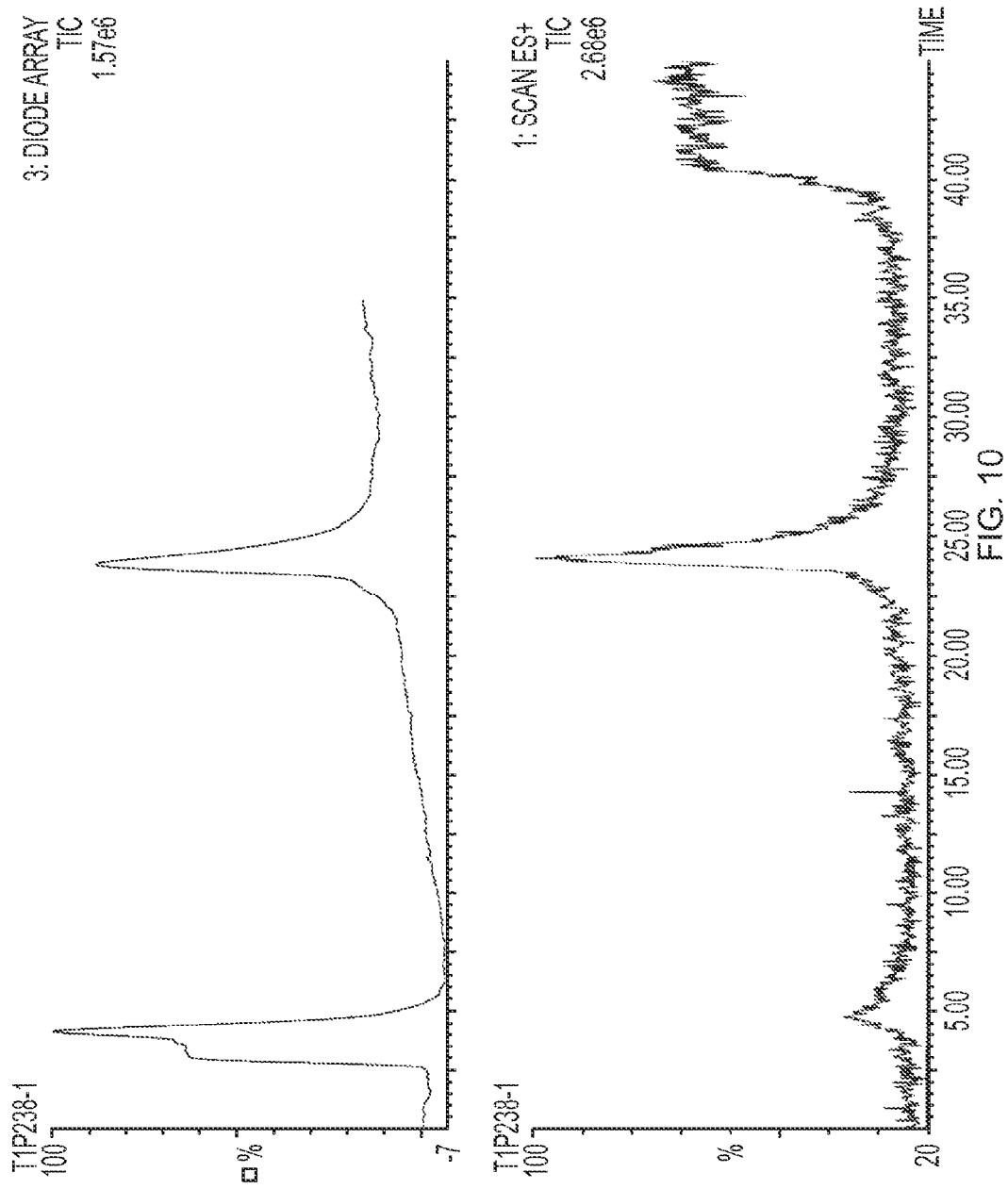
FIG. 10 depicts LC-MS of peptide 8: 45-65% acetonitrile in water in 30 min, C4 analytical column.
Figure 11:
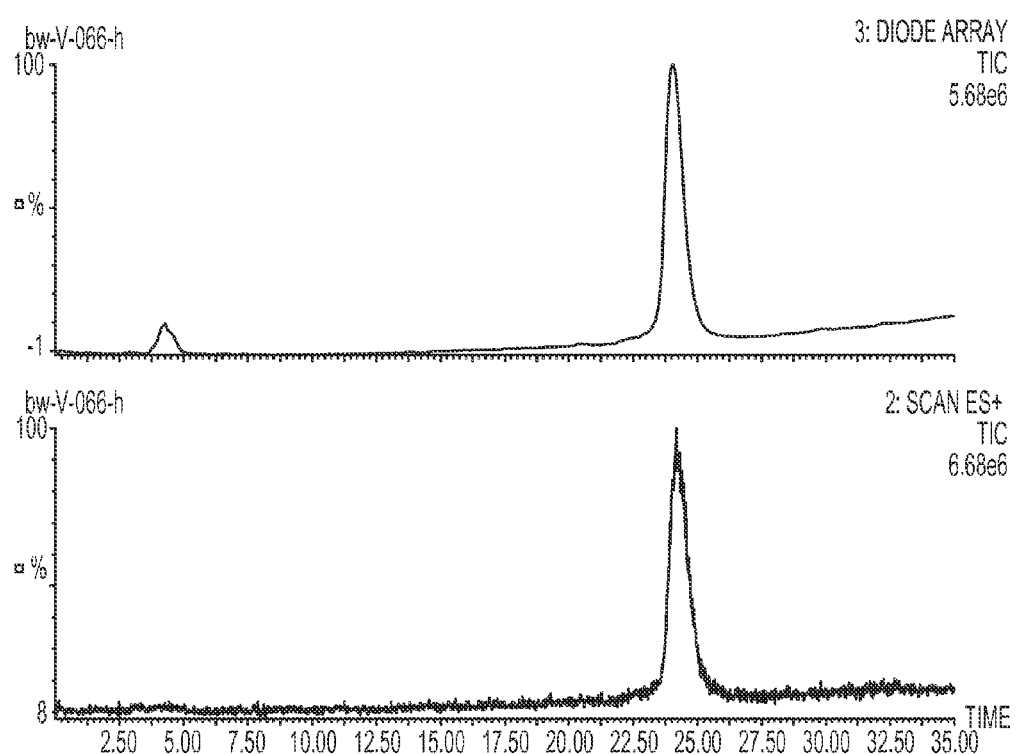
FIG. 11 depicts LC-MS of peptide 17: 40-80% acetonitrile in water over 25 min, C4 analytical column.
Figure 12:
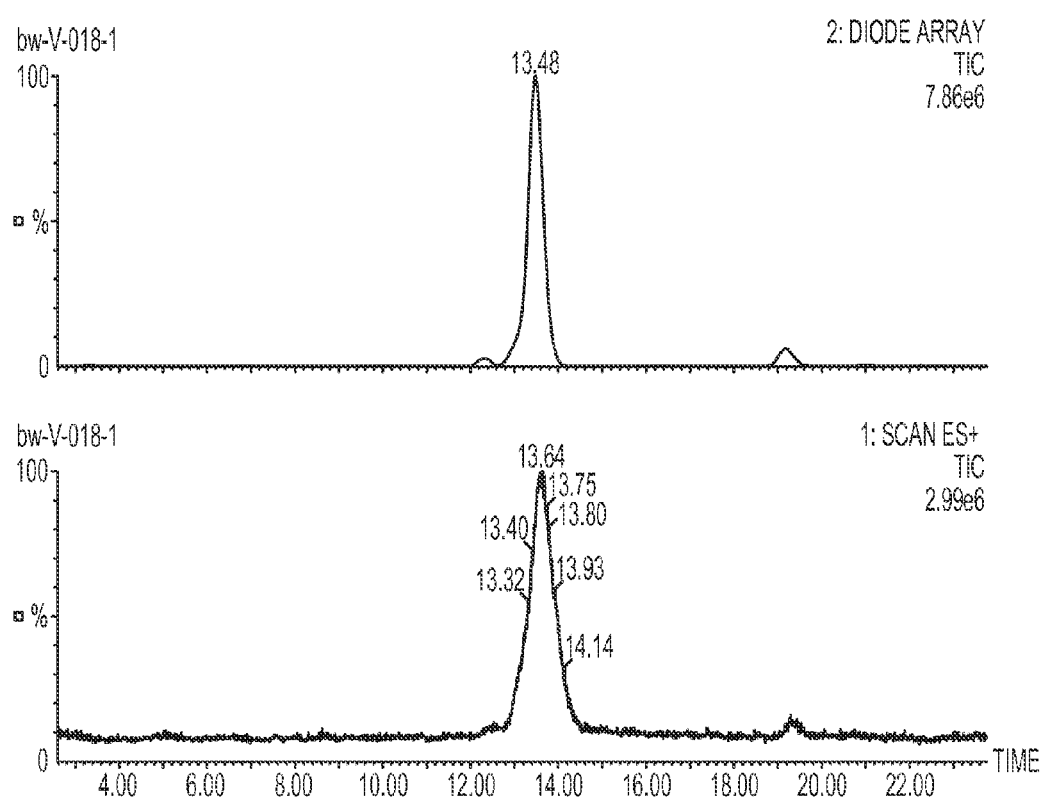
FIG. 12 depicts LC-MS of glycopeptide 9: 30-70% acetonitrile in water over 20 min.
Figure 13:
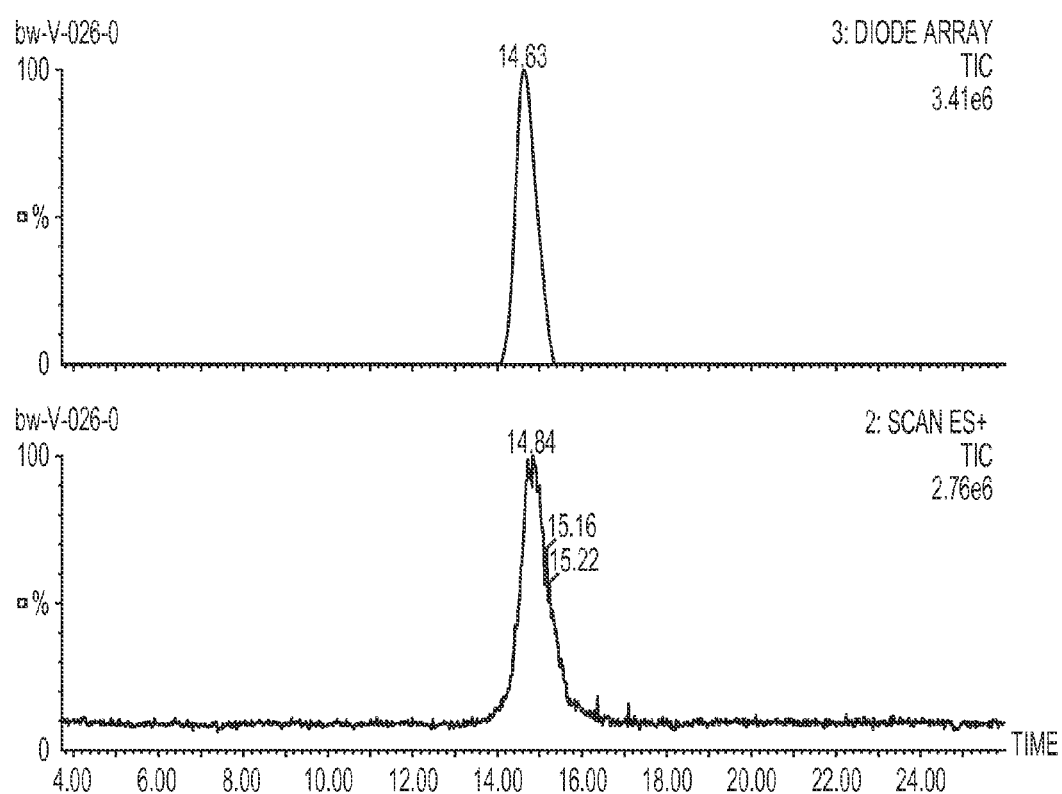
FIG. 13 depicts LC-MS of glycopeptide 1: 20-50% acetonitrile in water over 20 min.
Figure 14:
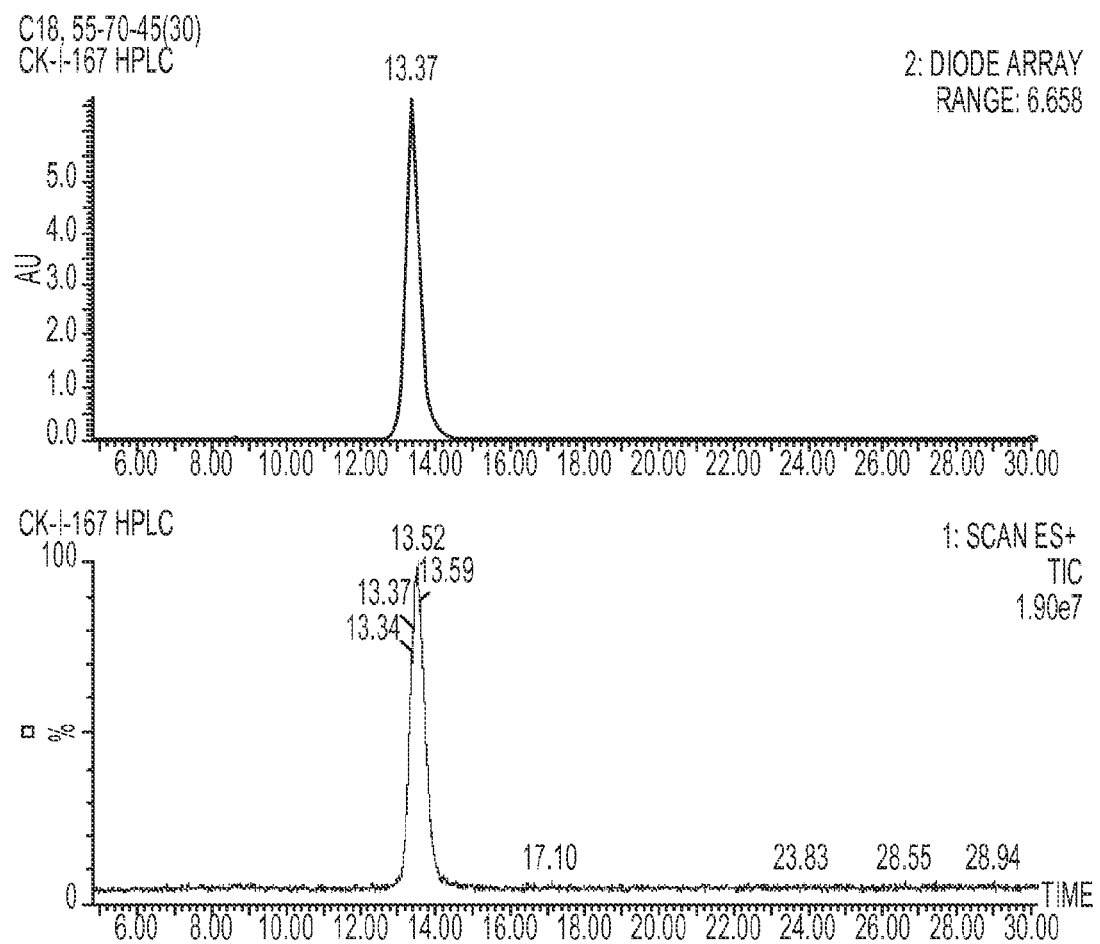
FIG. 14 depicts LC-MS of peptide 104: C18 analytical column, 55%-70% MeCN/H$_2$O over 30 min.
Figure 15:
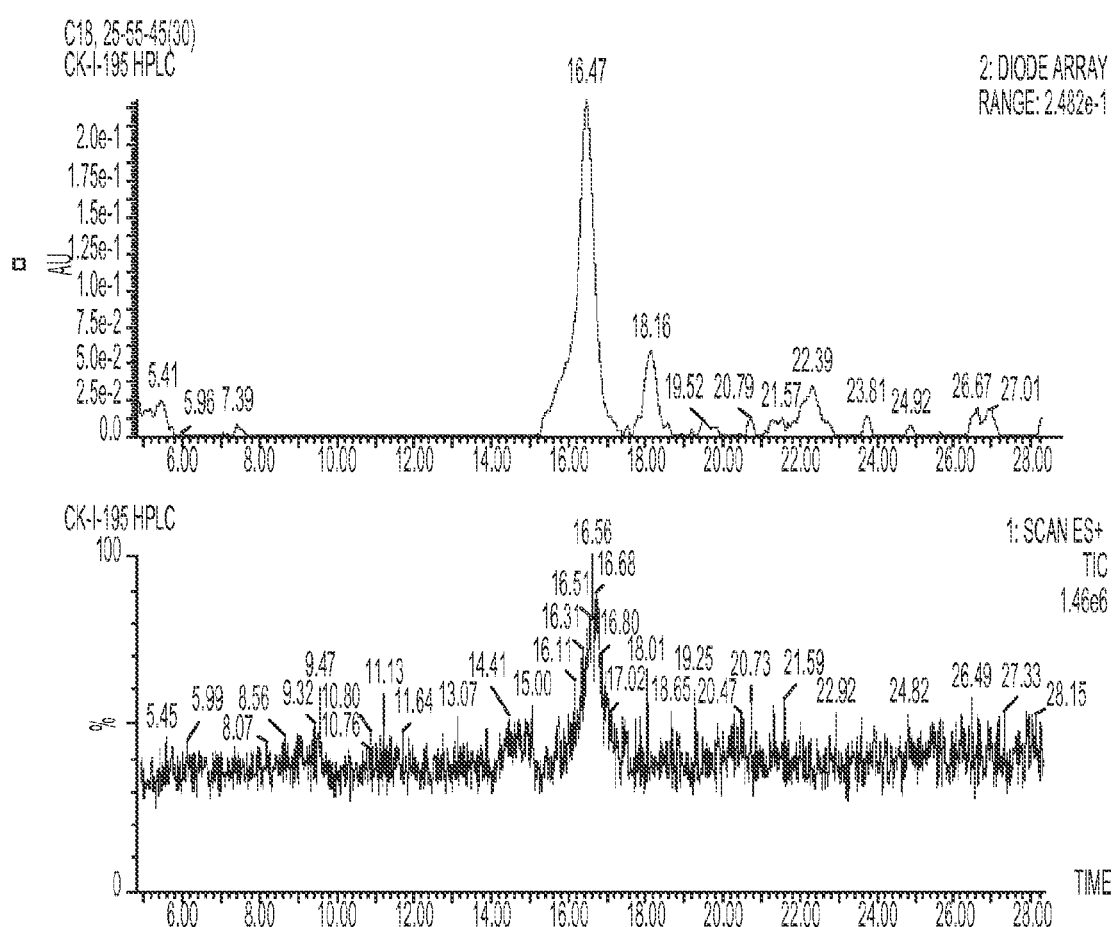
FIG. 15 depicts LC-MS of peptide 106: C18 analytical column, 25%-55% MeCN/H$_2$O over 30 min.
Figure 16:
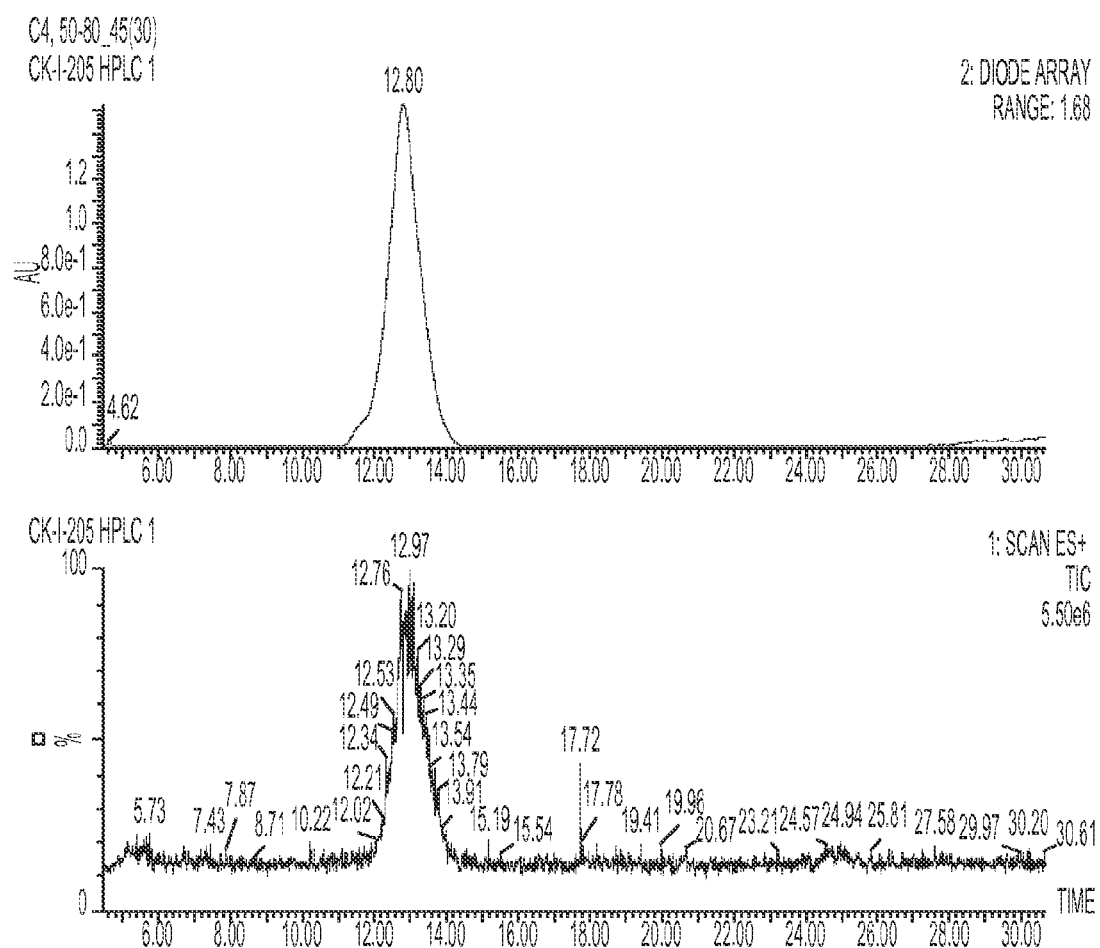
FIG. 16 depicts LC-MS of peptide 109: C18 analytical column, 25%-55% MeCN/H$_2$O over 30 min.
Figure 17:
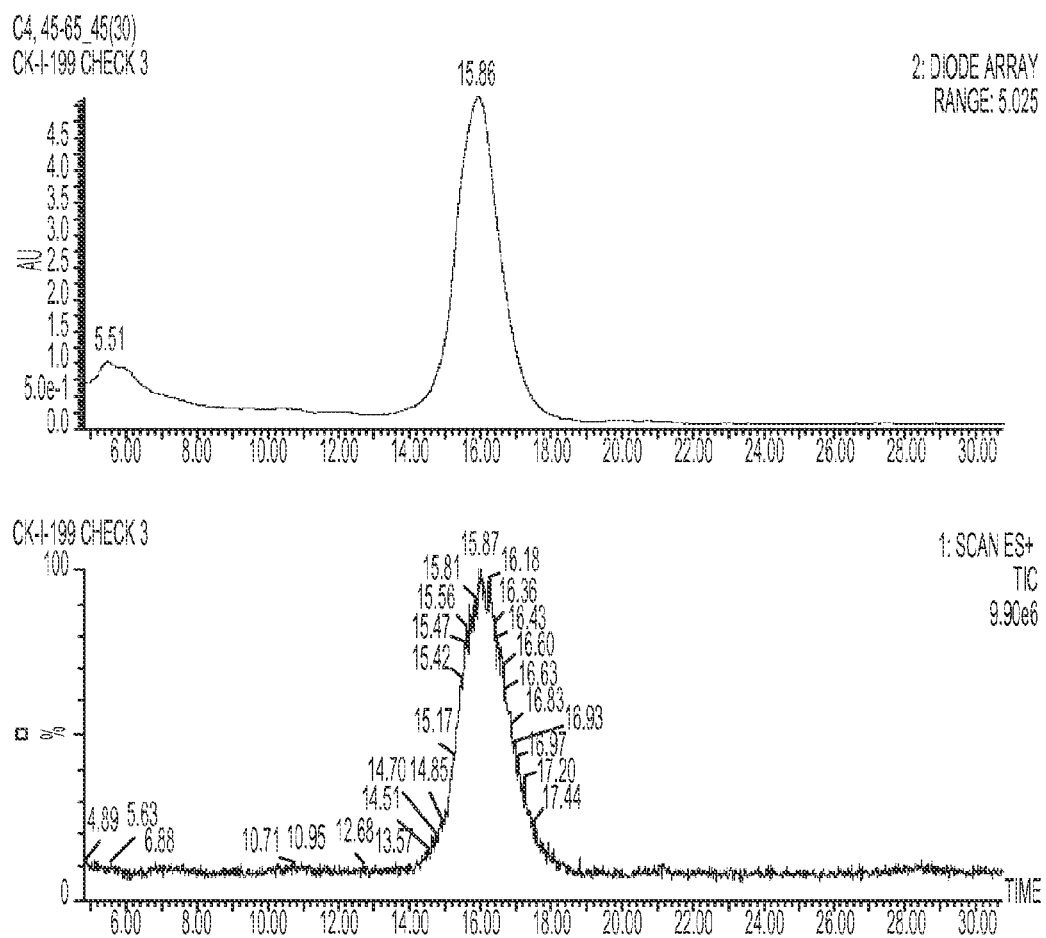
FIG. 17 depicts LC-MS of peptide 101: C4 analytical column, 45%-65% MeCN/H$_2$O over 30 min.

Upon generation of the N-terminal auxiliary, our previously developed methodology can be used to link two glycopeptides (FIG. 6). Here, the auxiliary intercepts the normal mechanism of NCL at the point of trans-thioesterification, leading to an intermediary unimolecular thioester. Rearrangement of this intermediate gives the native amide with the auxiliary still attached. Subsequent removal of the auxiliary under acidic conditions provides a "cysteine-free" Native Chemical Ligation.

Completion of an Exemplary Synthesis

The skilled practioner will recognize that piecing together the individual fragments of EPO using the inventive method can be accomplished in a number of ways. One such way is shown in Scheme 7. Here the glycoprotein is broken up into four smaller fragments, each containing a (possibly different) carbohydrate. In this iteration, we build the protein from the C-terminus to the N-terminus, although this doesn't always have to be the case. Thus, beginning with a fragment representing $Ala^{114}$-$Arg^{166}$, we ligate the fragment representing $Gln^{78}$-$Gly^{113}$, using "cysteine free" conditions. After "activation" of the latent auxilliary attached at the N-terminus of the newly fashioned glycopeptide, we perform a second "cysteine free" ligation, this time adding a fragment representing $Cys^{29}$-$Gly^{77}$. The final fragment, representing $Ala^1$-$Gly^{28}$, is attached using cysteine-based Native Chemical ligation, following deprotection of the thiol functionality at $Cys^{29}$. With the fully intact peptide backbone in place, a final deprotection to remove the ligation auxiliaries and any side-chain protecting groups that might be remaining, followed by protein folding will deliver the functional glycoprotein (Proper protein folding is not anticipated to be a problem as Kent and co-workers have demonstrated such folding occurs when the EPO backbone is modified by the attachment of polymers.).

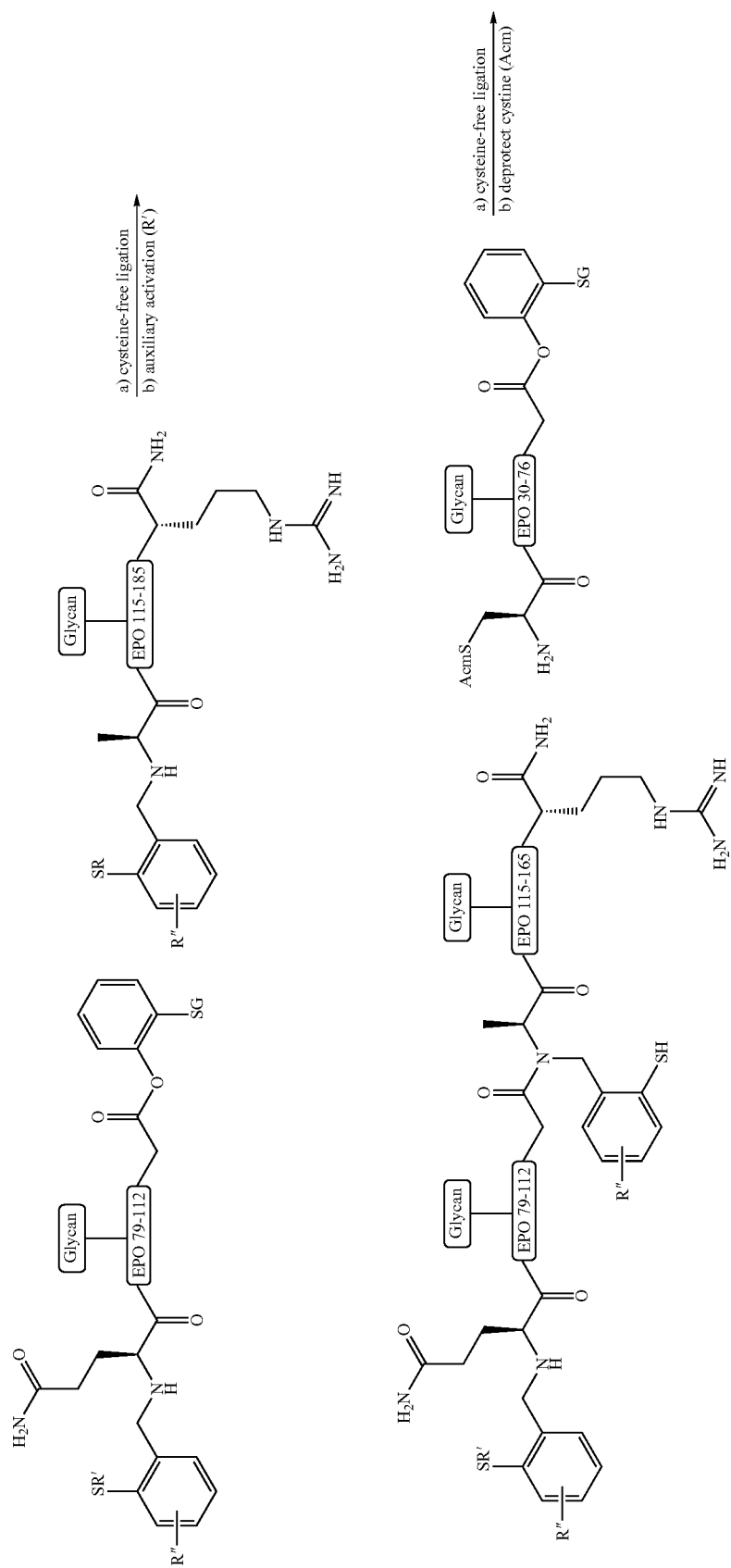
Scheme 7.
Completion of a fully synthetic homogeneous HuEPO.

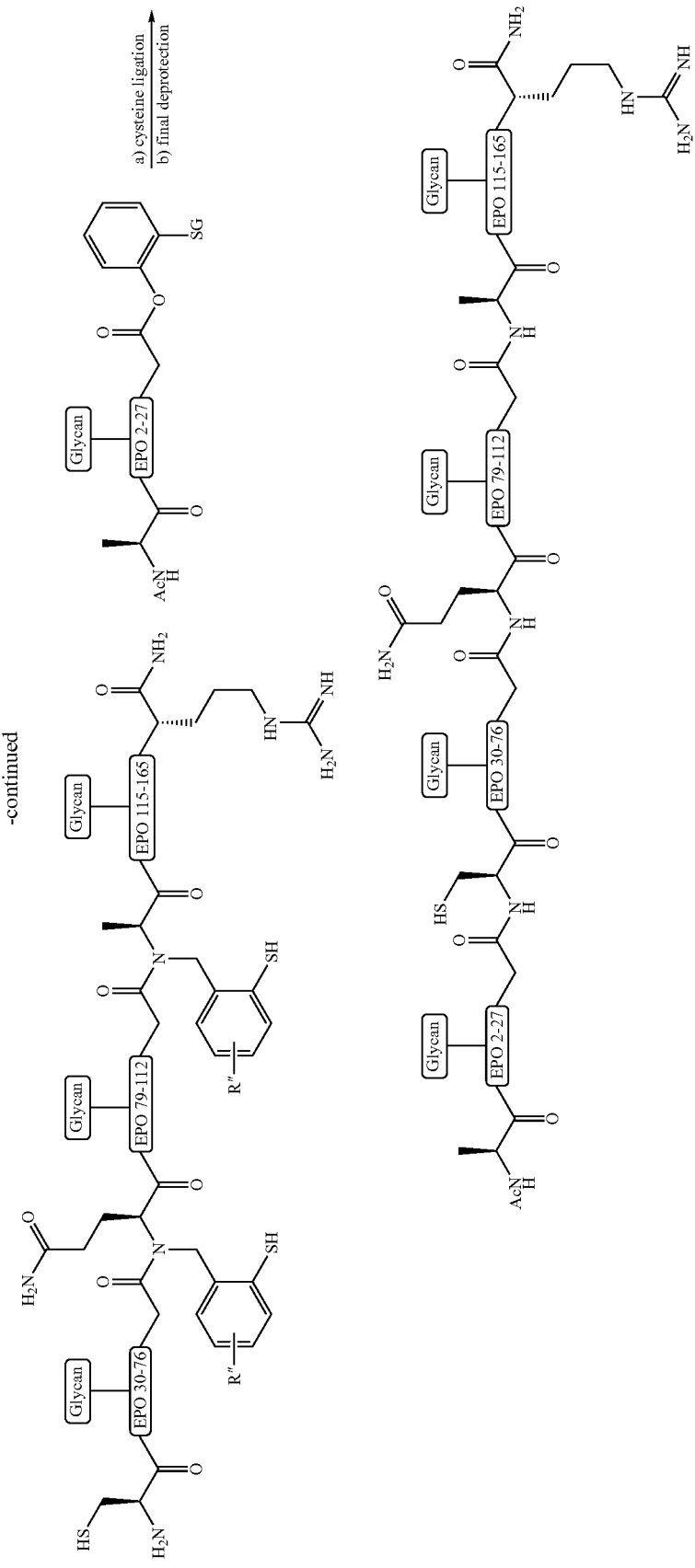

It is understood that the above synthetic approach is but one example of how homogeneous HuEPO may be pieced together using the inventive method in combination with the cysteine-dependent native chemical ligation methodology. A variety of other approaches, using different EPO peptide fragments, and/or using solely the inventive cysteine-free method fall within the scope of the invention.

Accordingly, there is provided herein a method for preparing glycopeptides or glycoproteins comprising at least two carbohydate domains covalently attached thereto. In certain embodiments, some or all of carbohydrate domains are O-linked. In certain other embodiments, some or all of carbohydrate domains are N-linked. In certain embodiments, the glycopeptide or glycoprotein comprises two or more carbohydate domains covalently attached thereto, wherein the glycopeptide or glycoprotein sequence between each point of attachment of the carbohydrate domains does not comprise a cysteine residue. In certain embodiments, the glycopeptide or glycoprotein comprises two or more carbohydate domains covalently attached thereto, wherein the glycopeptide or glycoprotein sequence between each point of attachment of the carbohydrate domains comprises a cysteine residue. In certain embodiments, the mutli-glycan glycopeptide or glycoprotein is prepared by cysteine-free Native Chemical Ligation. In certain embodiments, the mutli-glycan glycopeptide or glycoprotein is prepared by a combination of cysteine-free and cysteine-dependent Native Chemical Ligation (i.e., where at least one glycopeptide ligation step is accomplished by cysteine-free NCL, and at least one glycopeptide ligation step is accomplished by cysteine-dependent NCL). In certain embodiments, the method allows for coupling where each coupling partner is a glycopeptide itself. Symmetrical, non-symmetrical and mixed (N-linked and O-linked) glycopeptides can be obtained. In certain embodiments, the method involves the in situ generation of a thioester that is then used immediately in native chemical ligation.

It is understood that, although the discussion above regarding Cysteine-free Native Chemical Ligation focuses on the preparation of multiglycosylated peptides or proteins, the method may readily be adapted to other polyfunctionalized peptides and/or proteins. For example, peptides and/or proteins functionalized at more than one amino acid site with a pharmaceutically useful group or entity may be prepared by the method of the invention.

EQUIVALENTS

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. In but one illustrative example, protecting groups play an important role in the synthesis of the carbohydrate domains and synthetic conjugates, as described herein; however it will be appreciated by one of ordinary skill in the art that the present invention encompasses the use of various alternate protecting groups known in the art. Those protecting groups used in the disclosure including the Examples below are merely illustrative.

It should further be appreciated that, uless otherwise indicated, the contents of those cited references are incorporated herein by reference to help illustrate the state of the art. The following examples contain important additional information, exemplification and guidance which can be adapted to the practice of this invention in its various embodiments and the equivalents thereof.

EXAMPLES

The method of this invention can be understood further by the examples that illustrate some of the processes by which the inventive method may be practice. It will be appreciated, however, that these examples do not limit the invention. Variations of the invention, now known or further developed, are considered to fall within the scope of the present invention as described herein and as hereinafter claimed.

1) General Description of Synthetic Methods:

The practitioner has a a well-established literature of peptide, protein and glycoside chemistry to draw upon, in combination with the information contained herein, for guidance on synthetic strategies, protecting groups, and other materials and methods useful for practicing the method of this invention.

The various references cited herein provide helpful background information on preparing complex glycosides, glycosylated peptides and other glycosylated constructs that may be applied and/or adapted to the method of the present invention.

According to the present invention, any available techniques can be used to practice the method of the invention. For example, a variety of solution phase synthetic methods such as those discussed in detail below may be used. Alternatively or additionally, a variety combinatorial techniques, parallel synthesis and/or solid phase synthetic methods known in the art may be used.

Starting materials and reagents used in practicing the specific embodiments of the invention detailed below and herein are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", $2^{nd}$ ed. VCH Publishers. These schemes are merely illustrative of some embodiments of the present invention, and various modifications to these schemes can be made and will be suggested to a person of ordinary skill in the art having regard to this disclosure.

In practicing the invention, starting materials, intermediates, and compounds may be isolated and purified using conventional techniques, including filtration, distillation, crystallization, chromatography, and the like. They may be characterized using conventional methods, including physical constants and spectral data.

Methods for preparing glycopeptides (e.g., O- or N-linked glycopeptides) and for conjugating peptides and glycopeptides to carriers are known in the art. For example, guidance may be found in U.S. Pat. No. 6,660,714; U.S. patent application Ser. Nos. 09/641,742; 10/209,618; and 10/728,041; U.S. Provisional Patent Application Nos. 60/500,161; 60/500,708 and 60/560,147; and International Patent Application Nos. PCT/US03/38453, PCT/US03/38471 and PCT/

US2004/29047; each of the above-referenced patent documents are hereby incorporated by reference herein.

Overview

The development of increasingly efficient and general methods for the merging of complex peptidic fragments remains a central objective in the field of polypeptide and glycopolypeptide synthesis. A number of traditional native chemical ligation (NCL) techniques have been applied to the problem of polypeptide assembly through convergent ligation (Dawson et al., *Science,* 1994, 266, 776-779; Wilken et al., *Curr. Opin. Biotech.* 1998, 9, 412-426; Yeo et al., *Chem. Eur. J.* 2004, 10, 4664-4672). Nearly all of these require the presence of an N-terminal cysteine residue to function as the acyl acceptor. Given the relative scarcity of cysteine residues in nature, there remains a need for new NCL capabilities that do not require cysteine residue at the site of ligation.

Preparation of Polyglycosylated Proteins

The development of efficient methods for the preparation of homogeneous, fully synthetic polypeptides, and even proteins, displaying multiple sites of glycosylation is needed. One interesting target glycoprotein which the present invention allows synthetic access to is the naturally occurring erythropoietin alpha (EPO) (Ridley et al., *J. Natl. Med. Assoc.* 1994, 86, 129-135). This multiply glycosylated protein has found widespread therapeutic application in the treatment of anemia. Despite the clear-cut clinical importance of this compound, attempts to rigorously evaluate the role of glycosylation on the activity and stability of erythropoietin have thus far been complicated by the daunting difficulties associated with isolating significant quantities of homogeneous EPO (Kornfeld et al., *Annu. Rev. Biochem.* 1985, 54, 631-664; Roth, *Chem. Rev.* 2002, 102, 285-303). Making use of existing knowledge in the area of carbohydrate and glycopeptide total synthesis (Danishefsky et al., *Angew. Chem.* 1996, 108, 1482-1522; *Angew. Chem. Int. Ed.* 1996, 35, 1380-1419; S. J. Danishefsky et al., *Angew. Chem.* 2000, 112, 882-912; Angew. *Chem., Int. Ed.* 2000, 39, 836-863), the present invention establishes the first synthesis of fully synthetic, homogeneous erythropoietin. Although the examples below focus on the preparation of one EPO glycoform, the scope of the present invention extend to the preparation of a wide variety of EPO analogs, both naturally occurring and non-naturally occurring. Thus, the present invention allows access to isolated EPO analogs, which are useful for conducting SAR-type investigations. It is to be understood that the inventive method is applicable to the fully synthetic preparation of a wide variety of functionalized peptides and proteins. Accordingly, the present invention provides generally useful strategies and protocols of great utility to the entire field of glycoprotein synthesis, or functionalized proteins in general.

Erythropoietin is a 166-residue protein possessing four sites of glycosylation. Three of these are N-linked to asparagine residues and one is O-linked to a serine residue. Erythropoietin having only four cysteine residues, existing cysteine-dependent NCL methodologies would not be suitable for effecting a highly convergent erythropoietin synthesis, particularly in light of the fact that the four cysteine residues of erythropoietin do not segregate into nearly equal sized carbohydrate domains. By contrast, the present invention enables a maximally convergent route to erythropoietin, involving the ligation of four different glycopeptide fragments, the amino acid sequence of which is not determined by the position of cysteine residues. Rather, the person of ordinary skill in the art has great liberty in selecting the glycopeptide fragments to be joined through ligation. In particular, the person of ordinary skill in the art is not limited to using glycopeptide fragments having a cysteine-based acyl acceptor.

Scheme 8a projects, in the most general terms, a scenario wherein two differentially glycosylated peptide fragments (cf 1 and 2) are temporarily engaged through an auxiliary linker, (Warren et al., *J. Am. Chem. Soc.* 2004, 126, 6576-6578). While the O→S acyl transfer method which we have developed and its application to complex glycopeptide synthesis had not been reported, the general concept of chemical ligation of polypeptides through (i) an organizing preliminary attachment, (ii) acyl transfer, (iii) de-convolution with emergence of a peptide bond establishing the ligation has a distinguished intellectual history. For an early paper that can be so classified, see: Brenner et al., *Helv. Chim. Acta.* 1957, 40, 1497-1517. The key seminal advance was incubated in a series of papers by Kemp: Kemp et al., *Tetrahedron Lett.* 1981, 22, 181-184; Kemp et al., *Tetrahedron Lett.* 1981, 22, 185-186; Kemp et al., *J. Org. Chem.* 1981, 46, 490-498; Kemp, *Biopolymers* 1981, 20, 1793-1804; Kemp et al., *J. Org. Chem.* 1986, 51, 1821-1829; Kemp et al., *Tetrahedron Lett.* 1987, 28, 4637-4640; Fotouhi et al., *J. Org. Chem.* 1989, 54, 2803-2817; Kemp et al., *J. Org. Chem.* 1993, 58, 2216-2222) such that the C-terminal coupling fragment is activated as a thioester (3). Having been coaxed into proximity, the N-terminal coupling partner reacts with the thioester, thus forming the amide bond leading to peptide ligation (4). Removal of the auxiliary provides the doubly glycosylated peptide 5. In this way, the limitation of a cysteine situated acyl acceptor at the N-terminus is obviated.

Scheme 8.
Cysteine-Free Ligation Strategy.

(a)

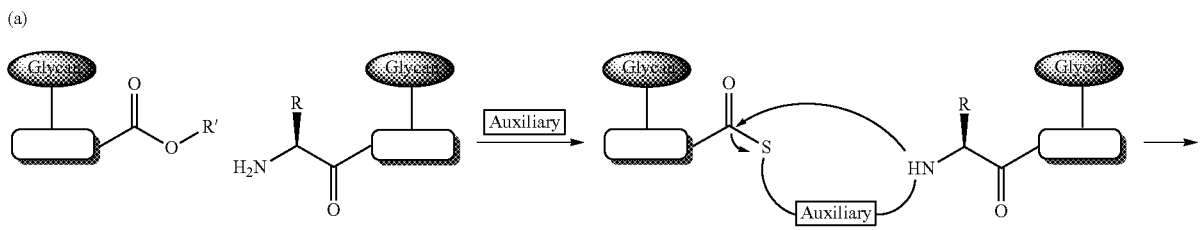

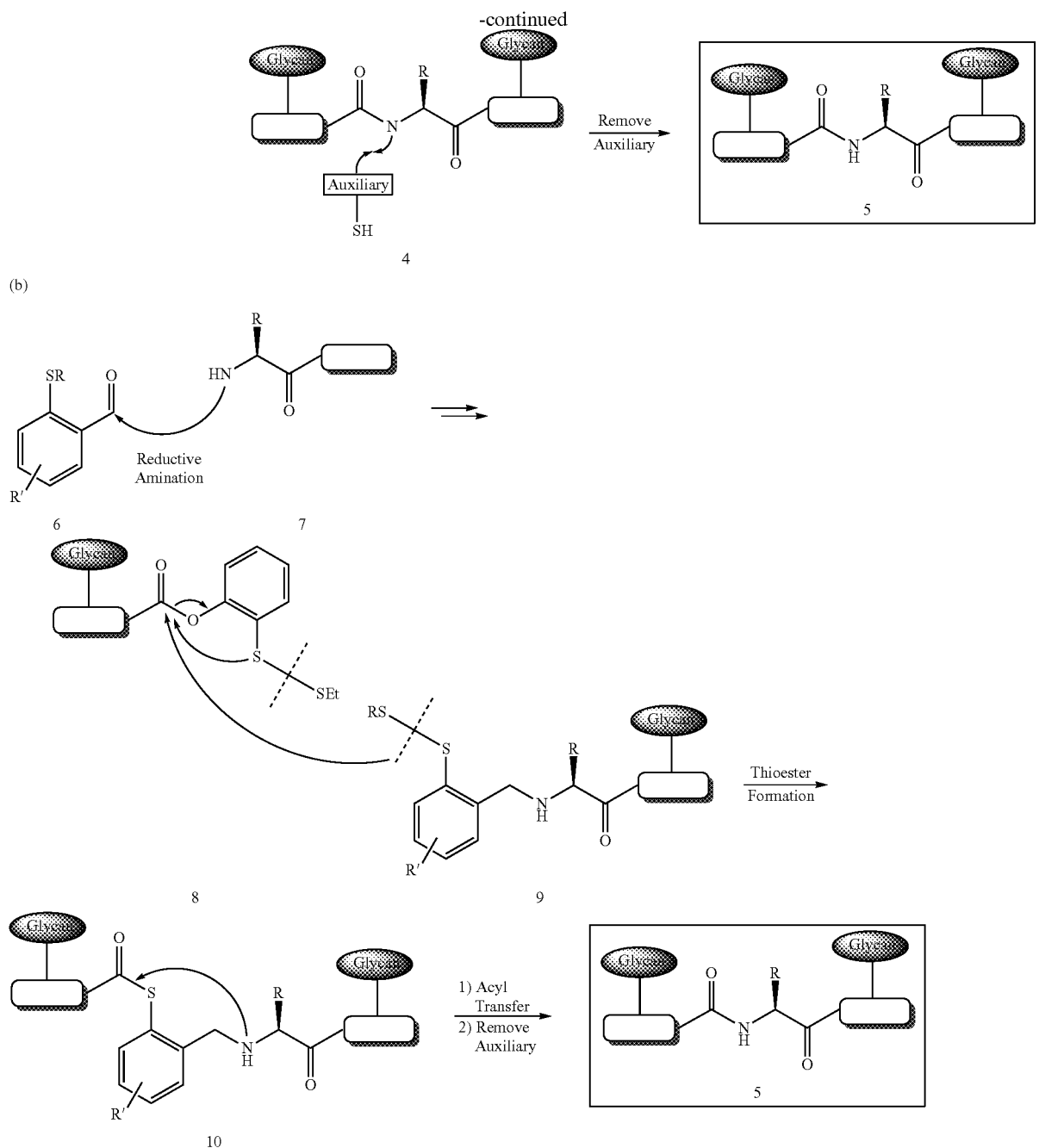

In certain embodiments, the inventive method comprises covalent appendage of a sulfur-displaying auxiliary of the type 6 to the N-terminus of an appropriate peptide fragment (7) through reductive amination (Macmillan et al., *Org. Lett.* 2004, 6, 4659-4662; Kawakami et al., *Org. Lett.* 2001, 3, 1403-1405). The present invention thus improves on a previously reported non-cysteine based ligation method (Offer et al., *J. Am. Chem. Soc.* 2002, 124, 4642-4646). The resultant intermediate is then converted to glycopeptide 9. The two fully functionalized glycopeptide fragments may then be coupled under conditions analogous to those that we had previously developed in the context of a cysteine-based NCL method. Thus, under disulfide reducing conditions, the C-terminal coupling partner, 8, containing a C-terminal phenolic ester is activated to form a thioester with the auxiliary sulfur functionality of the N-terminal fragment, thus providing an intermediate of the type 10. Amide bond formation followed by auxiliary removal provides the bifunctional glycopeptide 5.

In certain embodiments, the sulfur atom of the auxiliary is protected with a PMB protecting group, which can be deprotected under mild conditions, compatible with survival of glycopeptide functionality. Thus, aldehyde 11 was prepared through slight modification of a known procedure (Offer et al., *J. Am. Chem. Soc.* 2002, 124, 4642-4646). Reductive amination with hexapeptide 12 provided 13 in 60% yield. This ability to connect a substantial N-terminal domain to the auxiliary by reductive amination is an important feature of this methodology. Next, the disaccharide 14 was appended to the peptide through reducing end amination and aspartylation (Cohan-Anisfeld et al., *J. Am. Chem. Soc.* 1993, 115, 10531-10537). The —SPMB group was converted to an aromatic disulfide under mild conditions which would leave intact sensitive glycopeptide functionality. Compound 17 was obtained following treatment of 15 with sufenyl chloride 16 in TFE/DCM (Matsueda et al., *Chem. Lett.* 1981, 6, 737-740). Notably, this transformation represents an appealing alternative to previously described conditions, which typically require exposure to such harsh reagents as anhydrous HF or Hg(OAc)$_2$ and TFA (Macmillan et al., *Org. Lett.* 2004, 6, 4659-4662; Offer et al., *J. Am. Chem. Soc.* 2002, 124, 4642-4646).

Gly-Ala ligation was investigated first. Upon exposure to TCEP in PBS (pH 8.0), glycopeptides 17 and 18 each underwent reductive disulfide cleavage. Presumably, the C-terminal glycopeptide then suffered an O- to S-acyl transfer of the type previously described to generate the activated thioester (cf. 19). As anticipated, 19 and 20 were temporarily joined through a thioester exchange reaction. Following intramolecular acyl transfer, the fully functionalized glycopeptide 21 was isolated in approximately 40% yield.

Scheme 9.
(a) NaCNBH$_3$, MeOH/DMF, 60%; (b) 14, HATU, iPr$_2$NEt, DMSO, 62%; (c) 16, TFE/CH$_2$Cl$_2$, 70%.

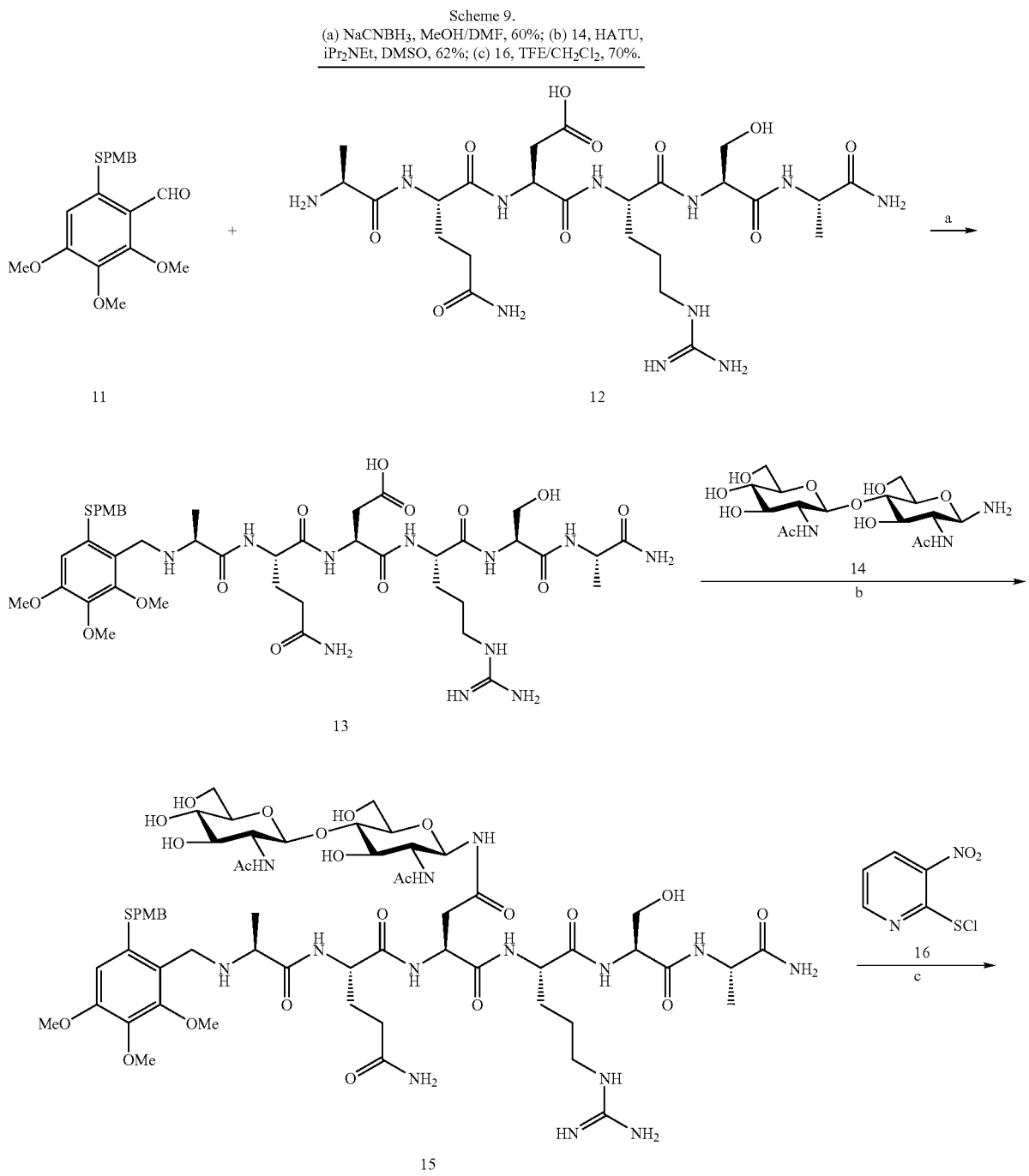

-continued
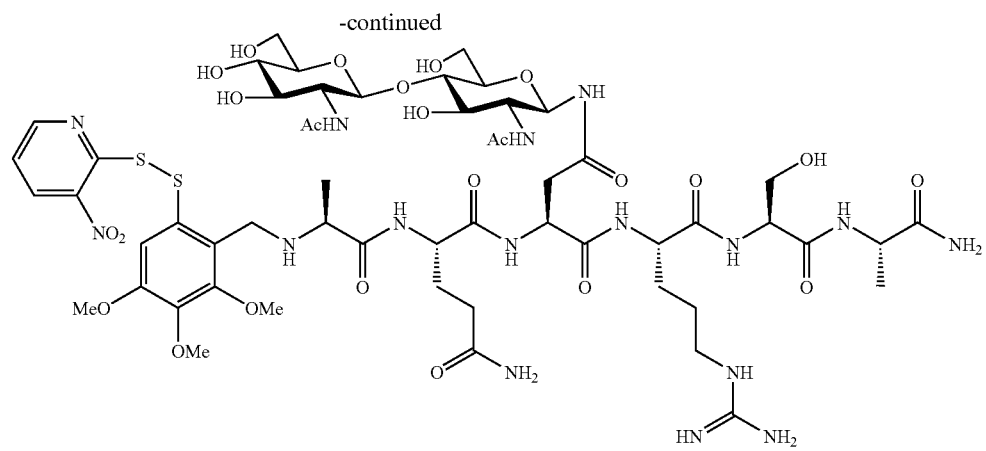
17

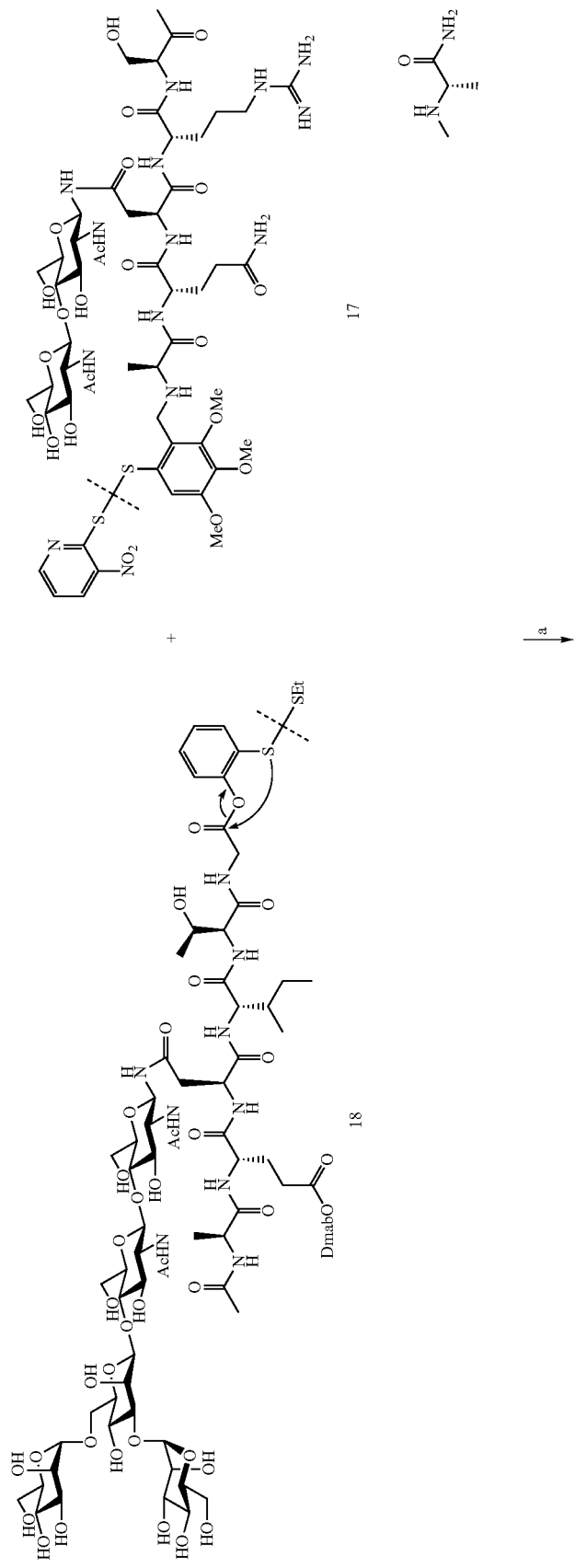

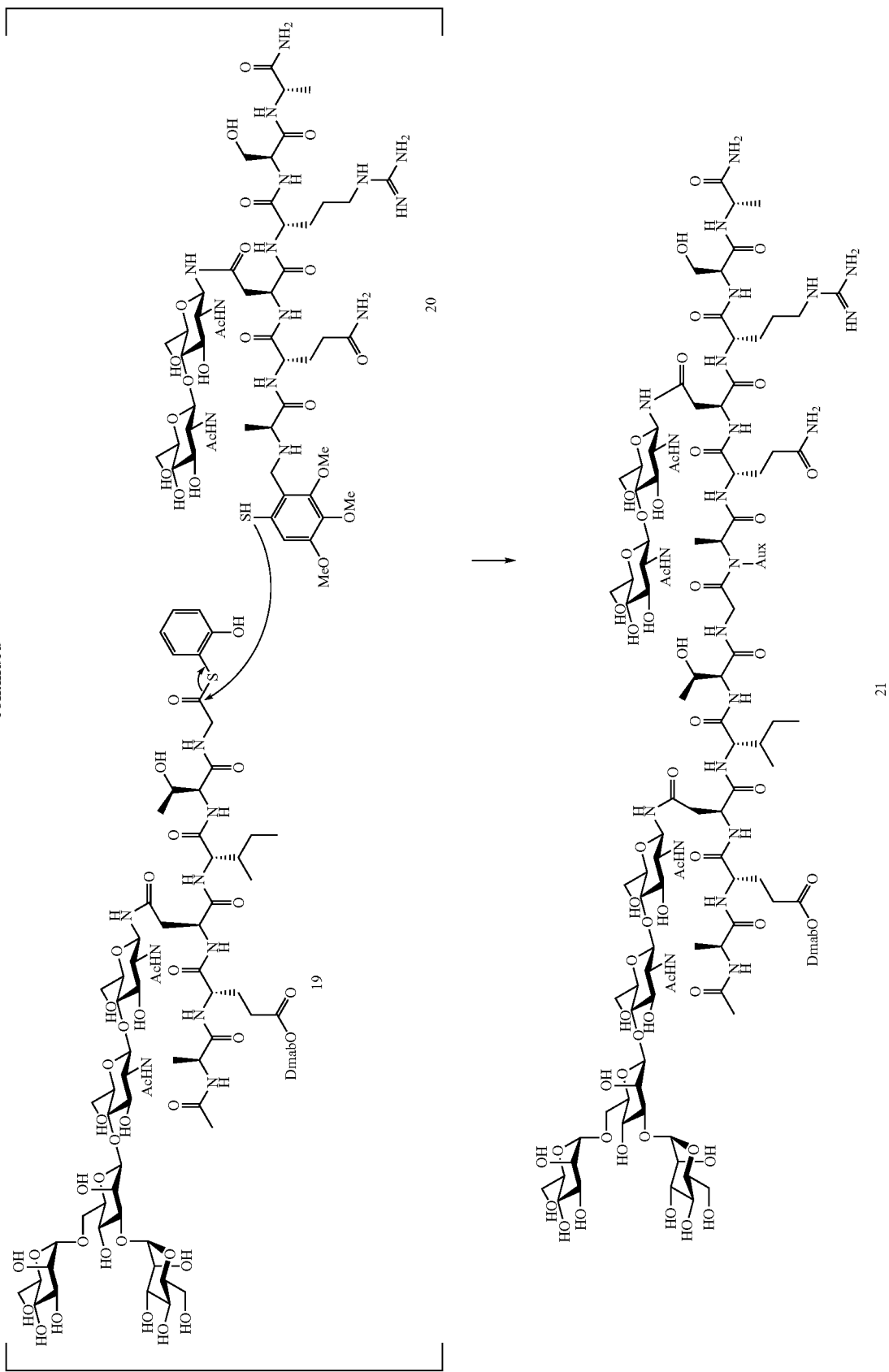

Scheme 11.
(a) TCEP, DMF, NaH$_2$PO$_4$, Na$_2$HPO$_4$, 32° C., 54%.
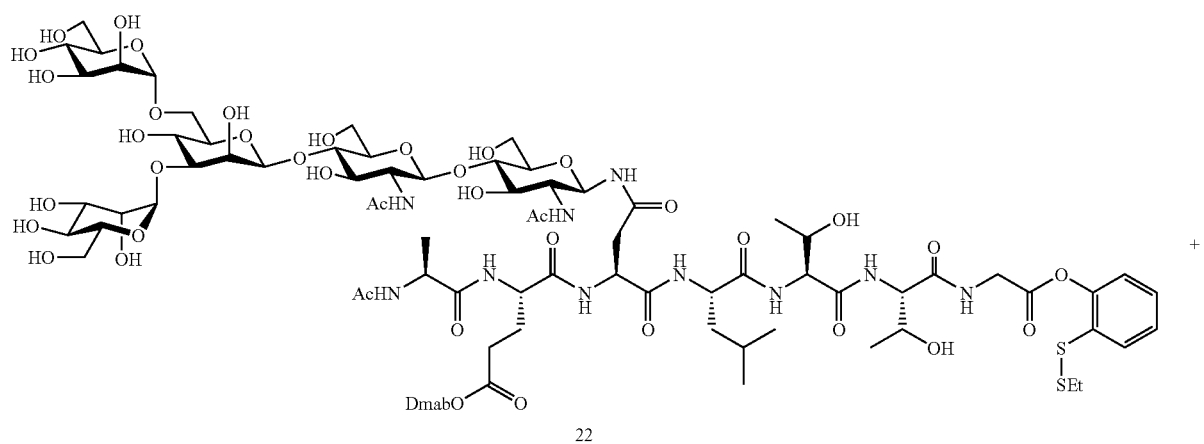
22
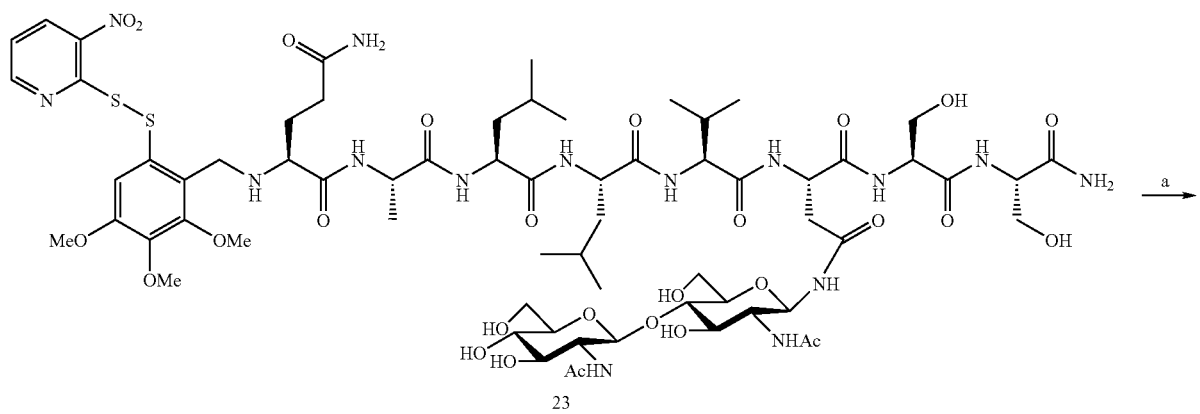
23
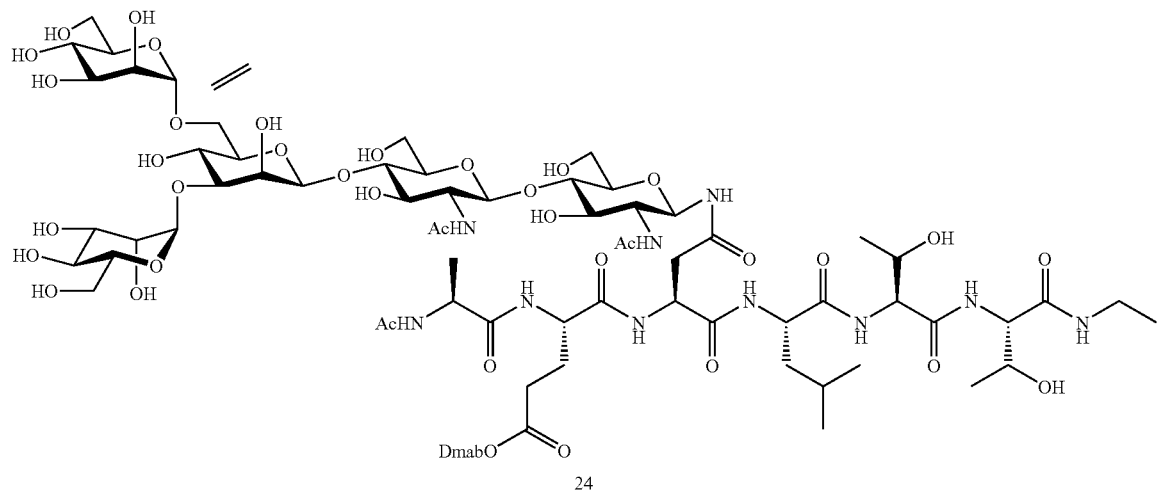
24

-continued
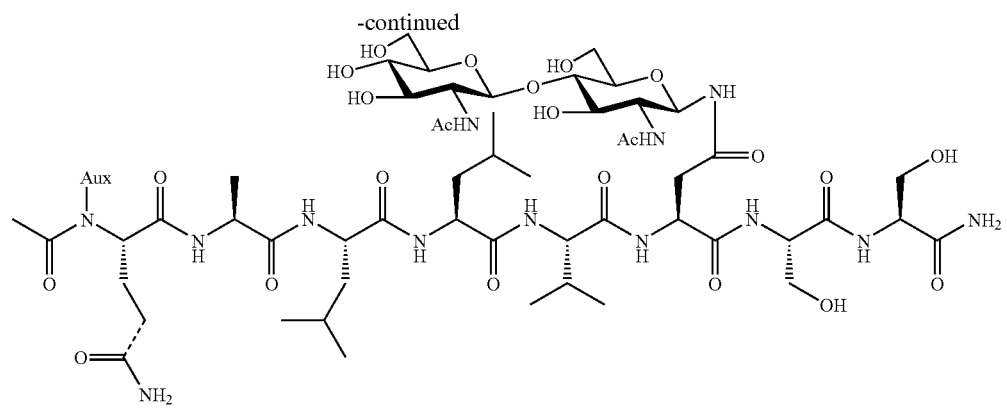

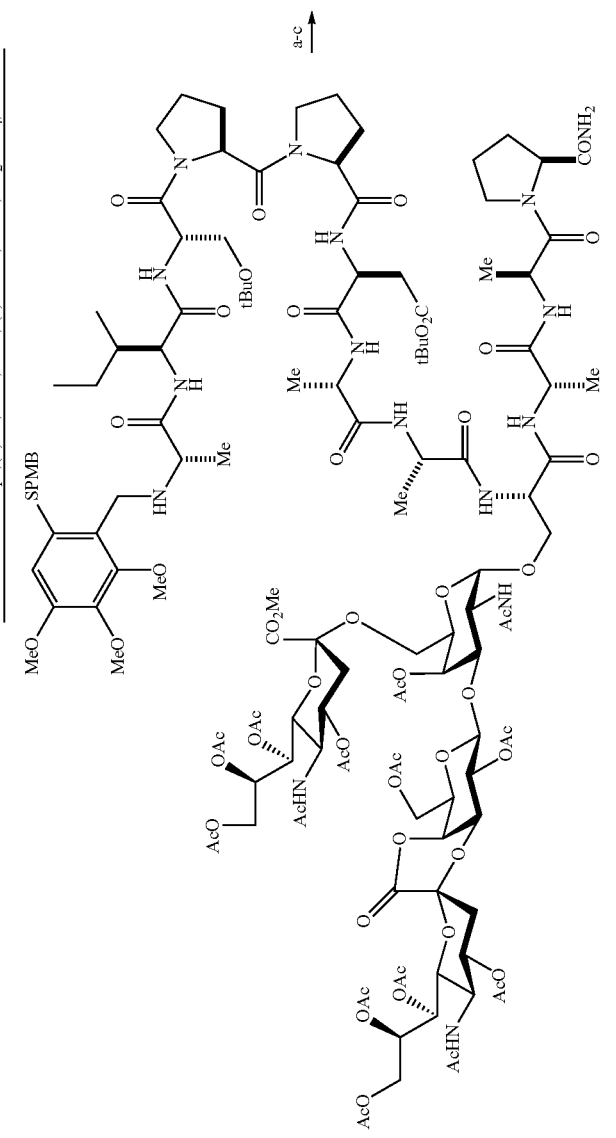
Scheme 12.
(a) TFA, PhOH, H₂O, TESH; (b) 0.1N NaOH, MeOH; (c) H₂NNH₂, MeOH, 61% over 3 steps;(d) 16, TFE, 67%; (e) TCEP, DMF, Na₂HPO₄, 65%.

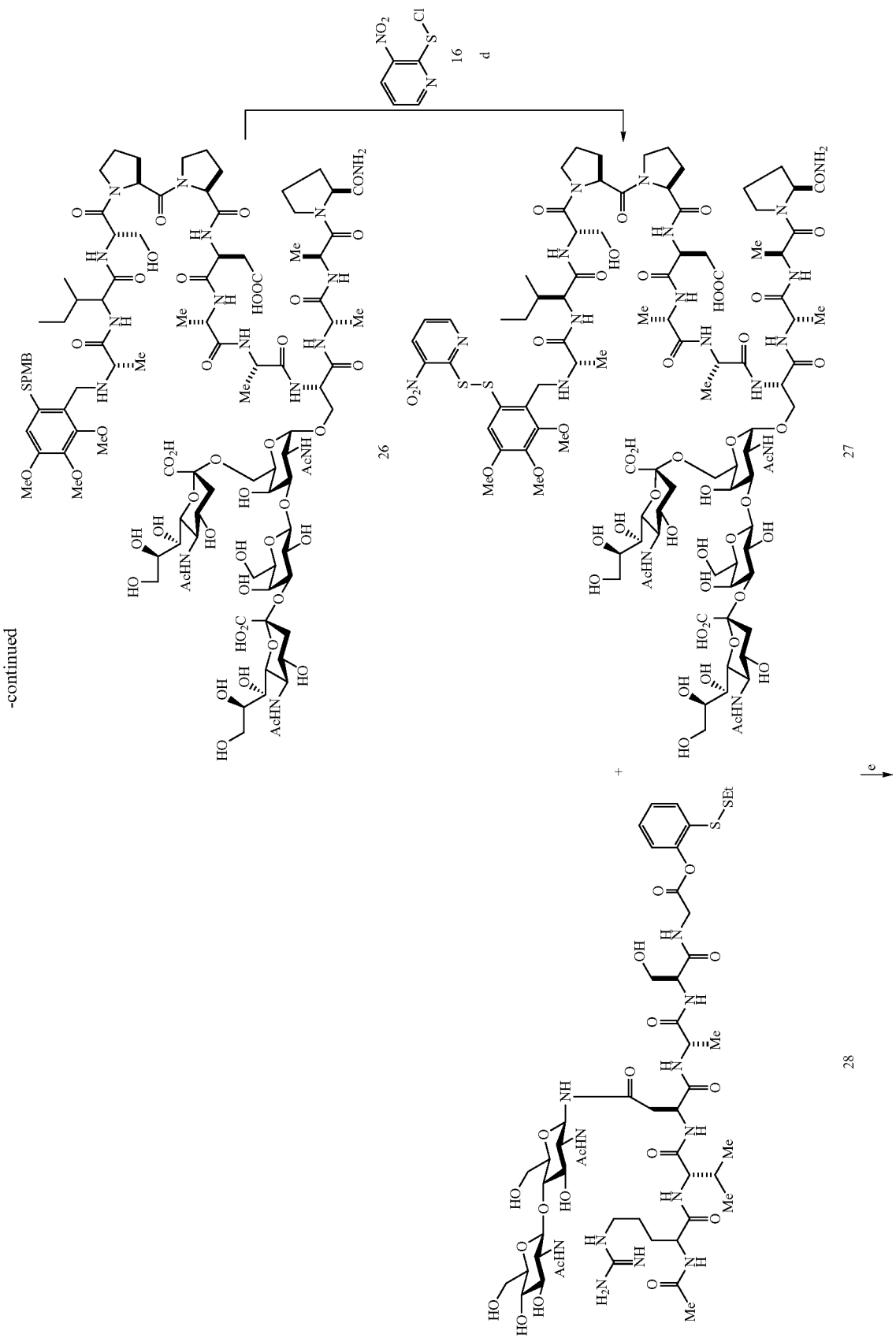

-continued
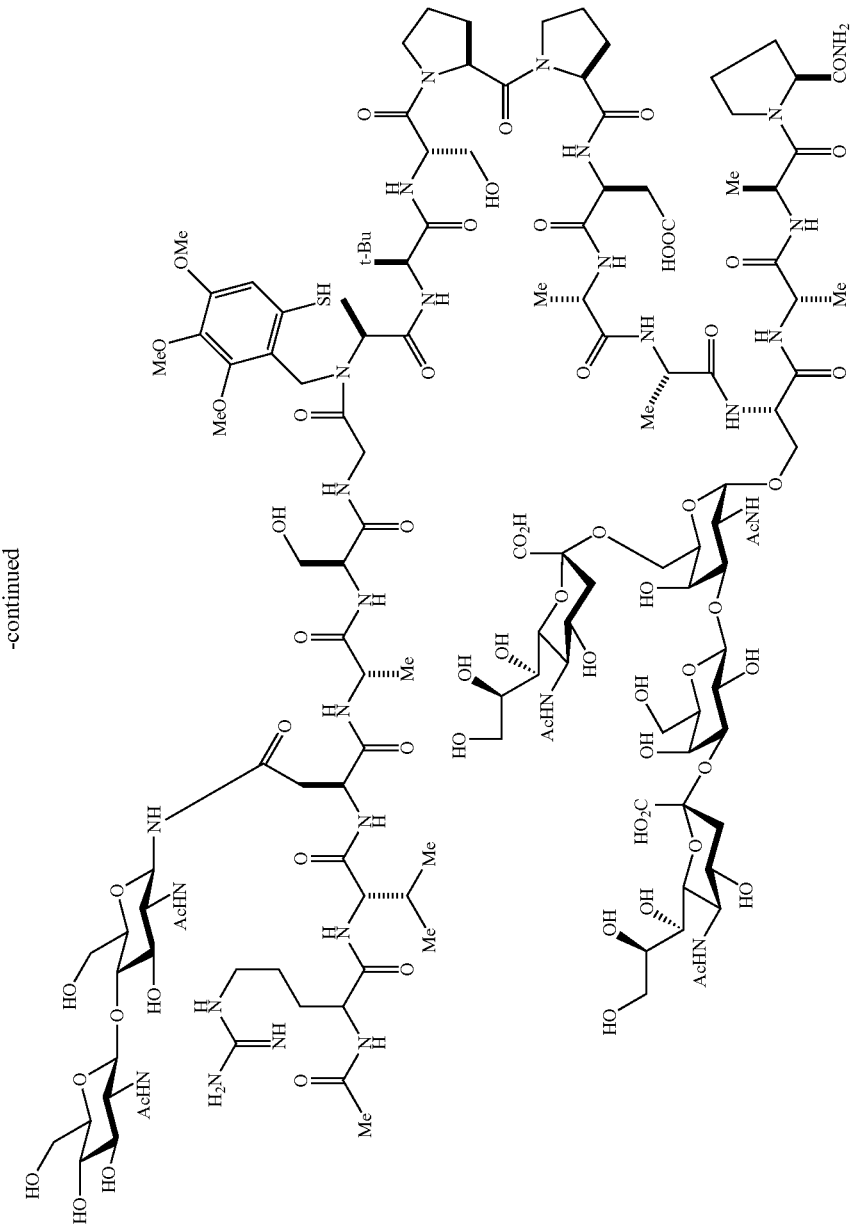

The generality of the method was then explored by attempting ligation at a more challenging Gly-Gln center. Thus, glycopeptides 22 and 23 were prepared and subjected to the reaction conditions described above (TCEP in pH 8.0 PBS buffer). Unfortunately, the isolated yield of 24 was found to be quite low, and a significant quantity of carboxylic acid arising from hydrolysis of 22 was observed. Without wishing to be bound to any particular theory, we postulated that, while in the previous instance (cf 17+18→21), the rate-determining step of the sequence had been the joining of the two fragments through transthioesterification, in the case at hand, the increased steric hindrance around the reacting center had caused the intramolecular acyl transfer to become rate-limiting. Consequently, hydrolysis of the tethered intermediate had the opportunity to intervene as a competitive side reaction. Although we were unable to improve upon the product distribution by adjusting the pH of the system, we did find that, by introducing DMF as a co-solvent with a small amount of $Na_2HPO_4$, we were able to isolate the ligation product 24 in a more acceptable 54% yield.

Having demonstrated the ability of the inventive method to successfully ligate two N-linked glycopeptide domains, we next sought to investigate its compatibility with O-linked glycodomains. Thus, intermediate 25 was advanced to 26 through a three-step sequence, as shown (Schwarz et al., *J. Am. Chem. Soc.* 1999, 121, 2662). The latter was converted to the N-terminal coupling partner, 27, according to the previously developed reaction conditions. Upon exposure to TCEP and DMF with $Na_2HPO_4$, 27 and 28 readily underwent cysteine-free native chemical ligation to provide glycopeptide 29, possessing both N-linked and O-linked carbohydrate domains. Notably, no carbohydrate decomposition products were observed.

The inventive methodology was then validated in the context of more complex glycan fragments, including those containing characteristic non-reducing and sialic acid moieties. The extent of sialidation is apparently a determinant of EPO stability (Tsuda et al., *Eur. J. Biochem.* 1990, 188, 405-411). Thus, the coupling of two glycopeptide fragments, each displaying an N-linked core pentasaccharide, was found to proceed smoothly to provide the bifunctional glycopeptide 30 (Scheme 13).

The development of appropriately mild conditions for the cleavage of the thiol auxiliary was investigated. In this context, TFA with scavenger has been used in similar types of systems. However, treatment of ligation product with 95% TFA with a TIPS scavenger resulted in a mixture of the desired native glycopeptide, along with one compound of the same molecular weight as the starting glycopeptide. The latter was tentatively assigned to be the thioester intermediate, arising from acid-mediated intramolecular acyl transfer from N- to S- (Vizzavona et al., *Bioorg. Med. Lett.* 2002, 12, 1963-1965). Presumably, the otherwise endothermic step is driven by irreversible protonation of the benzylic amine. In light of this finding, a two-step sequence was devised for the removal of the auxiliary. First, intermediate 24 was treated with methyl-p-nitrobenzene sulfonate (Tam et al., *Biopolymers*, 1998, 46, 319-327). This step accomplished selective methylation of the sulfur on the aromatic ring to provide intermediate 31. The latter was not purified. Rather, it was then exposed to the action of 95% TFA, thereby providing the native glycopeptide 32, free of any observable thioester byproduct.

Having established the success of the inventive ligation method in the context of a convergent bis-domainal glycopeptide synthesis, we explored the generalization of the method to the synthesis of longer peptide chains containing more than two sites of glycosylation. Thus, the applicability of the inventive method to coupling in reiterative fashion, multiple glycopeptide fragments was established. We recently disclosed a method by which to generate differentially glycosylated trifunctional glycopeptides based on a cysteine-dependent native chemical ligation protocol. As a demonstration of the applicability of our new non-cysteine NCL technology to complex targets, the combination of our cysteine-dependent and cysteine-free NCL protocols to the preparation of the multiply glycosylated peptide, 33 was explored. Thus, each of the three glycopeptide fragments (34, 35, and 23) are prepared according to glycal assembly and glycopeptide synthesis protocols that have been validated and optimized over the course of many years in our laboratory (Danishefsky et al., *Angew. Chem.* 1996, 108, 1482-1522; *Angew. Chem. Int. Ed.* 1996, 35, 1380-1419; S. J. Danishefsky et al., *Angew. Chem.* 2000, 112, 882-912; *Angew. Chem.*,

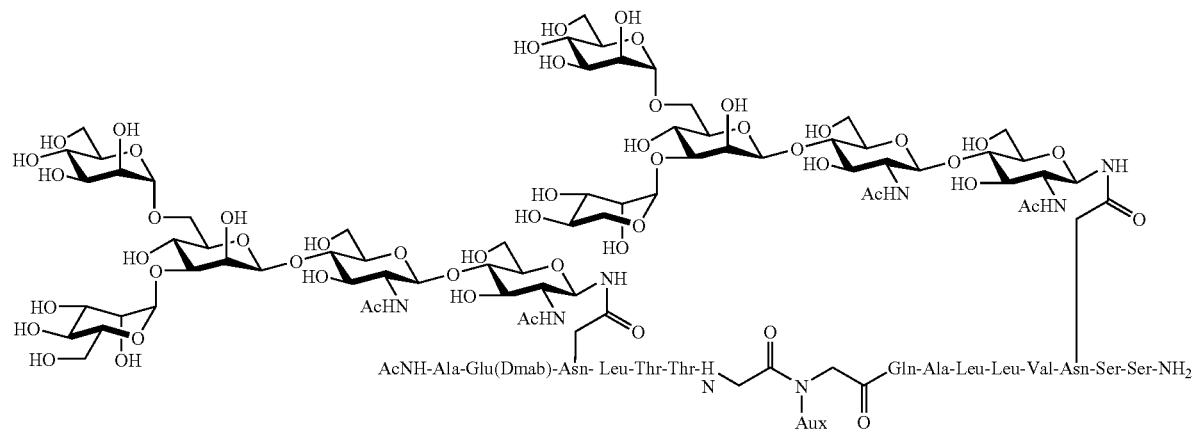

Scheme 13.
Bifunctional glycopeptide.

*Int. Ed.* 2000, 39, 836-863). Fragments 23 and 35 are then joined according to the inventivecysteine-free ligation method, to form the Gly-Gln junction. Next, following deprotection of the N-terminal cysteine residue, the bifunctional peptide is coupled with glycopeptide 34 through cysteine-based ligation to afford the fully functionalized target compound.

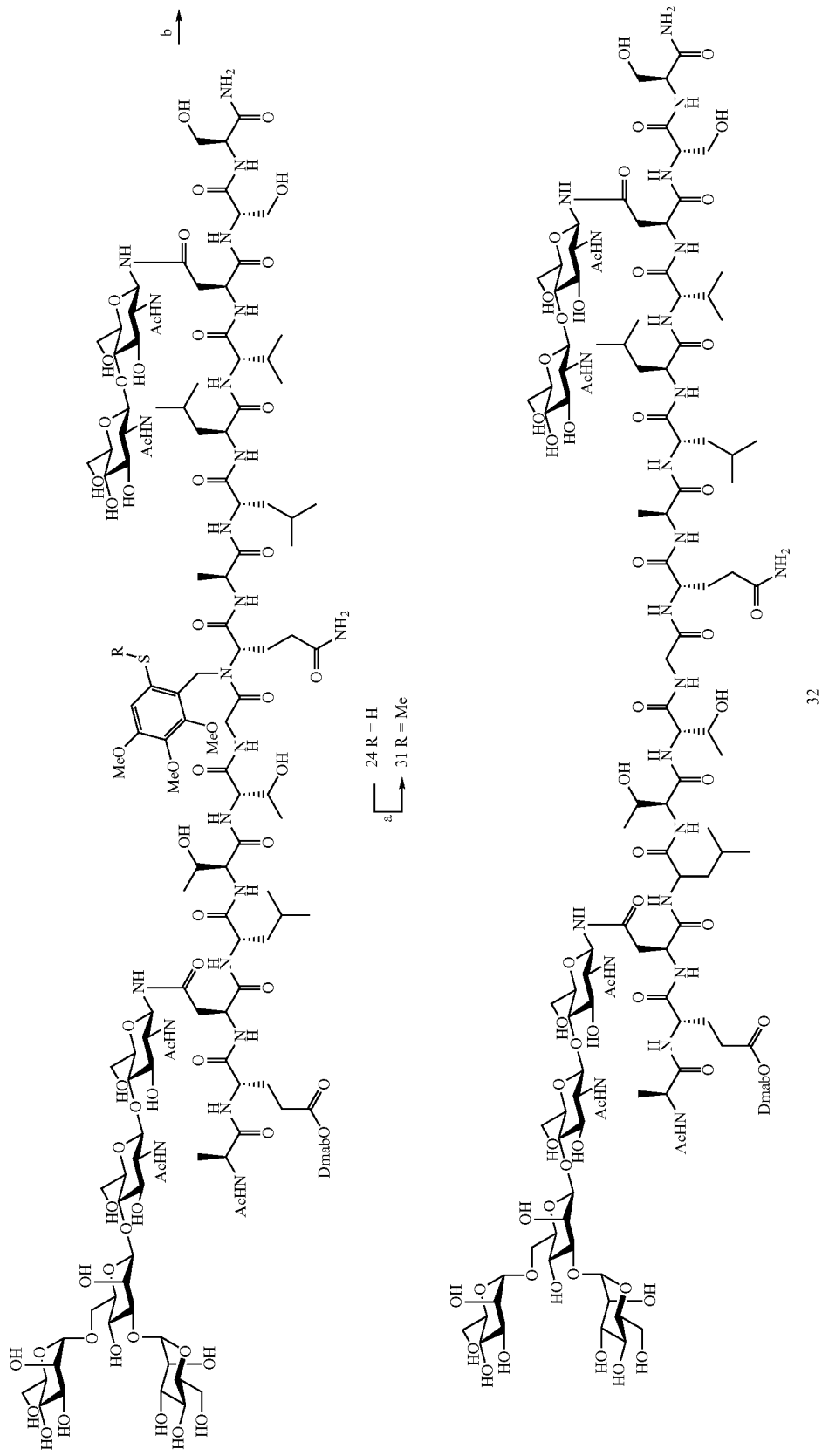

Scheme 15.
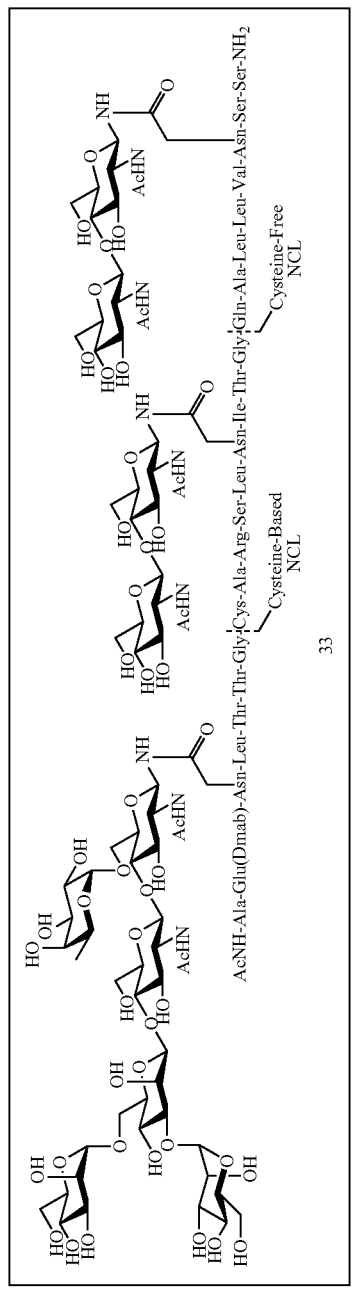
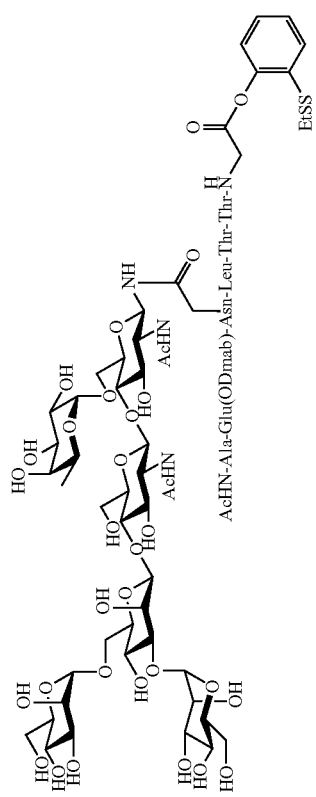
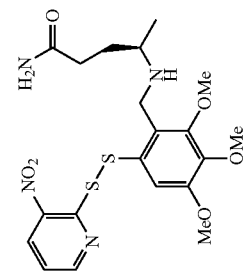
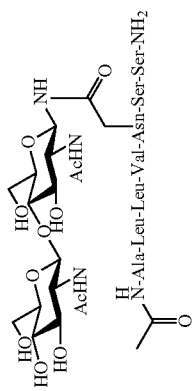

Thus, polypeptides 36 and 37 were prepared for the cysteine-free ligation event. It will be noted that the termini have been suitably equipped in anticipation of the reiterative sequence. Thus, peptide 37 bears the requisite N-terminal auxiliary for the cysteine-free coupling, while fragment 36, which will serve as the middle glycopeptide component, incorporates the C-terminal phenolic ester for the first cysteine-free ligation as well as a Thz-protected N-terminal cysteine residue which will be unmasked prior to the second, cysteine-based ligation event (Bang et al., *Angew. Chem.* 2004, 116, 2588-2592; *Angew. Chem. Int. Ed.* 2004, 43, 2534-2538).

Each peptide fragment was subjected to glycosylation with disaccharide 14, and, following conversion of the N-terminal auxiliary —SPMB group to the requisite disulfide, glycopeptides 35 and 23 were in hand. The coupling of the two fragments proceeded readily in the presence of TCEP to afford the ligated product 38 in 58% yield, along with 11% of the thioester 40. The latter could be converted to 38 upon treatment with thiophenol or MesNa (Kawakami et al., *Tetrahedron Lett.* 2005, 46, 8805-8807). The thiol auxiliary was removed according to the two-step sequence shown (cf 38→39); however, the auxiliary could also be maintained in the subsequent ligation event without causing detriment.

As we had previously demonstrated, the cysteine residue was readily unmasked through exposure of 38 to 10% morpholine in DMF (to remove the -Fmoc group) followed by treatment with an aqueous solution of MeONH$_2$.HCl. Native chemical ligation between 41 and 34 was carried out in the presence of MesNa and TCEP and afforded the multifunctional glycopeptide 42 in 57% yield.

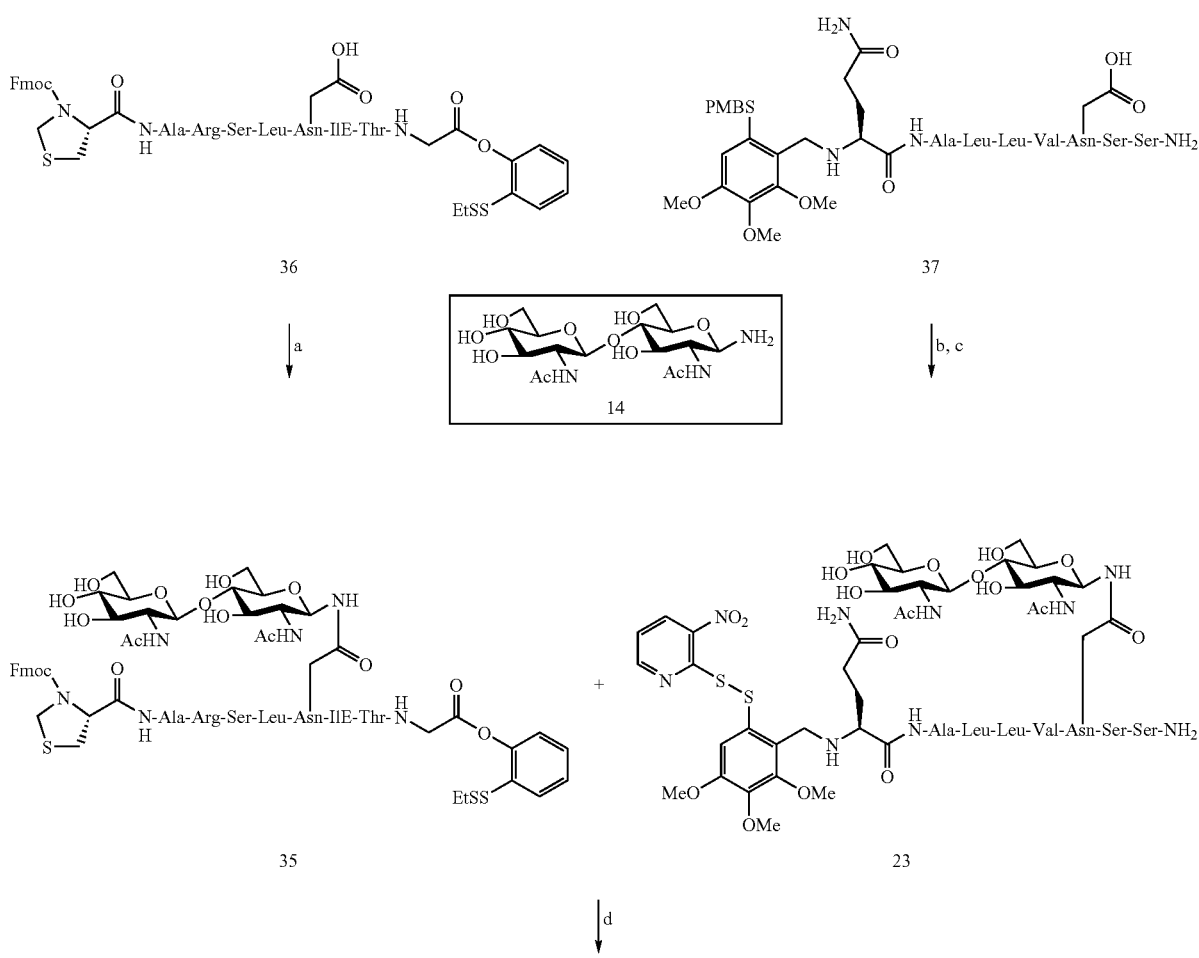

Scheme 16.
(a) 14, HATU, iPr$_2$NEt, DMSO, 72%; (b) 14, HATU, iPr$_2$NEt, DMSO, 83%;
(c) TFE, DCM, 16, 69%; (d) TCEP, DMF, Na$_2$HPO$_4$, 58% (38) + 11% (40);
(e) methyl p-nitrobenzene sulfonate; (f) 95% TFA; (g) PhSH or MesNa, PBS.

-continued
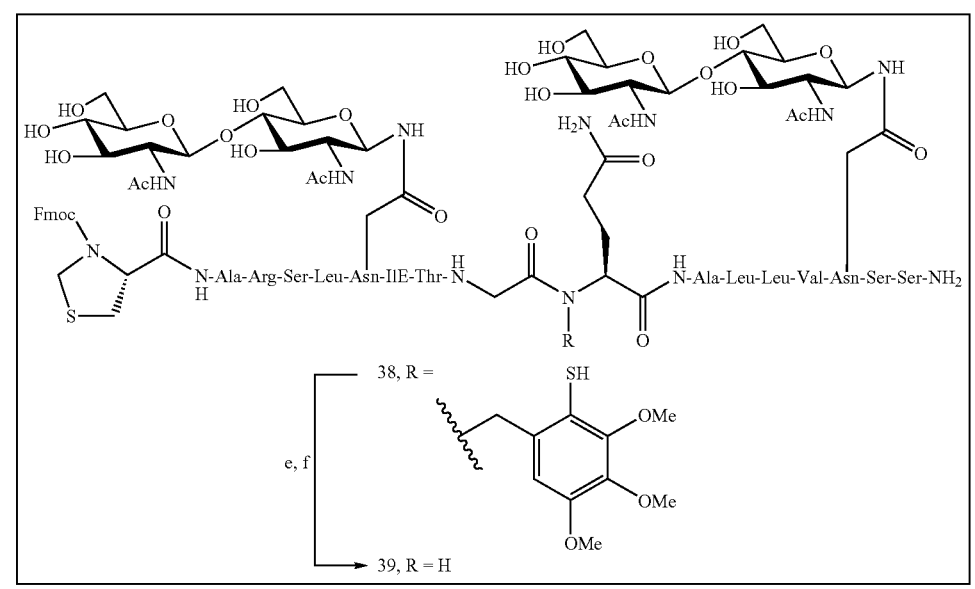
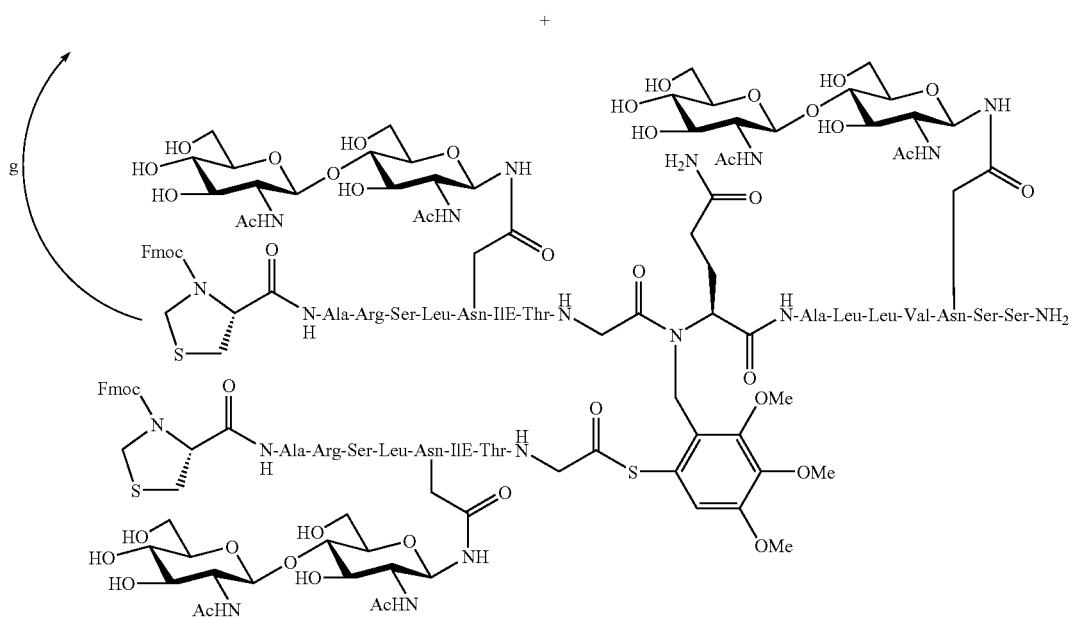

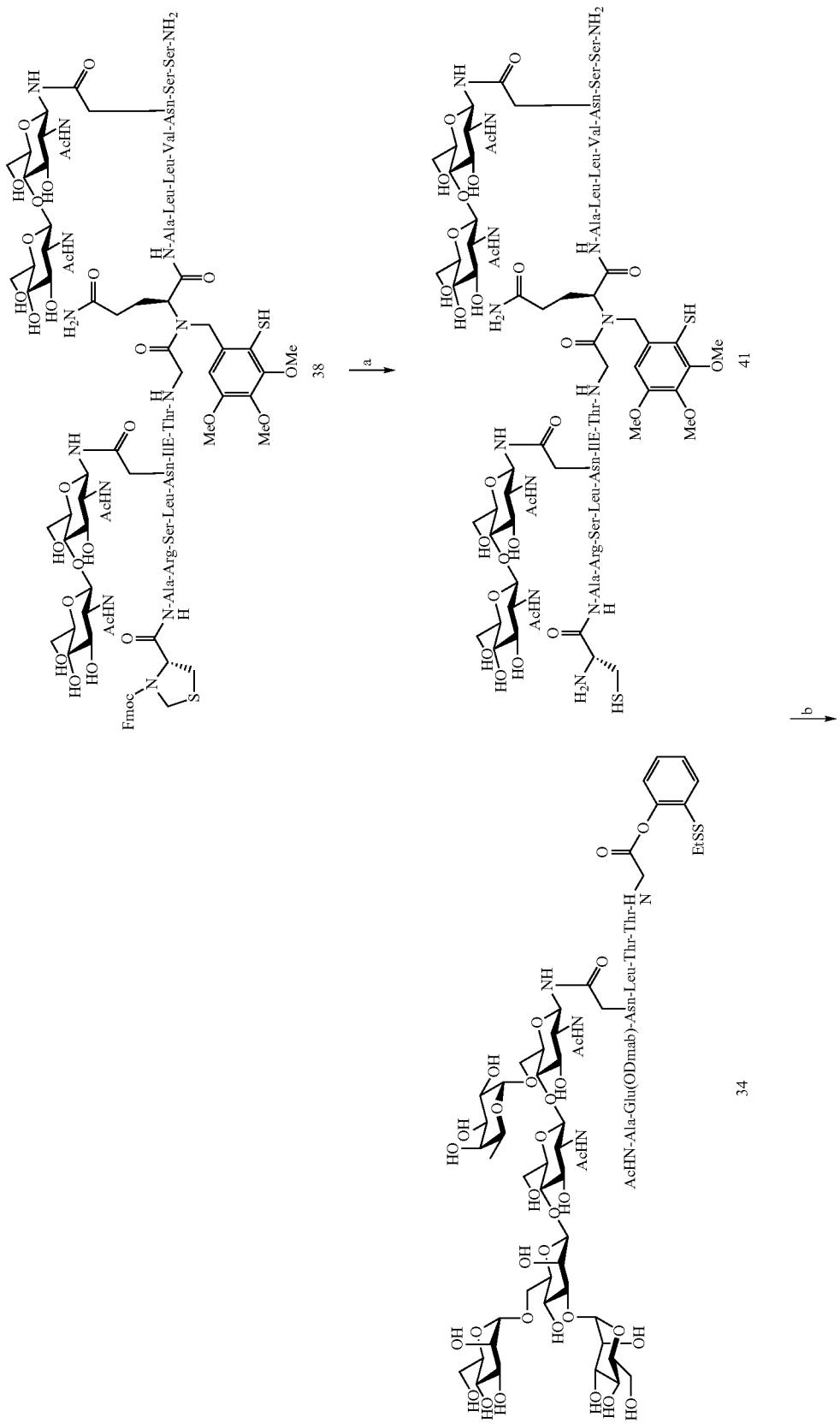
Scheme 17.
(a) (i) 10% morpholine in DMF; (ii) 0.4M MeONH$_2$·HCl, 60%;
(b) MesNa, TCEP, PBS (pH = 8.0), 57%.

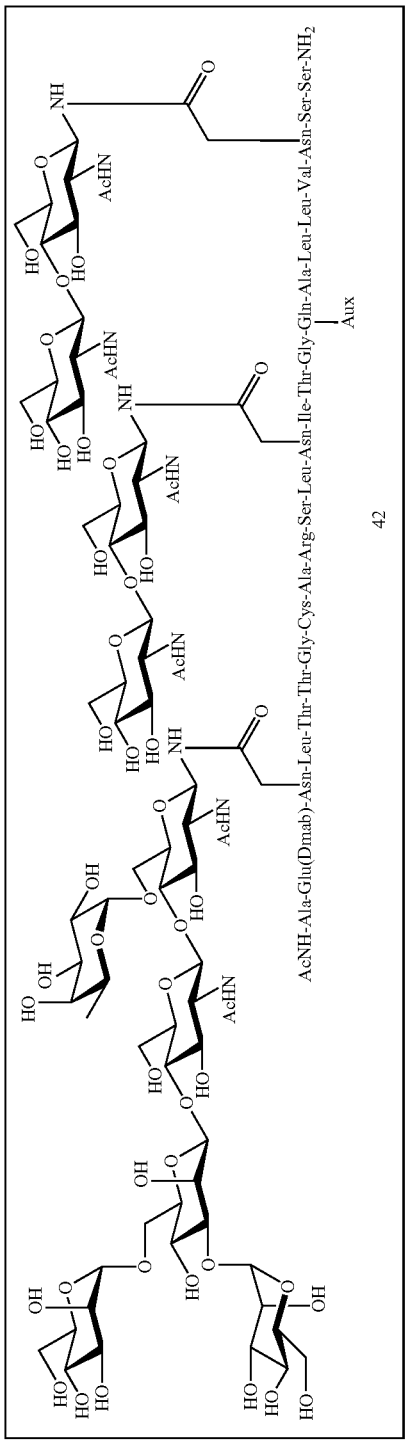

Preparation of Cyclic Peptides

The viability of our newly developed cysteine-free ligation protocol was demonstrated in another area of peptide chemistry of great interest to those at the forefront of chemistry and glycobiology; i.e., the synthesis of cyclic peptides (Verber et al., *Trends Neurosci.* 1985, 8, 392; Milner-White, *Trends Pharmacol. Sci.* 1989, 10, 70). Cyclic peptides often possess enhanced biological specificity, activity, and metabolic stability in comparison to their linear counterparts, as a consequence of their constrained conformations and their enhanced levels of resistance to protease digestion. While traditional strategies for cyclic peptide formation are restricted to macrolactam or disulfide formation, Tam and coworkers have disclosed that cyclic peptides can be accessed through native chemical ligation (Zhang et al., *J. Am. Chem. Soc.* 1997, 119, 2363; Tam et al., *Tetrahedron Lett.* 1997, 38, 5599; for other examples of the use of NCL in the synthesis of cyclic peptides, please see: Shao et al., *Tetrahedron Lett.* 1998, 39, 3911; Meutermans et al., *J. Am. Chem. Soc.* 1999, 121, 9790). Recently, our research group reported on a newly modified native chemical ligation protocol that allows for formation of cyclic peptides possessing a cysteine residue (Chen et al., *Tetrahedron Lett.* 2006, 47, ASAP). However, given the scarcity of cysteine residues in nature, this chemical appraoch has limitations. Clearly, the development of a broadly useful, cysteine-independent ligation protocol could well have profound ramifications for the field of cyclic peptide synthesis.

Thus, the linear polypeptide 43 was prepared through solid phase peptide synthesis. Reductive amination with aldehyde 11 served to introduce the N-terminal auxiliary (44). The C-terminus was functionalized through HATU-mediated esterification with phenol 45, providing 46. Following protecting group removal and exposure to 3-nitro-2-pyridine-sulfenyl chloride, the requisite disulfide cyclization precursor was in hand. Thus, the linear peptide bis-disulfide (47) was treated with tricarboxyethylphosphine (TCEP) and $Na_2HPO_4$ in DMF to provide the desired cyclized peptide (48) in good yield. Importantly, no dimers or oligomers were observed based on LC-MS analysis.

Scheme 18.
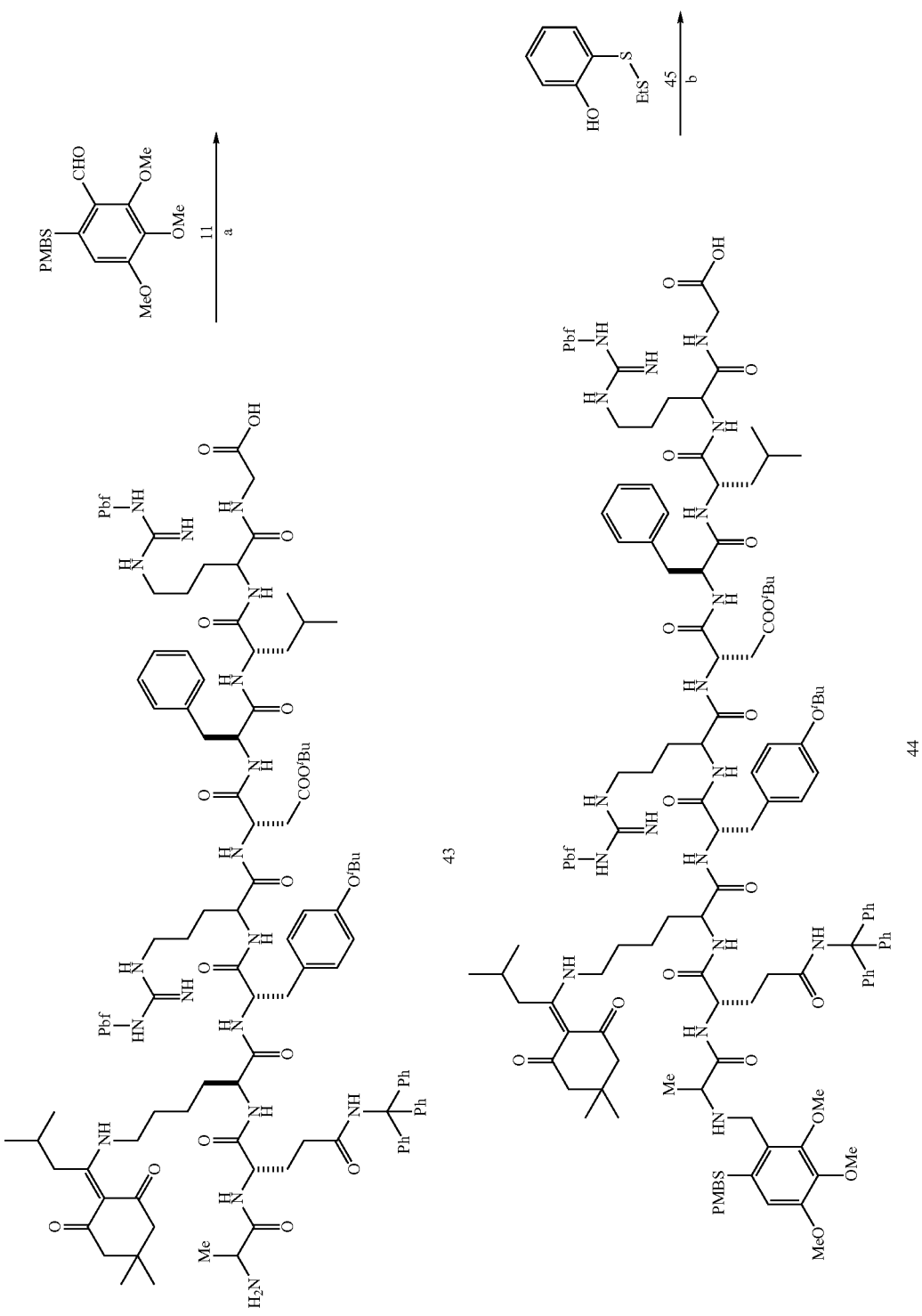

-continued
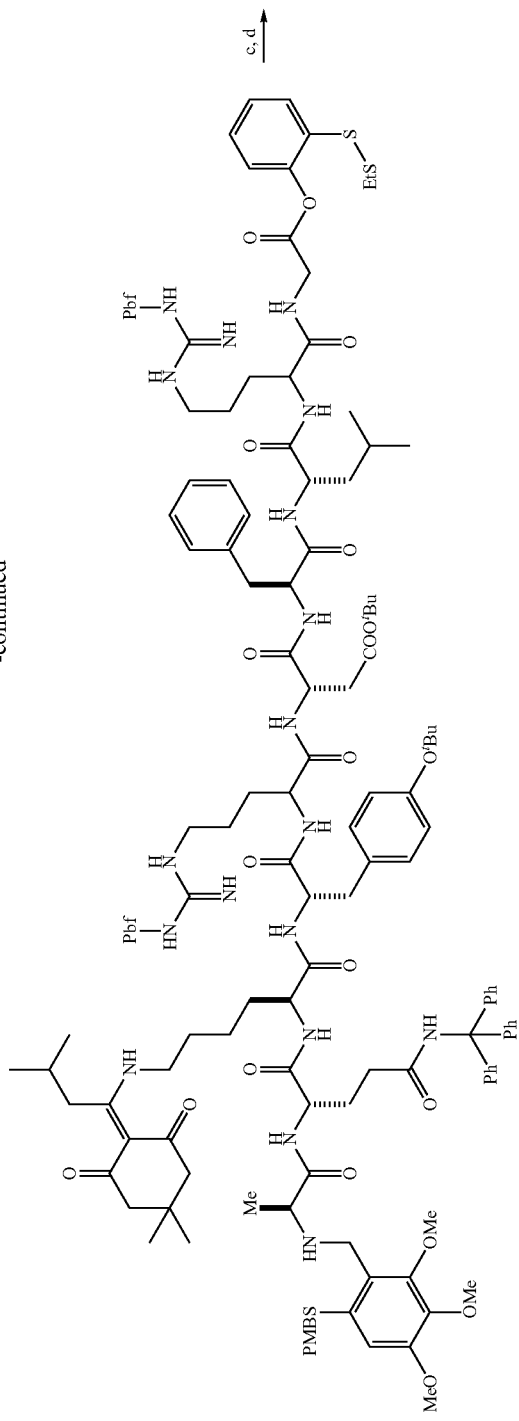
46
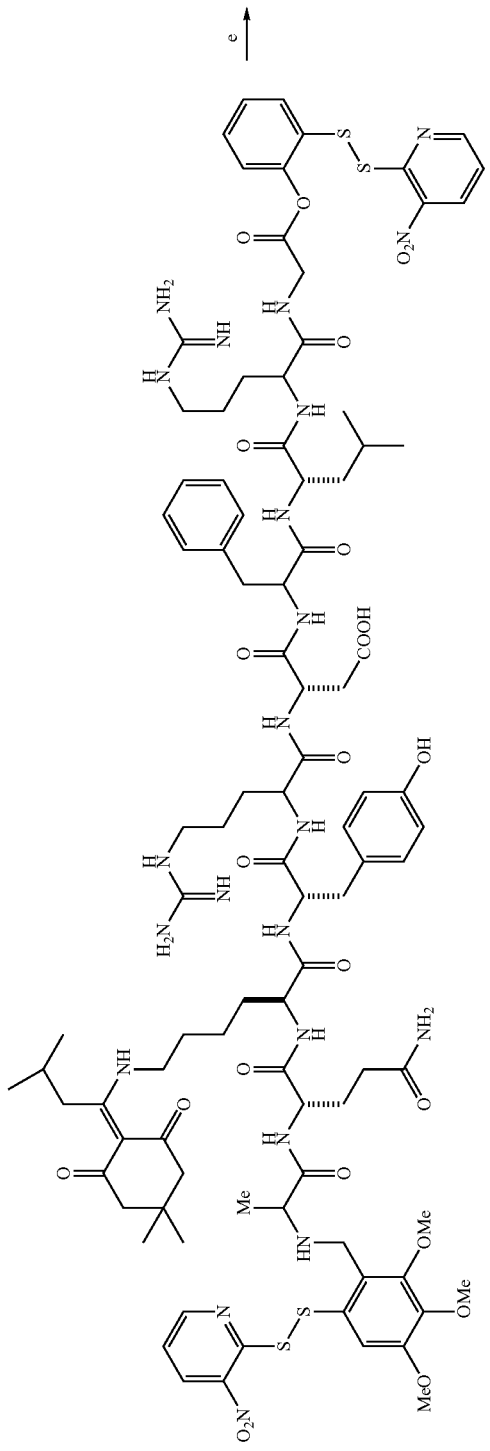
47

-continued
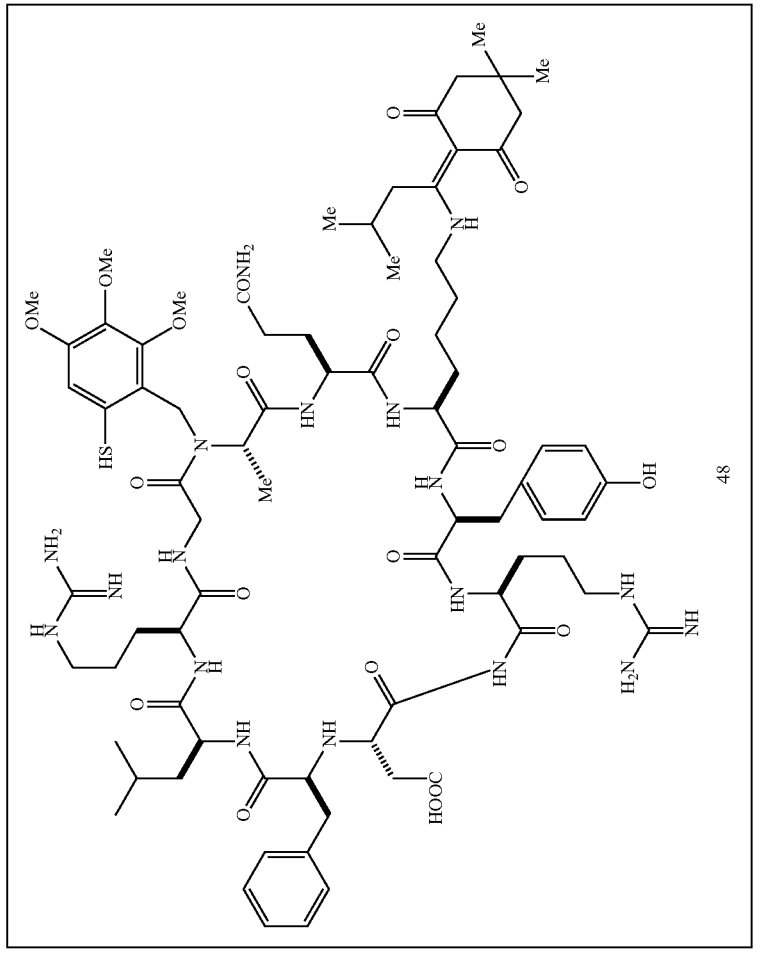
48
(a) 11, NaCNBH₃, MeOH, DMF, 66%; (b) 45, HATU, DIPEA, DMF: (c) TFA, PhOH, TESH, H₂O, 57% for two steps;(d) 16, TFE, 60%; (e) TCEP, Na₂HPO₄, DMF 78%.

It will be appreciated that the method can readily be applied to the preparation of multi-glycosylated cyclopeptides or proteins (e.g., comprising one or more non-adjacent glycosides covalently linked at designated sites).

General Reaction Procedures:

Unless mentioned specifically, reaction mixtures were stirred using a magnetically driven stirrer bar. Reactions involving air or moisture-sensitive reagents or intermediates were performed under argon or nitrogen atmosphere in glassware which had been heat gun or flame-dried under high vacuum. An inert atmosphere refers to either dry argon or dry nitrogen. Reactions were monitored either by thin layer chromatography, by proton nuclear magnetic resonance (NMR) or by high-pressure liquid chromatography (HPLC), of a suitably worked up sample of the reaction mixture.

Indicated reaction temperatures refer to those of the reaction bath, while room temperature (rt) is noted as 22° C. Preparative reactions were stirred magnetically. Tetrahydrofuran (THF), diethyl ether ($Et_2O$), methylene chloride ($CH_2Cl_2$), and toluene were obtained from a dry solvent system (activated alumina columns, positive pressure of argon). All other solvents were used as received in Sure/Seal bottles (Aldrich). Triethylamine ($Et_3N$), diisopropylethylamine (i-$Pr_2NEt$), pyridine, and 2,6-lutidine were distilled from $CaH_2$ immediately prior to use. All other reagents were purchased from Aldrich at the highest commercial quality and used without further purification.

General Work Up Procedures:

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent (e.g. ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulphite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous magnesium sulphate, and then filtered. The crude products were then isolated by removal of solvent(s) by rotary evaporation under reduced pressure, at an appropriate temperature (generally less than 45° C.).

General Purification Procedures:

Unless mentioned specifically, chromatographic purification refers to flash column chromatography on silica, using a single solvent or mixed solvent as eluent. Suitably purified desired product containing elutes were combined and concentrated under reduced pressure at an appropriate temperature (generally less than 45° C.) to constant mass. Final compounds were dissolved in 50% aqueous acetonitrile, filtered and transferred to vials, then freeze-dried under high vacuum before submission for biological testing.

Analytical Equipment:

HPLC: All separations involved a mobile phase of 0.05% TFA (v/v) in water (solvent A)/0.0425% TFA in acetonitrile (solvent B). Preparative, semipreparative, and analytical HPLC separations were performed using a Rainin HXPL solvent delivery system equipped with a Rainin UV-1 detector and one of the following Dynamax-60 Å C18 axial compression columns 250 mm in length equipped with a similarly packed guard column: 41.4 mm diameter (prep), 21.4 m diameter (semiprep), or 4.6 mm diameter (analytical). Separations were performed at flow rates of 48 mL/min (prep), 16 mL/min (semiprep), or 1 mL/min (analytical), and were monitored at a wavelength between 214 and 230 nm, depending on column loading. LCMS chromatographic separations were performed using a Waters 2695 Separations Module and a Waters 996 Photodiode Array Detector equipped with a Varian Microsorb C18 2×150 mm column at a flow rate of 0.2 mL/min.

ESMS and LCMS: Electrospray mass spectroscopy and LCMS analyses were obtained on a Waters Micromass ZQ mass spectrometer in conjunction with the Waters HPLC apparatus described above.

NMR: $^1H$ and $^{13}C$ NMR spectra were recorded on Bruker instruments in $CDCl_3$, $CD_3OD$ or $D_2O$ at 400 or 500 MHz for $^1H$ and 100 or 125 MHz for $^{13}C$.

Reagents: All commercial materials were used as received unless otherwise noted. The following solvents were obtained from a dry solvent system and used without further purification: THF, diethyl ether, toluene, and DCM. Reagents were obtained from Aldrich or as noted, with the following exceptions: amino acids and resins for solid phase peptide synthesis were purchased from NovaBiochem; Biosynthesis grade DMF from EM Science; and all other solvents from Fisher Scientific (HPLC grade).

Representative Experimental Procedures Relevant to Schemes 9-18:

Compound 13:

To a solution of crude peptide 12 (10 mg, 15.5 µmol) in MeOH/DMF (1.5 mL, 2/1) was added aldehyde 11 (16 mg, 46.5 µmol). The solution was stirred for 1 h, then $NaCNBH_3$ (2.9 mg, 46.5 µmol) was added. The reaction was stirred for 16 h, solvent was removed in vacuo and HPLC purification (20-60% acetonitrile in water over 20 min, $T_{retention}$=12.3 min) yielded peptide 13 (9 mg, 60%) as a white solid. ESI-MS: calcd. $C_{42}H_{63}N_{11}O_{14}S$, 977.3. found m/z 978.4 $[M+H]^+$.

Compound 15:

Peptide 13 (4.0 mg, 4.1 µmol) and disaccharide 14 (2.2 mg, 5.2 µmol) were placed in a vial with a flea-sized stirbar. Anhydrous DMSO (0.2 mL) was added and stirred 5 min. Freshly distilled $iPr_2NEt$ (1.4 µL, 8.2 µmol) was added to the reaction mixture followed by HATU (3.9 mg, 10.3 µmol). The solution turned to orange and stirred at room temperature for 1 h. The reaction was quenched by water (0.2 mL) and then subjected onto HPLC (15-45% acetonitrile in water, $T_{retention}$=12.9 min) to yield glycopeptide 15 (3.5 mg, 62%) as a white solid. ESI-MS: calcd. $C_{58}H_{90}N_{14}O_{23}S$, 1382.6. found m/z 1383.5 $[M+H]^+$.

Compound 17:

To a solution of glycopeptide 15 (3.2 mg, 2.3 µmol) in TFE (0.8 mL) was added a solution of sufenyl chloride 16 (0.5 mg, 2.4 µmol) in DCM (0.2 mL). The reaction was stirred for 1 h, and more 16 (0.1 mg) was added. The solvent was removed in vacuo after 30 min and then subjected to HPLC (15-45% acetonitrile in water, $T_{retention}$=12.6 min) to yield glycopeptide 17 (2.3 mg, 70%) as a light yellow solid. ESI-MS: calcd. $C_{55}H_{84}N_{16}O_{24}S_2$, 1416.5. found m/z 1418.0 $[M+H]^+$.

Compound 24:

To a mixture of glycopeptide 22 (1.4 mg, 0.66 µmol) and 23 (1.1 mg, 0.68 µmol) was added a solution of TCEP (1.0 mg) in DMF with small amount of $NaH_2PO_4$ and $Na_2HPO_4$ at room temperature. The reaction was stirred for 8 h at 32° C., then subjected to HPLC (20-60% acetonitrile in water, $T_{retention}$=16.1 min) to yield glycopeptide 24 (1.2 mg, 54%) as a white solid. ESI-MS: calcd. $C_{145}H_{230}N_{24}O_{65}S$, 3379.5. found m/z 1691.8 $[M+2H]^{2+}$.

Compound 32:

To a solution of glycopeptide 24 (0.2 mg, 0.06 µmol) in PBS (0.1 mL, pH 8.5) was added a solution of methyl p-nitrobenzenesulfonate (1.2 mg, 6 µmol) in MeCN. The reaction was stirred 1 h, and quenched with 25% TFA in $H_2O$ (5 uL). The mixture was washed with $Et_2O$ twice and the solvent was removed in vacuo. The crude material was dissolved in 95% TFA (0.2 mL) at room temperature. The reaction was stirred for 16 h, then the solvent was removed by $N_2$ stream. The residue was purified by HPLC (20-60% acetonitrile in water, $T_{retention}$=13.8 min) to yield the deprotected glycopeptide 32 as a white solid. ESI-MS: calcd. $C_{135}H_{218}N_{24}O_{62}$, 3167.5. found m/z 1585.5 $[M+2H]^{2+}$.

Compound 26:

To a vial containing glycopeptide 25 (12.0 mg, 4.11 µmol) was added 95% TFA in $H_2O$. The resultant reaction mixture was stirred at 0° C. for 1 h and warmed to room temperature and stirred at room temperature for additional 2 h. The excess solvents were evaporated with a stream of $N_2$ to dryness. The resulting residue was redissolved in MeOH (0.6 mL) and added aqueous NaOH (0.1 N, 0.6 mL) at 0° C. The reaction mixture was warmed to room temperature gradually and stirred at room temperature overnight. The reaction mixture was neutralized with acidic amberlyst resin and concentrated to give a solid which was further exposed to a solution of hydrazine in MeOH to remove all the remaining acetates to provide a residue which was purified with HPLC (20-50% acetonitrile (0.04% TFA) in water (0.05 TFA) over 20 min) to give glycopeptide 26 (5.9 mg, 2.51 µmol) with an unprotected glycophorin: $T_{retention}$=13.89 min, ESI-MS calcd $C_{100}H_{152}N_{16}O_{46}S$ $[M+2H]^{2+}$ 1174.2. found $[M+2H]^{2+}$ 1174.3.

Compound 27:

To a solution of compound 26 (2.1 mg, 0.90 µmol) in trifluoroethanol (1 mL) was added a solution of 3-nitro-2-pyridinylsulfenyl chloride (0.3 mg, 1.35 µmol) in $CH_2Cl_2$ (0.5 mL) at room temperature. The resultant reaction mixture was stirred at room temperature for 30 min and concentrated. The residue was redissolved in acetonitrile and water and purified by high performance liquid chromatography (20-50% acetonitrile in water over 20 min, $T_{retention}$=13.27 min) to give disulfide 27 (1.4 mg, 0.60 µmol): ESI-MS calcd $C_{97}H_{146}N_{18}O_{47}S_2$ $[M+2H]^{2+}$ 1191.2. found $[M+2H^+]$ 1191.34.

Compound 29:

To a vial with glycopeptides 27 (0.4 mg) and 28 (0.2 mg) was added a solution of TCEP in DMF (0.2 mL, 10 mg TCEP in 1 mL DMF) and sodium monohydrogen phosphate (2 mg). The reaction was monitored by LC-MS. Once the reaction is completed, the reaction mixture was diluted with water and acetonitrile and purified by HPLC (15-45% acetonitrile in water over 20 min, $T_{retention}$=15.62 min) to give compound 29: ESI-MS calcd $C_{133}H_{212}N_{28}O_{64}S$ $[M+2H]^{2+}$ 1630.3. found $[M+2H]^{2+}$ 1630.6.

Compound 44:

To a solution of crude peptide 43 (30 mg, 12.94 µmol) in MeOH (1 mL) was added a solution of aldehyde 11 (13.5 mg, 38.8 µmol) at room temperature. The resulting reaction mixture was stirred at room temperature for 2 h before a solution of sodium cyanoborohydride (4.0 mg, 64.7 µmol) in MeOH (0.5 mL). The reaction mixture was stirred at room temperature overnight before it was concentrated with a stream of nitrogen gas. The resultant residue was purified by HPLC (80-100% acetonitrile in water over 20 min, $T_{retention}$=14.39 min) to give the reductive amination product 44 (22.5 mg, 8.5 µmol) in 66% isolation yield: ESI-MS calcd $C_{140}H_{188}N_{18}O_{27}S_3$ $[M+2H]^{2+}$ 1327.0. found $[M+2H]^{2+}$ 1327.1.

Compound 46:

To a solution of peptide 44 (7.5 mg, 2.83 µmol) in DMF (0.5 mL) was added diisopropyl ethyl amine (1.5 µL, 8.49 µmol) and HATU (3.2 mg, 8.49 µmol). The resulting reaction mixture was stirred at room temperature for 5 min before a solution of phenol 45 (1.6 mg, 8.49 µmol) in DMF (0.2 mL) was added. The reaction mixture was stirred at room temperature for 3 h before it was concentrated in vacuo. The resultant residue was used for next step without further purification.

To a vial with crude phenolic ester (2.83 µmol) was added a mixture of trifluoroacetice acid, triethylsilane, water and phenol (3 mL/0.1 mL/0.2 mL/66 mg). The reaction mixture was stirred at room temperature for 2 h before it was concentrated. Addition of ice-cooled diethyl ether to the vial removed phenol and precipitated the peptide which was purified by HPLC (40-85% acetonitrile in water over 20 min, $T_{retention}$=11.44 min) to give phenolic ester 46a (3.2 mg, 1.61 µmol) in a 57% isolation yield over two steps: ESI-MS calcd $C_{95}H_{133}N_{18}O_{21}S3$ $[M+2H]^{2+}$ 981.3. found $[M+2H]^{2+}$ 981.4.

Compound 48:

To a solution of phenolic ester 46 (3.2 mg, 1.61 µmol) in trifluoroethanol (1 mL) was added a solution of 3-nitro-2-pyridinylsulfenyl chloride (0.7 mg) in $CH_2Cl_2$ (0.3 mL). The resultant reaction mixture was stirred at room temperature for 30 min and concentrated with a stream of nitrogen gas to give a residue which was purified by HPLC to generate a mixture of disulfides in which compound 47 is the major compound. All the disulfides can be reduced with TCEP to give the same thiol phenol.

To a vial with the disulfide mixture 47 (1.5 mg) was added a solution of TCEP (5 mg) in DMF (1.5 mL) and sodium monohydrogen phosphate (2 mg). The reaction was stirred at room temperature for 4 h before the reaction mixture was purified by HPLC (40-85% acetonitrile in water over 20 min, $T_{retention}$=10.88 min) to give the cyclic peptide 48 (1 mg, 78%): ESI-MS calcd $C_{79}H_{116}N_{18}O_{19}S$ $[M+2H]^{2+}$ 827.5. found $[M+2H]^{2+}$ 827.6.

Scheme 19. Synthesis of Disaccharide Acceptor
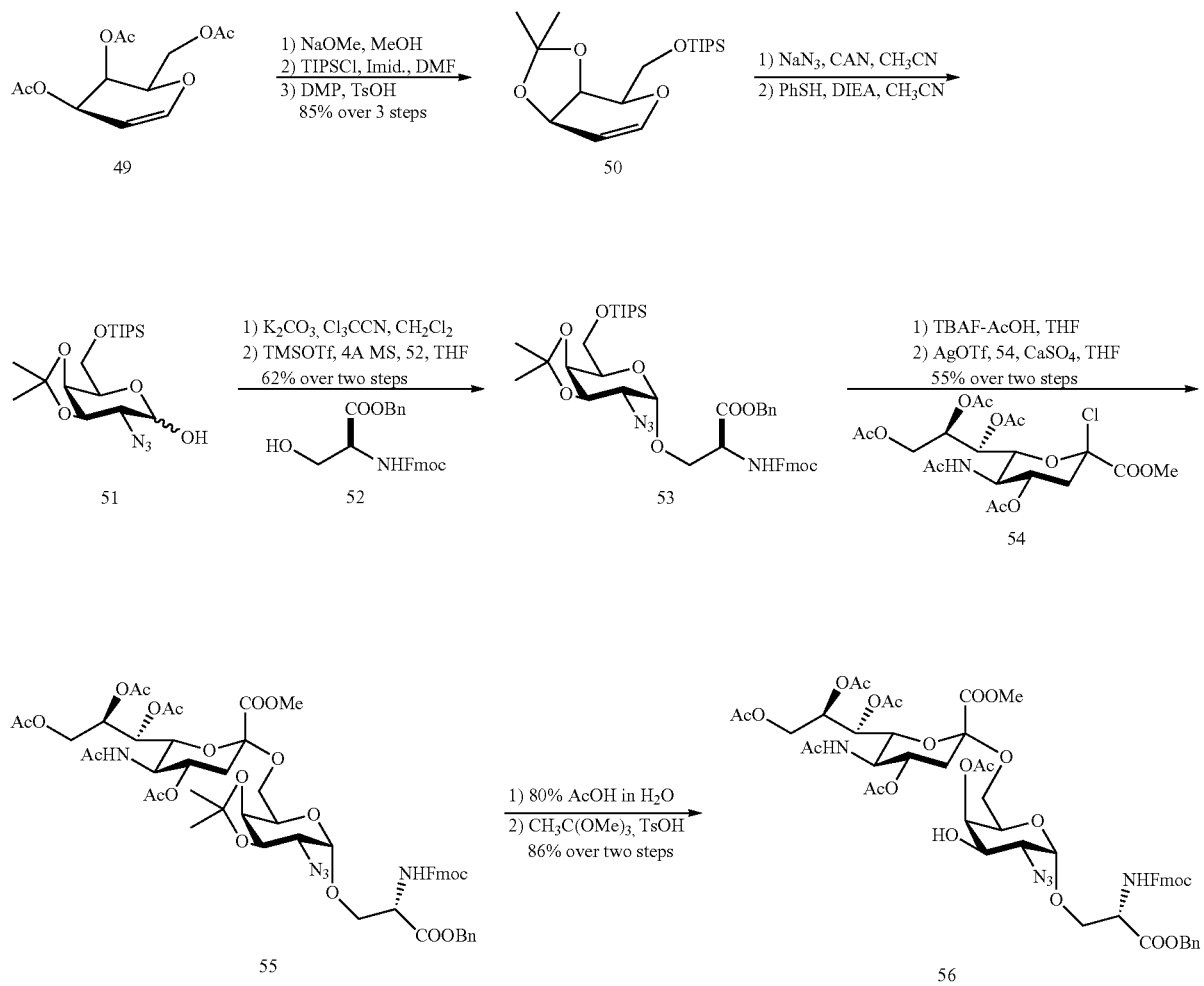
Scheme 20. Synthesis of Protected Glycophorin
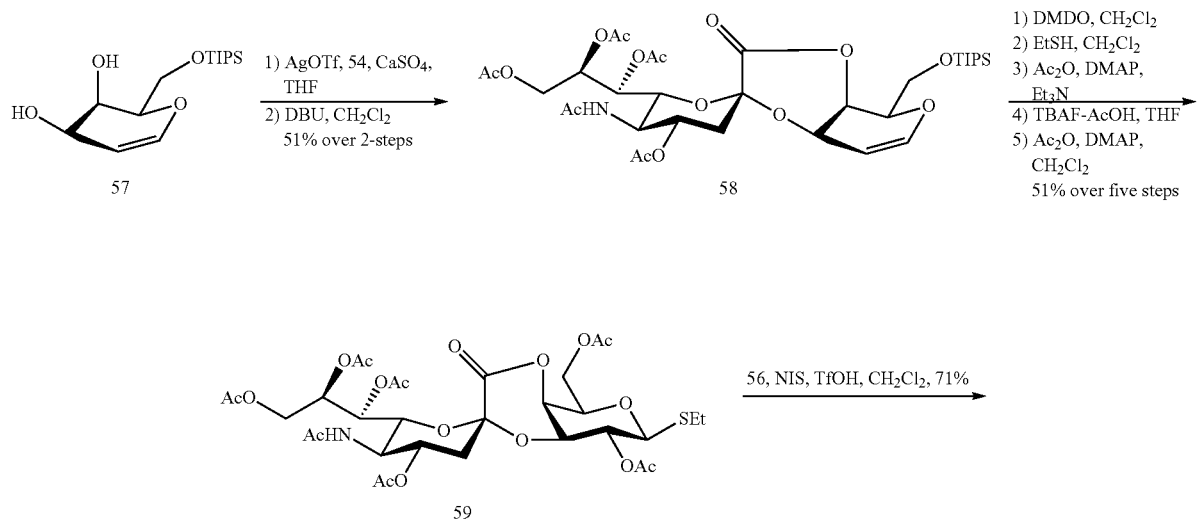

-continued
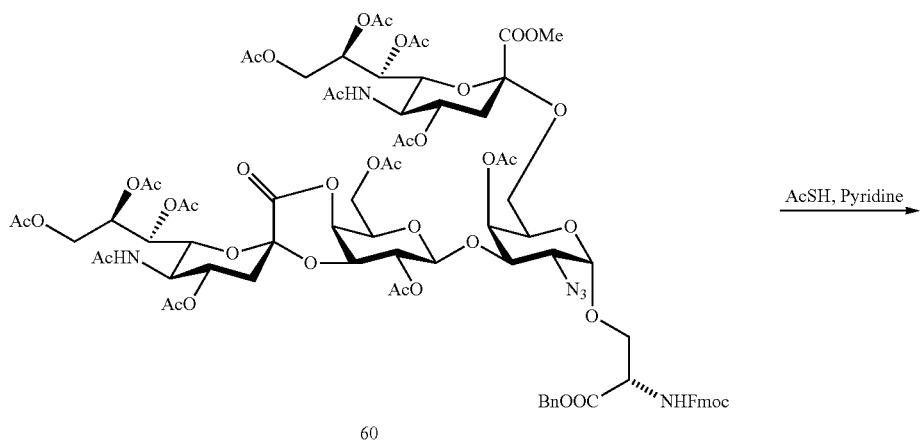
60
AcSH, Pyridine →
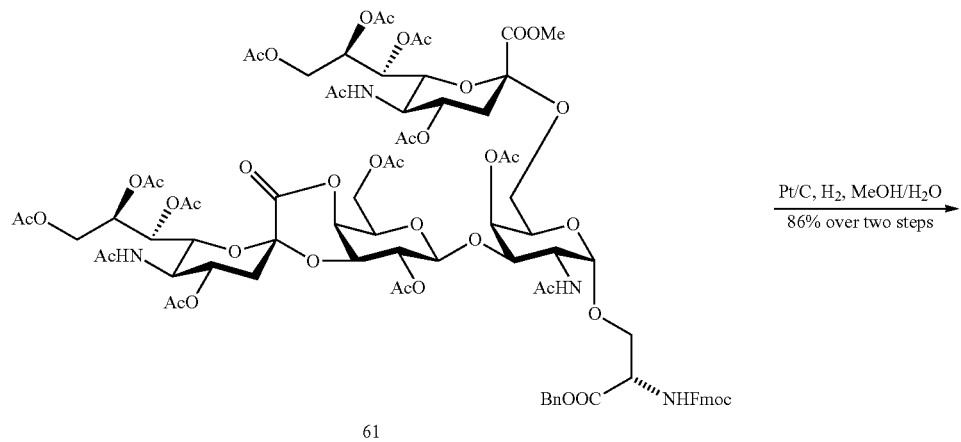
61
Pt/C, H₂, MeOH/H₂O
─────────────
86% over two steps →
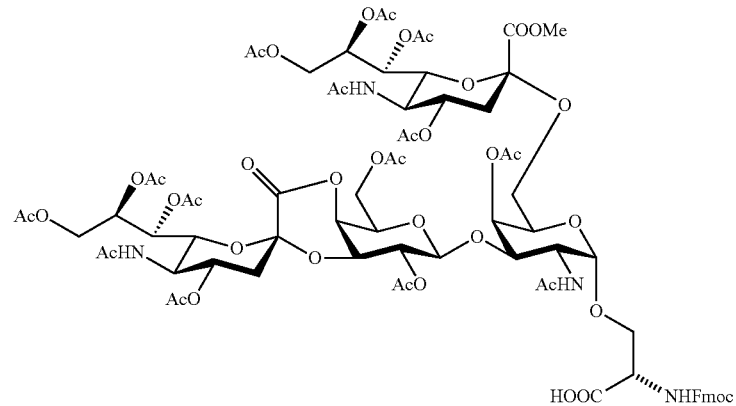
62

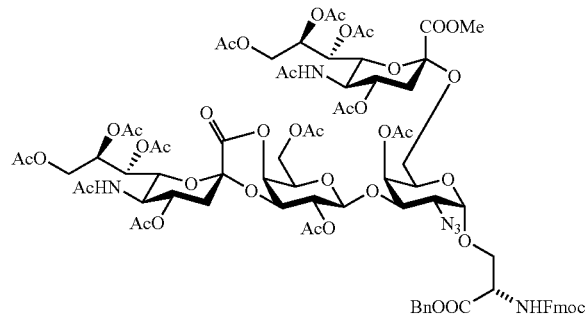

60

Sialylated acceptor 56 (115 mg, 0.013 mmol) and thioglycoside 59 (62 mg, 0.083 mmol) were azeotroped benzene (3×10 mL). NIS (48.4 mg, 0.215 mmol), 0.32 g of 4 Å MS, and 7 mL of CHCl$_2$ were then added. The resultant suspension was cooled to 0° C. A freshly prepared solution of triflic acid (1% solution in CH$_2$Cl$_2$, 0.73 mL) was then added dropwise over 3 min at 0° C. The ice-water bath was removed and the reaction mixture was stirred at rt for 20 min before it was quenched with addition of saturated aqueous NaHCO$_3$. The organic layer was washed with water (10 mL) and saturated aqueous Na$_2$S$_2$O$_3$ (10 mL). And the combined aqueous layers were extracted with CH$_2$Cl$_2$ (3×10 mL). The combined organic layers were dried over Na$_2$SO$_4$, filtered, and concentrated in vacuo to give a residue which was purified by silica gel flash column chromatography (20% CH$_2$Cl$_2$ in EtOAc to 5% MeOH in CH$_2$Cl$_2$) to give the desired tetrasaccharide 60 (106 mg, 0.058 mmol) as a white solid: ESI-MS C$_{82}$H$_{98}$N$_6$O$_{40}$, cald. 1806.58. found [M+Na]$^+$ 1829.8.

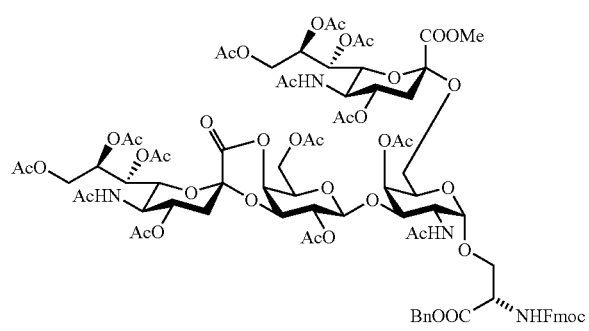

61

To a solution of tetrasaccharide 60 (88 mg, 0.049 mmol) in pyridine (2.5 mL) was added thiolacetic acid (2.5 mL) at 0° C. The resultant reaction mixture was gradually warmed to rt and stirred at rt overnight before the excess thiolacetic acid was removed with a stream of nitrogen follwed by toluene azeotrope (3×10 mL). The crude product was purified by silica gel flash column chromatography (40% hexanes in EtOAc, 5% MeOH in CH$_2$Cl$_2$) to give the desired acetylamine 61 (86 mg, 0.047 mmol) as a white solid: ESI-MS C$_{84}$H$_{102}$N$_4$O$_{41}$, cald. 1822.60. found [M+Na]$^+$ 1845.7.

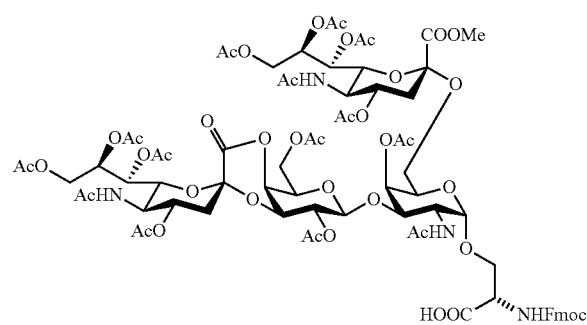

62

To a solution of compound 61 (8.5 mg, 4.66 μmol) in MeOH (1.5 mL) and water (0.1 mL) was added platinum (10% on carbon, 1 mg). The reaction system was purged with hydrogen for three times. And the reaction mixture was stirred at rt for 2 days before the mixture was filtered by a short column with celite to give a crude product which was purified by silica gel flash column chromatography (5-15% MeOH in CH$_2$Cl$_2$) to give the desired acetylamine 62 (7.2 mg, 0.042 mmol) as a white solid: ESI-MS C$_{77}$H$_{96}$N$_4$O$_{41}$, cald. 1732.56. found [M−H]$^−$ 1731.7.

Scheme 21.
Synthesis of Glycopeptide representing AA114-AA166 of Erythropoietin with a Tn on Ser[126].

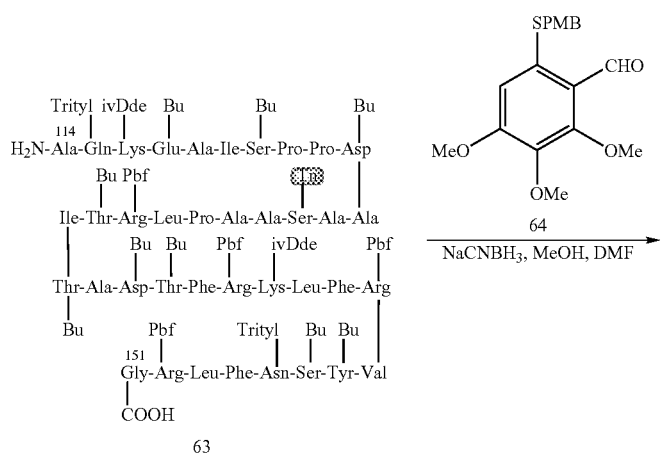

63

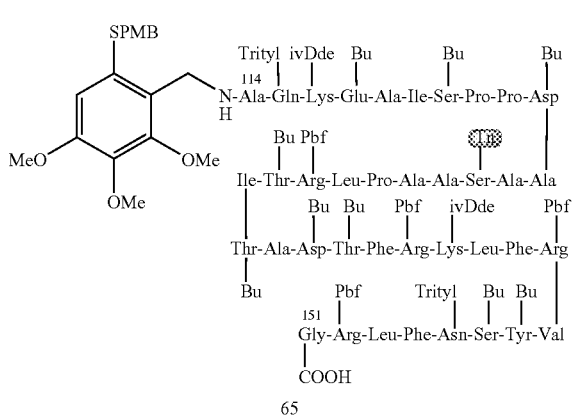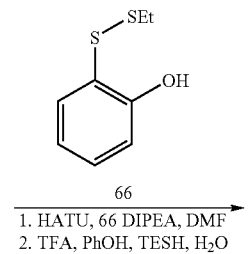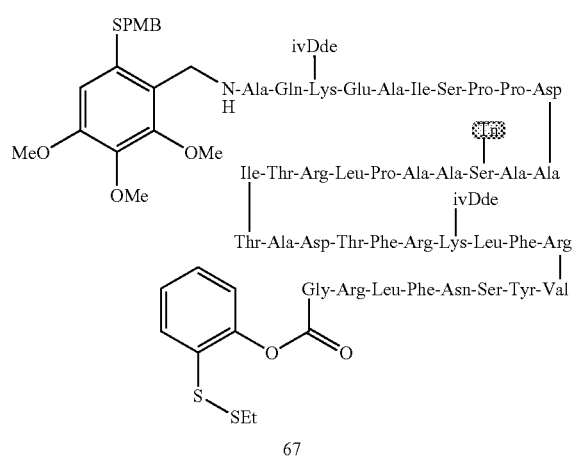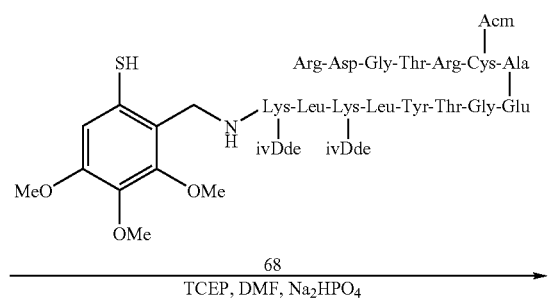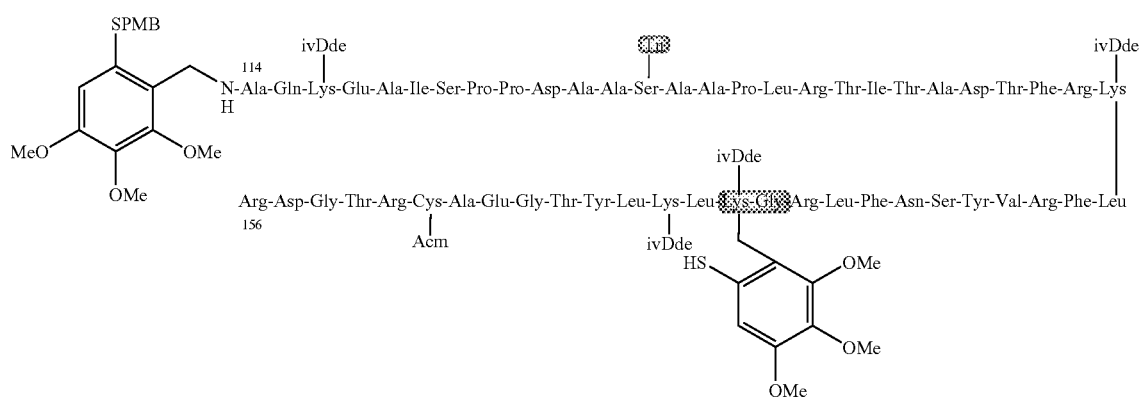

Scheme 22. Abbreviations in Scheme 21.

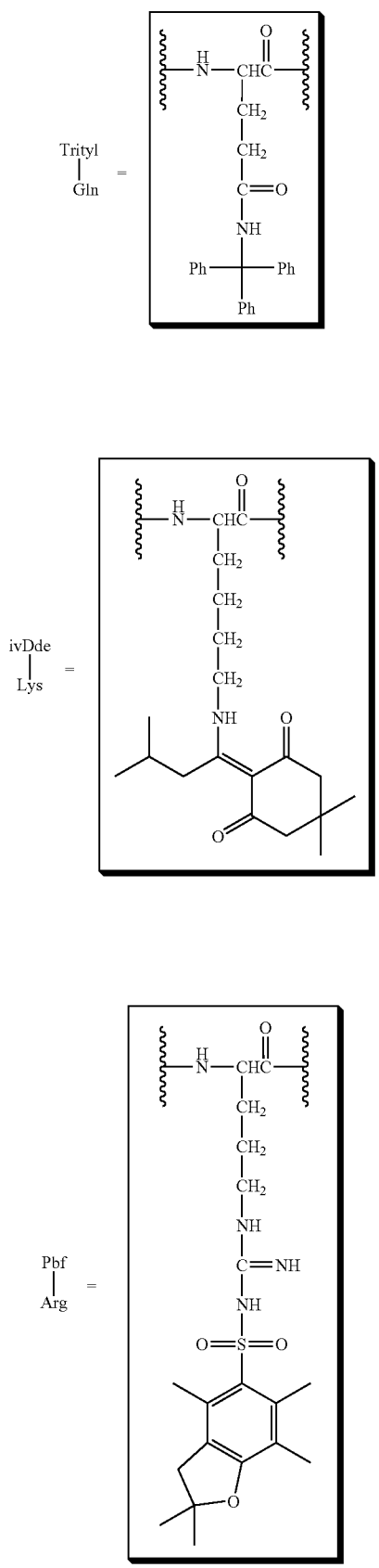

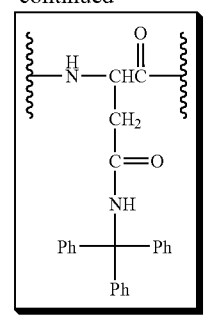

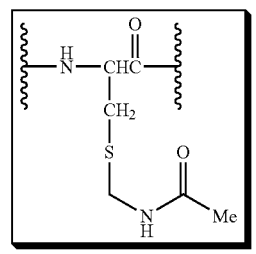

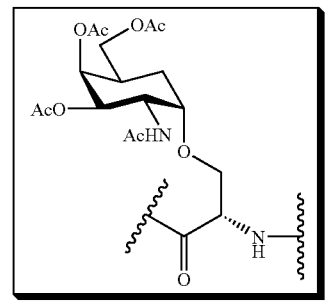

The preparation of glycopeptide 63 was carried on peptide solid phase synthesizer using HATU as the coupling reagent, diisopropylethyl amine as the base, TGT chloro-trityl resin. For each cycle, 4 equivalent of HATU, 4 equivalent of the individual amino acid and 8 equivalent of the base were employed. After the first 25 cycles completed, the resin was transferred to a sinister flask and treated with 1 equivalent of Tn-Ser-OH, 1 equivalent of HATU, 1 equivalent of HOAt and 2 equivalent of diisopropyl ethyl amine in DMF for 45 min and repeated the same coupling reaction for one more time. The resin was thoroughly washed with DMF. Then the resin was exposed to 20% piperidine in DMF for 5 min twice. The resin was thoroughly washed with DMF and transferred to the solid phase peptide synthesizer for the rest of 12 amino acids introduction. Finally, the resin was transferred to a sinister flask and was subjected to 30% 2,2,2-trifluoroethanol in methylene chloride for 1 h and filtered. The filtrate was concentrated and precipitated by addition of ice-cooled diethyl ether to give solid crude peptide 63. The crude peptide was used for the next step without further purification.

To a solution of the crude peptide 63 (30 mg, 4.33 µmol) in MeOH (0.5 mL) was added a solution of aldehyde 64 (4.5 mg, 12.9 µmol) in DMF (0.2 mL). The resulting solution was stirred at rt for 2 h before a solution of sodium cyanoborohydride (1.4 mg, 21.6 µmol) in MeOH (0.1 mL) was added. The resulting reaction mixture was stirred at rt overnight before it was concentrated and washed with water (3 mL). The aqueous layer was extracted with $CHCl_3$ (3×10 ml). The combined organic layers were dried over $Na_2SO_4$ and filtered and concentrated to give a residue containing 65, which was used for the next step without further purification.

The crude carboxylic acid 65 was dissolved in DMF (0.5 mL) and treated with HATU (3 eq.) and DIPEA (6 eq.) for 5 min before a solution of phenol 66 (5 eq.) was added. The resultant reaction mixture was stirred at rt for 3 h before it was concentrated in vacuo. The residue was exposed to a co-solvent system (TFA/H$_2$O/TESH, 94:4:2) and Phenol for 3 h to remove the side chain protecting groups. The excess solvents were removed and the phenol was removed by addition of diethyl ether. The resultant residue was purified with HPLC to give compound 67. ESI-MS: $C_{254}H_{383}N_{55}O_{70}S_3$, Calcd. $[M+3H]^{3+}$, 1808.61. found 1808.78; Calcd. $[M+4H]^{4+}$, 1356.71. found 1356.65.

To a vial with glycopeptide 67 (0.1 mg) and polypeptide 68 (0.1 mg) equipped with a flea-sized stir bar was added a solution of TCEP in DMF (2 mg/0.2 mL) and solid Na$_2$HPO$_4$. The resulting reaction mixture was stirred at rt and monitered with LC-MS. After stirring at rt overnight, the reaction was completed. A MS-peak corresponding the desired ligated product 69 was observed.

Scheme 23. Exemplary synthesis of the hexasaccharide glycan.

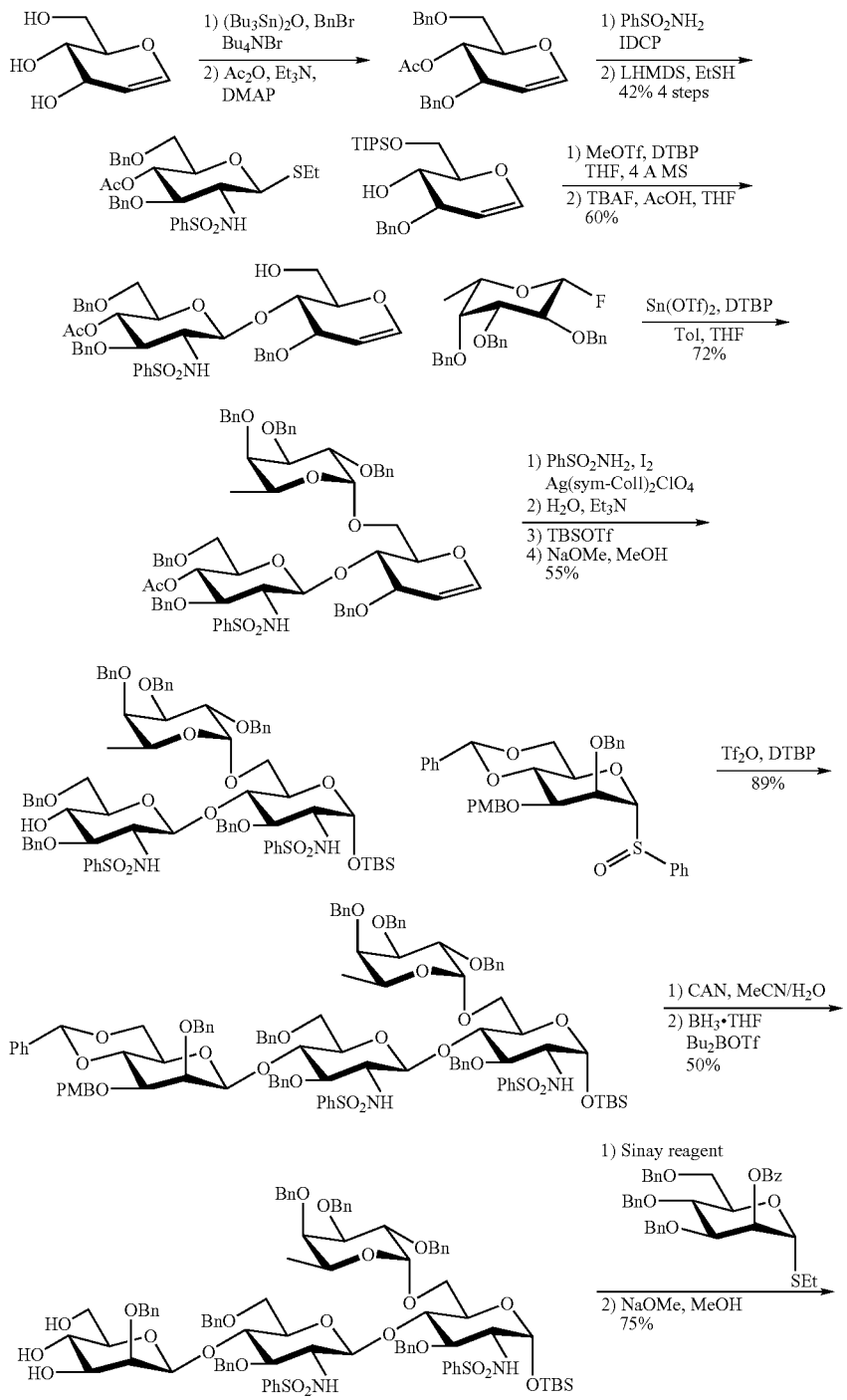

-continued
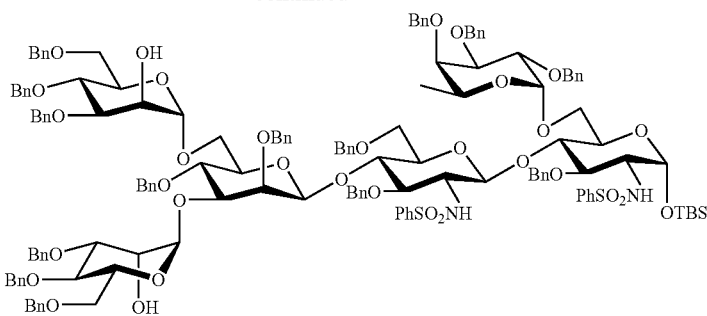
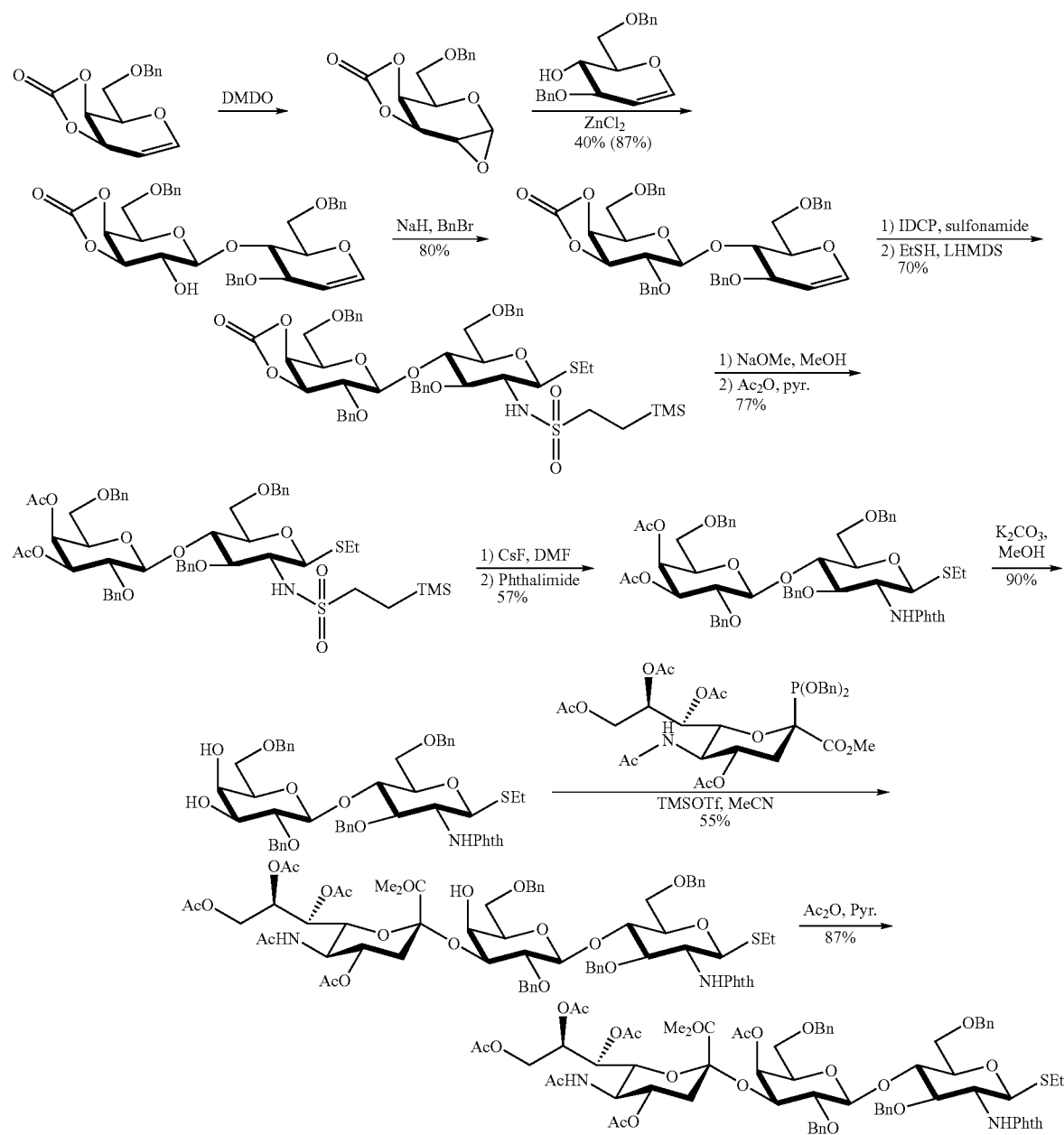
Scheme 24. Exemplary synthesis of the "wing" trisaccharide glycan.

Scheme 25. Exemplary preparation of 11-mer and 12-mer sugars.
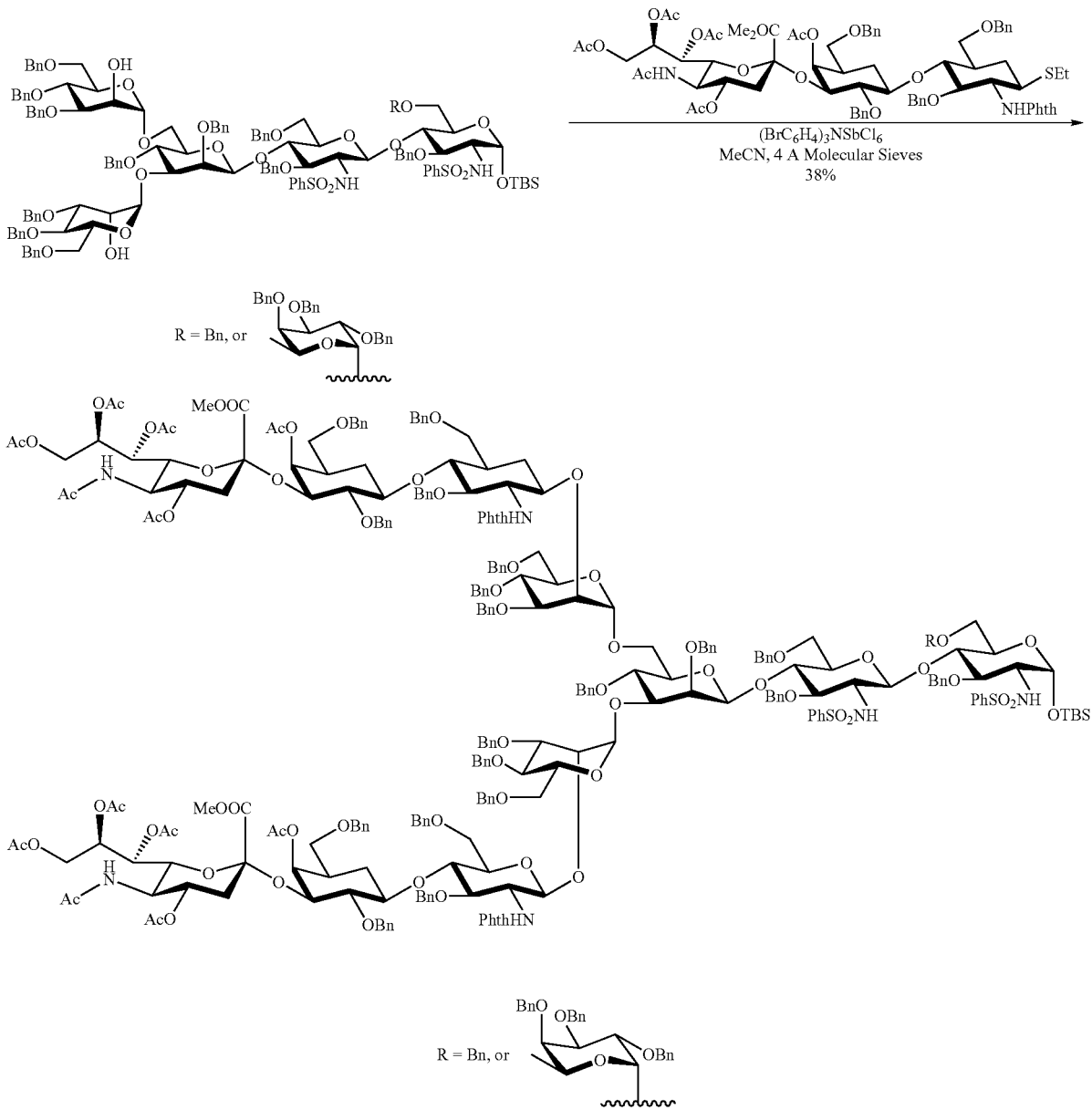
Scheme 26. Representative Experimental Procedure for the Biscoupling.
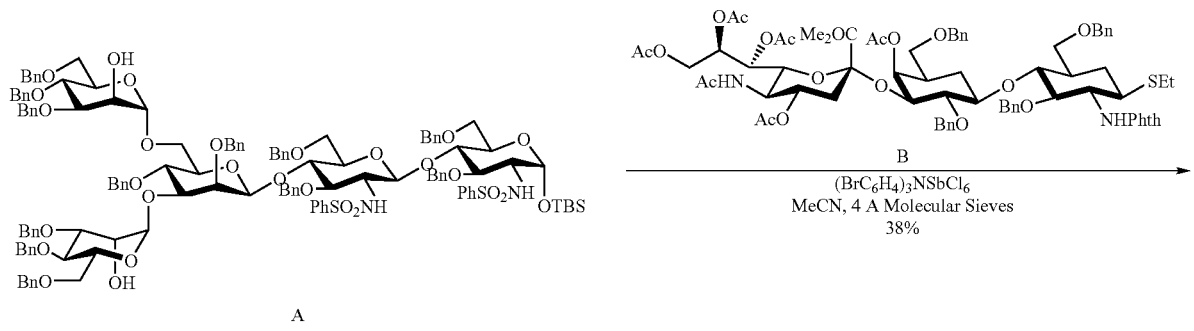

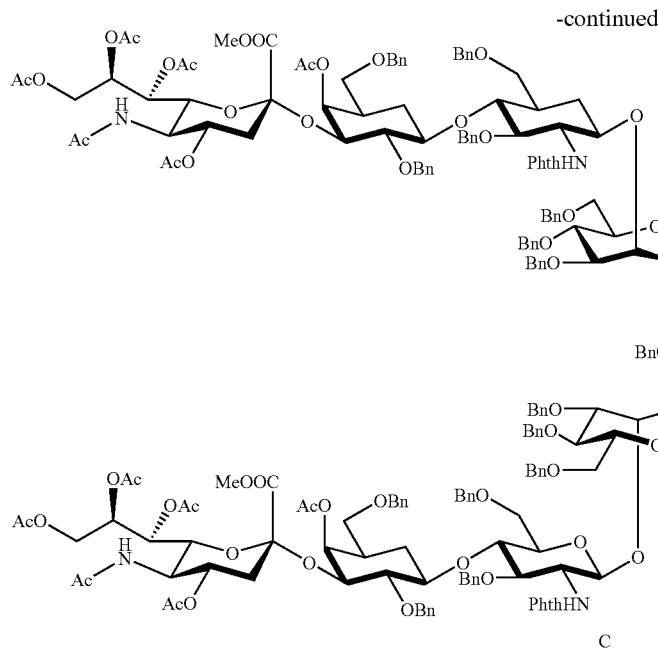
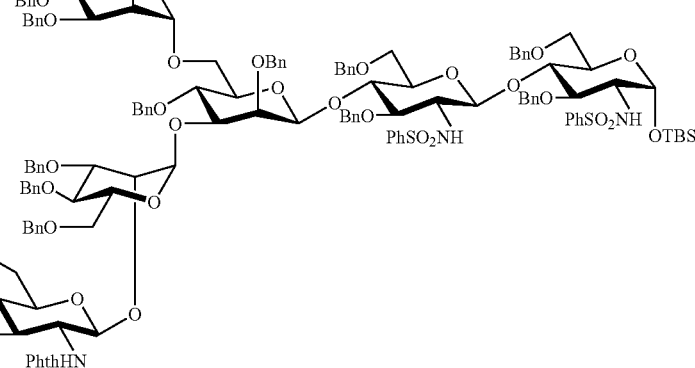

C

Pentasaccharide A (12 mg, 5.1 μmol) and trisaccharide B (25 mg, 18.0 μmol) were combined and concentrated with dry toluene three times, then placed on high vacuum pump for 3 h. The mixture was dissolved in MeCN (2 mL) with freshly dried 4 A molecular sieves. The mixture was stirred at room temperature for 30 min, then cooled to 0° C. Sinay reagent was added to the mixture, and the reaction was stirred in the dark for 15 h. Excess amount of Et$_3$N (0.1 mL) was added to the reaction, and the mixture was filtered through a short plug of silica gel and celite, washed by EtOAc. The filtrate was concentrated under vacuo and the residue was purified by flash chromatography (DCM:MeOH=60:1 to 40:1) to yield the 11-mer sugar C (9.5 mg, 38%) as a white solid along with monocoupling product.

3) Exemplary Reiterative Cysteine-Dependent Native Chemical Ligation Synthetic Methodology Towards the Synthesis of Homogeneous HuEPO.

As discussed herein, glycoproteins constitute an important class of biomacromolecules, and a great deal of effort has been directed toward the understanding of the role of glycosylation in various critical protein functions, such as protein folding, proteolytic stability, and cell adhesion (Varki, *Glycobiology* 1993, 3, 97; Helenius, *Mol. Biol. Cell* 1994, 2, 253; Ruderer et al., *J. Bacteriol.* 1991, 173, 3539; Klausner et al., *Cell* 1990, 62, 611; Roth, *Chem. Rev.* 2002, 102, 285-303; Grogan et al., *Annu. Rev. Biochem.* 2002, 71, 593-634; Nilsson et al., *Annu. Rev. Biophys. Biomol. Struct.* 2005, 34, 91-118; Ratner et al., *ChemBioChem.* 2004, 5, 1375-1383). Furthermore, a number of glycoproteins are known to possess valuable and exploitable therapeutic activities. Prominent examples include, but are not limited to, erythropoietin, (Szymkowski, *Curr. Opin. Drug Discov. & Devel.* 2005, 8, 590-600; Pavlou et al., *Nature Biotech.* 2004, 22, 1513-1519; Jelkmann et al., *Ann Hematol.* 2004, 83, 673-686; Ridley et al., *J. Natl. Med. Assoc.* 1994, 86, 129-135) which is commonly used in the treatment of anemia, the various isoforms of prostate specific antigen (Okada et al., *Biochim. Biophys. Acta* 2001, 1525, 149-160; Dudkin et al., *J. Am. Chem. Soc.* 2004, 126, 736-738) and candidate antigens which could serve as the basis for gp120-directed HIV vaccines (Geyer et al., *J. Biol. Chem.* 1988, 263, 11760-11767; Mandal et al., *Angew. Chemie Int. Ed.* 2004, 43, 2557-2561; Geng et al., *Angew. Chemie Int. Ed.* 2004, 43, 2562-2565). Presumably, Nature's complex apparatus for accomplishing post-translational glycosidation is there to impart some advantage to the glycoprotein product. However, despite considerable interest, the field of glycobiology faces a nontrivial obstacle to the rigorous investigation of the implications of protein glycosidation. The isolation of significant quantities of homogeneous glycoprotein from natural sources is exceedingly difficult (Kornfeld et al., *Annu. Rev. Biochem.* 1985, 54, 631-664). The present invention provides a widely applicable method allowing access to the de novo preparation of meaningful amounts of structurally homogeneous glycoproteins including, for example, erythropoietin.

Methods for constructing O-linked glycopeptides are known in the art. Similarly, N-linked glycopeptides may be synthesized by preparing, through total synthesis, complex oligosaccharide units and appending them to small peptide fragments through a Kochetkov-Lansbury amination-aspartylation protocol (Wang et al., *Angew. Chem.* 2001, 113, 1778-1782; *Angew. Chem. Int. Ed.* 2001, 40, 1728-1732; Wang et al., *Angew. Chem.* 2000, 112, 3798-3802; *Angew. Chem. Int. Ed.* 2000, 39, 3652-3656). Methodologies aimed at ligating a fully synthetic carbohydrate-peptide domain to another peptide fragment using cysteine-based native chemical ligation are also known in the art (for the paper teaching the powers of cysteine-based antive chemical ligation, see: Dawson et al., *Science*, 1994, 266, 776-779; Miller et al., *Angew. Chem.* 2003, 115, 447-450; *Angew. Chem., Int. Ed.* 2003, 42, 431-434). A methodology has been reported that involves coupling two fully functionalized carbohydrate-peptide fragments, thus rendering possible the preparation of multiply glycosylated proteins with a high level of convergence (Scheme 27). That methodology involves in situ generation of a thioester from a glycopeptide possessing a C-terminal phenolic ester (Scheme 27). This fragment can then be coupled with a second glycopeptide displaying an N-terminal cysteine residue to provide a homogeneous, fully synthetic polypeptide incorporating two N-linked oligosaccharide domains (Warren et al., *J. Am. Chem. Soc.* 2004, 126, 6576-6578).

Scheme 27.
Cysteine-Based Native Chemical Ligation of Glycopeptides

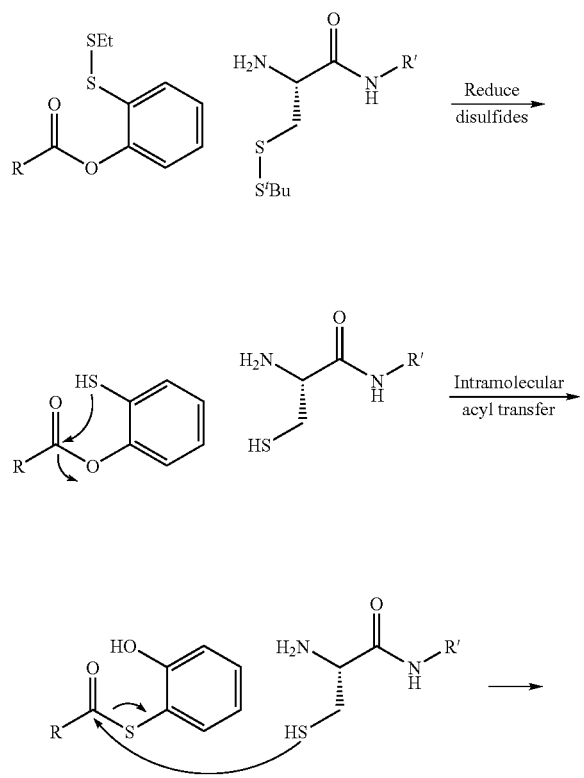

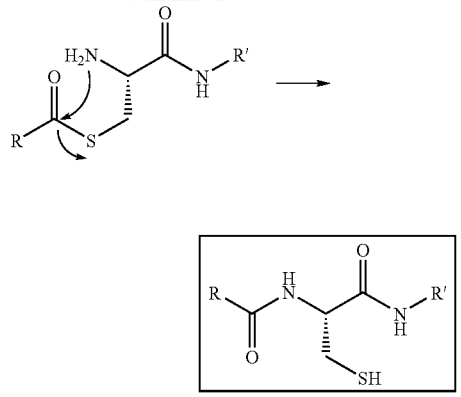

We describe herein a reiterative process making use of the above-methodology, thus allowing access to the generation of complex glycoproteins displaying multiple sites of glycosylation. Thus, as outlined in Scheme 28, two glycopeptide fragments (70 and 71) may be joined in the first step through the cysteine-dependent native chemical ligation method. The C-terminal coupling partner (70) possesses a masked cysteine residue at its N-terminus. Following removal of the N- and S-protecting groups, the newly formed glycopeptide (74) is coupled once again with a third synthetic glycopeptide unit (73). Deprotection of the N-terminus and the cysteine residue of the coupled product (75) provides a large polypeptide unit containing three different oligosaccharide domains. A 1,3-thiazolidine-4-carboxo (Thz) group, which Kent and coworkers had employed in their total synthesis of crambin, (Bang et al., *Angew. Chem.* 2004, 116, 2588-2592; *Angew. Chem. Int. Ed.* 2004, 43, 2534-2538) is expected to work well, as this particular protecting group may be cleavable under mild conditions, which are compatible with survival of the potentially labile glycopeptide ensemble. As depicted in Scheme 28, the resulting N-terminal cysteine-based acyl acceptor may be subjected to reiteration of the scheme, thus leading to elongation of the glycopeptidic construct.

Scheme 28. General Strategy for Reiterative Coupling of Glycopeptides.

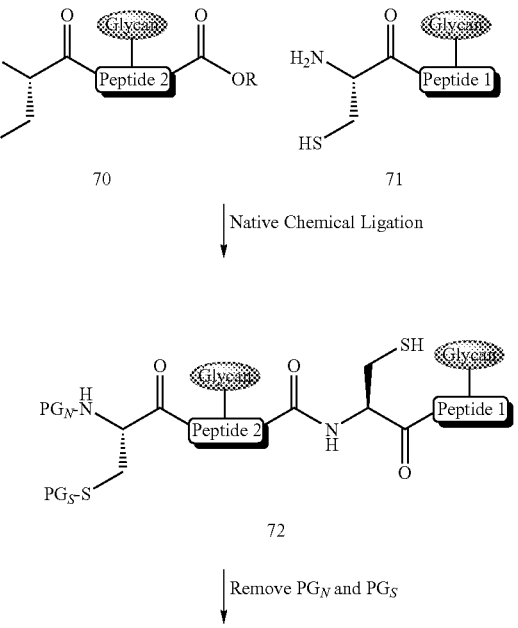

-continued
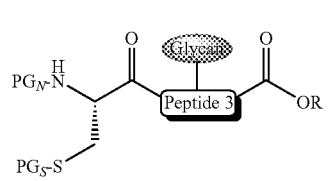
73
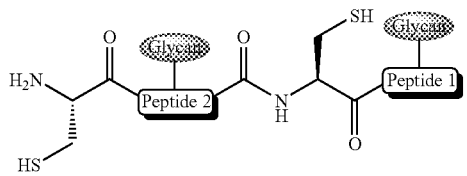
74
1) Native Chemical Ligation
2) Remove PG$_N$ and PG$_S$
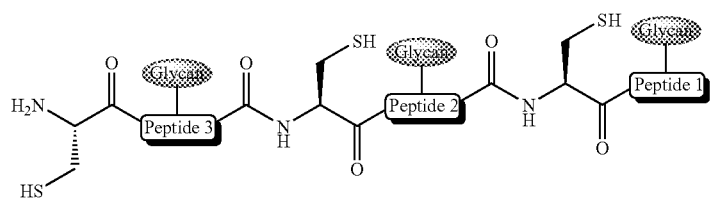
75

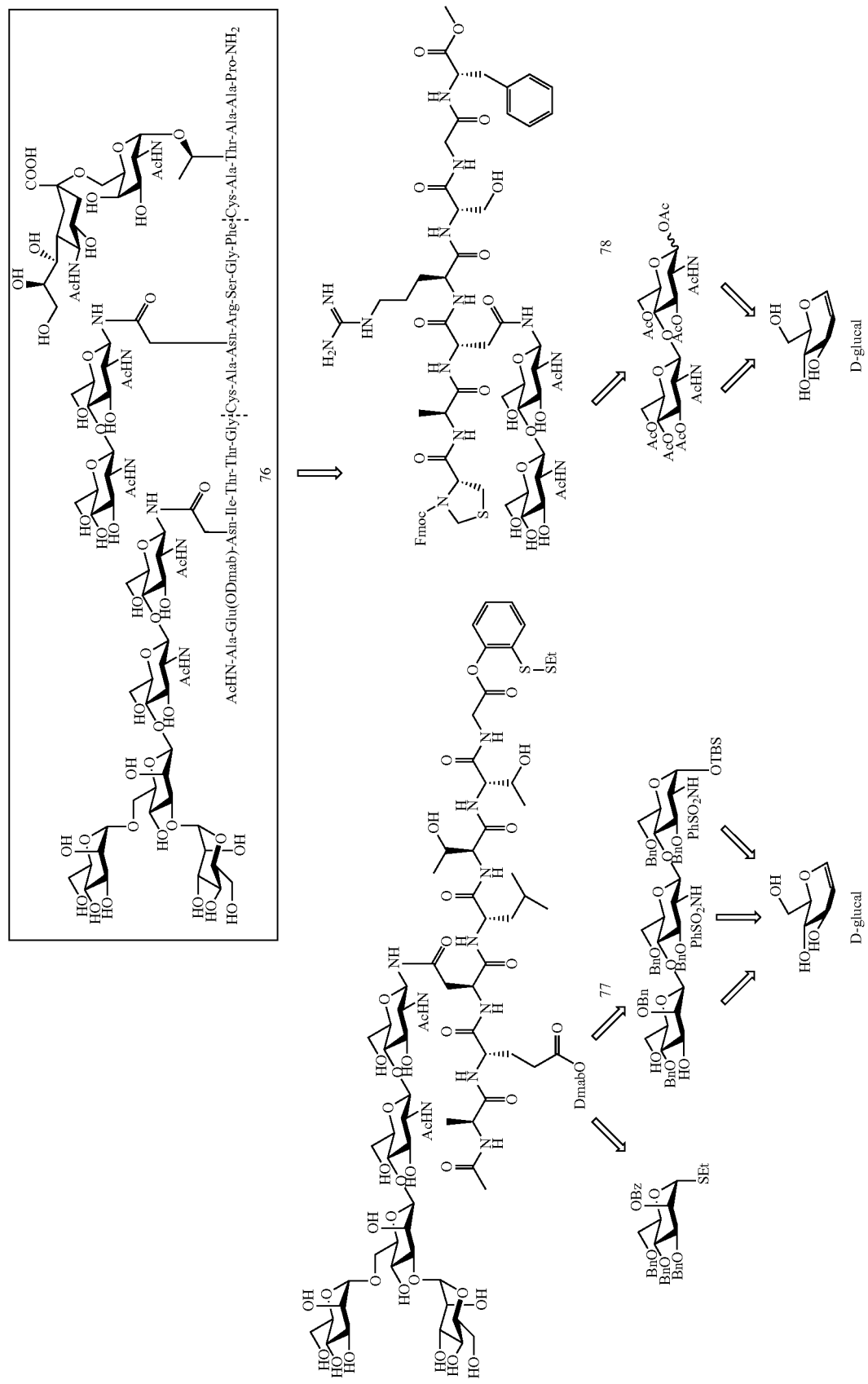

-continued
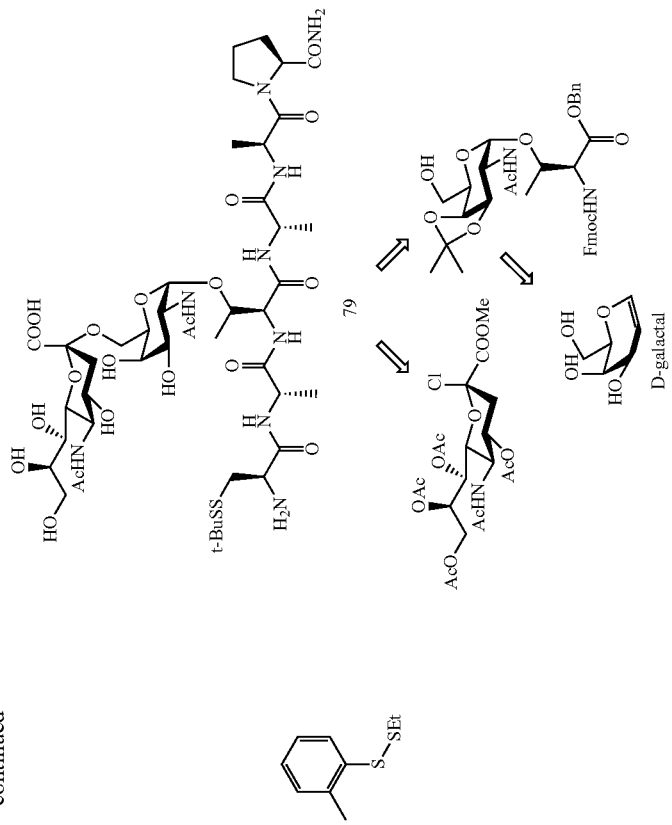

The success of this iterative method was established by the preparation of the target glycopeptide 76, which is comprised of 20 amino acids and three different oligosaccharide domains, two of which contain N-linkages to Asn residues, and one of which is O-linked to a Thr residue (Scheme 29). Accordingly, glycopeptide 76 is assembled through reiterative couplings of individual glycopeptide fragments 77, 78, and 79. The coupling precursor fragments leading to the 77, 78, and 79 domains were synthesized according to well-established methods (Danishefsky et al., *Angew Chem.* 1996, 108, 1482-1522; *Angew. Chem. Int. Ed.* 1996, 35, 1380-1419).

pling site. Following removal of the amino acid protecting groups (cf 81 to 82), aspartylation (Likhosherstov et al., *Carbohydr. Res.* 1986, 146, C1-C5; Cohen-Anisfeld et al., *J. Am. Chem. Soc.* 1993, 115, 10531-10537) with glycosylamine 83 (prepared from chitobiose through amination (Likhosherstov et al., *Carbohydr. Res.* 1986, 146, C1-C5) provided 78 in 68% yield.

The preparation of the O-linked glycopeptide, 79, is outlined in Scheme 31. As shown, the synthesis began with the previously described glycosylamino acid, 84 (Schwartz et al., *J. Am. Chem. Soc.* 1999, 121, 2662-2673). The remainder of

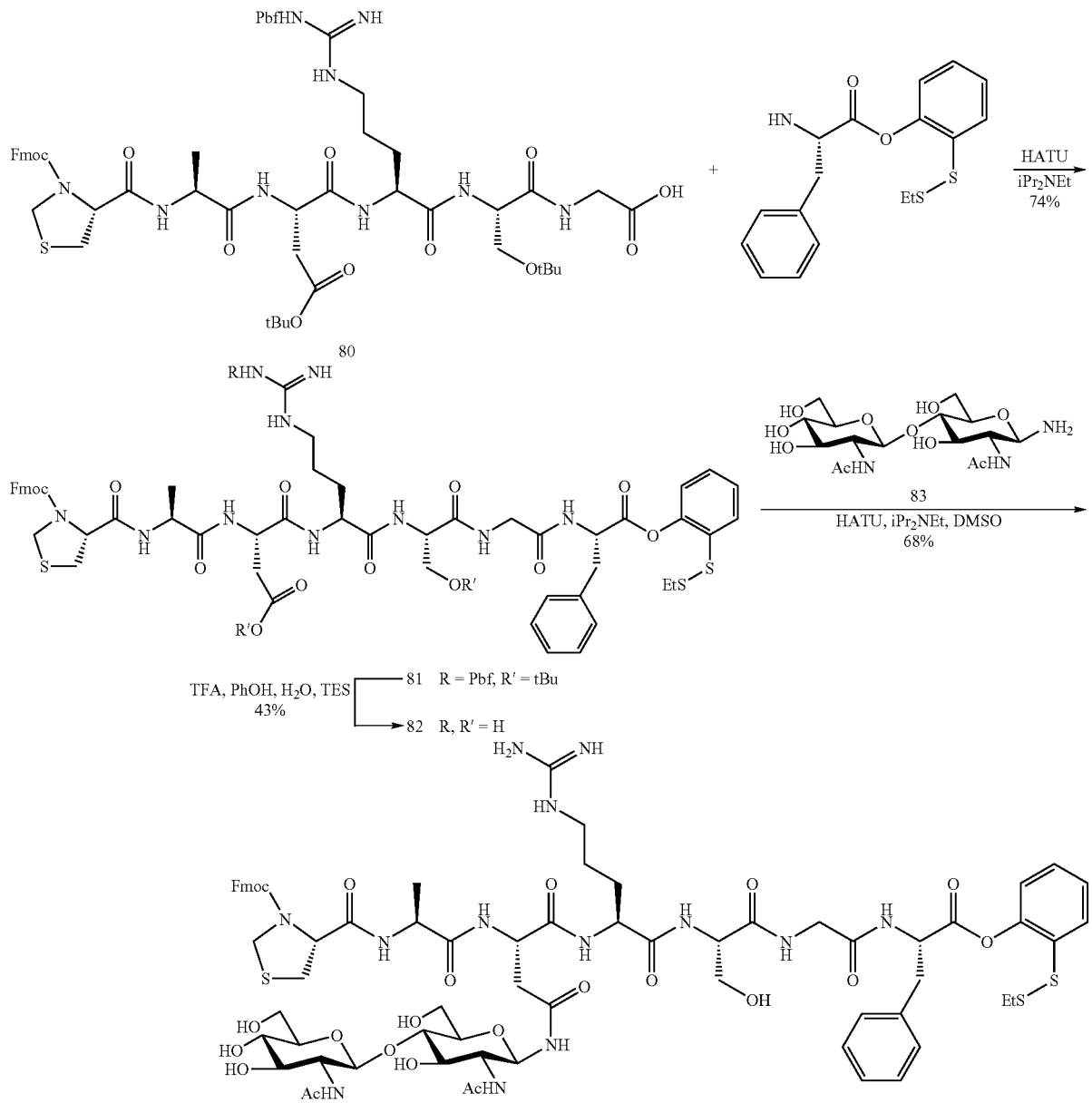

Scheme 30. Preparation of Coupling Partner 78.

Thus, peptide 80 was prepared through Fmoc based synthesis (Scheme 30). Coupling of 80 with the phenolic ester of phenylalanine, as shown, provided peptide 81, possessing the appropriate functionalization at the future C-terminal coupling site.

the peptide was then appended to the N- and C-termini of the threonine glycosylamino acid to afford, following deprotection, the coupling partner 79, possessing an N-terminal cysteine residue.

Scheme 31. Preparation of Coupling Partner 79.
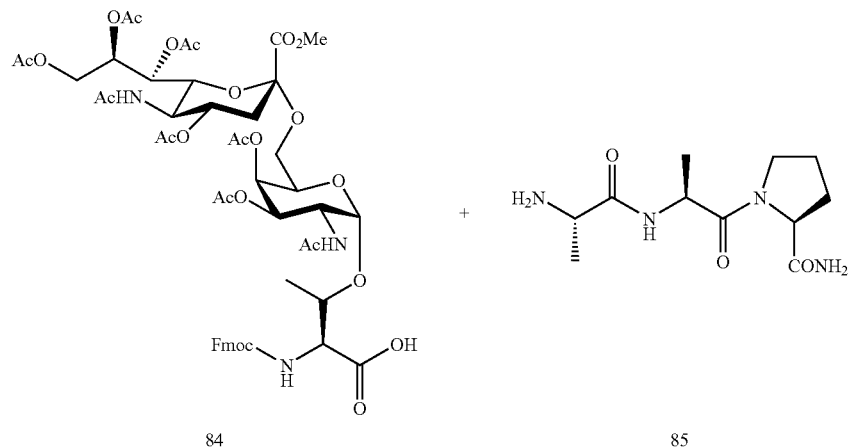
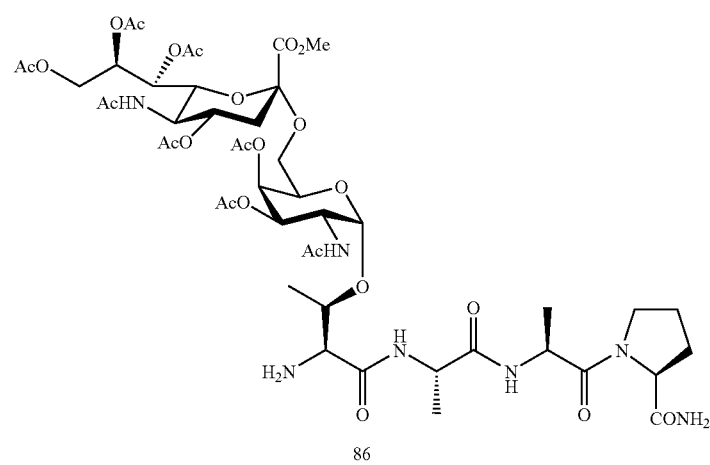
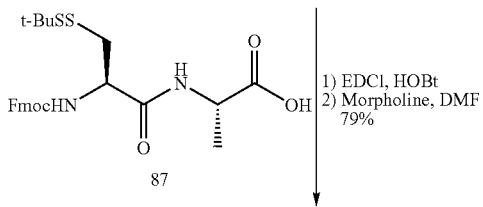

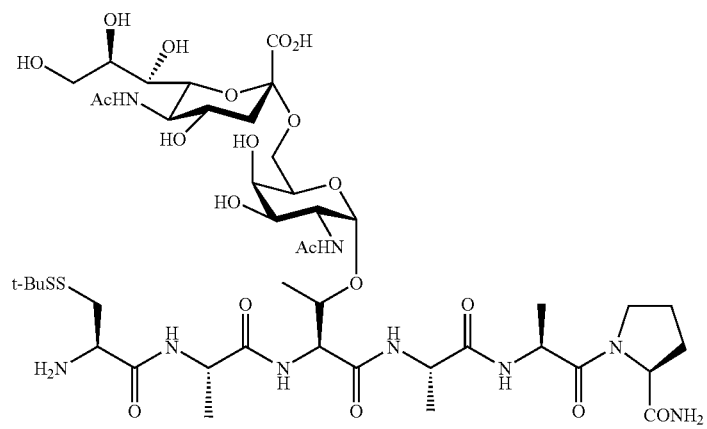
79
Scheme 32. Preparation of Coupling Partner 77.
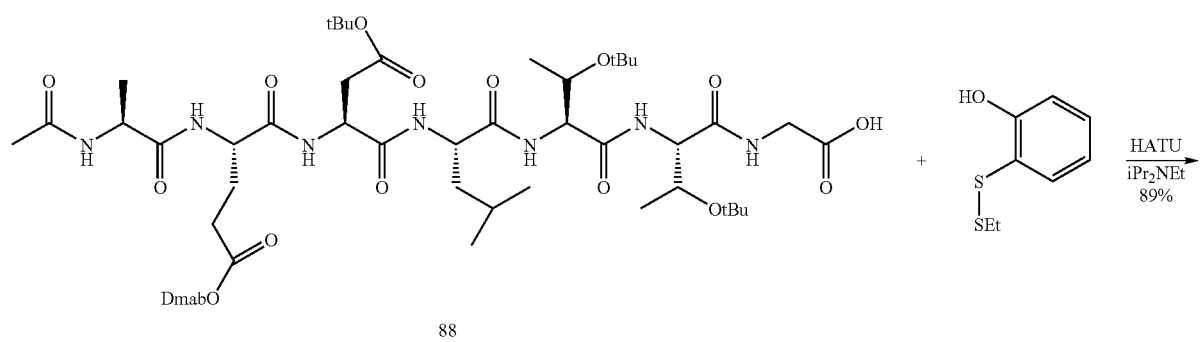
88
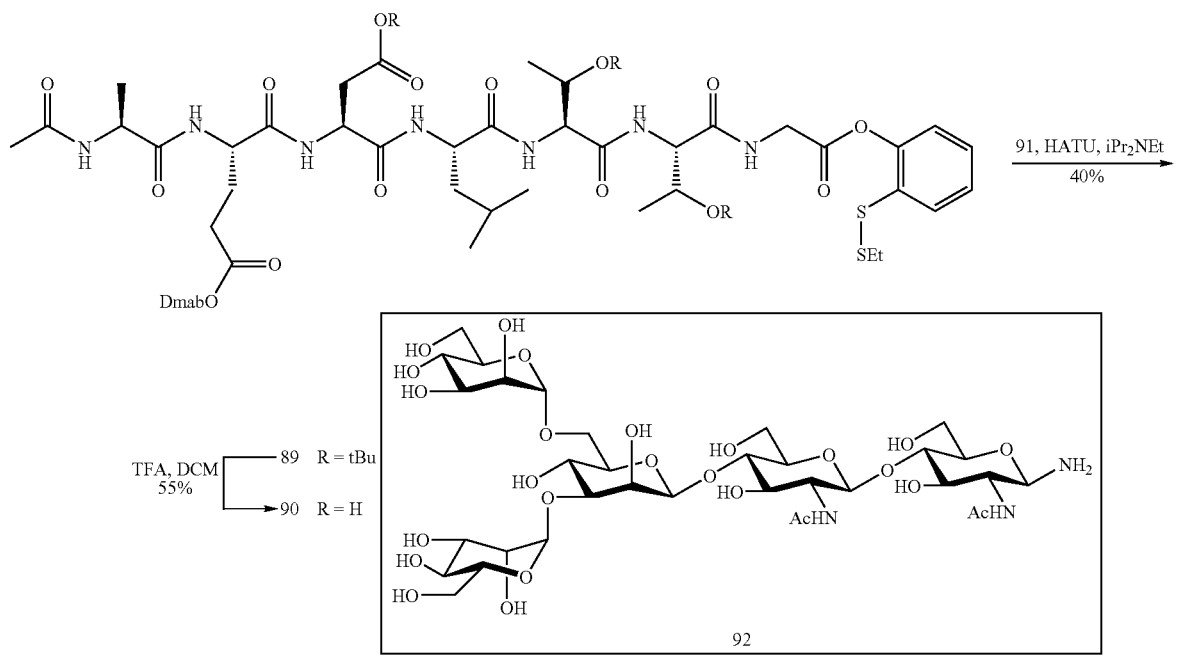

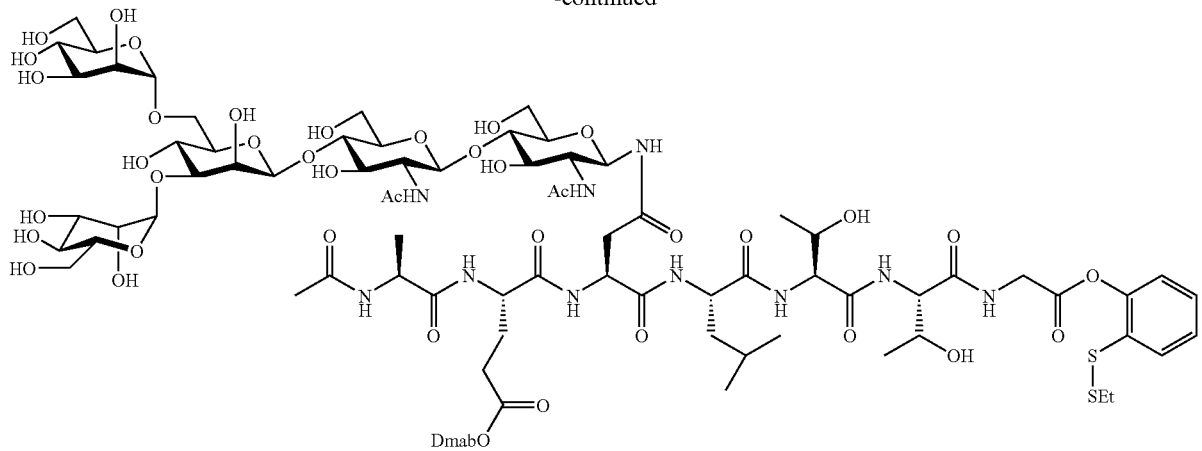

77

As shown in Scheme 32, peptide 88, prepared through Fmoc solid phase synthesis, was converted to coupling fragment 77 via standard esterification, deprotection, and aspartylation techniques. We note that, in the case of 77, the glutamic acid residue was equipped with the readily removable Dmab [1-(4,4-dimethyl-2,6-dioxocyclohexylidene)-3-methylbutyl)amino benzyl)] protecting group, thereby enabling selective appendage of the oligosaccharide domain to the aspartic acid residue (Chan et al., *J. Chem. Soc., Chem. Commun.*, 1995, 21, 2209-2211).

Upon treatment with MesNa (2-mercaptoethanesulfonic acid sodium salt) in a phosphate buffered saline solution (pH=7.4), glycopeptide fragments 78 and 79 smoothly underwent ligation within 20 hours, as indicated by LC-MS analysis, to afford a bifunctional glycopeptide in approximately 50% yield (Scheme 31), via acyl migration, transferring the entire C-terminal glycopeptidyl domain from O to S (cf structure 93). Without wishing to be bound to any particular theory, structure 93 is converted to the corresponding MesNa ester, which subsequently undergoes NCL with the N-terminal cysteine residue of 79 (Scheme 33). Deprotection of the N-terminal Thz and Fmoc functionalities was effected by treatment of the glycopeptide with 10% morpholine in DMF, followed by an aqueous solution of MeONH$_2$.HCl, to afford the deprotected intermediate 84 in 57% yield.

Finally, the second native chemical ligation between 94 and 77 proceeded cleanly under the previously described conditions to provide the complex, structurally homogeneous glycopeptide 76, in 38% yield (Scheme 33).

In summary, we have demonstrated the synthesis of a multifunctional glycopeptide through reiterative cysteine-dependent native chemical ligation. The compatibility of both N-linked and O-linked glycans in this process is noteworthy. Its ability to encompass the biologically important sialic acid glycosides is particularly encouraging. Thus, cysteine-dependent native chemical ligation, combined with the inventive cysteine-free native chemical ligation method provide highly powerful and versatile tools for achieving the total synthesis of multiply glycosylated, clinically valuable complex glycoproteins in homogeneous form.

Scheme 33.
Synthesis of 76 Through Reiterative Glycopeptide Coupling Sequence.
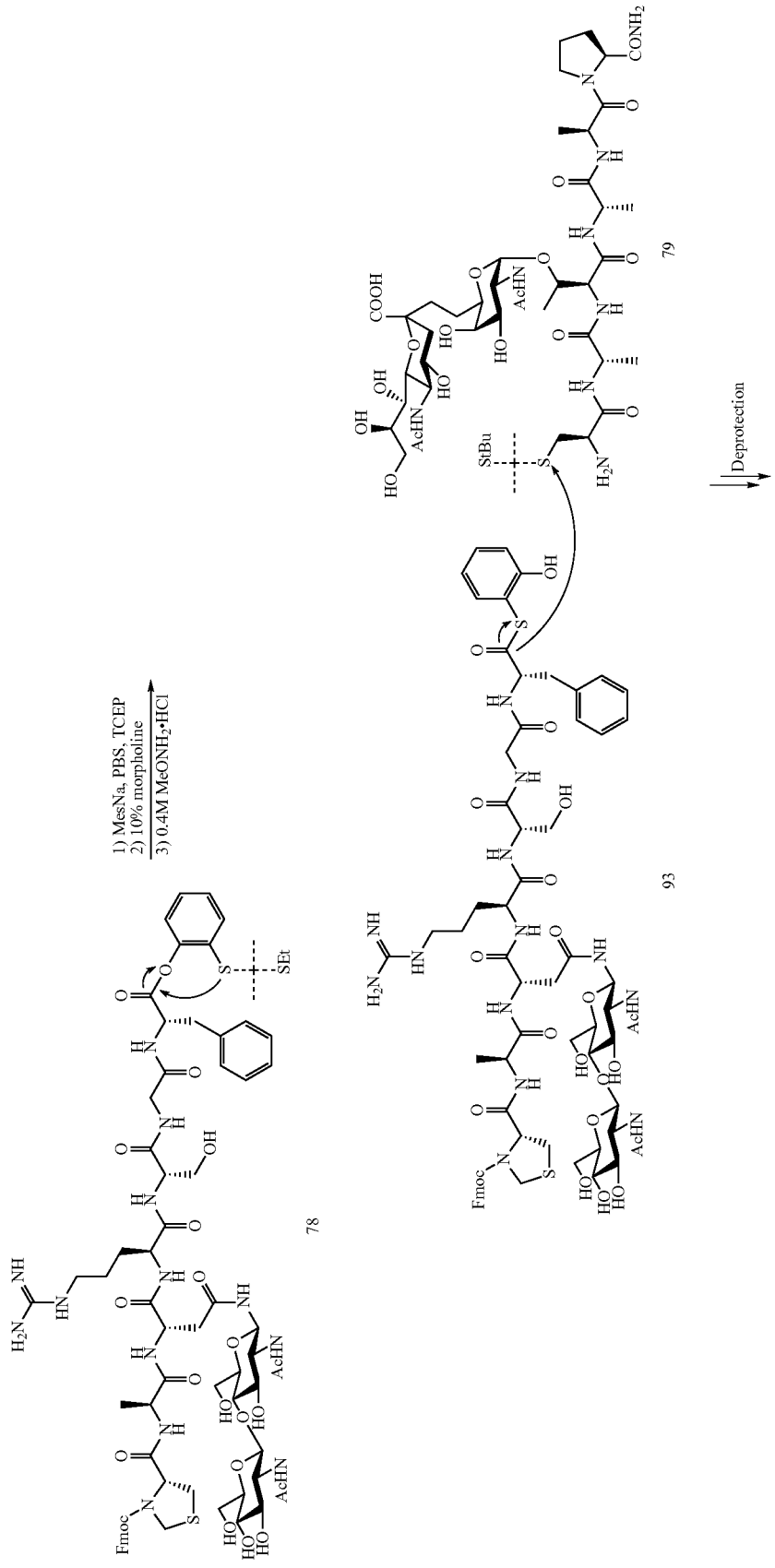

-continued
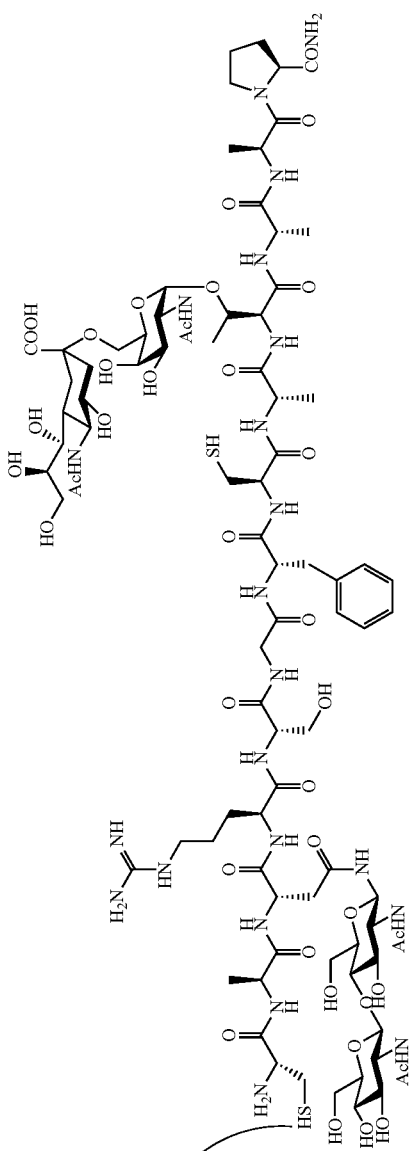
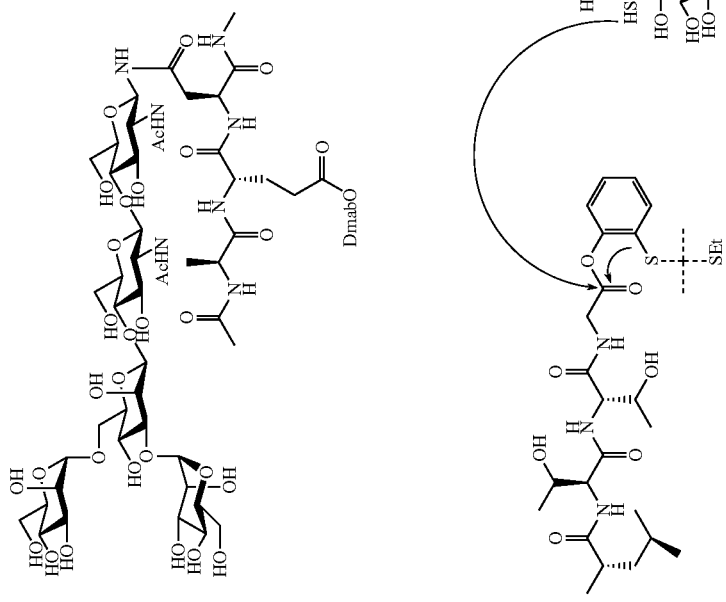
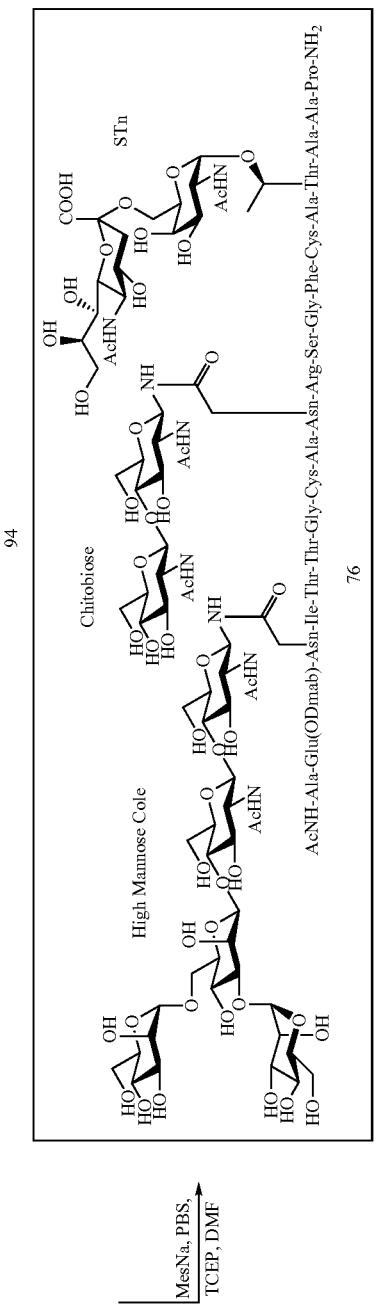

General Protocol to Prepare Peptidyl Phenolic Ester

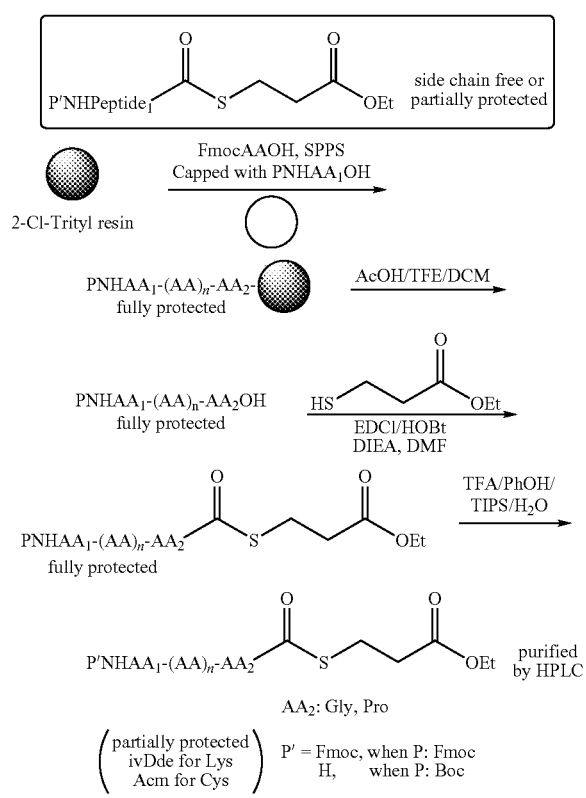

Protected peptides were prepared by standard solid-phase synthesis on preloaded 2-chlorotrityl resin using standard amide coupling conditions HATU/DIEA; final cleavage was effected by treatment with AcOH/TFE/DCM (2:2:6) for 2×1 hour to yield peptidyl acids in good yield. The peptidyl acids (in good purity) were used in the next step without further purification. There were two different ways to install the C-terminal phenolic ester: direct phenolic ester coupling when $AA_2$ is Gly or Pro; attaching the premade $NH_2AA_2OPh$ by amide coupling when $AA_2$ is non-Gly amino acid.

General Protocol to Prepare Peptide with C-Terminal Alkyl-Thioester

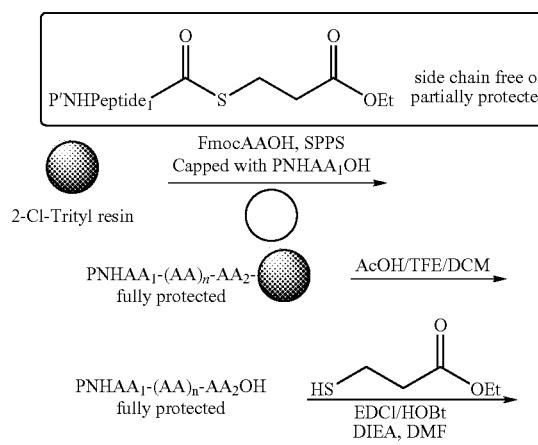

General Protocol to Prepare N-Linked Glycopeptidyl Phenolic Ester for Coupling

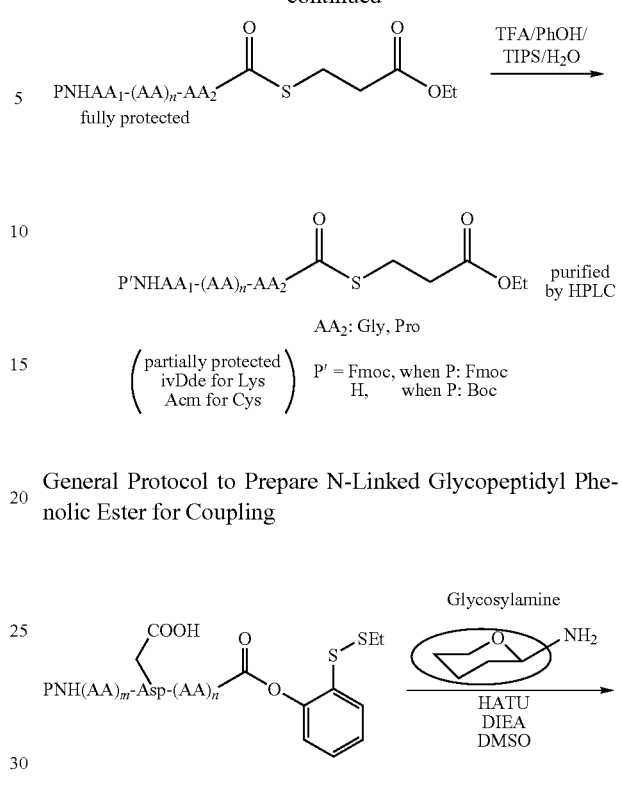

General condition: To a solution of glycosylamine (5 μmol) and peptide (15 μmol) in anhydrous DMSO (0.5 mL) was added DIEA (5.3 μL, 30 μmol), followed by HATU (11.4 mg, 30 μmol). The reaction was stirred at room temperature for 30 minutes to 2 hours and then subjected directly to reverse-phase HPLC purification to give desired glycopeptide.

General Condition for Peptide Coupling Using Phenolic Ester-Directed Amide Coupling Mediated by AgCl

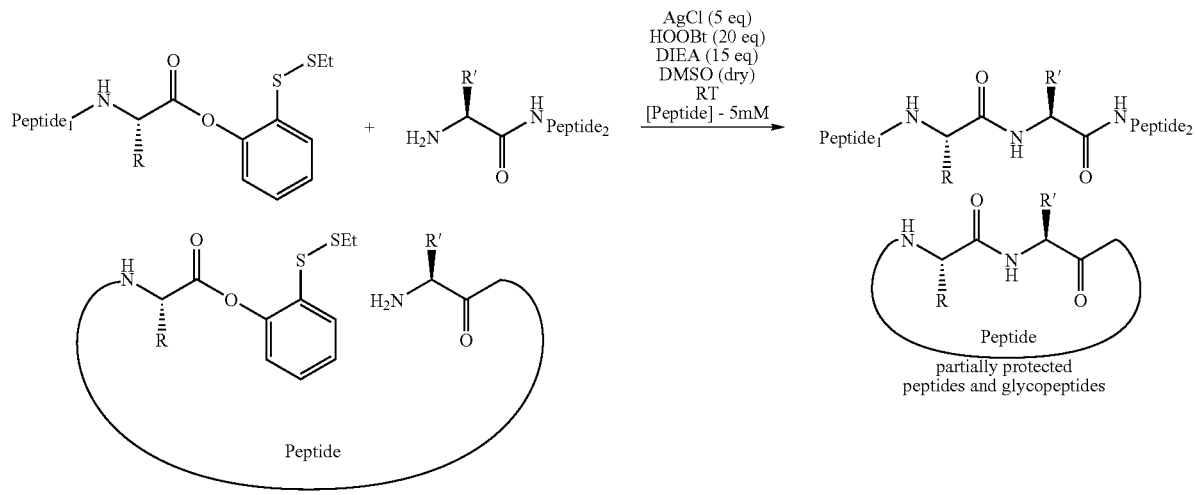

General Condition:

Peptide$_1$ (5 μmol), Peptide$_2$ (5 μmol), and HOOBt (16.3 mg, 100 μmol) were dissolved in anhydrous DMSO (1.0 mL) containing DIEA (13.1 μL, 75 μmol). AgCl (3.6 mg, 25 μmol) was then added, and the resulting mixture was stirred in the dark for 4 to 24 hours. 5 μL aliquot of the reaction mixture was taken out and diluted with 100 μL of $CH_3CN/H_2O(1/1)$ for LC-MS analysis. The reaction mixture was diluted with 3 mL of $CH_3CN/H_2O(1/1)$, and filtered to remove insoluble silver salt, and then loaded onto HPLC for final purification. For the synthesis of cyclicpeptide, the single peptide precursor (5 μmol) was used, and the other reagents and condition remained the same.

General Condition for Peptide Coupling Using Phenolic Ester-Directed Amide Coupling Mediated by TCEP.HCl

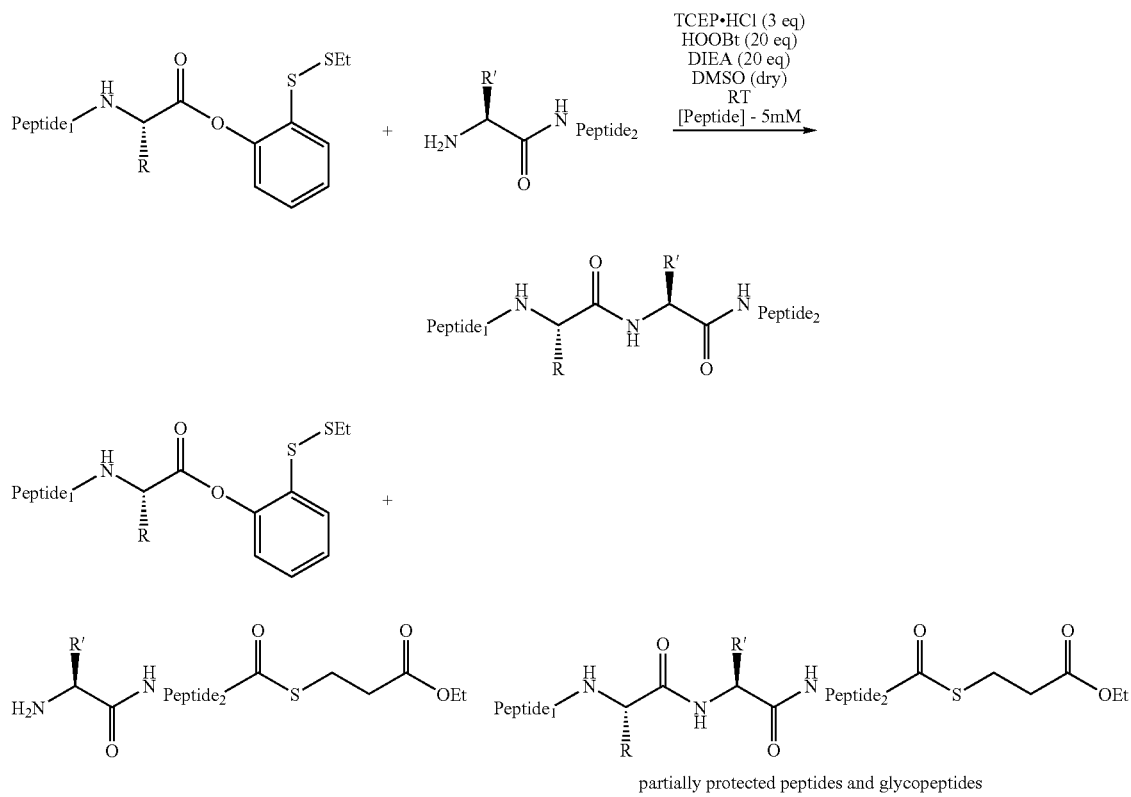

General Condition:

Peptide₁ (5 μmol), Peptide₂ (5 μmol), and HOOBt (16.3 mg, 100 μmol) were dissolved in anhydrous DMSO (1.0 mL) containing TCEP.HCl (4.3 mg, 15 μmol). The resulting mixture was stirred at RT for 15 minutes. DIEA (17.4 μL, 100 μmol) was then added, and the reaction mixture was stirred for additional 4 to 24 hours. 5 μL aliquot of the reaction mixture was taken out and diluted with 100 μL of CH₃CN/H₂O(1/1) for LC-MS analysis. The reaction mixture was diluted with 3 mL of CH₃CN/H₂O(1/1), and filtered to remove insoluble silver salt, and then subjected to HPLC for purification.

General Protocol for Desulfurization Mediated by Radical Reactions:

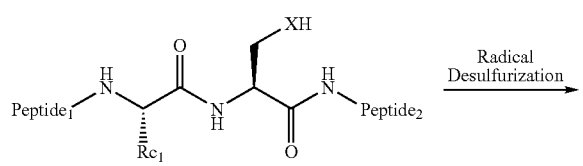

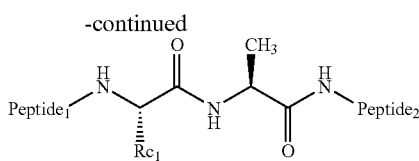

Desulfurization reactions were performed in aqueous condition. The solution was degassed by bubbling argon through for 10 minutes before each use. The phosphine (phosphate or isocyanide) was added, and then thiol was added. The radical initiator was added at the end. The reaction mixture was keep at room temperature or higher temperature for 45 minutes to 20 hours. The desulfurization reaction was followed by LC-MS. The reaction mixture was subjected directly to reverse-phase HPLC purification to give desired analyl peptide.

Example 1

Synthesis of Peptidic Fragments of Erythropoietin Using Secondary Amino Acid Surrogates In this example, we describe an efficient and general method for the generation of complex peptidic fragments, possessing a C-terminal phenolic ester and/or a N-terminal auxiliary. These peptidic fragments can then be merged with an oligosaccharide unit and/or small glycopeptide to provide the desired glycopeptide segments.

Results

We started from the synthesis of the peptidic fragment, EPO(78-113), a 36-amino acid polypeptide chain with a N-terminal auxiliary and a C-terminal phenolic ester. In particular, this fragment contains 17 hydrophobic residues, which is more than 47% of the sequence. The synthesis of fully-protected EPO(78-113) was initially carried out under our standard laboratory conditions with resulting low crude purities of less than 10%0/obtained. Subsequent dissolving and purification of the peptide to high purity proved difficult. Confirmation of the parent peak by LC-MS analysis indicated that the major product was from the Asp$^{96}$ aspartimide formation reaction, which is a ring-closing reaction between the nitrogen of the α-amide bond and the β-carboxy side chain, resulting in the loss of the ester protecting group Dmab and the formation of a variety of aspartimide-related by-products. Repeat synthesis EPO(78-113) and synthesis of shorter peptidic fragments, EPO(89-13) and EPO(98-113), using standard Fmoc-derivatives, also failed.

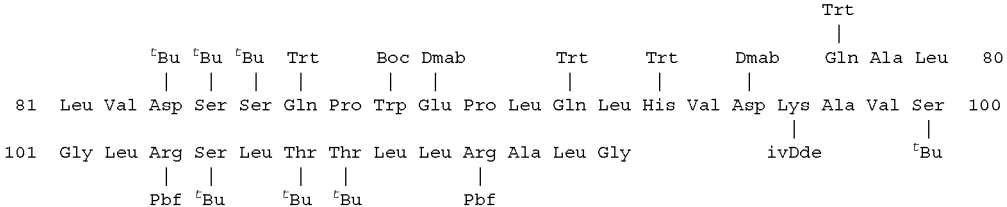

Amino Acid Sequence of Fully-Protected EPO(78-113).

It was synthesize using standard Fmoc (9-fluorenylmethyloxycarbonyl) chemistry. The glutamic acid and aspartic acid residues were equipped with the readily removable Dmab [1-(4,4-dimethyl-2,6-dioxocyclohexylidene)-3-methylbutyl) amino benzyl)] protecting groups and the lysine residue with ivDde [1-(4,4-dimethyl-2,6-dioxocyclohex-1-ylidene)-3-methylbutyl], whereas all the other amino acids are protected with protecting groups most commonly used in Fmoc-based SPPS (solid phase peptide synthesis) as follows in blue color. Ser and Thr, with t-butyl; Arg, with Pbf (2,2,4,6,7-pentamethyldihydrobenzofuran-5-sulfonyl); Gln, Asn and His, with trityl; Trp, with Boc and Asp, corresponding to Asn 83, with t-butyl. The use of Dmab and ivDde enables selective appendage of the oligosaccharide domain to the aspartic acid residue 83 and the auxiliary to the N-terminus of this fragment.

To improve the peptide synthesis yields and purities, as well as the solubilities of crude products, we attempted various strategies, including the replacement of the synthesized chlorotrityl resin with commercially available NovaSyn® TGT resin (preloaded with Fmoc-amino acids), the use of Ser/Thr-derived oxazolidines (pseudoprolines) and Dmb (2,4-dimethoxybenzyl)dipeptides, 1, 2, 3 and 4 shown below. While 1, 2 and 4 are available in large scale, 3 had to be prepared from a multistep synthesis. These dipeptides could be incorporated into the growing peptide chain in the same manner as normal amino acids activated by HATU. The synthesis outlined below exploited all the beneficial properties of these strategies and produced >80% purity EPO(78-113) at 85% as determined by LC-MS. The aspartimide formation reaction was completely eliminated and the solubility of the peptide product was highly improved, as high as 4.6 mM concentration could be easily achieved in MeOH.

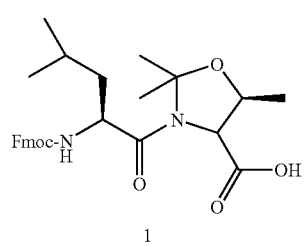
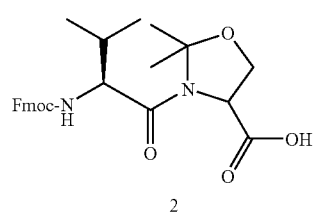

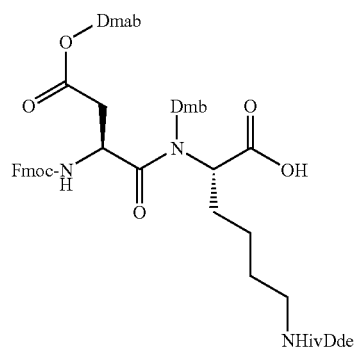
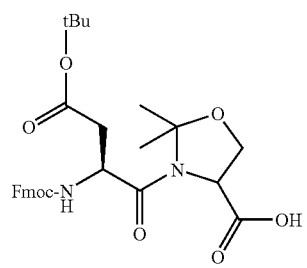

A

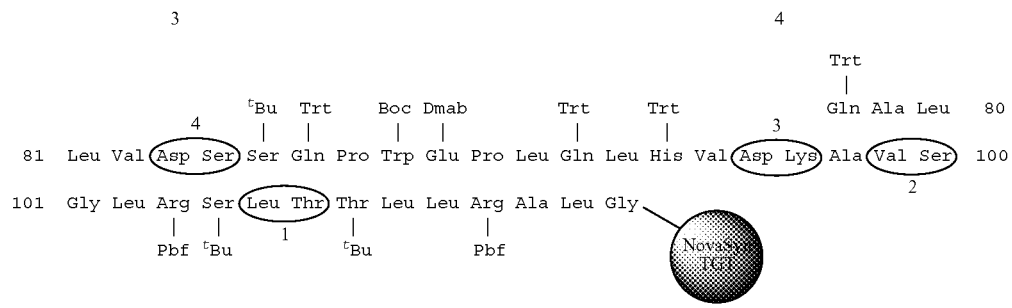

B

Pseudoproline and Dmb Dipeptides (A) and Overview of the Strategies Used to Enhance the Synthetic Efficiency of the Peptidic Fragment of EPO(78-113) (B).

The resin is represented as a cartoon. The dipeptides are highlighted by black circles.

At this point, we envisioned that to join with the other two fragments, EPO(29-77) and EPO(114-166) under conditions analogous to those that we had previously developed in the context of a cysteine-free NCL method, the peptidic fragment of EPO(78-113) should be equipped with a N-terminal auxiliary and a C-terminal phenolic ester. Thus, the auxiliary-bearing fragment was prepared from the fully-protected peptidic fragment 5 through slight modification of a known procedure developed in our laboratory. Ester formation reaction with 2-(ethyldithio)-phenol provided phenolic ester 7 in 50% yield as estimated by LC-MS. Finally, treatment of 7 with 88% TFA with a TIPS scavenger resulted in the desired peptidic fragment 8. It was further purified by $C_4$ reverse phase column and ready for the selective appendage of the oligosaccharide domain to the aspartic acid residue 83.

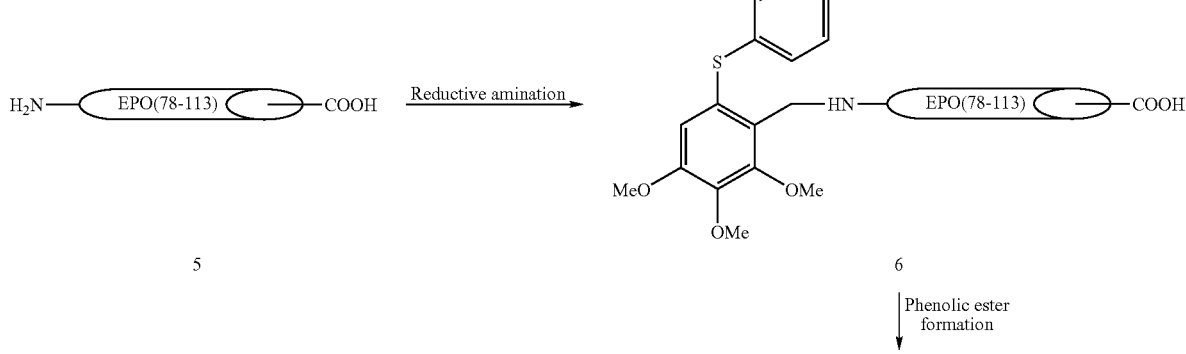

Phenolic ester formation

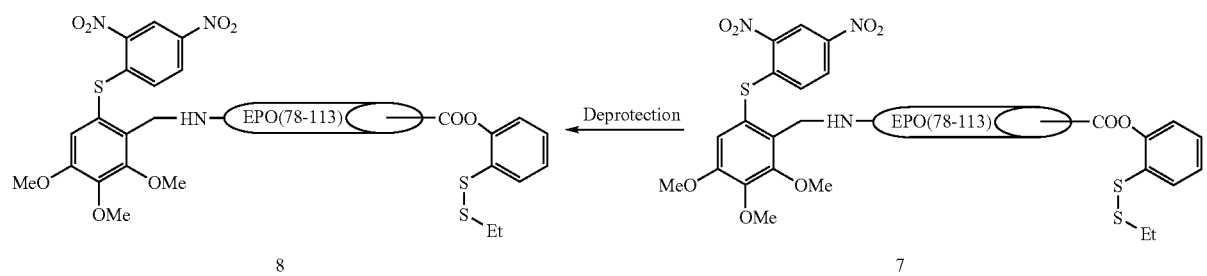

8 ← Deprotection ← 7 peptides are depicted in blue, and the deprotected one in black.

With 8 in hand, we were now prepared to investigate the viability of our strategy in the synthesis of peptidic fragments of EPO(29-77). According to the general guidelines for the use of secondary amino-acid surrogates, the synthesis of peptidic fragments of EPO(29-77) was designed as shown below. We have obtained all the dipeptides and N-alkylated amino acids. We will prepare this fragment through the similar method as we developed for the synthesis of EPO(77-113).

Secondary Amino Acid Surrogates (A) and Overview of the Plan for the Synthesis of the Peptidic Fragment of EPO (28-77) (B).

The resin is represented as a cartoon. The secondary amino acid surrogates are highlighted by black circles.

Initial attempts at the synthesis of peptide fragment EPO (1-28) failed also due to significant aspartimide formation. Careful analysis revealed that the $Asp^8$-$Ser^9$ is the problematic sequence. While t-Bu protecting group could be used to minimize the side reaction, Dmab on the aspartic acid side chain is necessary to differentiate between $Asp^8$ and $Asp^{24}$.

A

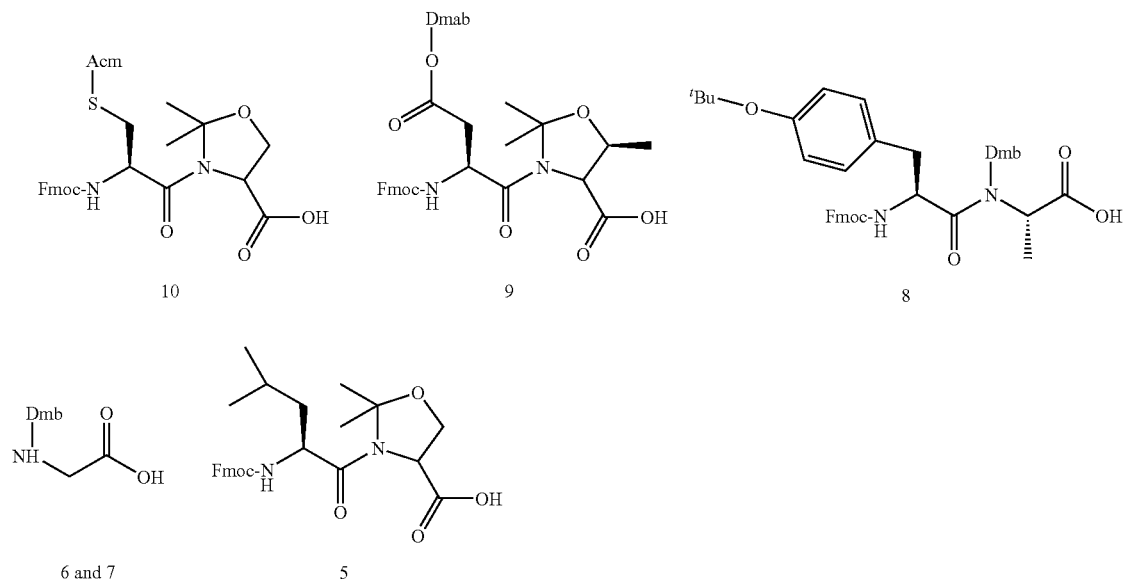

B

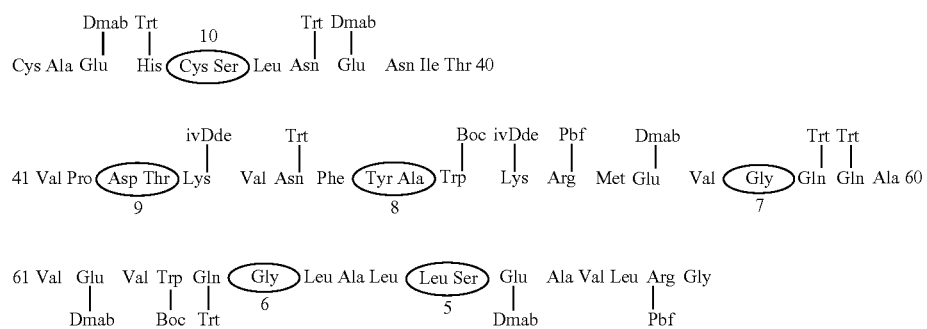

Thus, to avoid the aspartimide byproduct, a pseudoproline dipeptide 15 was prepared for the peptide synthesis. With the dipeptide 15 incorporated as a single residue, Fmoc SPPS proceeded smoothly to afford the desired peptide 16 after acidic cleavage from resin. Phenolic ester formation followed by TFA treatment led to polypeptide 17, ready for future incorporation of N-linked glycan.

AcHN-Ala-Pro-Pro-Arg(pbf)-Leu-Ile-Cys-(Acm)-Asp-(ODmab)-Ser($\psi^{Me,Me}$)pro-Arg(pbf)-Val-Leu-Glu-(ODmab)-Arg(pbf)-Tyr(tBu)-Leu-Leu--Glu(ODmab)-Ala-Lys(ivDde)-Glu(ODmab)-Ala-Glu(ODmab)-Asp(tBu)-Ile-Thr(tBu)-Thr(tBu)-Gly-OH

16

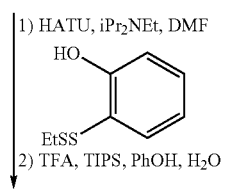

AcHN-Ala-Pro-Pro-Arg-Leu-Ile-Cys-(Acm)-Asp-(ODmab)-Ser-Arg-Val-Leu-Glu-(ODmab)-Arg-Tyr-Leu-Leu--Glu(ODmab)-Ala-Lys(ivDde)-Glu(ODmab)-Ala-Glu(ODmab)-Asp-Ile-Thr-Thr-Gly-OAr

17 EPO (1-28)

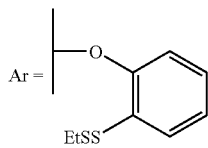

Preparation of the Peptidic Fragment of EPO(28-77).

The viability of our pseudoproline dipeptide strategy was also demonstrated in a parallel synthesis study of the peptidic fragments of EPO(128-166). The use of commercially available dipeptides Fmoc-Asp(OtBu)-Thr($\psi^{Me,Me}$Pro)-OH, Fmoc-Tyr(tBu)-Ser($\psi^{Me,Me}$Pro)-OH and Fmoc-Tyr(tBu)-Thr($\psi^{Me,Me}$Pro)-OH highly improved the synthetic efficiency.

Experimentals

Fmoc-Asp(ODmab)-(Dmb)Lys(ivDde)-OH 3

As shown below, Fmoc-Lys(ivDde)-OAllyl was deprotected by piperidine in 81% yield. Reductive amination gave 20 in 65% yield. Amide coupling between 19 and Fmoc-Asp (Dmab)-OH afforded dipeptide 21. Removal of the allyl ester finished dipeptide 3. ESI-MS: calcd. $C_{67}H_{82}N_4O_{13}$, 1150.59. found m/z 1151.8 [M+H]$^+$, 1173.8 [M+Na]$^+$, 1189.8 [M+K]$^+$.

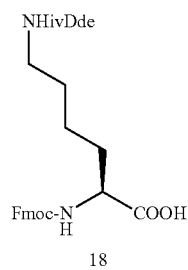

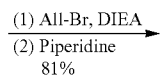

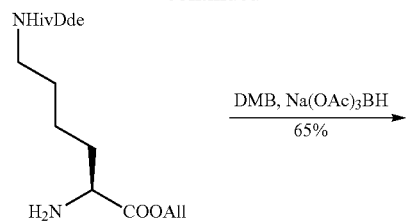

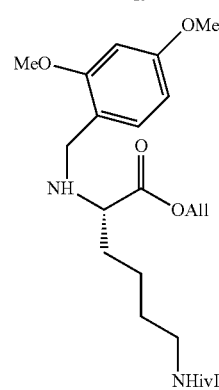

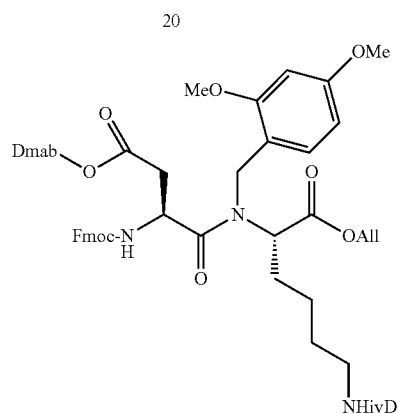

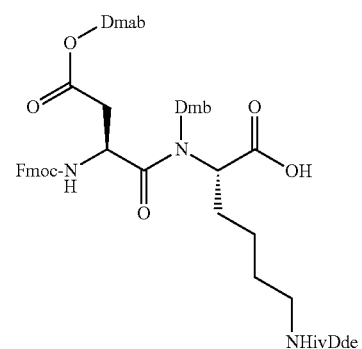

Synthesis of Dipeptide Fmoc-Asp(ODmab)-(Dmb)Lys(ivDde)-OH.

Fmoc-Tyr(tBu)-(Dmb)Ala-OH 8.

As shown, reductive amination of 22 gave 23 in 30% yield. Amide coupling between 23 and Fmoc-Tyr(tBu)-OH afforded dipeptide 24. Removal of the allyl ester finished dipeptide 8. Product was confirmed by NMR and ESI-MS.

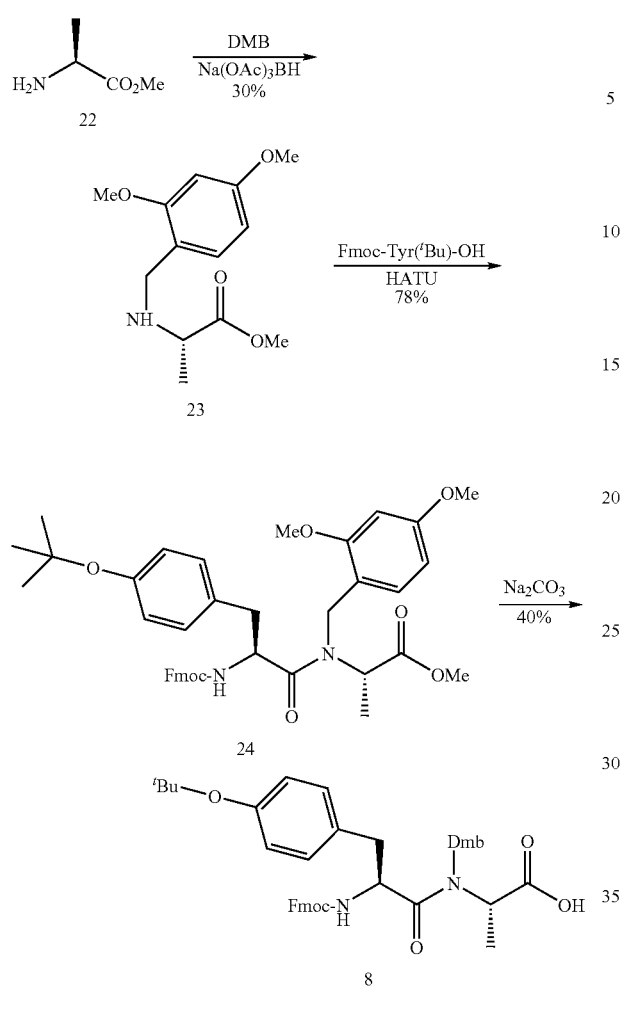

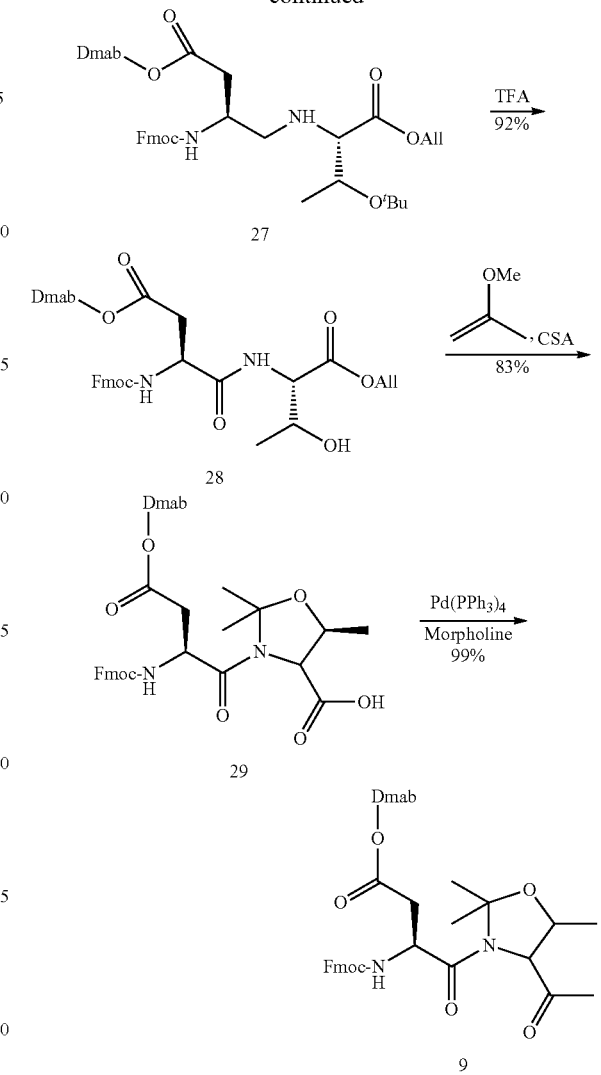

Synthesis of Dipeptide Fmoc-Tyr(tBu)-(Dmb)Ala-OH.

Fmoc-Asp(Dmab)-Thr($\psi^{Me,Me}$Pro)-OH 9.

Amide coupling between 26 and Fmoc-Asp(Dmab)-OH afforded dipeptide 28 after deprotection. Formation of oxazolidine ring was accomplished with treatment of 2-dimethoxypropene and PPTS. Removal of the allyl ester finished dipeptide 9, which is ready for solid-phase peptide synthesis. ESI-MS: calcd. $C_{46}H_{53}N_3O_{10}$, 807.37. found m/z 808.4 [M+H]$^+$, 831.2 [M+Na]$^+$, 846.4 [M+K]$^+$.

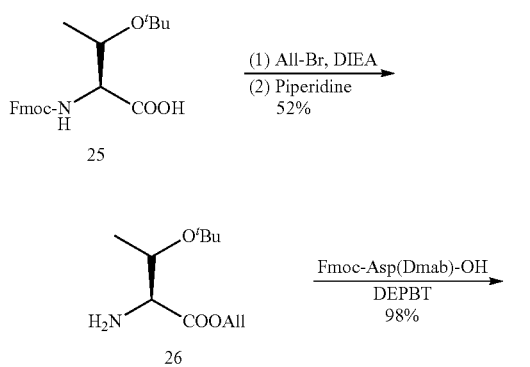

Synthesis of Dipeptide Fmoc-Tyr(tBu)-(Dmb)Ala-OH.

Fmoc-Cys(Acm)-Ser($\psi^{Me,Me}$Pro)-OH 10.

Amide coupling between 31 and Fmoc-Cys(Acm)-OH afforded dipeptide 33 after deprotection. Formation of oxazolidine ring was accomplished with treatment of DMP (2,2-dimethoxypropane) and PPTS. Removal of the allyl ester finished dipeptide 1, which is ready for solid-phase peptide synthesis. Product was confirmed by NMR and ESI-MS.

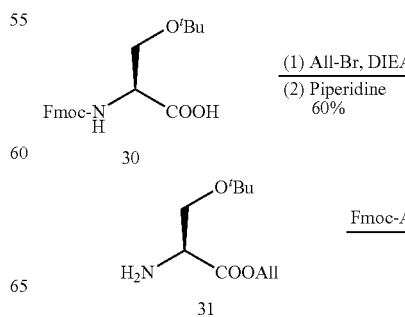

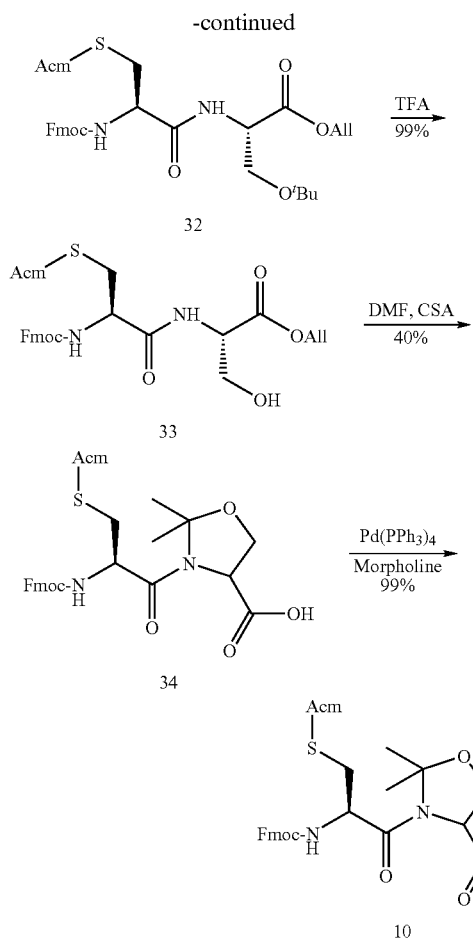

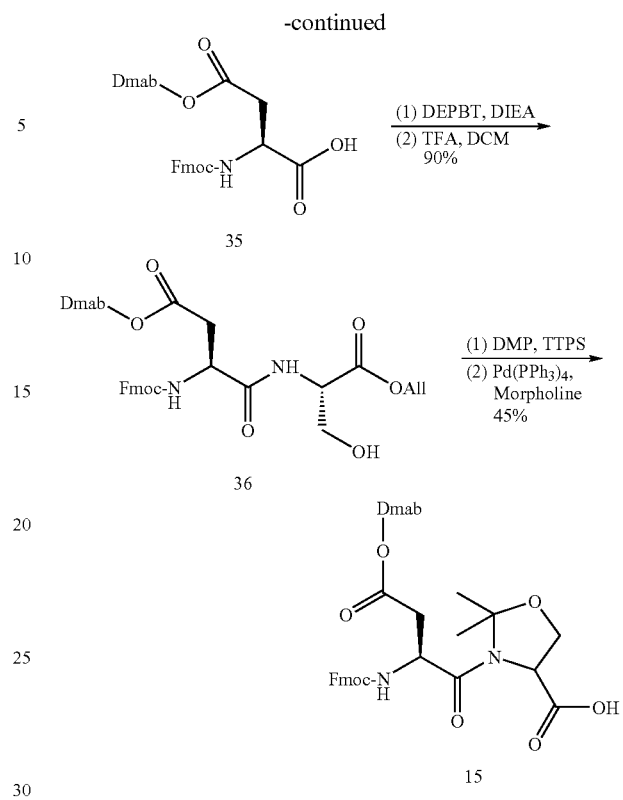

Synthesis of Dipeptide Fmoc-Cys(Acm)-Ser($\psi^{Me,Me}$Pro)-OH 10.

Fmoc-Asp(ODmab)-Ser($\psi^{Me,Me}$Pro)-OH 15.

Amide coupling between 30 and 35 afforded dipeptide 36 after deprotection. Formation of oxazolidine ring was accomplished with treatment of DMP (2,2-dimethoxypropane) and PPTS. Removal of the allyl ester finished dipeptide, which is ready for solid-phase peptide synthesis. $^1$H NMR (CDCl$_3$, 400 MHz) δ 7.69 (d, J=12.0 Hz, 2H), 7.52-7.47 (m, 3H), 7.34 (d, J=8.0 Hz, 4H), 7.29-7.24 (m, H), 7.08 (d, J=8.0 Hz, 2H), 5.62 (d, J=9.0 Hz, 1H), 5.11 (s, 2H), 4.86 (d, J=6.0 Hz, 1H), 4.76-4.73 (m, 1H), 4.31-4.29 (m, 3H), 4.17-4.14 (m, 2H), 3.00-2.86 (m, 3H), 2.78-2.70 (m, 1H), 2.46 (s, 2H), 2.37 (s, 2H), 1.85-1.78 (m, 1H), 1.75-1.58 (m, 1H), 1.68 (s, 3H), 1.50-1.40 (m, 1H), 1.47 (s, 3H), 1.05 (s, 6H), 0.75 (s, 3H), 0.73 (s, 3H); $^{13}$C NMR (CDCl$_3$, 100 MHz) δ 176.8, 172.3, 170.7, 168.0, 155.9, 144.1, 143.6, 141.5, 141.4, 137.1, 135.3, 129.2, 128.0, 127.3, 126.9, 125.5, 125.3, 120.2, 108.0, 97.2, 67.8, 67.3, 66.0, 59.5, 51.0, 50.6, 47.2, 38.6, 38.5, 30.2, 29.8, 28.4, 25.3, 23.0, 22.8.

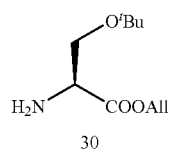

Synthesis of Dipeptide Fmoc-Asp(ODmab)-Ser($\psi^{Me,Me}$Pro)-OH 15.

Peptide 8 ESI-MS: calcd. C$_{252}$H$_{381}$N$_{53}$O$_{65}$S$_3$, 5285.73. found m/z 1763.74 [M+3H]$^{3+}$, 1323.36 [M+4H]$^{4+}$.

LC-MS: 45-65% acetonitrile in water in 30 min, C4 analytical column.

Peptide 17. ESI-MS: calcd. C$_{263}$H$_{386}$N$_{44}$O$_{59}$S$_3$, 5200.8. found m/z 1735.7 [M+3H]$^{3+}$, 1302.2 [M+4H]$^{4+}$.

LC-MS: 40-80% acetonitrile in water over 25 min, C4 analytical column.

Example 2

Mature Homogeneous Erythropoietin Building Blocks by Chemical Synthesis The EPO 22-37 Glycopeptide Domain Presenting the Fully N-Linked Dodecasaccharide In an earlier publication directed to the erythropoietin (EPO) problem, we related the synthesis of the protected biantennary dodecamer glycan 4 (Wu et al., *Tetrahedron Lett.* 2006, 47, 5577-5579). The synthesis commenced with the preparation of hexasaccharide (2) and trisaccharide (3), through recourse to glycal assembly methods developed in our laboratory and through application of the Crich-Kahne direct mannosylation protocol (Danishefsky et al., *Angew. Chem. Int. Ed.* 1996, 35, 1380-1419; Danishefsky et al., *Angew. Chem. Int. Ed.* 2000, 39, 836-863; Crich et al., *J. Org. Chem.* 1997, 62, 1198-1199; Crich, D.; Sun, S. *Tetrahedron* 1998, 54, 8321-8348; Kahne et al., *J. Am. Chem. Soc.* 1989, 111, 6881-6882). Under Sinay radical cation activation conditions, coupling of 2 with excess amounts of 3 successfully provided the fully protected dodecasaccharide 4 (Zhang et al., *Carbohydr. Res.* 1992, 236, 73-88; Marra et al., *Synlett* 1990, 572-574).

253 254
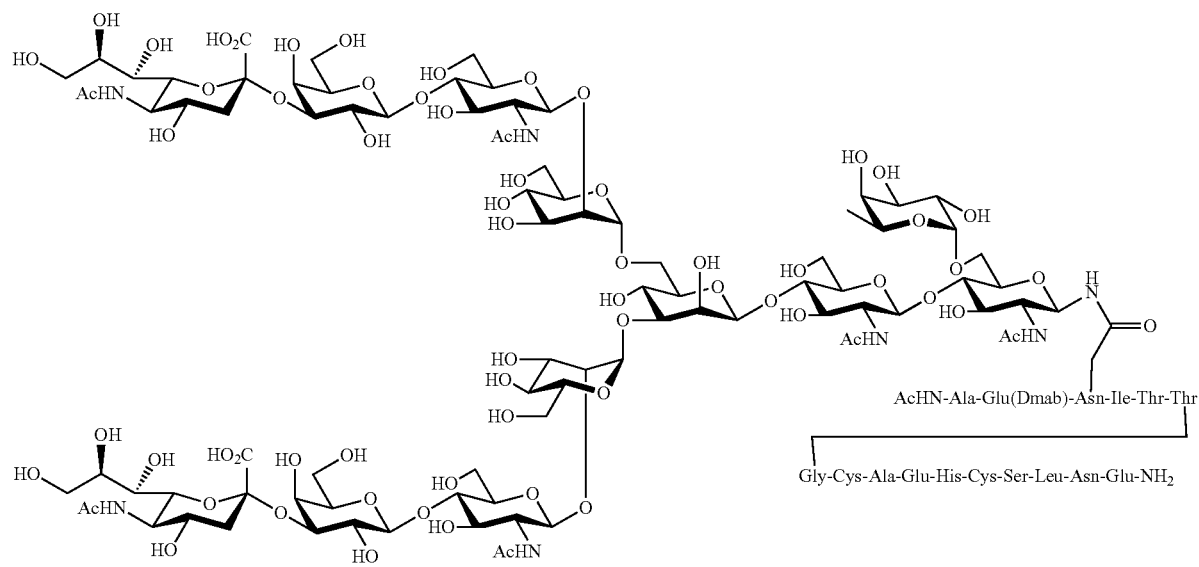
EPO (22-37) glycopeptide (1).
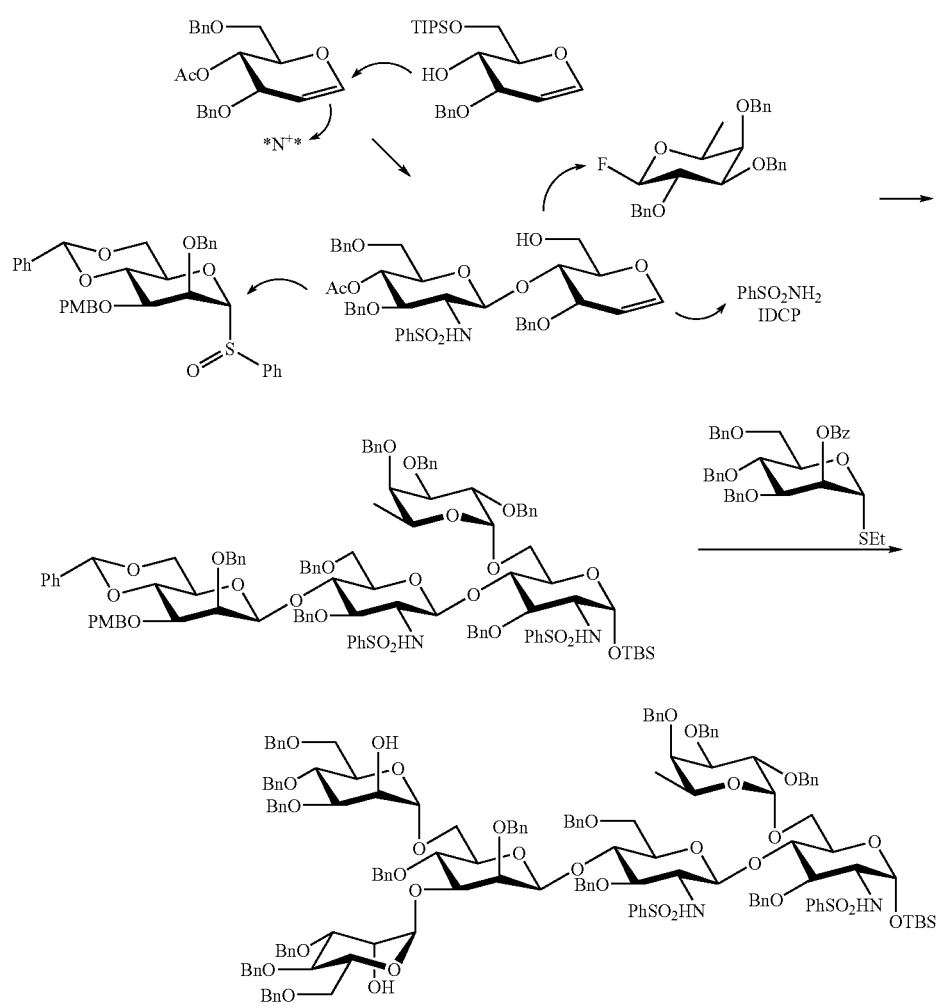

-continued
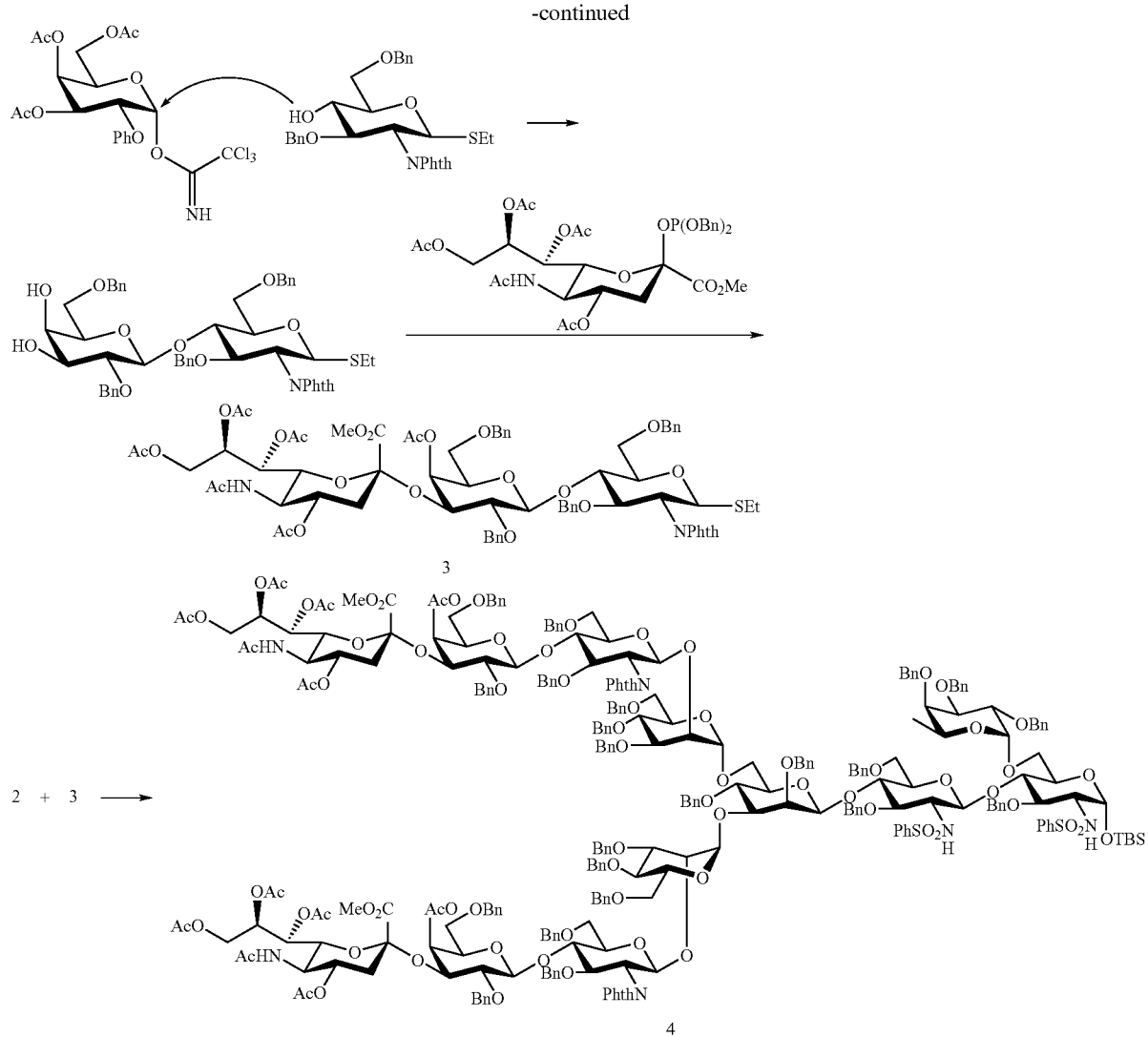
Synthesis of the Protected Glycan of the EPO Dodecasaccharide.
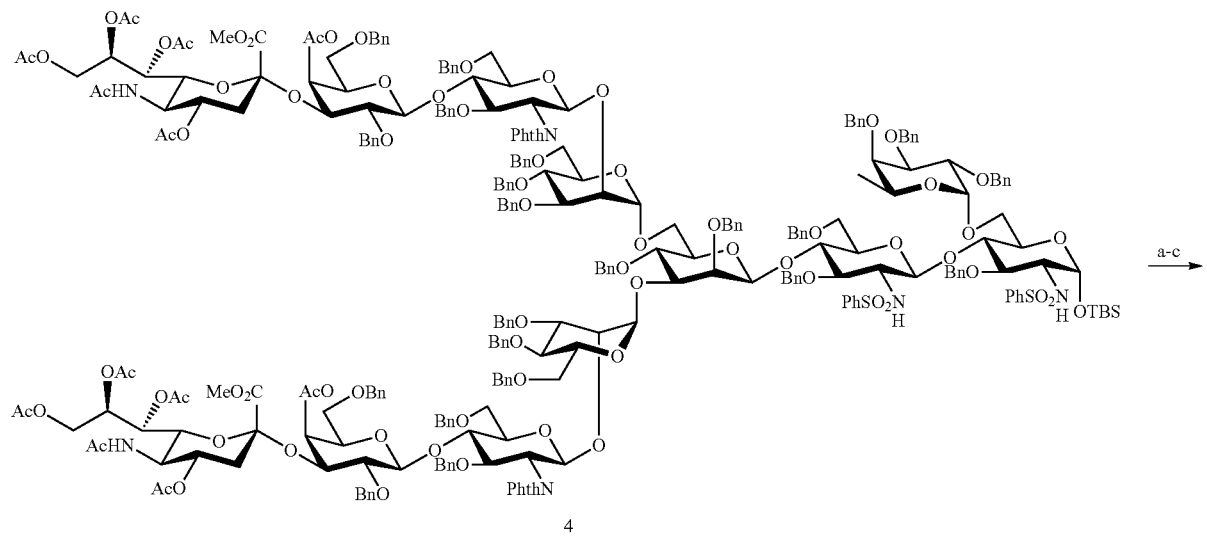 a-c →

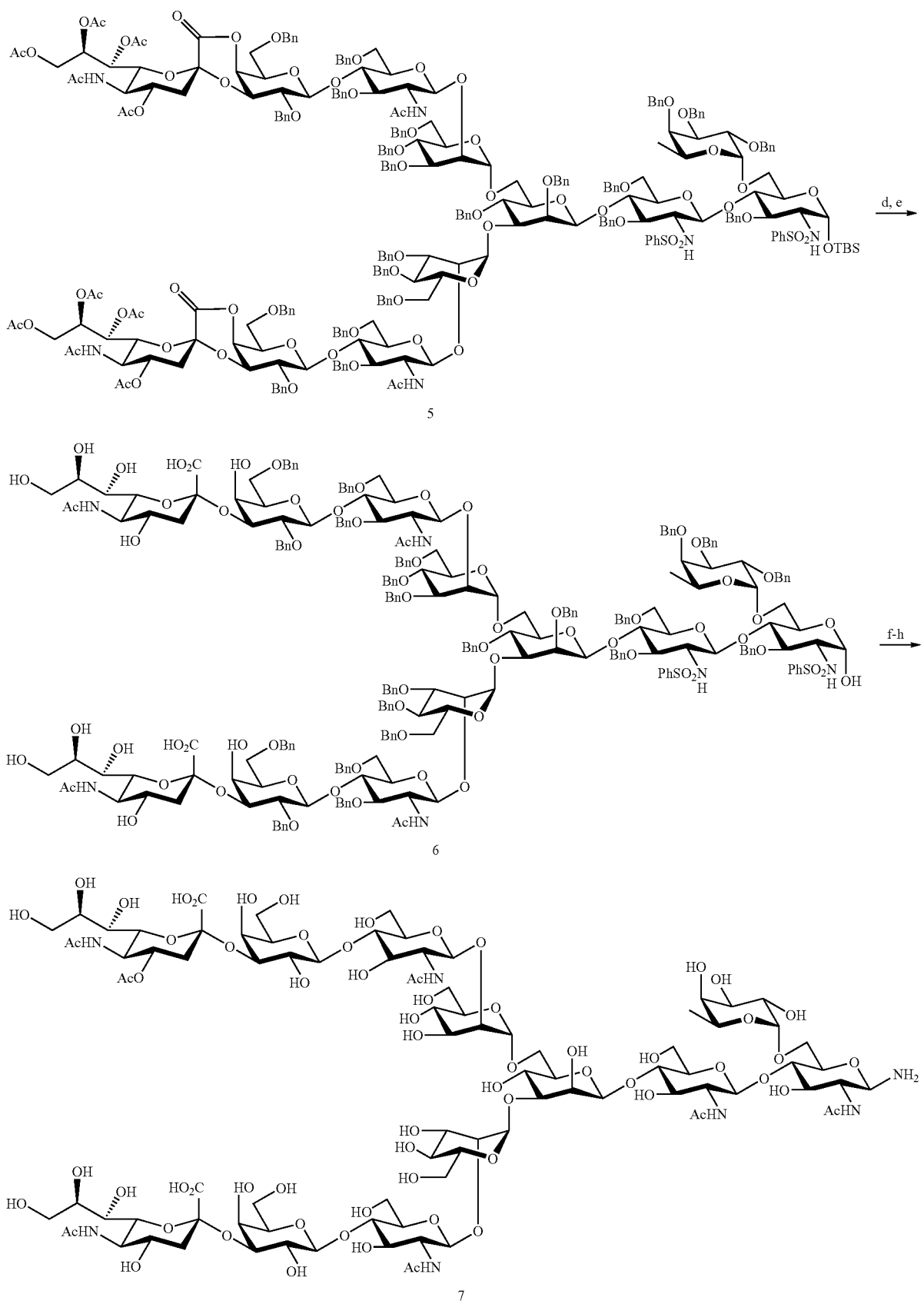

Synthesis of 7:

a) NaOMe, MeOH; b) H$_2$NCH$_2$CH$_2$NH$_2$; c) Ac$_2$O, pyr.; d) TBAF, AcOH; e) NaOMe, MeOH/H$_2$O; f) Na, NH$_3$; g) Ac$_2$O, NaHCO$_3$; h) NH$_4$HCO$_3$, H$_2$O (63% overall yield).

Given the degree of functionalization of dodecasaccharide 4, careful consideration had to be given to the sequence of the deprotection pathway. First, the methyl esters of the erstwhile sialic acid functionalities would be unmasked, along with the ten acetyl protecting groups, in order to achieve compatibility with conditions required for the subsequent phthalamide removal. In practice, hydrolysis of the methyl esters, accompanied by removal of the resident acetyl protecting groups, provided an appropriate substrate for cleavage of the two phthalamide moieties through exposure to ethylenediamine (Dudkin et al., J. Am. Chem. Soc. 2004, 126, 736-738). This intermediate was subjected to peracetylation to afford the bis-lactone intermediate 5. The next step involved the removal of the anomeric TBS ether through exposure to TBAF. Subsequent solvolysis gave rise to intermediate 6 (Scheme 2).

At this stage, we were obliged to face an important challenge in this sequence—the concomitant removal of the 22 benzyl ethers and the two phenyl sulfonamides of the ensemble with maintenance of the anomeric hydroxyl group. Fortunately, exposure of 6 to Birch reduction conditions (Na/NH$_3$), following previously developed procedures, indeed accomplished the global deprotection (Wang et al., Angew. Chem. Int. Ed. 2000, 39, 3652-3656; Wang et al., Angew. Chem. Int. Ed. 2001, 40, 1728-1732; Iserloh et al., Tetrahedron Lett. 2002, 43, 7027-7030; Wang et al., Tetrahedron 2006, 62, 4954-4978). Finally, Kochetkov anomeric amination conditions readily provided the glycosylamine 7 in good overall yield from the fully protected 4 (Likhosherstov et al., Carbohydr. Res. 1986, 146, C$_1$-C$_5$). The realization of compatibility of the sialic acid residues with the Kochetkov amination conditions was particularly welcome.

With the deprotected dodecasaccharide in hand, we turned our attentions to the ultimate goal of merging the glycan with the EPO peptide fragment. Toward that end, peptide 8, which corresponds to EPO (22-28), was prepared under previously described conditions, and equipped with a C-terminal phenolic ester (Scheme 3) (Warren et al., J. Am. Chem. Soc. 2004, 126, 6576-6578). Aspartylation between 7 and 8, with concurrent lactone formation, provided 9 (Cohen-Anisfeld et al., J. Am. Chem. Soc. 1993, 115, 10531-10537). At this stage, we investigated the feasibility of native chemical ligation between 9 and the EPO (29-37) peptide, itself available through solid-phase peptidesynthesis. Happily, under improved conditions (PBS, PhSH, TECP), ligation using our O→S migration based method proceeded smoothly to afford 1, corresponding to the full EPO 22-37 glycopeptide domain, in good overall yield (Warren et al., J. Am. Chem. Soc. 2004, 126, 6576-6578; Chen et al., J. Am. Chem. Soc. 2006, 128, 7560-7462; Johnson et al., J. Am. Chem. Soc. 2006, 128, 6640-6646).

In summary, the synthesis of an important fragment contained in the naturally occurring glycoprotein, erythropoietin, has been accomplished by strictly chemical means. Toward this end, the complex dodecasaccharide domain of EPO has been successfully assembled, deprotected, and coupled to the requisite peptide fragment through aspartylation. Furthermore, the peptide domain has been elongated following application of our recently developed native chemical ligation methodology. The assembly of 1 clearly lays the groundwork for the realization of the ultimate goals, as described above. A corresponding advance in the construction of mature O-linked glycopeptides is described in the paper which follows.

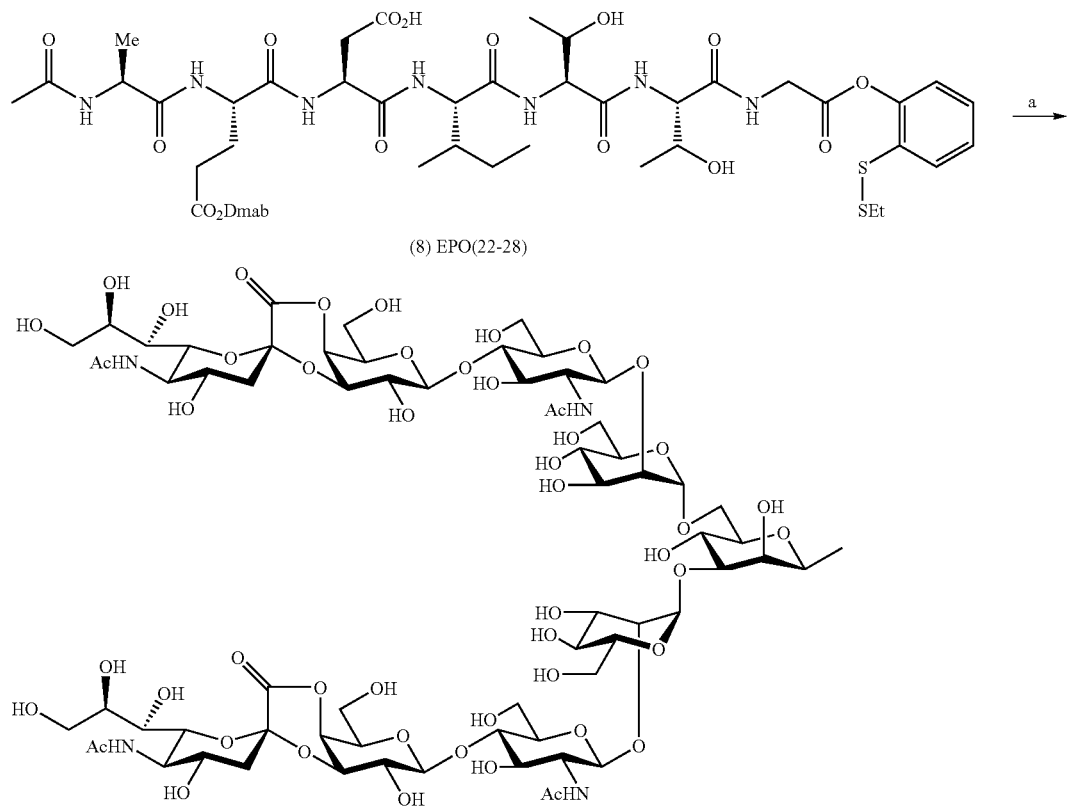

(8) EPO(22-28)

-continued
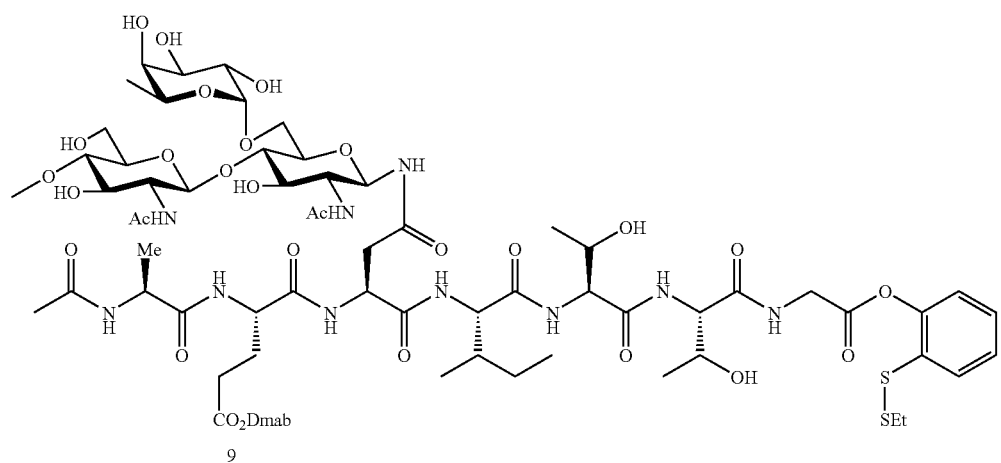
9
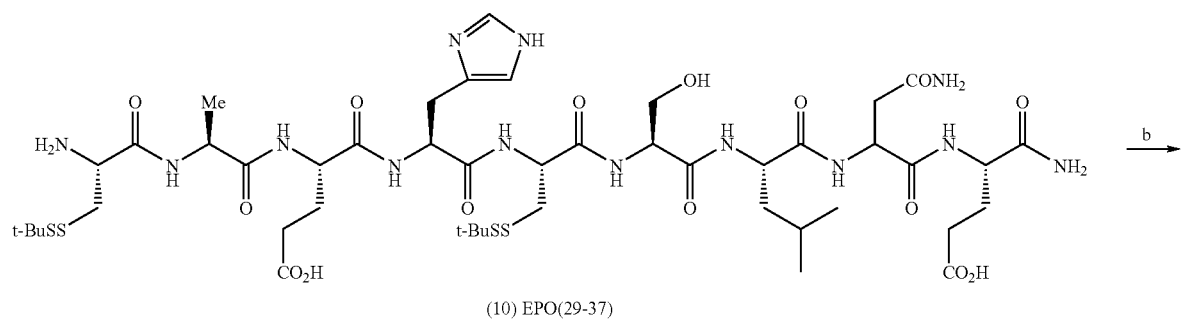
(10) EPO(29-37)
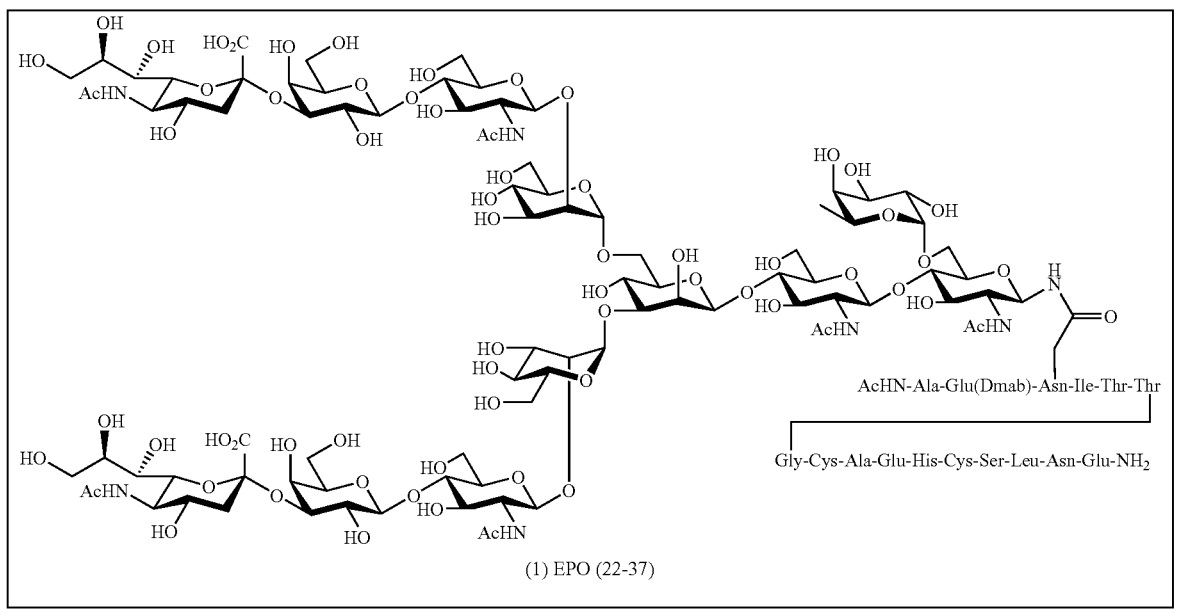
(1) EPO (22-37)

Synthesis of EPO (22-37) (1):

a) 7, HATU, iPr$_2$NEt, DMSO, 40%, b) PBS, 1% PhSH, TCEP, 56%.

Experimentals

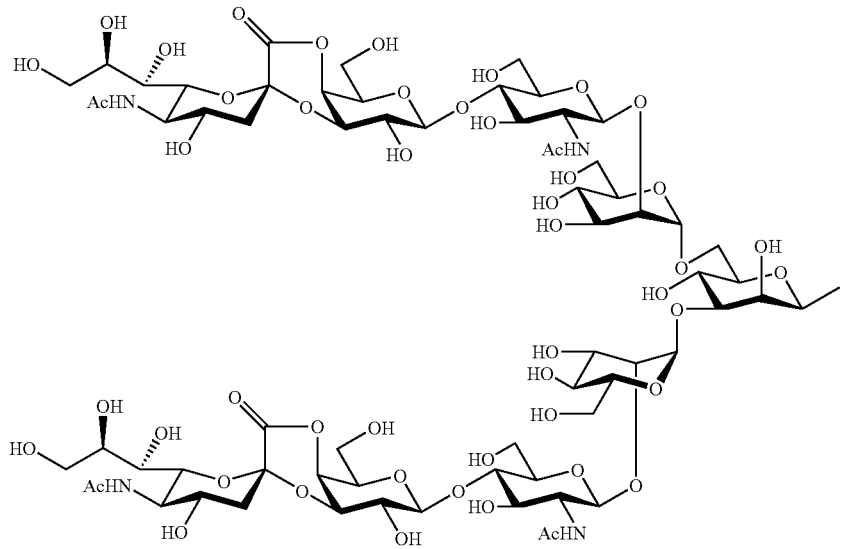

9

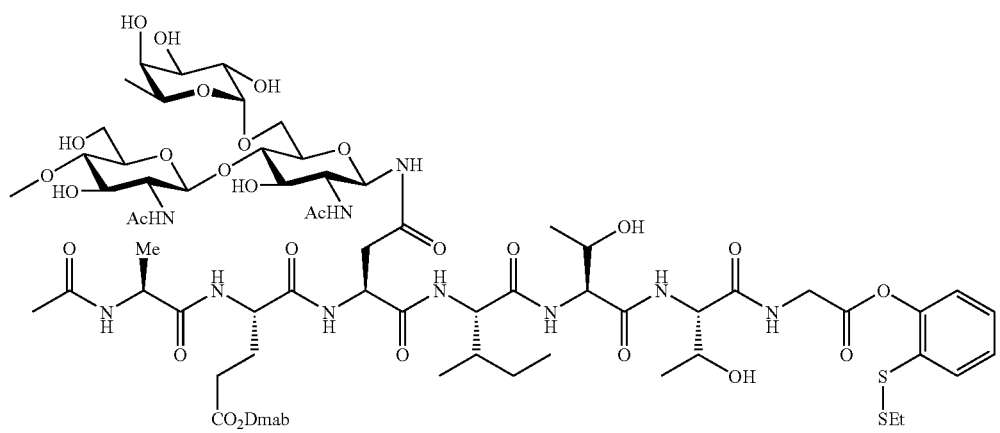

To a solution of glycosylamine 7 (1.0 mg, 0.42 µmol) and peptide 8 (2.2 mg, 1.8 µmol) in dry DMSO (0.7 mL) was added iPr$_2$NEt (4 µL, 23 µmol), followed by HATU (2.0 mg, 5.2 µmol). The reaction was stirred at room temperature for 30 min and then subjected directly to reverse-phase HPLC purification (C18 semi-prep, 30-70% acetonitrile in water in 20 min) to give glycopeptide 9 (0.6 mg, 40%) as a white solid. (T$_{rent}$=13.5 min). ESI-MS: calcd. C$_{148}$H$_{225}$N$_{15}$O$_{79}$S$_2$, 3540.4. found m/z 1772.0 [M+2H]$^{2+}$.

LC-MS: 30-70% acetonitrile in water over 20 min.

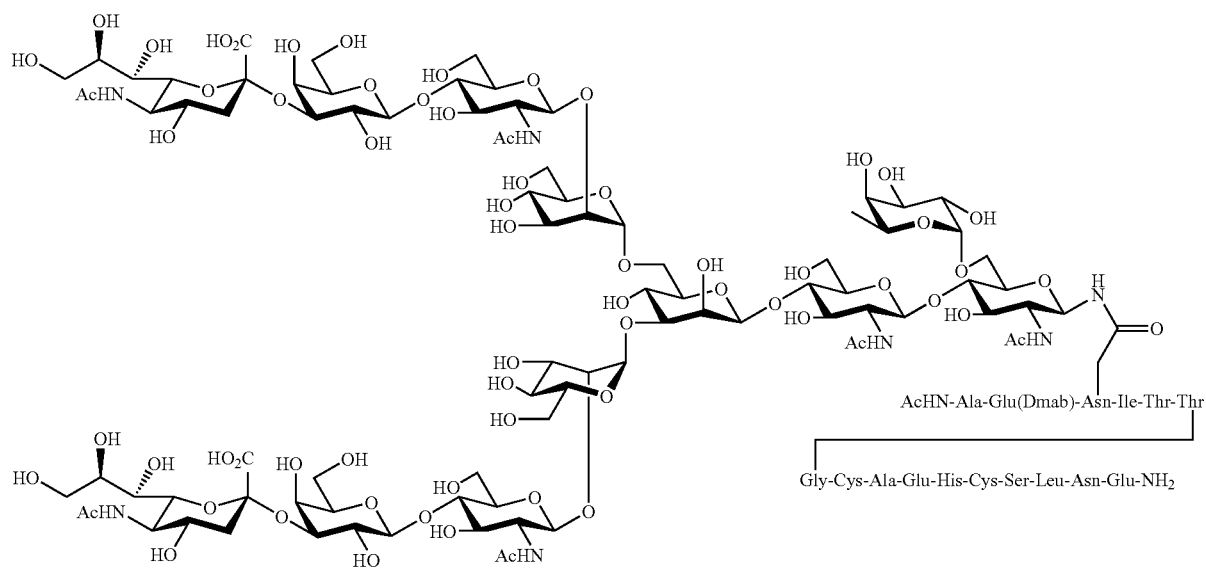

To a solution of glycopeptide 9 (1.0 mg, 0.28 μmol) and peptide 10 (1.8 mg, 1.5 μmol) in PBS (1% PhSH, pH 8.0, 0.6 ml) and DMF (0.3 mL) was added TCEP.HCl (2 mg). The reaction was stirred at room temperature for 4 h, then directly subjected to reverse-phase HPLC (C18 semi-prep, 20-50% acetonitrile in water in 20 min) to give glycopeptide 1 (0.7 mg, 56%) as a white solid ($T_{rent}$=13.5 min). ESI-MS: calcd. $C_{178}H_{280}N_{280}O_{95}S_2$, 4393.7. found m/z 1466.5 $[M+3H]^{3+}$.

LC-MS: 20-50% acetonitrile in water over 20 min.

Example 3
Mature Homogeneous Erythropoietin-Level Building Blocks by Chemical Synthesis: The EPO 114-166 Glycopeptide Domain, Presenting its O-Linked Glycophorin The naturally occurring glycoprotein, erythropoietin (EPO), is a 166-residue protein possessing four carbohydrate domains (Lai et al., E. *J. Biol. Chem.* 1986, 261, 3116-3121). The synthesis of the EPO 22-37 fragment displaying the mature N-linked dodecasaccharide domain has been described (Wu et al., *Tetrehedron Lett.* 2006, 47 *Proceeding Communication*). Herein, we describe the synthesis of the EPO 114-166 glycopeptide, presenting the glycophorin glycan at $Ser^{126}$ (1).

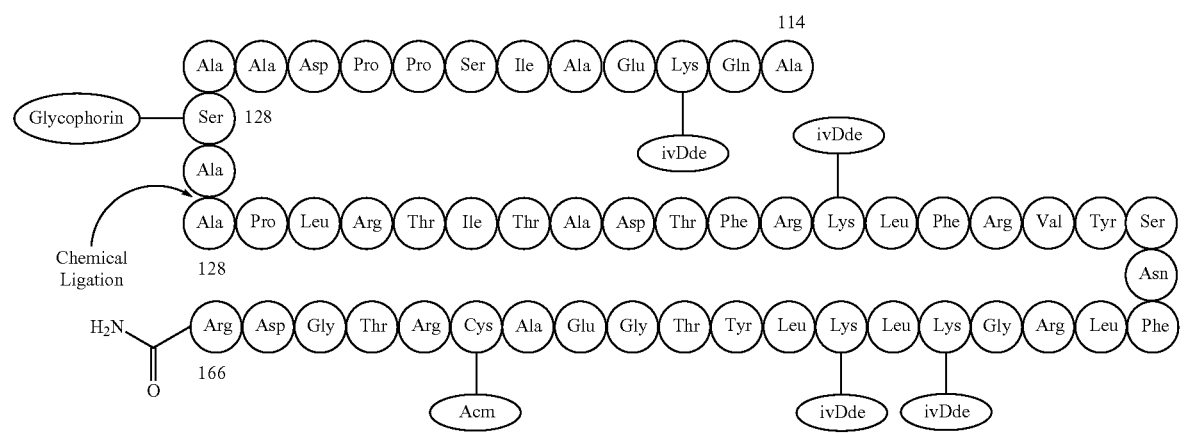

EPO 114-166 glycopeptide (1).

A synthetic plan toward erythropoietin with a view toward optimal convergency was developed. The program would entail synthesis of the required peptide fragments, each of which would be equipped with a mature carbohydrate domain. These glycopeptides would then be merged by exploiting chemical ligation methods developed elsewhere (Offer et al., *J. Am. Chem. Soc.* 2002, 124, 4642-4646; Offer et al., *Org. Lett.* 2000, 2, 23-26), as well as in our laboratory (Warren et al., *J. Am. Chem. Soc.* 2004, 126, 6576-6578; b) Wu et al., *Angew. Chem. Int. Ed.* 2006, 45, 4116-4125; Chen et al., *Tetrehedron Lett.* 2006, 47, 1969-1972; Wu et al., *Tetrehedron Lett.* 2006, 47, 5219-5223). One of the target fragments, 1, containing the 53 amino acid residues from $Ala^{114}$ to $Arg^{166}$ with a glycophorin domain attached at $Ser^{126}$.

Several strategies might have been pursued toward the synthesis of 1. One obvious approach would involve utilizing the glycophorin-presenting serine as a cassette and preparing the entire fragment, from the C to N terminus, through iterative Fmoc-based solid phase peptide synthesis (SPPS). In the context of this complex target, however, the costs associated with the significant loss of the valuable serine glycosylamino acid (cf. 3) and the low overall yields typically associated with the preparation of such large peptide fragments in this manner rendered such a non-convergent strategy quite unattractive.

Rather, we favored an approach that would make use of glycopeptide ligation methods (Wu et al., *Angew. Chem. Int. Ed.* 2006, 45, 4116-4125), which can be employed to join together two peptide fragments, one of which bears an O-linked carbohydrate. Given the difficulties in achieving non-cysteine native chemical ligation with sterically hindered amino acids, we elected to disconnect 1 at the $Ala^{127}$-$Ala^{128}$ junction. We envisioned employing our newly developed cysteine-free chemical ligation techniques. In the event that this application proved to be non-feasible or impractical it would be possible to resort to a cysteine-based method, which would simply require a subsequent desulfurization to convert Cys to Ala (Yan et al., *J. Am. Chem. Soc.* 2001, 123, 526-533).

Our synthesis of the $Ala^{114}$-$Ala^{127}$ coupling fragment (7) would first require the preparation of ample quantities of the Ser-glycophorin glycosylamino acid (2). In light of the well-documented challenges associated with the selective appendage of O-linked carbohydrates to serine and threonine residues, we elected to employ the cassette approach, developed some years earlier in our laboratory, in anticipation of just such a need (Schwarz et al., *J. Am. Chem. Soc.* 1999, 121, 2662-2673). In the case at hand, the cassette method was successfully applied to reaching the glycophorin-presenting glycosylamino acid, wherein an Fmoc-masked serine benzyl ester would be O-linked to a galactosamine moiety at an early stage of the synthesis. This intermediate was ultimately advanced to the fully protected glycosylamino acid 2 (Schwarz et al., *J. Am. Chem. Soc.* 1999, 121, 2662-2673).

In order to avoid compatibility issues associated with removal of the Fmoc group at a later stage in the synthesis, it was replaced with a Boc function, following the one-step protocol developed by Joullie (Li et al. *Tetrehedron Lett.* 1993, 34, 1413-1415). Hydrogenation of the benzyl ester provided carboxylic acid 3. EDC and HOOBt-mediated amide coupling between 3 and 4 proceeded without epimerization (Kuroda et al., *Int. J. Pept. Protein Res.* 1992, 40, 294; Sakakibara, *Biopolymers* 1995, 37, 17). These results are in accord with those reported by Sakakibara, who observed that the use of HOOBt as an additive in peptide coupling reactions is superior to the more commonly employed HOBt reagent (Li et al., *Org. Lett.* 1999, 1, 91-93). Treatment of the resultant amide with 4M HCl in dioxane afforded the dipeptide amine HCl salt 5. The latter was successfully coupled with the fully protected polypeptide 6 (itself obtained through SPPS), in the presence of EDC and HOOBt in TFE and $CHCl_3$, to afford the desired amide along with small amounts of TFE ester. The resultant compound was exposed to the action of 95% TFA and water to furnish glycopeptide 7, presenting the protected glycophorin domain.

The next task was that of preparing the $Ala^{128}$-$Arg^{166}$ polypeptide coupling fragment, bearing a Tmb group on the N-terminus. Due care was taken to ensure that the $Cys^{161}$ protecting group would be orthogonal to the functionality masking the Tmb thiol moiety. It was ultimately found that when the $Cys^{161}$ thiol was masked as an S-acetamidomethyl group (Acm), the Tmb could be equipped with a 2,4-dinitrophenyl (DNP) group, which would be selectively removed upon exposure to sodium 2-mercapto-ethanesulfonate (MESNa) and $K_2CO_3$ in MeOH (Halcomb et al., *J. Am. Chem. Soc.* 1991, 113, 5080-5082).

Having devised what seemed to be a feasible protecting group strategy, we prepared the poylpeptide 8 using a peptide amide linker on a polystyrene resin. Reductive amination between aldehyde 9 and peptide 8, following methodology which we had developed earlier (Wu et al., *Angew. Chem. Int. Ed.* 2006, 45, 4116-4125), yielded 10, equipped with the Tmb auxiliary at $Ala^{128}$. Treatment with MESNa exposed the required free thiophenol (see compound 11), which would couple with glycopeptide 7.

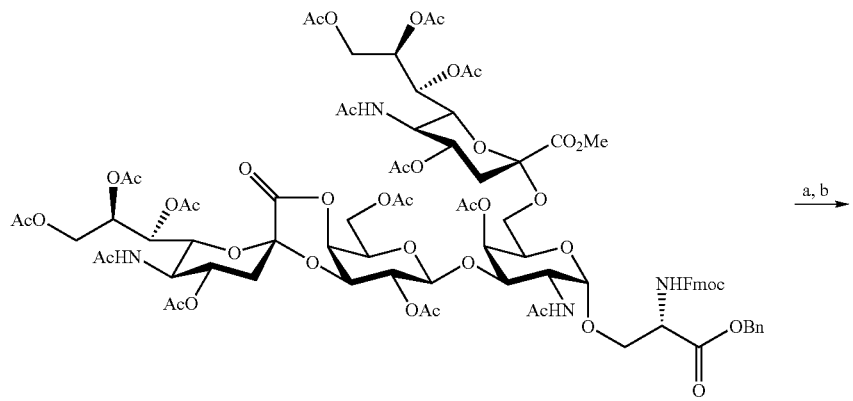

2

-continued
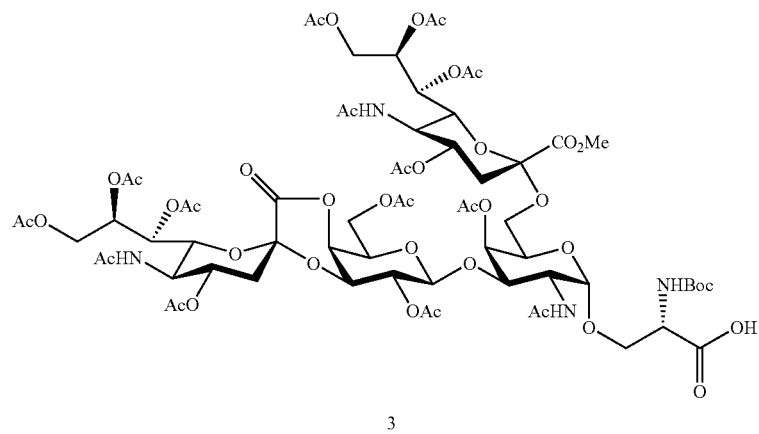
3
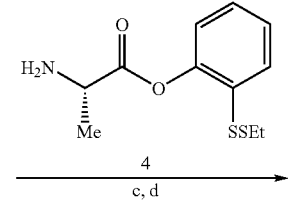
4
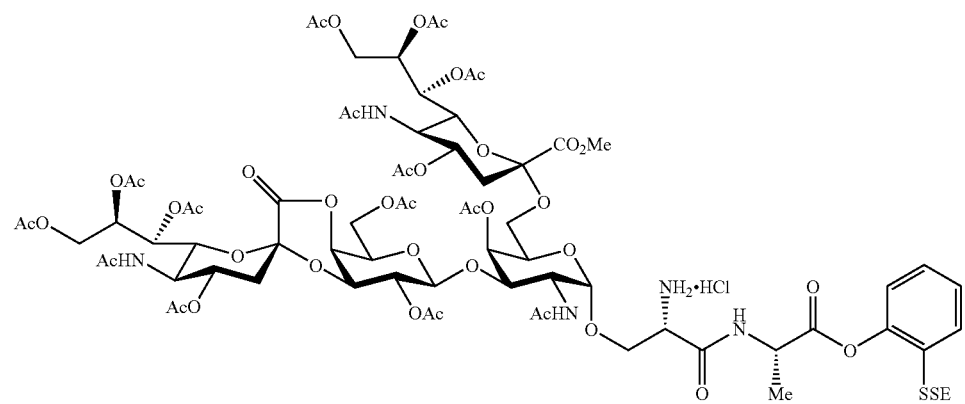
5
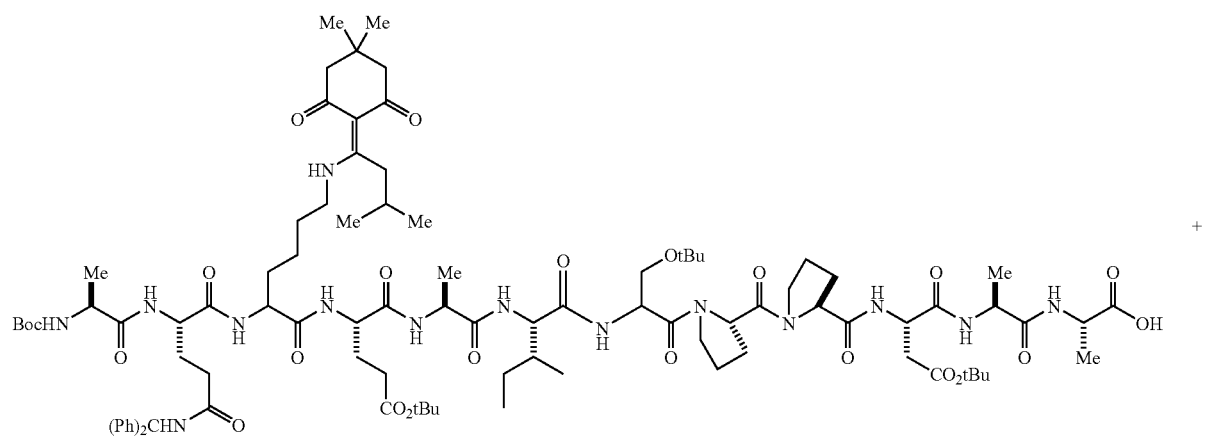
6
+

-continued
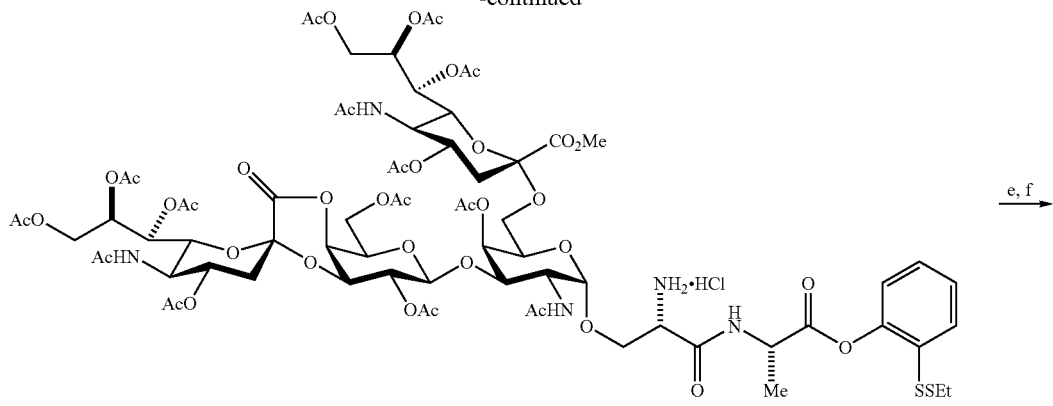
6
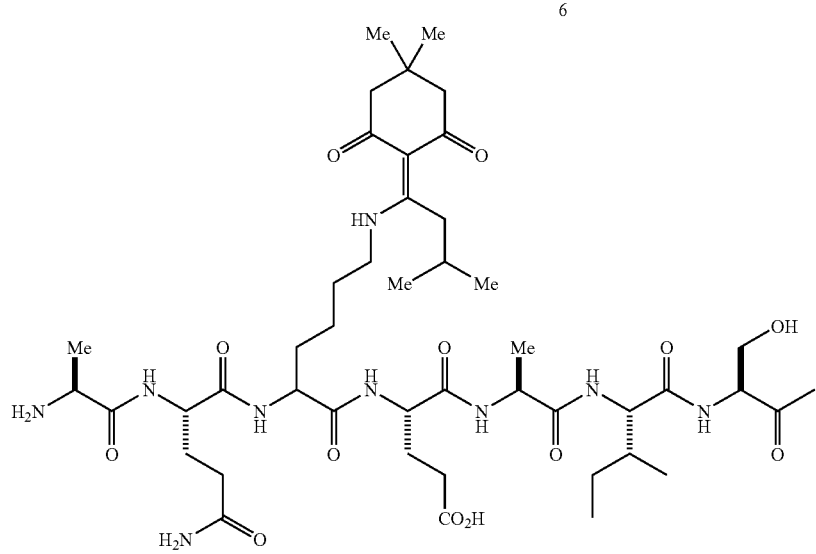
7
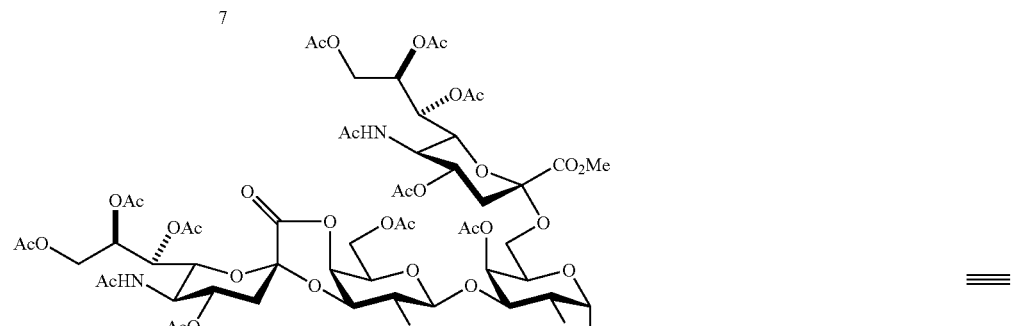
≡
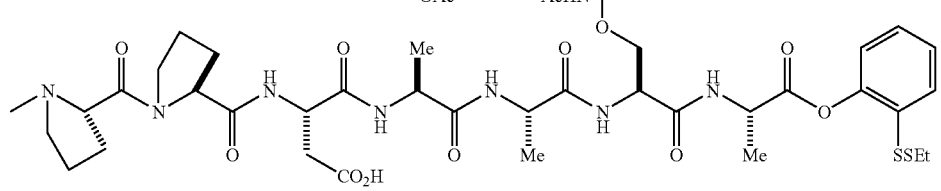
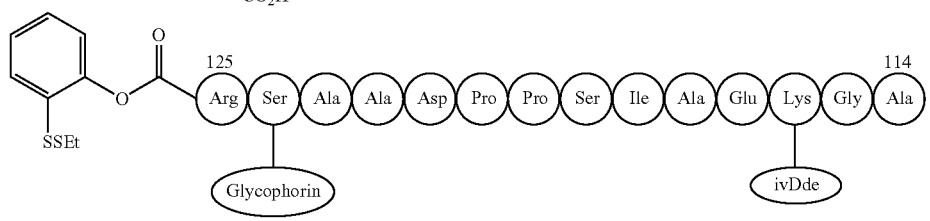

Synthesis of Compound 7.

a) Boc$_2$O, KF, Et$_3$N, DMF, b) H$_2$, Pd/C, MeOH, 78% over two steps, c) EDC, HOOBt, DMF, CH$_2$Cl$_2$, 4, d) 4M HCl in dioxane, e) EDC, HOOBt, TFE, CHCl$_3$, f) TFA, H$_2$O, PhOH, TESH, 46% over four steps.

S→N migration), culminating in 12. Initially, two peaks corresponding to the desired molecular weight were observed early on by LC-MS. These were assumed to arise from the ligated adduct and the intermediate thioester through which the two peptide fragments were temporarily joined prior to

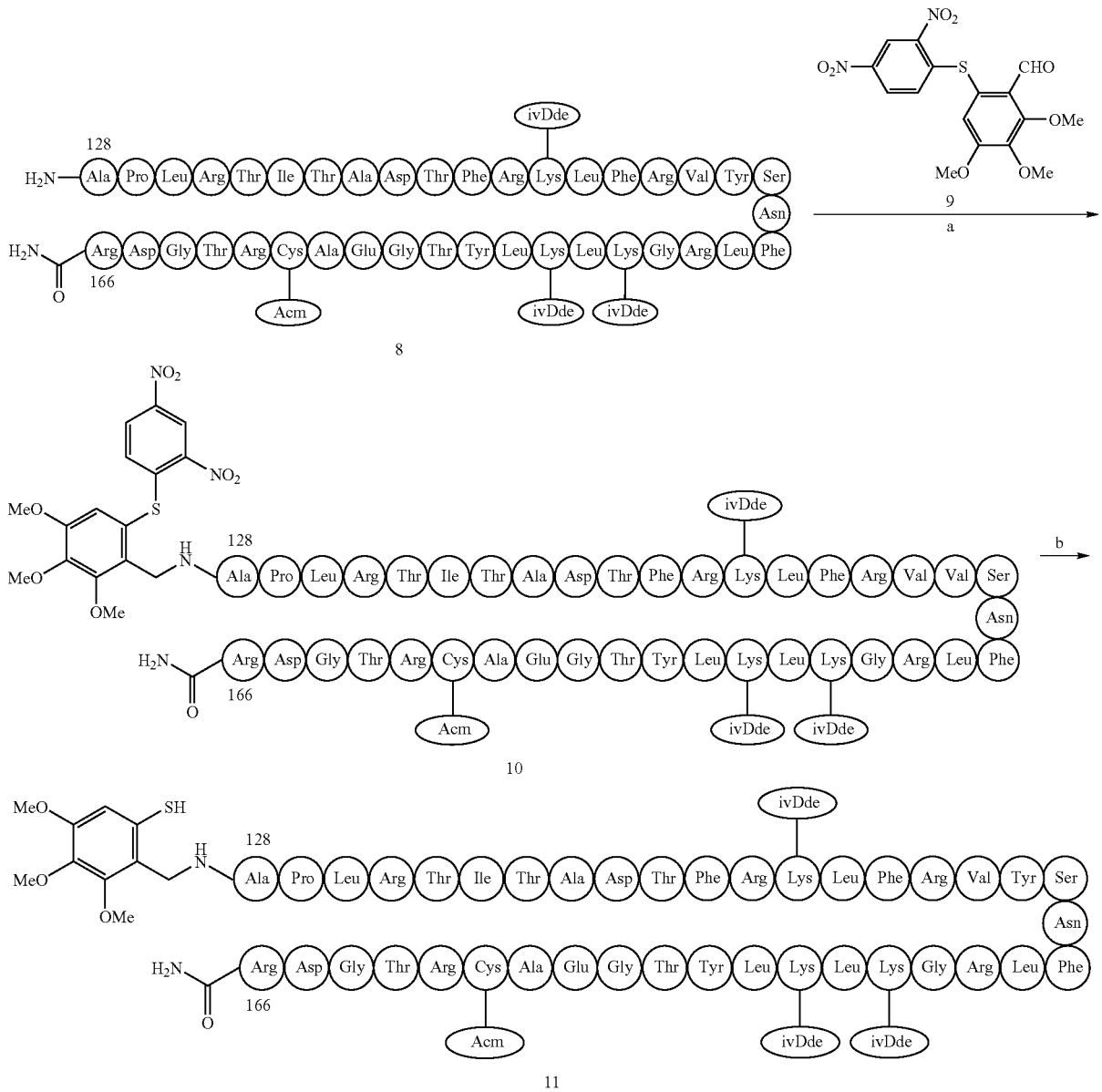

Synthesis of Compound 11.

a) NaCNBH$_3$, 9, MeOH, DMF, 63%, b) MESNa, K$_2$CO$_3$, MeOH, 88%.

In the event, the two peptides (7 and I) were subjected to concurrent treatment with TCEP in DMF, followed by sodium phosphate. We were expecting to exploit our recently established O→S migration, upon cleavage of the disulfide linkage in 7 (Chen et al., *J. Am. Chem. Soc.* 2006, 128, 7460-7462). It was presumed that the O→S intramolecular transacylation would be followed by an second trans acylation (intermolecular thioester exchange) with the liberated thiol linkage 11, generated from 10. The process advanced through another transacylation, (this time an intramolecular the actual ligation event, (i.e. S→N migration). After 24 h at room temperature, only one peak remained. The product was isolated and confirmed to be the desired amide (12), as opposed to the thioester intermediate. Interestingly, the terminating intramolecular S→N migration was found to be reversible, as evidenced by the fact that the coupled thioester reappeared upon treatment with 95% trifluoroacetic acid ((b) Wu et al., *Angew. Chem. Int. Ed.* 2006, 45, 4116-4125)). In order to block the undesired reverse N→S acyl migration pathway, the thiol group of the ligated product was selectively methylated to provide 13. We note that the successful methylation of intermediate 12 provides further evidence for the assignment of the latter as an amide bearing a free thiol functionality.

In order to demonstrate the compatibility of the glycan moiety with standard auxiliary removal conditions, the methylated glycopeptide 13 was subjected to 95% TFA and 5% TIPSH for 2 h. Following removal of solvents and treatment with phosphate buffer, the target glycopeptide 1 was isolated intact, without loss of the glycophorin domain.

Experimentals

To a solution of compound 2 (23.4 mg, 12.8 µmol) in DMF (0.6 mL) was added potassium fluoride (7.4 mg, 0.13 mmol) and triethylamine (5.4 µL) followed by addition of a solution of t-butyl dicarbonate (8.4 mg) in DMF (0.1 mL) at rt. The

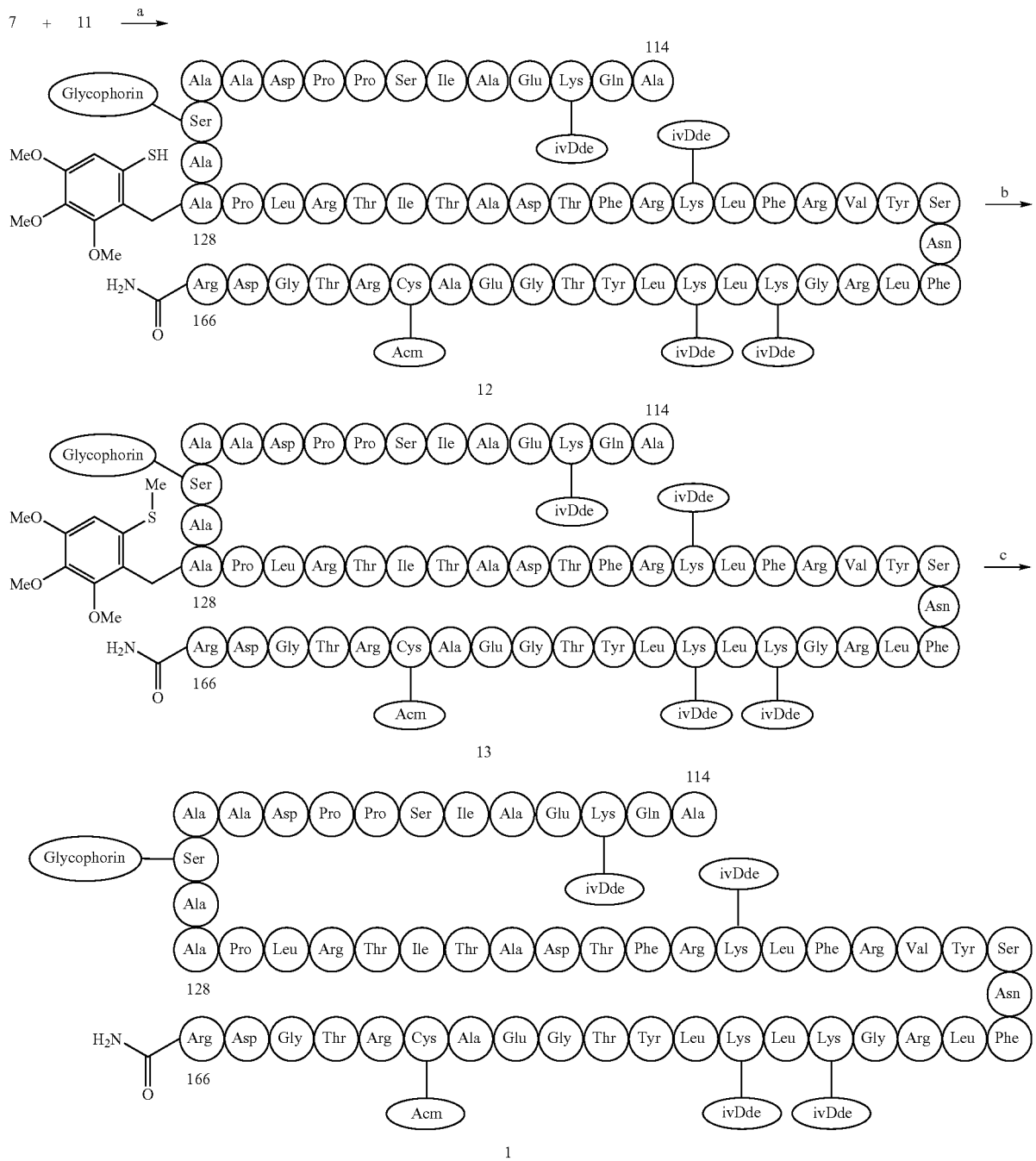

Synthesis of Compound 1.

a) TCEP, DMF, Na$_2$HPO$_4$, 57%, b) methyl 4-nitrobenzenesulfonate, PBS, 7.7, 81%, c) TFA, TIPSH.

In summary, we have described herein the preparation of the Ala$^{114}$-Arg$^{166}$ domain of EPO, bearing the requisite glycophorin domain by chemical synthesis.

resulting reaction mixture was stirred at rt for 24 h before it was diluted with ethyl acetate (5 mL). The organic layer was washed with 5% aqueous HCl (5 mL) and brine (5 mL). The combined aqueous layers were extracted with ethyl acetate (3×5 mL). The combined organic layers were dried over Na$_2$SO$_4$ and filtered and concentrated in vacuo. The residue was purified via silica gel column chromatography (EtOAc to 5% MeOH in $CH_2Cl_2$) to give the desired product (21 mg). MS (ESI): $C_{74}H_{100}N_4O_{41}$ Calc. 1700.59, Observed 1700.40.

To a solution of the Boc-protected benzyl ester (21 mg) in methanol (1.5 mL) was added 5% Pd/C (10 mg). The reaction vessel was equipped with a hydrogen balloon. The reaction mixture was allowed to stirred at rt for 7 h before it was filtered through a pad of silica gel and rinsed with 50% $CH_2Cl_2$ in MeOH. The resulting mixture was concentrated to give compound 3 (16.1 mg) and used for the next step without further purification.

To a solution of amine 4 (10.1 mg, 34.5 μmol) and acid 3 (18.5 mg, 11.5 μmol) in DMF (0.4 mL) and $CH_2Cl_2$ (0.4 mL) were added HOOBt (3.8 mg) and a solution of EDC (3.5 mg) in DMF (0.2 mL) at 0° C. The reaction mixture was stirred at 0° C. for 30 min before it was warmed to rt and stirred for 3 h. The reaction mixture was diluted with ethyl acetate (5 mL) and washed with 5% HCl (5 mL) and brine (5 mL). The combined aqueous layers were extracted with ethyl acetate (3×5 mL). The combined organic layers were dried over $Na_2SO_4$ and filtered and concentrated in vacuo. The resultant residue was purified with silica gel column chromatography (5% MeOH in $CH_2Cl_2$) to give the desired compound: MS (ESI): $C_{78}H_{107}N_5O_{42}S_2$ Calc. 1849.58, Exp. 1849.67, which was treated with 4M HCl in dioxane (1 mL) for 1 h at rt. Removal of all solvents followed by addition of cold ethyl ether (5 mL) precipitated the amine HCl salt 5, which was used for the next step without further purification.

To a solution of dipeptide amine HCl salt 5 (5.13 μmol) and polypeptide acid 6 (15 mg, 7.70 μmol) in trifluoroethanol (0.15 mL) and chloroform (0.45 mL) was added HOOBt (1.7 mg) and a solution of EDC (1.8 μL) in chloroform (0.1 mL) at 0° C. The resultant reaction mixture was allowed to stir at 0° C. for 30 min before it was warmed to rt and stirred at rt for 4 h. All solvents were removed by a stream air of nitrogen and the resultant residue was treated with a mixed solvents of TFA (90%), $H_2O$ (2.5%), TESH (2.5%), PhOH (5%) for 2 h. Then all solvents were removed and added ice-cold ether (5 mL) to precipitate the product, which was purified with HPLC (C-18 column, 35-50% acetonitrile in water over 20 min) to give the desired phenolic ester 7 (7.4 mg, 46% over 4 steps): MS (ESI): $C_{137}H_{199}N_{19}O_{60}S_2$, Calc. 3134.25, Observed 1568.84 $(M+2H^+)$.

Peptide 8 was prepared with amine linker polystyrene resin using Fmoc-based solid phase peptide synthesis protocol. The product was obtained after cleavage from resin with 95% TFA, 2.5% $H_2O$ and 2.5% TIPSH. The pure compound was purified with HPLC (C-4 column, 45-65% acetonitrile in water over 30 min). MS (ESI): $C_{245}H_{389}N_{63}O_{61}S$, Calc. 5221.90, Observed 1307.02 $(M+4H^+)$, 1046.52 $(M+5H^+)$.

To a solution of peptide 8 (10 mg) in MeOH (0.8 mL) was added a solution of aldehyde 9 (5 mg) in DMF (0.3 mL). The resultant reaction mixture was stirred at rt for 4 h before a solution of sodium cyanoborohydride (4 mg) in MeOH (0.2 mL). The reaction mixture was stirred at rt for 20 h before it was concentrated and redissolved in $H_2O$ and acetonitrile for HPLC purification (C4 column, 45-65% acetonitrile in water over 30 min) to give compound 10 (6.7 mg, 63%): MS (ESI): $C_{261}H_{403}N_{65}O_{68}S_2$, Calc. 5599.95, Observed 1401.98 $(M+4H^+)$, 1121.86 $(M+5H^+)$.

To a solution of compound 10 (4 mg) in MeOH (0.8 mL) was added MESNa (1.5 mg) and $K_2CO_3$ (1.5 mg). The resultant reaction mixture was stirred at rt for 30 min before it was concentrated and re-dissolved in water and acetonitrile for HPLC purification (C4 column, 45-65% acetonitrile in water over 30 min) to give compound 11 (3.4 mg, 88%): MS (ESI): $C_{255}H_{401}N_{63}O_{64}S_2$, Calc. 5433.95, Observed 1360.39 $(M+4H^+)$, 1088.54 $(M+5H^+)$.

To a vial with peptides 7 (2 mg) and 11 (2 mg) was added a solution of TCEP (1.0 mg) in DMF (0.8 mL) and sodium phosphate (1.5 mg). The resultant reaction mixture was allowed to stir at rt for 22 h before it was diluted with water and acetonitrile for HPLC purification (C4 column, 50-75% acetonitrile in water over 30 min) to give the ligated product 12 (3.4 mg, 57%): MS (ESI): $C_{34}H_{590}N_{82}O_{123}S_2$, Calc. 8382.19, Observed 2097.89 $(M+4H^+)$, 1678.76 $(M+5H^+)$, 1398.88 $(M+6H^+)$, 1199.53 $(M+7H^+)$.

To a solution of the ligated product (3.4 mg) in phosphate buffer (pH 7.72, 1.0 mL) was added a solution of methyl 4-nitrobenzenesulfonate (1.5 mg) in acetonitrile (0.15 mL) at rt. The resultant reaction mixture was allowed to stir at rt for 1 h before it was diluted with water and acetonitrile for HPLC purification (C4 column, 50-75% acetonitrile in water over 30 min) to give the ligated product 13 (2.7 mg, 81%): MS (ESI): $C_{385}H_{592}N_{82}O_{123}S_2$, Calc. 8396.19, Observed 2101.18 $(M+4H^+)$, 1681.29 $(M+5H^+)$, 1401.42 $(M+6H^+)$, 1201.30 $(M+7H^+)$.

To a vial with the methylated product (0.5 mg) was added a co-solvent of TFA (0.95 mL) and triisopropylsilane (0.05 mL) at rt. The resultant reaction mixture was allowed to stir at rt for 2 h before it was concentrated and redissolved in a PBS buffer (1 mL) for 1 h. It was diluted with water and acetonitrile for HPLC purification (C4 column, 50-75% acetonitrile in water over 30 min) to give the final product 1: MS (ESI): $C_{374}H_{578}N_{82}O_{120}S_1$, Calc. 8170.14, Observed 2044.98 $(M+4H^+)$, 1635.96 $(M+5H^+)$, 1363.93 $(M+6H^+)$, 1169.13 $(M+7H^+)$.

Example 4

Mature Homogeneous Erythropoietin Building Blocks by Chemical Synthesis: The EPO 1-28 Glycopeptide Domain Presenting the Fully N-Linked Dodecasaccharide and a C-Terminal Thioester In this example is described the synthesis of the EPO 1-28 glycopeptide (101) possessing both the N-linked dodecasaccharide at $Asn^{24}$ and a C-terminal thioester handle.

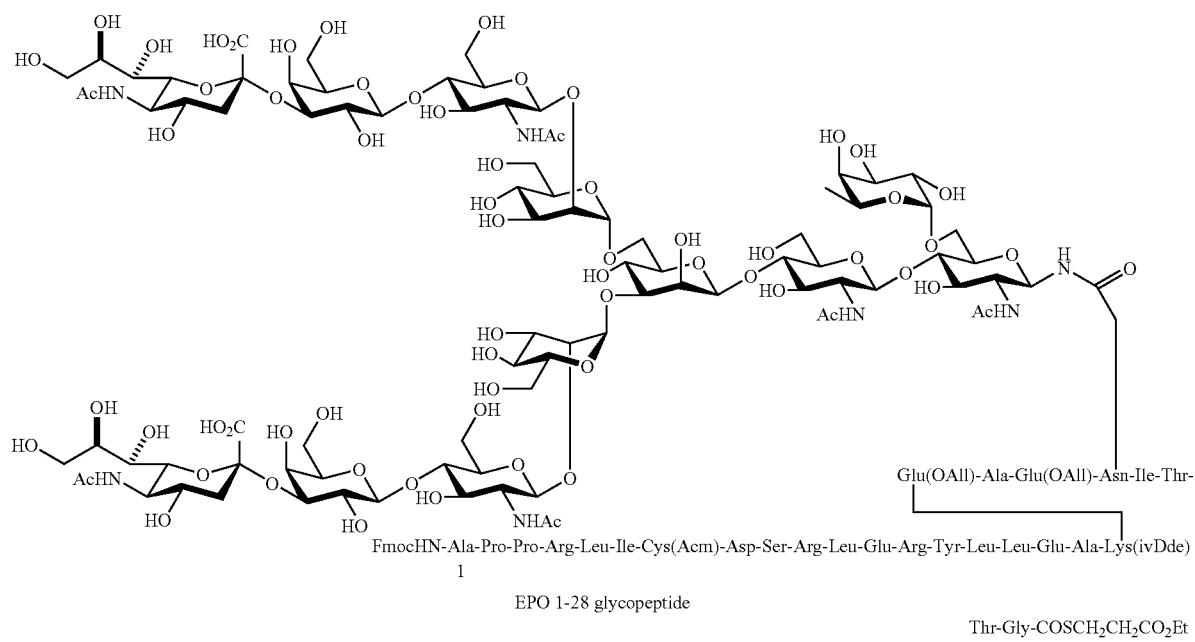
EPO 1-28 glycopeptide
Experimentals
Scheme for 102 → 103
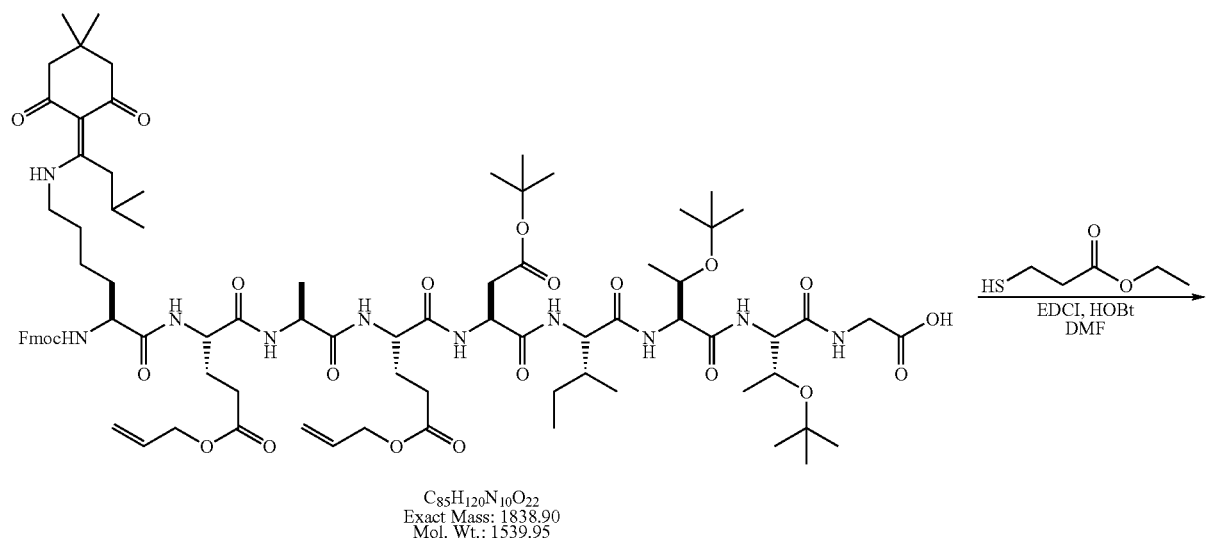
$C_{85}H_{120}N_{10}O_{22}$
Exact Mass: 1838.90
Mol. Wt.: 1539.95
102

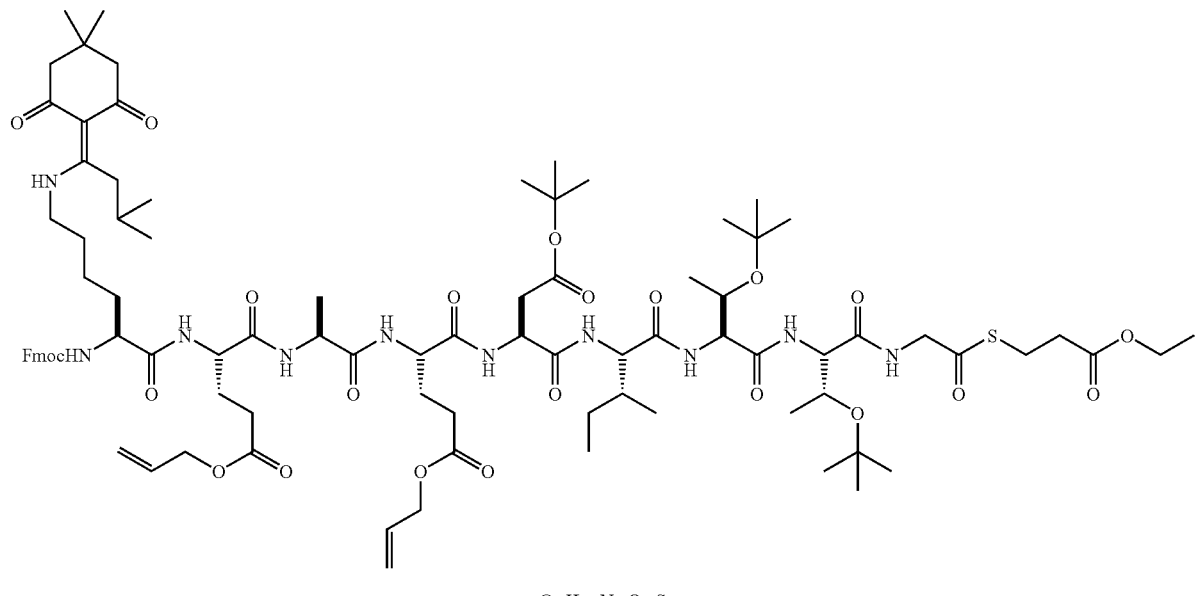

$C_{90}H_{134}N_{10}O_{23}S$
Exact Mass: 1754.93
Mol. Wt.: 1756.15

103

Peptide 102 (35 mg, 0.021 mmol), EDCI (41 mg, 0.21 mmol), and HOBt (29 mg, 0.21 mmol) were dissolved in DMF (2.0 mL). Then ethyl 3-mercaptopropionate (54 µL, 0.43 mmol) was added. The colorless solution was stirred at rt for 15 h. The DMF was removed under a positive stream of air to give a clear film. Purification by flash chromatography (silica gel, 5% MeOH/CH$_2$Cl$_2$) provided the desired product 103 (34 mg, 91%). ESI-MS: Calcd. For $C_{90}H_{134}N_{10}O_{23}S$: 1754.93. Found: m/z 1756.14 [M+H]$^+$.

Scheme for 103 → 104

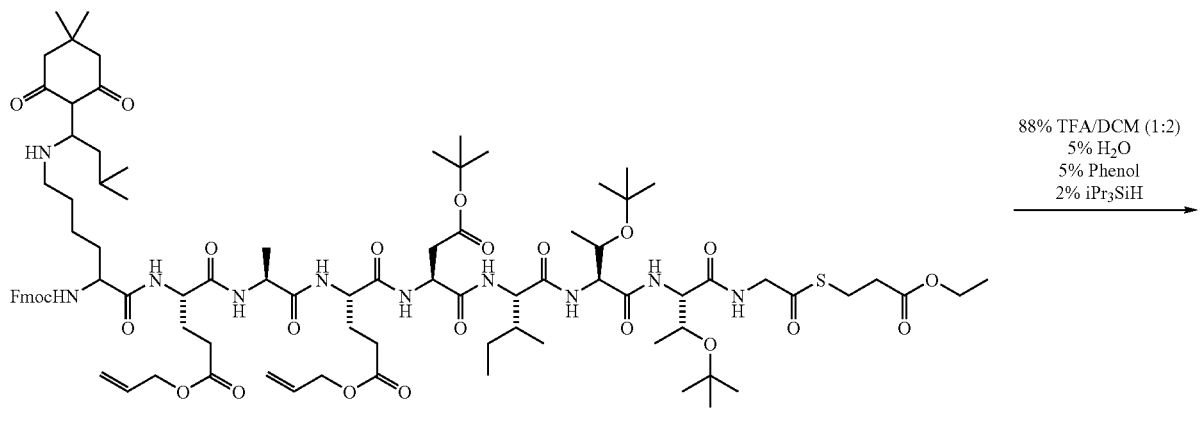

$C_{90}H_{134}N_{10}O_{23}S$
Exact Mass: 1754.93
Mol. Wt.: 1756.15

103

88% TFA/DCM (1:2)
5% H$_2$O
5% Phenol
2% iPr$_3$SiH

-continued

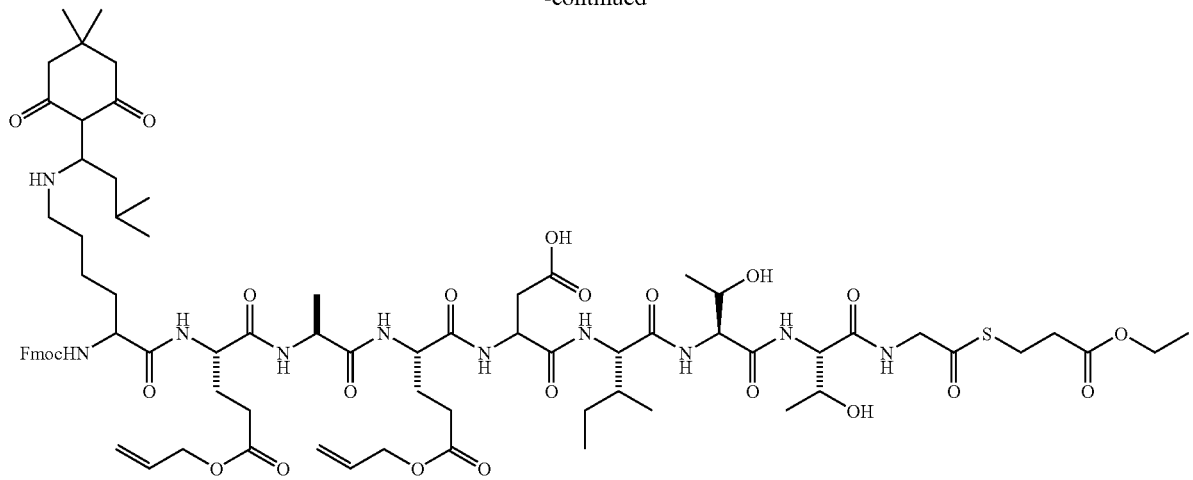

C$_{78}$H$_{110}$N$_{10}$O$_{23}$S
Exact Mass: 1586.75
Mol. Wt.: 1587.83

104

Peptide 103 (34 mg, 0.019 mmol) was dissolved in a deprotection cocktail (2.0 mL, 88% of a 1:2 CH$_2$Cl$_2$/TFA solution, 5% H$_2$O, 5% Phenol, 2% iPr$_3$SiH). The colorless solution was stirred at rt for 2 h. The reaction mixture was transferred to a polypropylene vial and concentrated under a stream of air. The resulting residue was triturated with cold Et$_2$O (3×7 mL). Each time, the precipitate/Et$_2$O mixture was placed in a centrifuge for 5 min and then the Et$_2$O was carefully decanted. The resulting off-white solid was placed under house-vacuum overnight. The solid was purified via RP-HPLC(C18 semi-prep column, 55%→70% MeCN/H$_2$O over 30 min, 262 nm, 16 mL/min) to provide peptide 104 (7 mg, 23%) as a white solid (T$_{rent}$=13.5 min). ESI-MS: Calcd. For C$_7$H$_{110}$N$_{10}$O$_{23}$S: 1586.75. Found: m/z 1587.83 [M+H]$^+$.

LC-MS for 104: C18 analytical column, 55%→70% MeCN/H$_2$O over 30 min.

Scheme for 104 → 106.
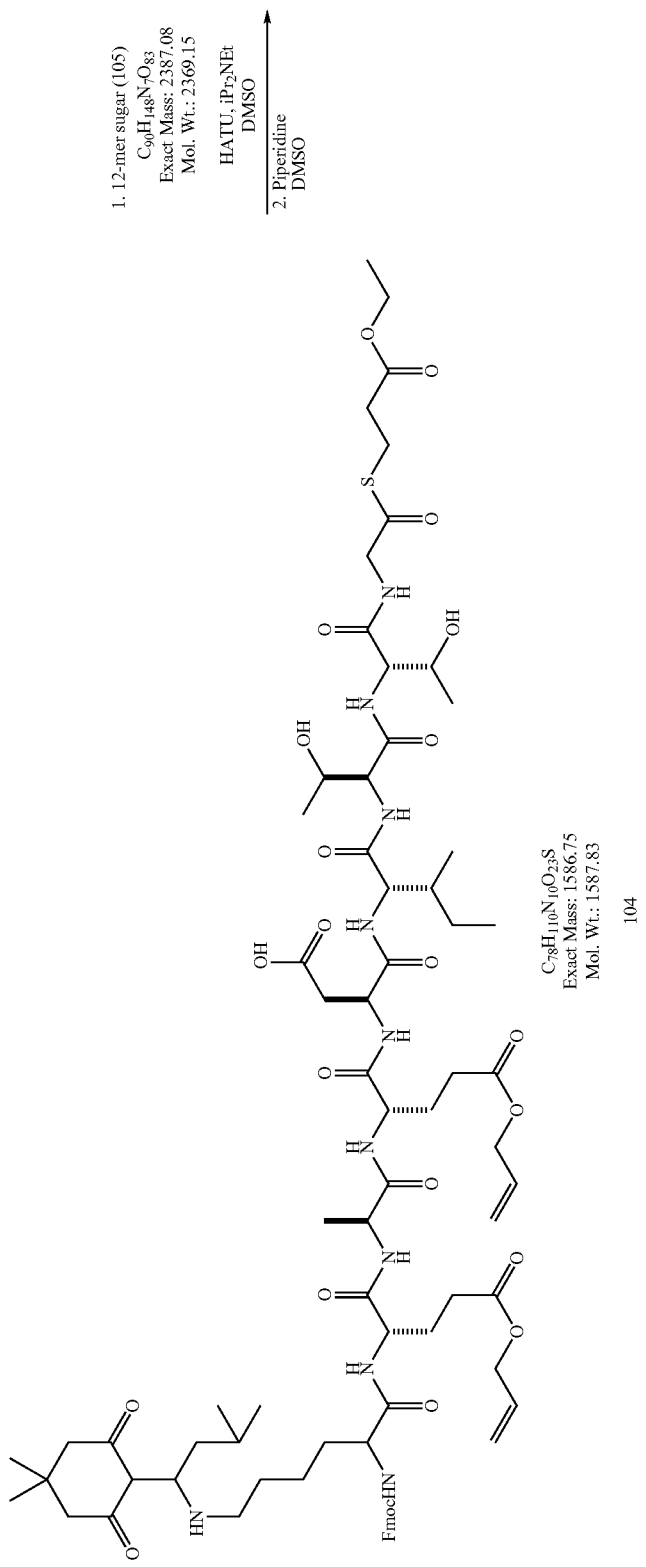

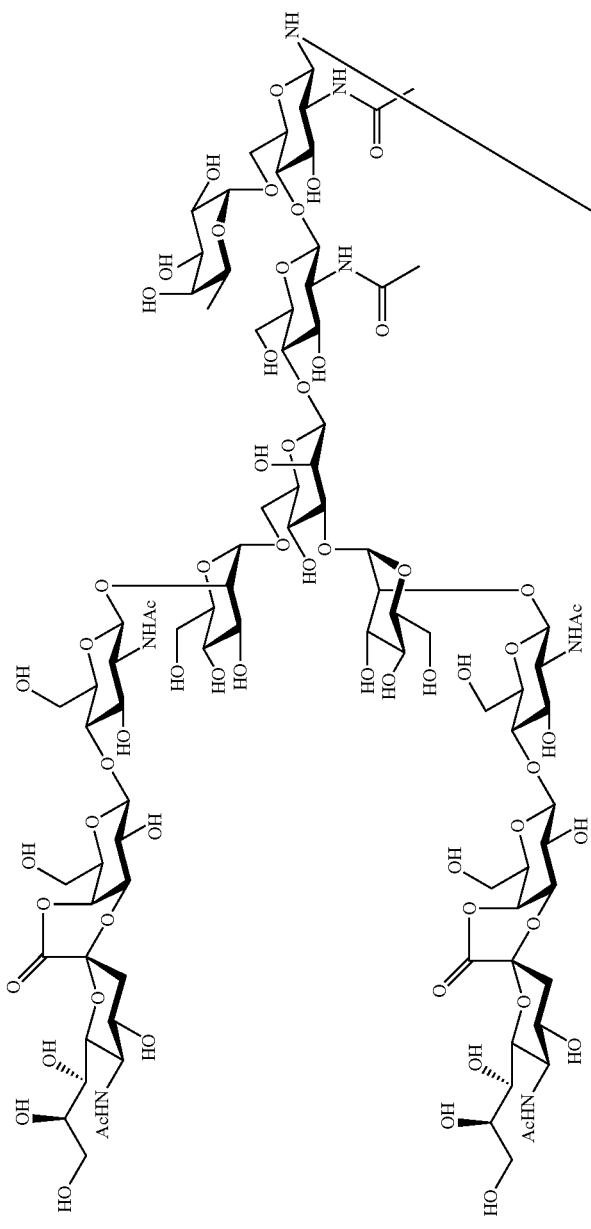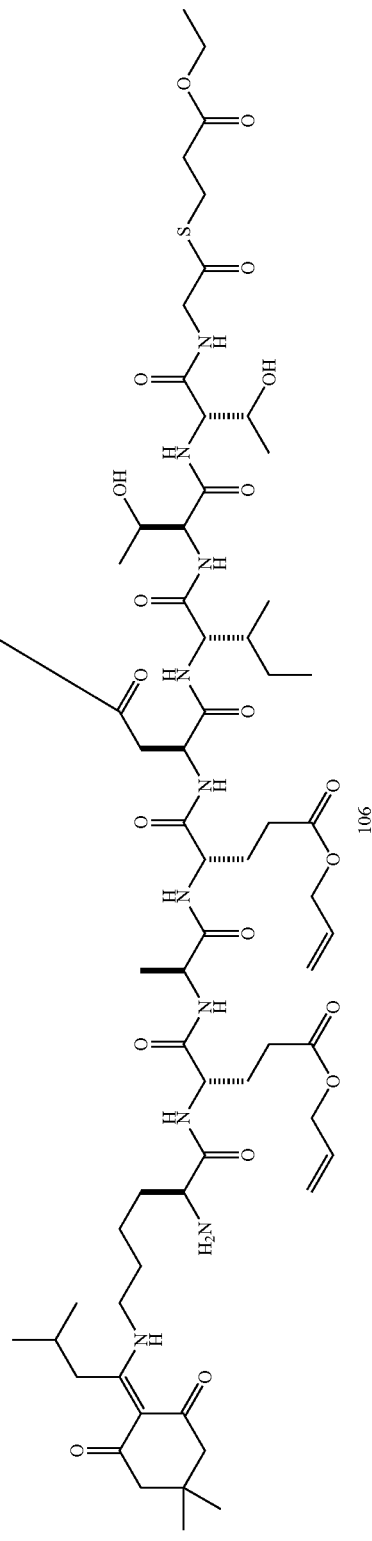

The HATU stock solution was prepared by dissolving HATU (20 mg, 0.053 mmol) in DMF (0.5 mL). The iPr$_2$NEt stock solution was prepared by adding iPr$_2$NEt (10 μL, 0.06 μmol) in DMF (1.0 mL). The piperidine stock solution was prepared by adding piperidine (10 μL, 0.10 μmol) in DMF (0.5 mL). Peptide 104 (1.0 mg, 0.59 μmol) and 12-mer sugar 105 (0.7 mg, 0.30 μmol) were placed in an oven-dried vial with stir bar. An aliquot of the HATU stock solution (25 μL, 2.4 μmol) and an aliquot of the iPr$_2$NEt stock solution (20 μL, 1.2 μmol) were added to the vial sequentially. The resulting yellow solution was stirred at rt for 1.5 h. Then an aliquot of the piperidine stock solution (25 μL, 5.3 μmol) was added to the reaction and the yellow color became more intense. The reaction was stirred for an additional 2 h, at which point the reaction was quenched by addition of MeCN/H$_2$O (500 μL, 1:1). The solution was loaded directly onto the RP-HPLC column and purified (C18 semi-prep column, 25%→55% MeCN/H$_2$O over 30 min, 260 nm, 16 mL/min) to provide glycopeptide 106 (0.35 mg, 35%) as a white solid ($T_{rent}$=16.5 min). ESI-MS: Calcd. for $C_{153}H_{243}N_{17}O_{83}S$: 3678.50. Found: m/z 1840.72 $[M+2H]^{2+}$.

LC-MS for 106: C18 analytical column, 25%→55% MeCN/H$_2$O over 30 min

Scheme for 107 → 109
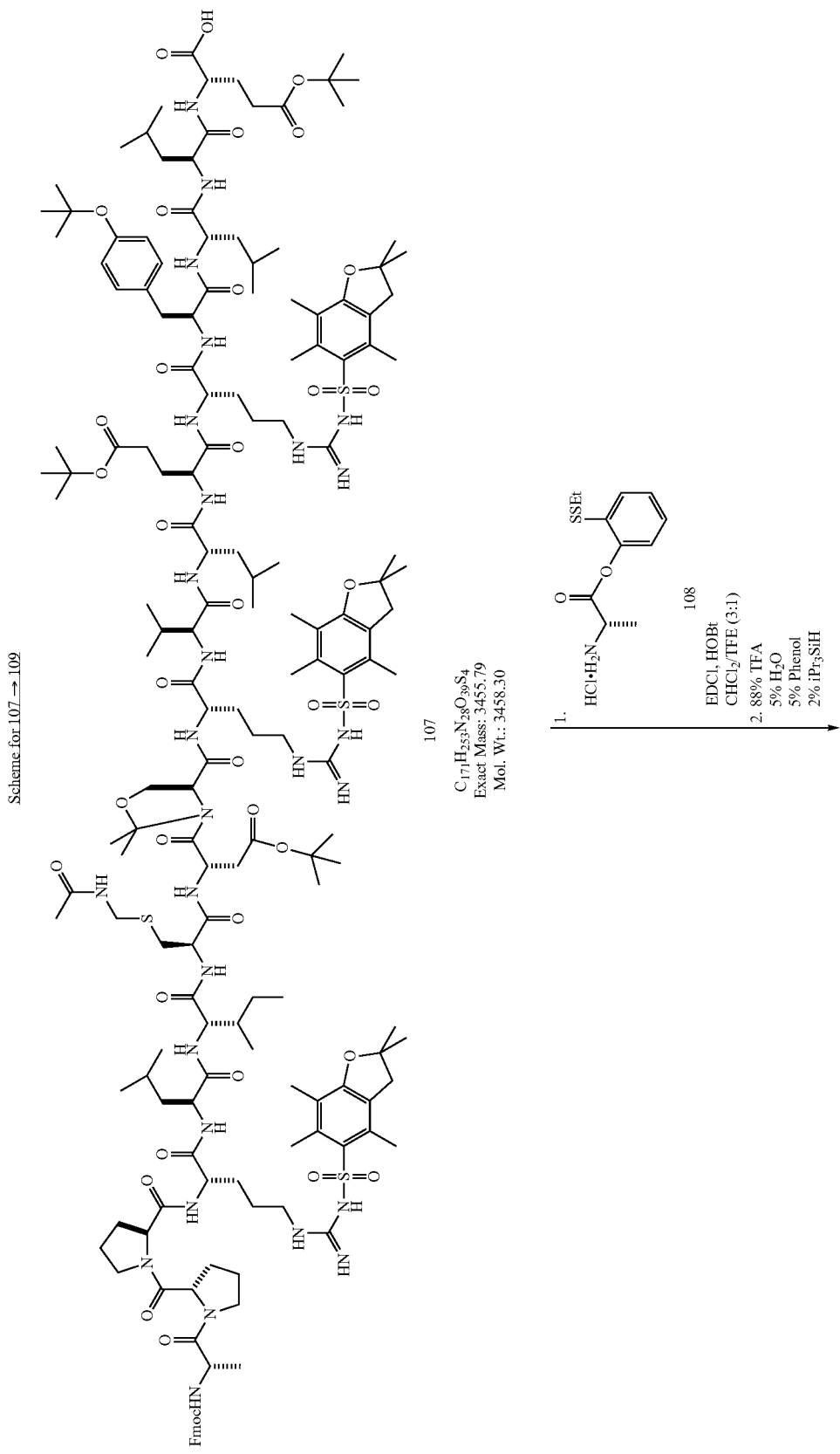
107
C₁₇₁H₂₅₃N₂₈O₃₉S₄
Exact Mass: 3455.79
Mol. Wt.: 3458.30
1. HCl·H₂N— (108)
   EDCI, HOBt
   CHCl₂/TFE (3:1)
2. 88% TFA
   5% H₂O
   5% Phenol
   2% iPr₃SiH

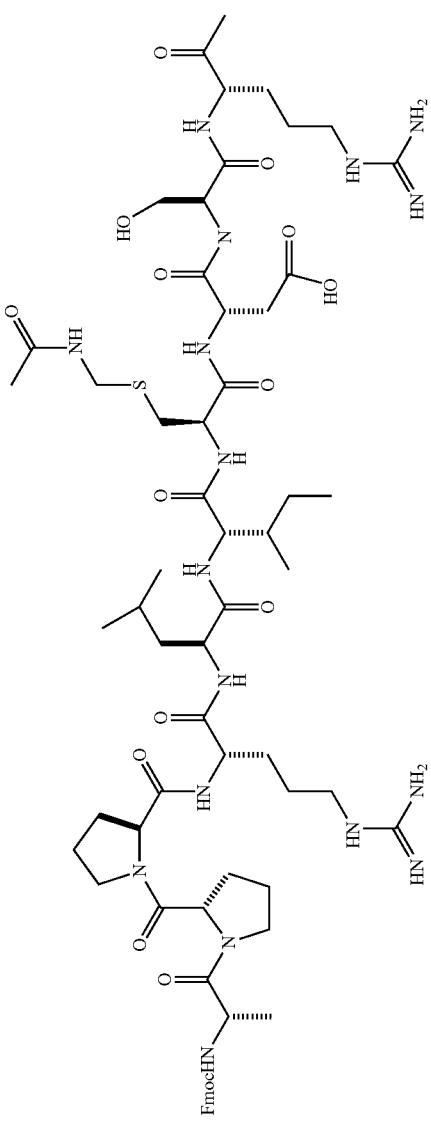

Peptide 107 (31 mg, 9.0 μmol) and the ortho-disulfide phenolic ester 108 (10 mg, 34 μmol) were weighed into an oven-dried vial. The solids were dissolved in $CHCl_3$/TFE (2 mL, 3:1) to give a colorless solution. EDCI (5.1 mg, 27 μmol) and HOBt (1.5 mg, 11 μmol) were added to the reaction. After stirring for 14.5 h, the solvent was removed under a stream of air and the residue placed under high vacuum for 1 h. The resulting peach-colored foam was dissolved in a deprotection cocktail (2.0 mL, 88% TFA, 5% $H_2O$, 5% Phenol, 2% $iPr_3SiH$) and stirred at rt for 3 h. The reaction mixture was transferred to a polypropylene vial and concentrated under a stream of air. The resulting residue was triturated with cold $Et_2O$ (3×7 mL). Each time, the precipitate/$Et_2O$ mixture was placed in a centrifuge for 5 min and then the $Et_2O$ was carefully decanted. The resulting peach-colored solid was placed under house-vacuum overnight. The solid was purified via RP-HPLC (C18 semi-prep column, 55%→80% MeCN/$H_2O$ over 30 min, 266 nm, 16 mL/min) to provide peptide 109 (12 mg, 50%) as a white solid ($T_{rent}$=12.9 min). ESI-MS: Calcd. for $C_{124}H_{187}N_{29}O_{31}S_3$: 2674.31. Found: m/z 1338.79 $[M+2H]^{2+}$, 893.11 $[M+3H]^{3+}$.

LC-MS for 109: C18 analytical column, 25%→55% MeCN/$H_2O$ over 30 min.

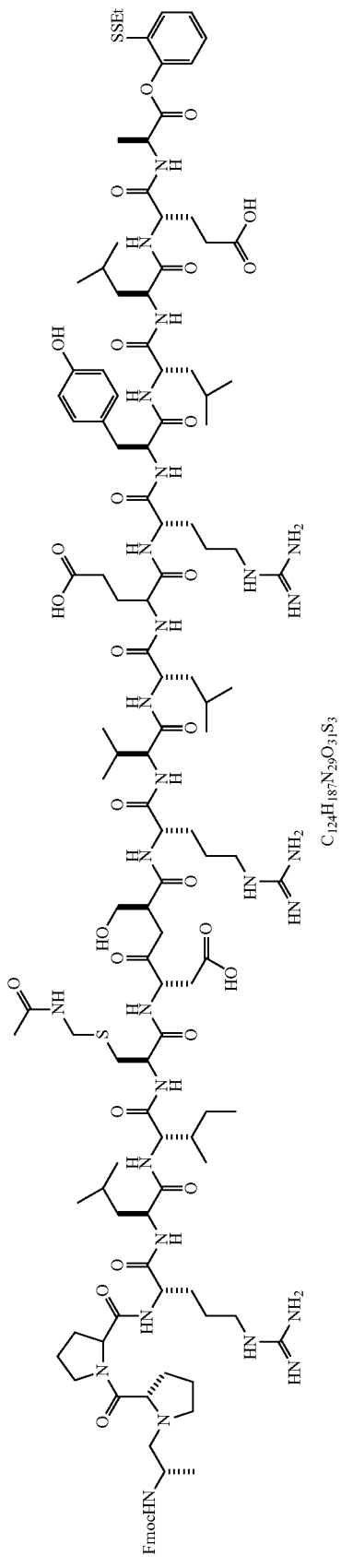
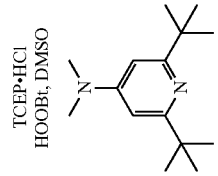
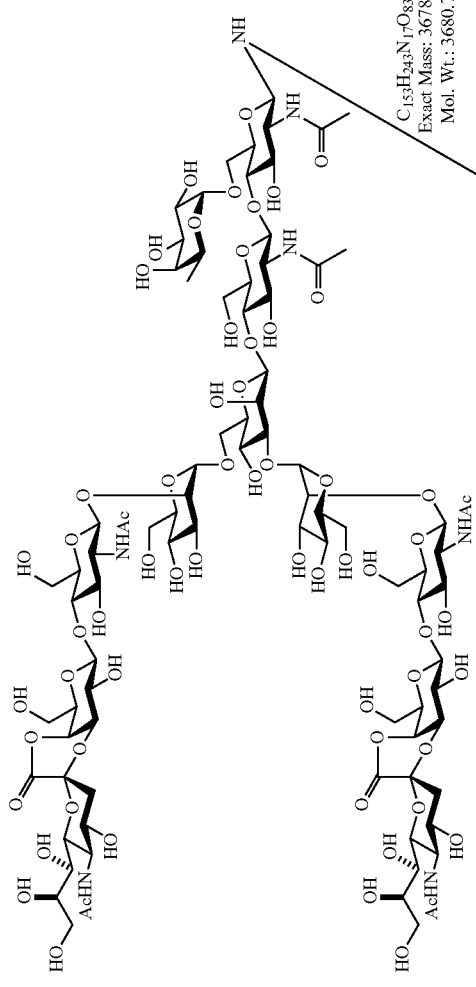

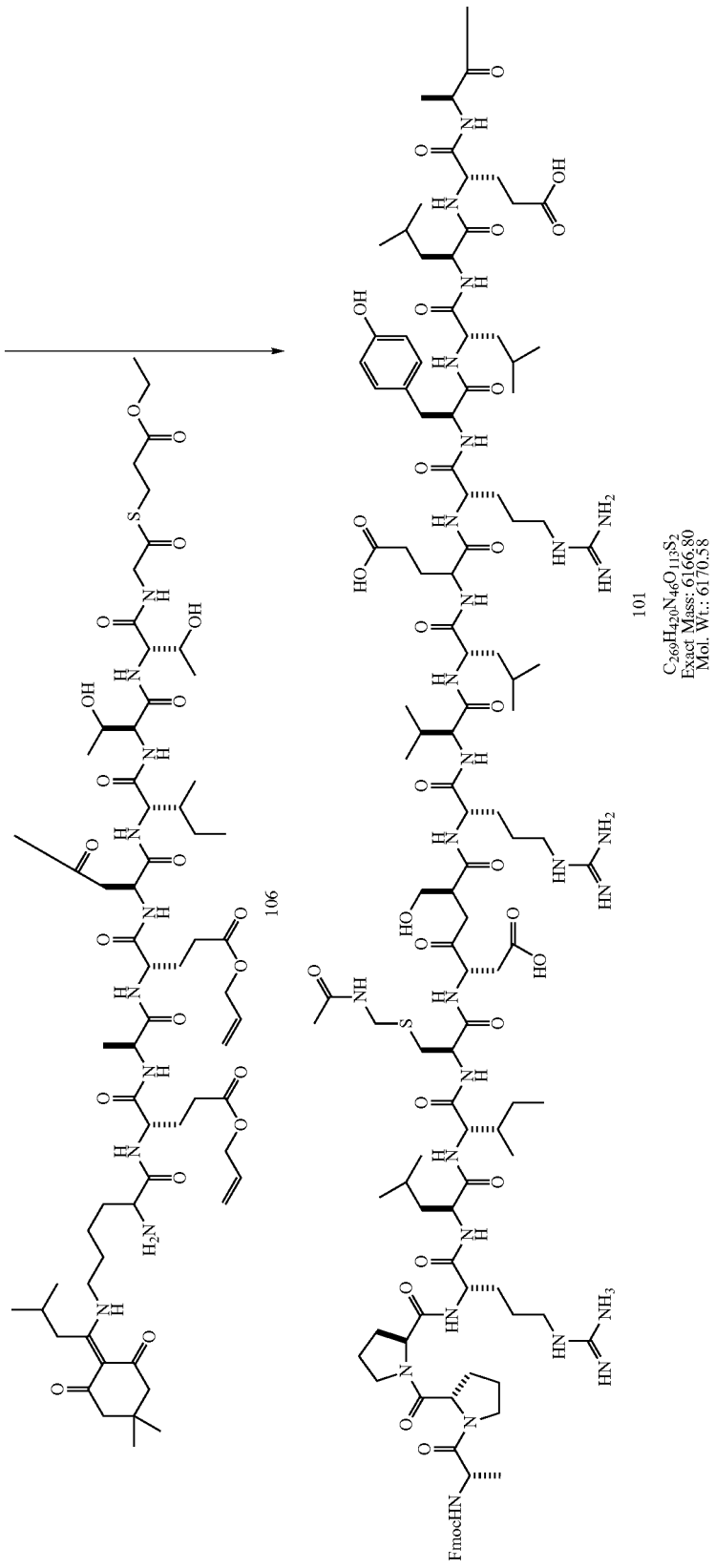

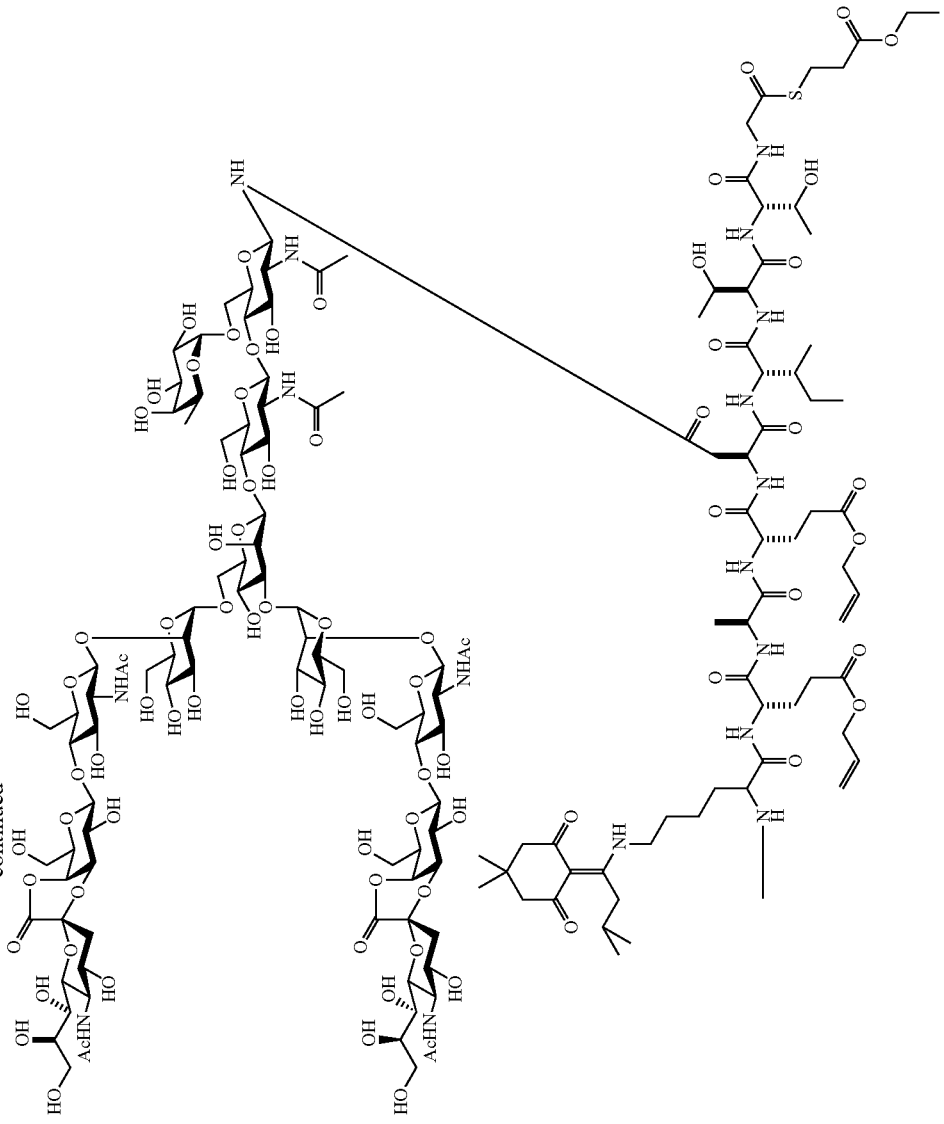
-continued

The HOOBt stock solution was prepared by dissolving HOOBt (15 mg, 0.092 mmol) in DMF (1.0 mL). Peptide 109 (2.5 mg, 0.95 μmol), glycopeptide 106 (0.35 mg, 0.095 μmol), TCEP.HCl (0.27 mg, 0.95 μmol), and 2,6-di-tbutyl-4-dimethylaminopyridine (0.6 mg, 2.4 μmol) were weighed into an oven-dried vial. An aliquot of the HOOBt stock solution (20 μL, 1.9 μmol) was added to the solids to give a yellow mixture. The reaction was stirred at rt for a total of 114 h, at which point it was quenched by addition of MeCN/$H_2O$ (700 μL, 1:1). The solution was loaded directly onto the RP-HPLC column and purified (C4 semi-prep column, 45%→55% MeCN/$H_2O$ over 30 min, 256 nm, 16 mL/min) to provide glycopeptide 101 as an of-white solid ($T_{rent}$=15.8 min). ESI-MS: Calcd. for $C_{269}H_{420}N_{46}O_{113}S_2$: 6166.80. Found: m/z 1543.36 $[M+4H]^{4+}$, 2057.57 $[M+3H]^{3+}$.

LC-MS for 101: C4 analytical column, 45%→65% MeCN/$H_2O$ over 30 min.

Example 5

Mature Homogeneous Erythropoietin Building Blocks by Chemical Synthesis The EPO 78-113 Glycopeptide Domain Presenting the Fully N-Linked Dodecasaccharide Herein, we describe the synthesis of the EPO 78-113 glycopeptide (110) possessing the N-linked dodecasaccharide at $Asn^{83}$.

Experimentals

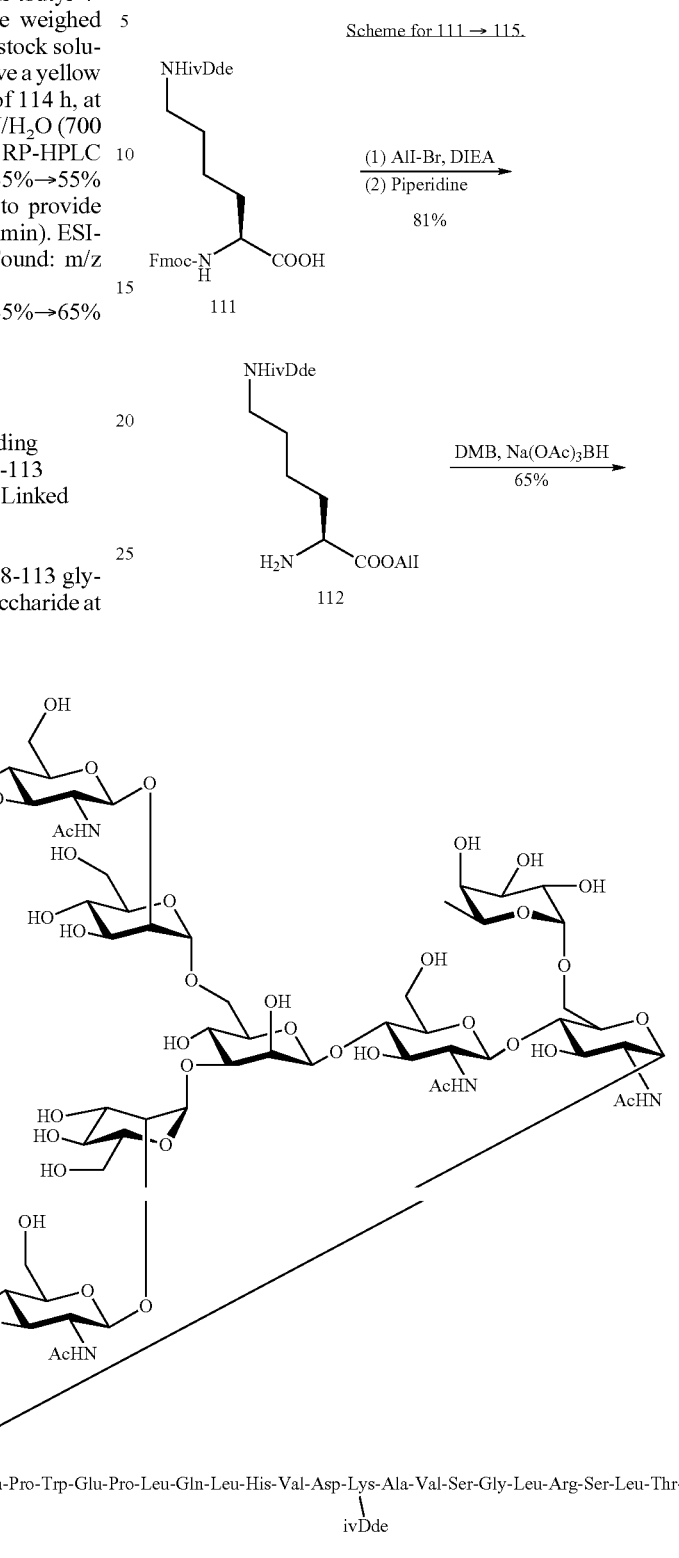

110

EPO 78-113 glycopeptide.

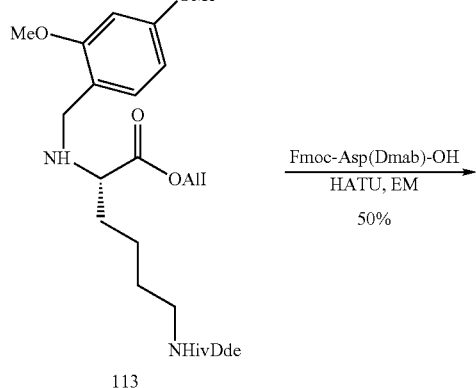

113

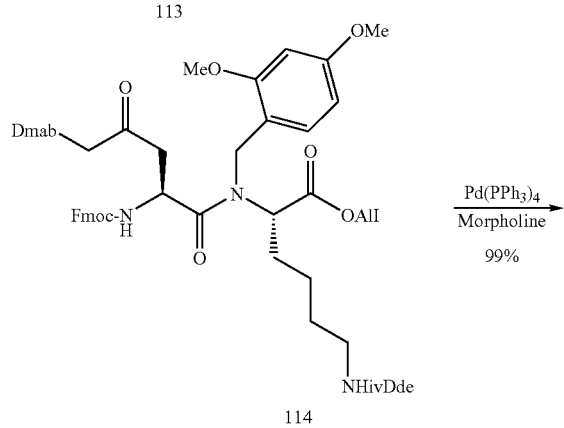

114

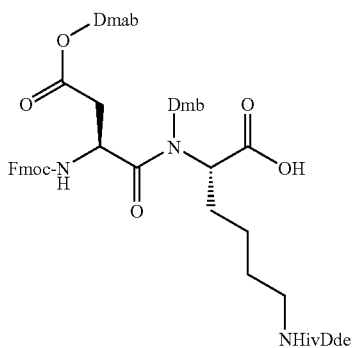

115

Fmoc-Asp(ODmab)-(Dmb)Lys(ivDde)-OH 115.

Fmoc-Lys(ivDde)-OAllyl was deprotected by piperidine in 81% yield. Reductive amination gave 113 in 65% yield. Amide coupling between 113 and Fmoc-Asp(Dmab)-OH afforded dipeptide 114. Removal of the allyl ester finished dipeptide 115. ESI-MS: calcd. $C_{67}H_{82}N_4O_{13}$, 1150.59. found m/z 1151.8 [M+H]$^+$, 1173.8 [M+Na]$^+$, 1189.8 [M+K]$^+$.

116

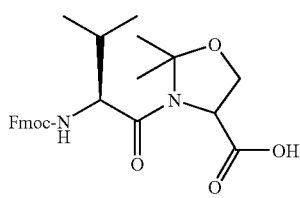 117

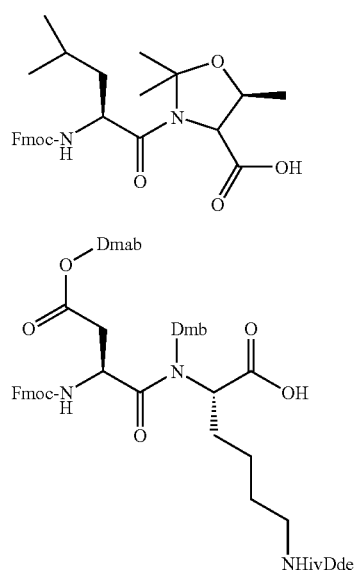

115

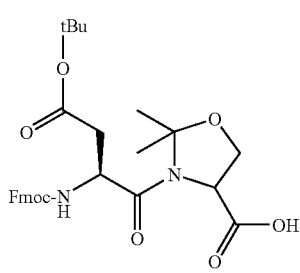 118

```
                  118    tBu  Trt        Boc Dmab       Trt      Trt    115          Trt
                   |      |    |          |   |          |        |      |        Gln Ala Leu   80
 81   Leu Val  Asp Ser   Ser Gln Pro Trp Glu Pro Leu Gln Leu His Val Asp Lys Ala Val Ser     100
                                                                                   117
101   Gly Leu Arg Ser  Leu Thr  Thr Leu Leu Arg Ala Leu Gly
                 |      |   |    |               |
                Pbf    tBu 116  tBu             Pbf
```

Dipeptide Fragments 115-118 and the Fully Protected EPO (78-113) Peptidic Fragment.

The synthesis of fully-protected EPO(78-113) was carried out under the standard Fmoc (9-fluorenylmethyloxycarbonyl) chemistry using NovaSyn® TGT resin, which was pre-loaded with Fmoc-Gly. The dipeptide derivatives 116, 117, 118 (Ser/Thr-derived oxazolidines), and the synthetic 2,4-dimethoxybenzyl dipeptides 115 were incorporated into the growing peptide chain in the same manner as normal amino acids activated by HATU. The synthesis produced >80% purity EPO(78-113) at 85% as determined by LC-MS after being cleaved from the resin by $CH_2Cl_2$:TFE:AcOH=8:1:1. ESI-MS: calcd. $C_{369}H_{509}N_{51}O_{68}S_2$, 6806.74. found m/z 2271.8 $[M+3H]^{3+}$.

To a solution of crude fully protected peptide 119 (37.4 mg, 5.48 μmol) in 1.2 ml MeOH was added benzylaldehyde solution (3.2 mg in 0.4 ml DMF). The solution was stirred at RT for 5 h, then 1.0 mg $NaCNBH_3$ in 0.2 ml MeOH was added. The reaction was stirred for 4 h. Solvent was removed. The product was precipitated by ether and used for next reaction without further purification. To a solution of 120 in 0.25 ml DMF was added DIEA (3 μl, 20 μmol), HATU (10 mg, 25 μmol) and 2-(ethyldithio)-phenol (3 mg, 15 μmol). The solution was stirred at RT for 2 h. The product was precipitated by water and freeze-dried. 5 mg 121 was treated with TFA:TIPSH:$H_2O$=95:2.5:2.5 1 ml at RT for 3 h. The solution was removed. The product 122 was precipitated by ether and purified by HPLC. Peptide 122 ESI-MS: calcd. $C_{252}H_{381}N_{53}O_{65}S_3$, 5285.73. found m/z 1763.74 $[M+3H]^{3+}$, 1323.36 $[M+4H]^{4+}$.

Fmoc-EPO(78-87)—OAr (123) with Dodecamer Sugar

Scheme for 119 → 122

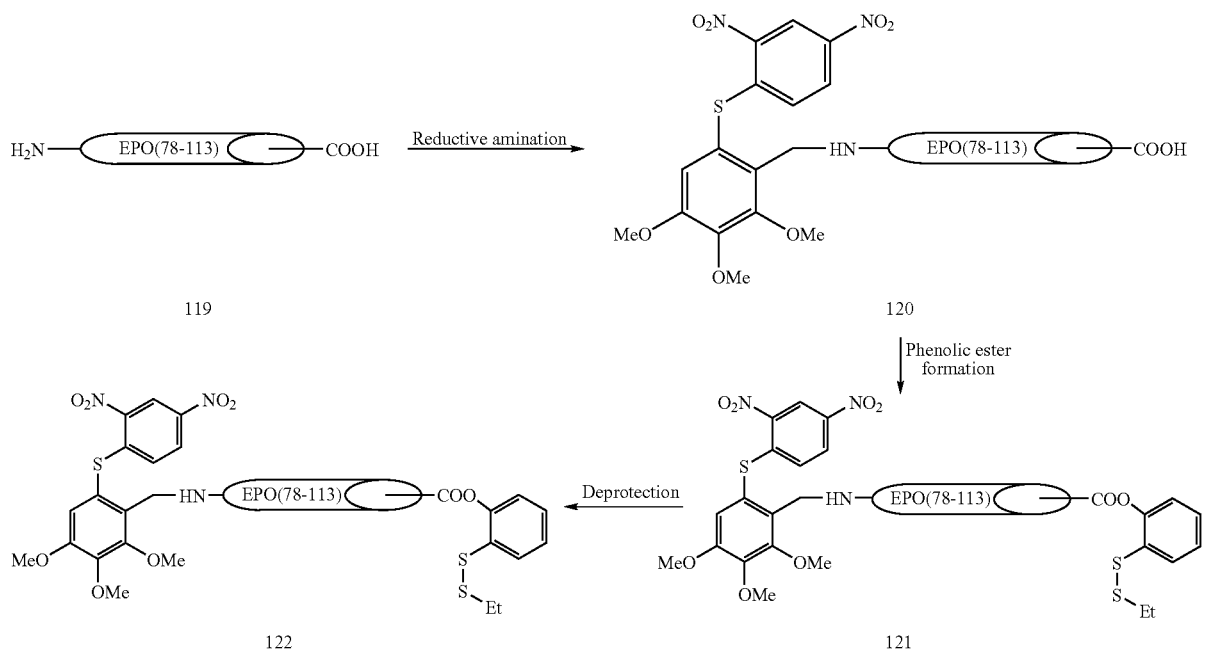

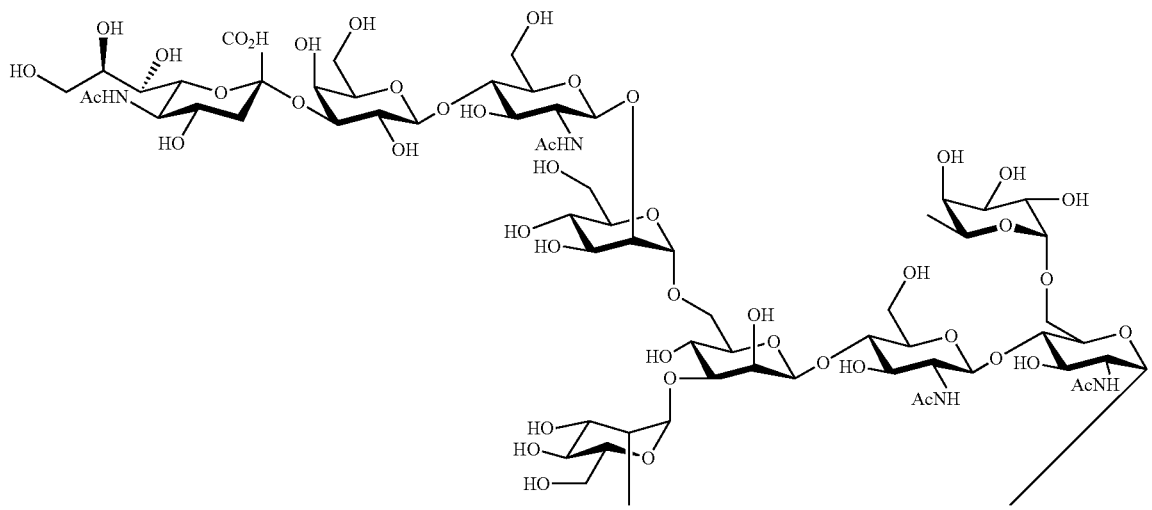

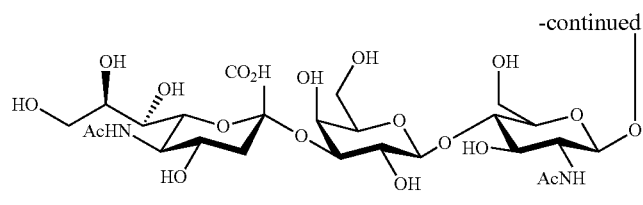

FmocGln-Ala-Leu-Leu-Val-Asn-Ser-Ser-Gln-ProO
123

The synthesis of fully-protected EPO(78-87) was carried out under the standard Fmoc (9-fluorenylmethyloxycarbonyl) chemistry using NovaSyn® TGT resin, which was preloaded with Fmoc-Pro. The dipeptide derivatives Fmoc-Asp(OtBu)-Ser($\psi^{Me,Me}$Pro)-OH were incorporated into the growing peptide chain in the same manner as normal amino acids activated by HATU. The fully protected peptide Fmoc-EPO(78-87)-OH was cleaved from the resin by $CH_2Cl_2$:TFE:AcOH=8:1:1. To a solution of crude fully protected peptide Fmoc-EPO(78-87)-OH (9 mg, 4.7 µmol) in 1 ml $CH_2Cl_2$ was added DCC (4.5 mg, 21 µmol), DMAP (0.24 mg, 1.9 µmol) and 2-(ethyldithio)-phenol (7.2 mg, 4 µmol). The solution was stirred at RT for 4 h. The product was precipitated by ether. The product was then deprotected by TFA:TIPSH:$H_2O$=95:2.5:2.5 and purified by HPLC. To a solution of peptide Fmoc-EPO(78-87)-OH (0.3 mg, 0.17 µmol) and dodecamer sugar 105 (0.4 mg, 0.17 µmol) in DMSO was added HATU (0.5 mg, 1.4 µmol) and DIEA (0.09 mg, 0.7 µmol). The solution was stirred at RT for 20 min. The product 123 was purified by HPLC. Glycopeptide Fmoc-EPO(78-87)-OAr 123, ESI-MS: calcd. $C_{158}H_{239}N_{19}O_{82}S_2$, 3778.46. found m/z 1890.42 $[M+2H]^{2+}$.

The synthesis of H-EPO(88-13)-OH was carried out under the standard Fmoc (9-fluorenylmethyloxycarbonyl) chemistry using NovaSyn® TGT resin, which was preloaded with Fmoc-Gly. The dipeptide derivatives Fmoc-Val-Ser($\psi^{Me,Me}$Pro)-OH and Fmoc-Leu-Thr($\psi^{Me,Me}$Pro)-OH were incorporated into the growing peptide chain in the same manner as normal amino acids activated by HATU. The H-EPO(78-87)-OH was cleaved from the resin by TFA:TIPSH:$H_2O$=95:2.5:2.5 and purified by HPLC. Peptide H-EPO(88-113)-OH, ESI-MS: calcd. $C_{143}H_{235}N_{37}O_{38}$, 3078.76. found m/z 1541.04 $[M+2H]^{2+}$; 1027.92 $[M+3H]^{3+}$.

To a solution of glycopeptide Fmoc-EPO(78-87)-OAr 123 (0.3 mg, 0.08 µmol) and H-EPO(88-13)-OH (0.3 mg, 0.1 µmol) in DMSO was added AgCl (0.1 mg, 0.8 µmol), HATU (0.7 mg, 5 µmol) and DIEA (0.36 mg, 3 µmol). The solution was stirred at RT for 24 h. The product was purified by HPLC. Glycopeptide Fmoc-EPO(78-113)-OH 110, ESI-MS: calcd. $C_{293}H_{464}N_{56}O_{119}$, 6671.2. found m/z 2224.70 $[M+3H]^{3+}$; 1669.34 $[M+4H]^{4+}$.

Example 6

Mature Homogeneous Erythropoietin Building Blocks by Chemical Synthesis: The EPO 88-166 Glycopeptide Domain Presenting its O-Linked Glycophorin Herein, we describe the synthesis of the EPO 88-166 glycopeptide (124) possessing the O-linked dodecasaccharide at $Ser^{126}$.

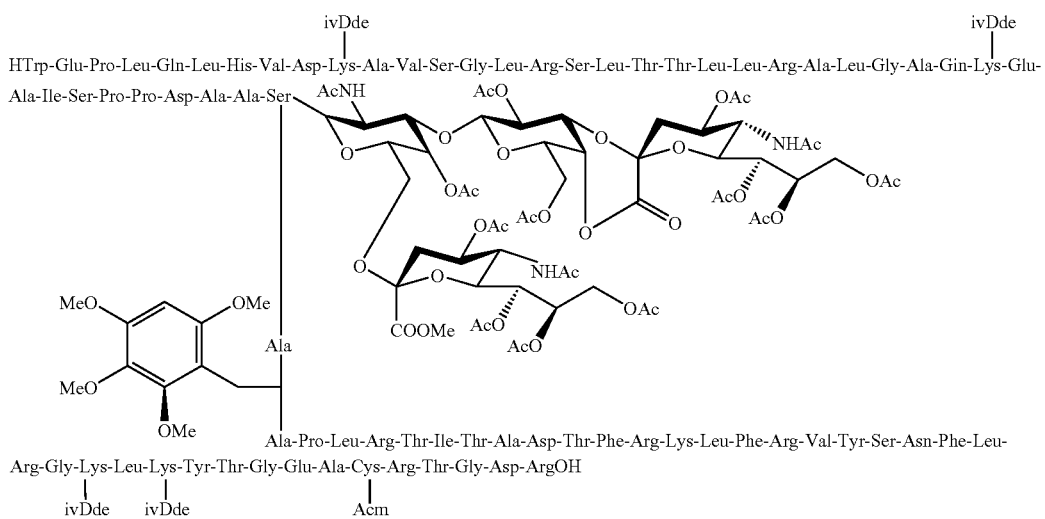

EPO 88-166 glycopeptide (124).

To a solution of glycopeptide H-EPO(14-166)-OH (0.5 mg, 0.06 μmol) and Fmoc-EPO(88-113)-OH (0.5 mg, 0.14 μmol) in DMSO was added AgCl (0.1 mg, 0.8 μmol), HATU (0.7 mg, 5 μmol) and DIEA (0.36 mg, 3 μmol). The solution was stirred at RT for 24 h. The product was purified by HPLC. Glycopeptide Fmoc-EPO(88-166)-OH, ESI-MS: calcd. $C_{543}H_{834}N_{118}O_{163}S_2$, 11680. found m/z 1670.31 $[M+7H]^{7+}$; 1462.29 $[M+8H]^{8+}$.

To a solution of glycopeptide Fmoc-EPO(88-166)-OH (0.5 mg, 0.06 μmol) in DMSO was added 20% piperidine 10 μl. The solution was stirred at RT for 1 h. The product was purified by HPLC. Glycopeptide H-EPO(88-166)-OH 124, ESI-MS: calcd. $C_{528}H_{824}N_{118}O_{161}S_2$, 11457.94. found m/z 1638.79 $[M+7H]^{7+}$; 1434.30 $[M+8H]^{8+}$.

Example 7

Chemical Synthesis of Homogenous Erythropoietin Fragment by Phenolic Ester-Directed Amide Coupling: The EPO 102-166 Glycopeptide Domain, Presenting O-Linked Glycophorin The $2^{nd}$-generation synthesis of the EPO 102-166 glycopeptide, presenting the glycophorin glycan at $Ser^{126}$ is described in this Example. The key chemical ligation of intermediates 133 and 134 to generate the desired product 135 is enabled by our phenolic ester-directed amide coupling mediated by AgCl in the presence of HOOBt, DIEA in DMSO.

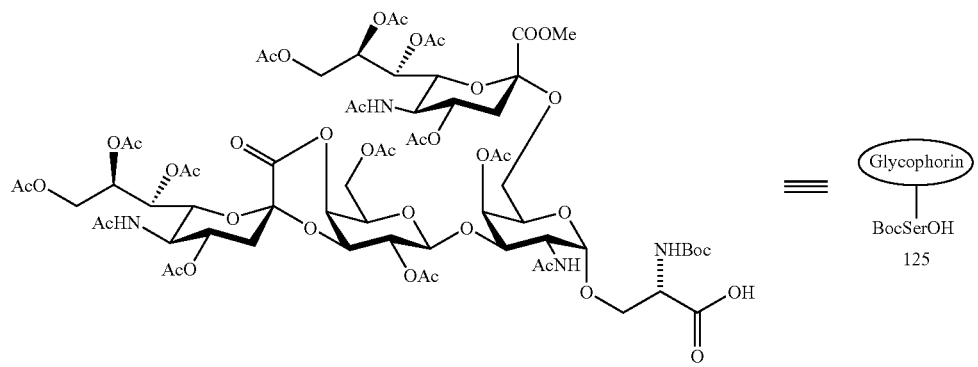

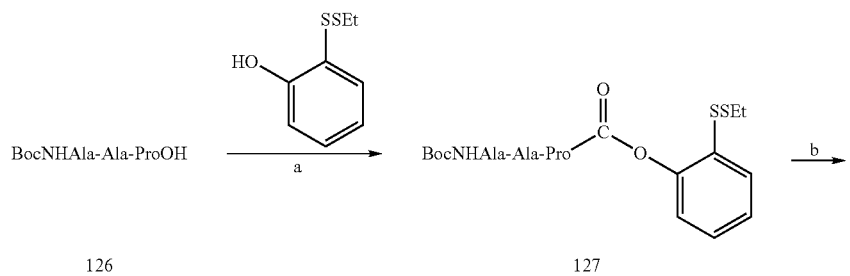

126    127

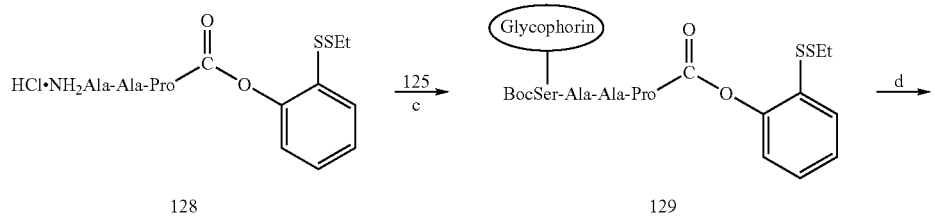

128    129

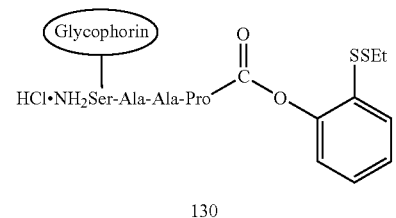

130

Synthesis of EPO Fragment 126-129:
 a) EDCI, HOBt, DIEA, DMF, RT, 12 h, 88%; b) 4M HCl in Dioxane, RT, 2 h, 95%; c) EDC, HOOBt, DMF/DCM, RT, 6 h, 81%; d) 4M HCl in Dioxane, RT, 2 h, 93%.
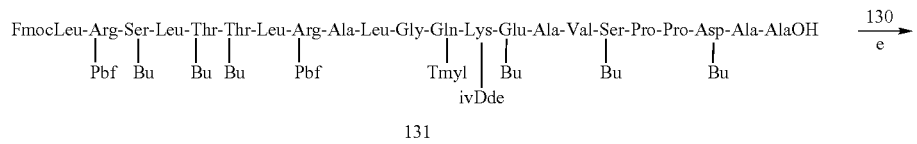
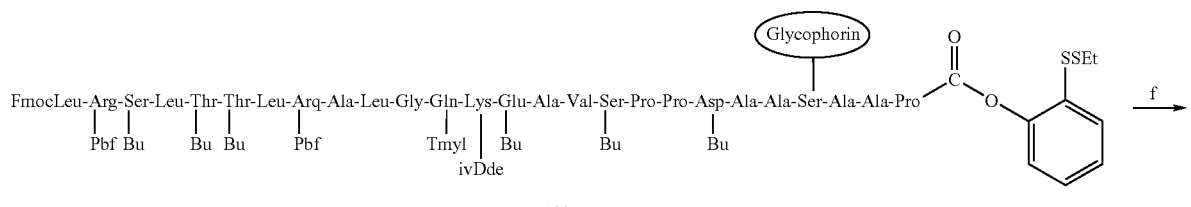
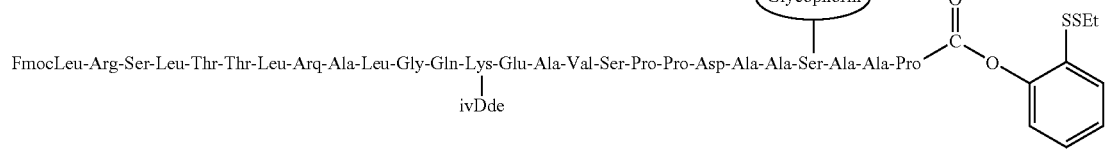
Synthesis of EPO Fragment 102-129:
 e) EDC, HOOBt, DMF/DCM, RT, 6 h; f) TFA/PhOH/TIPS/H₂O, RT, 2 h, 55% over 2 steps.
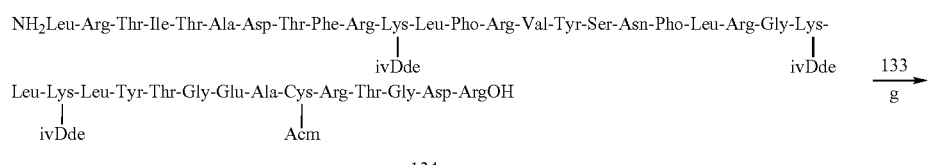
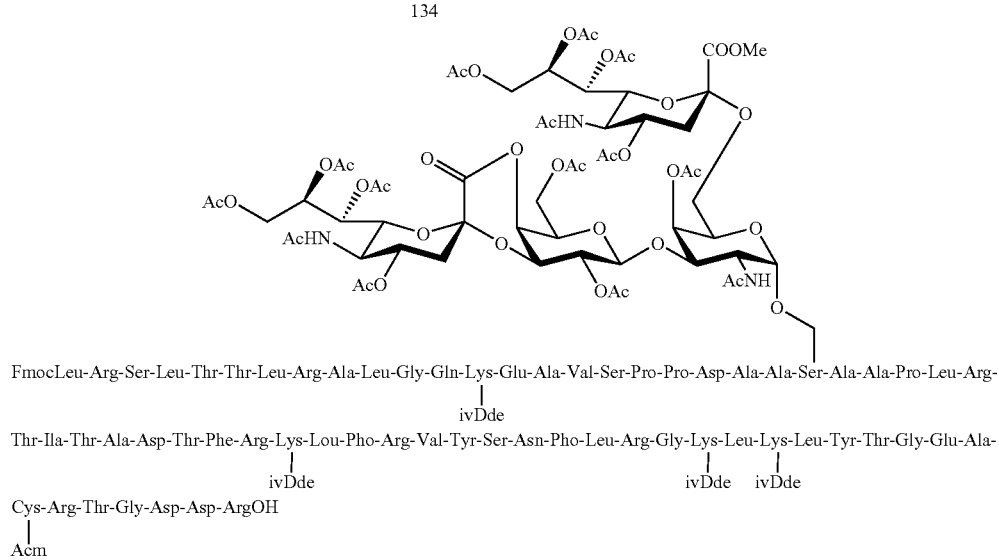

Synthesis of EPO Fragment 102-166:
  g) AgCl, HOOBt, DIEA, DMSO, RT, 3 d, 70%.

Experimentals

To a solution of compound 133 (10.0 mg, 2.1 μmol), compound 134 (21.0 mg, 4.2 μmol), and HOOBt (6.8 mg, 42 μmol) in anhydrous DMSO (1.0 mL) was added AgCl (1.5 mg, 10.5 μmol) and DIEA (5.5 μl, 32 μmol) at rt. The resulting reaction mixture was stirred in dark at rt for 3 days before it was diluted with 3 mL of $CH_3CN/H_2O$ (1/1). The solution was filtered and subjected to reverse phase HPLC purification. (C4 column, Rt: 19-20 min, 50-85% $CH_3CN$ in $H_2O$ over 30 min) to give the final product 135 (14 mg): MS (ESI): $C_{446}H_{691}N_{99}O_{138}S$ Calc. 9673.98, Observed 1935.3 (M+5H$^+$), 1613.7 (M+6H$^+$), 1383.2 (M+7H$^+$), 1210.4 (M+8H$^+$).

Example 8

Chemical Synthesis of a Complex Glycopeptide Building Block Related to Erythropoietin Fragment by Phenolic Ester-Directed Amide Coupling: The 29-Mer Glycopeptide, Containing One 12mer N-Linked Glycan and One O-Linked Glycophorin The chemical synthesis of the complex bi-functional glycopeptide 142 with a C-terminal alkyl thioester is described in this Example. The key chemical ligation of glycopeptides 137 and 141 to generate the desired product 142 is enabled by our phenolic ester-directed amide coupling mediated by TCEP-HCl in the presence of HOOBt, DIEA in DMSO.

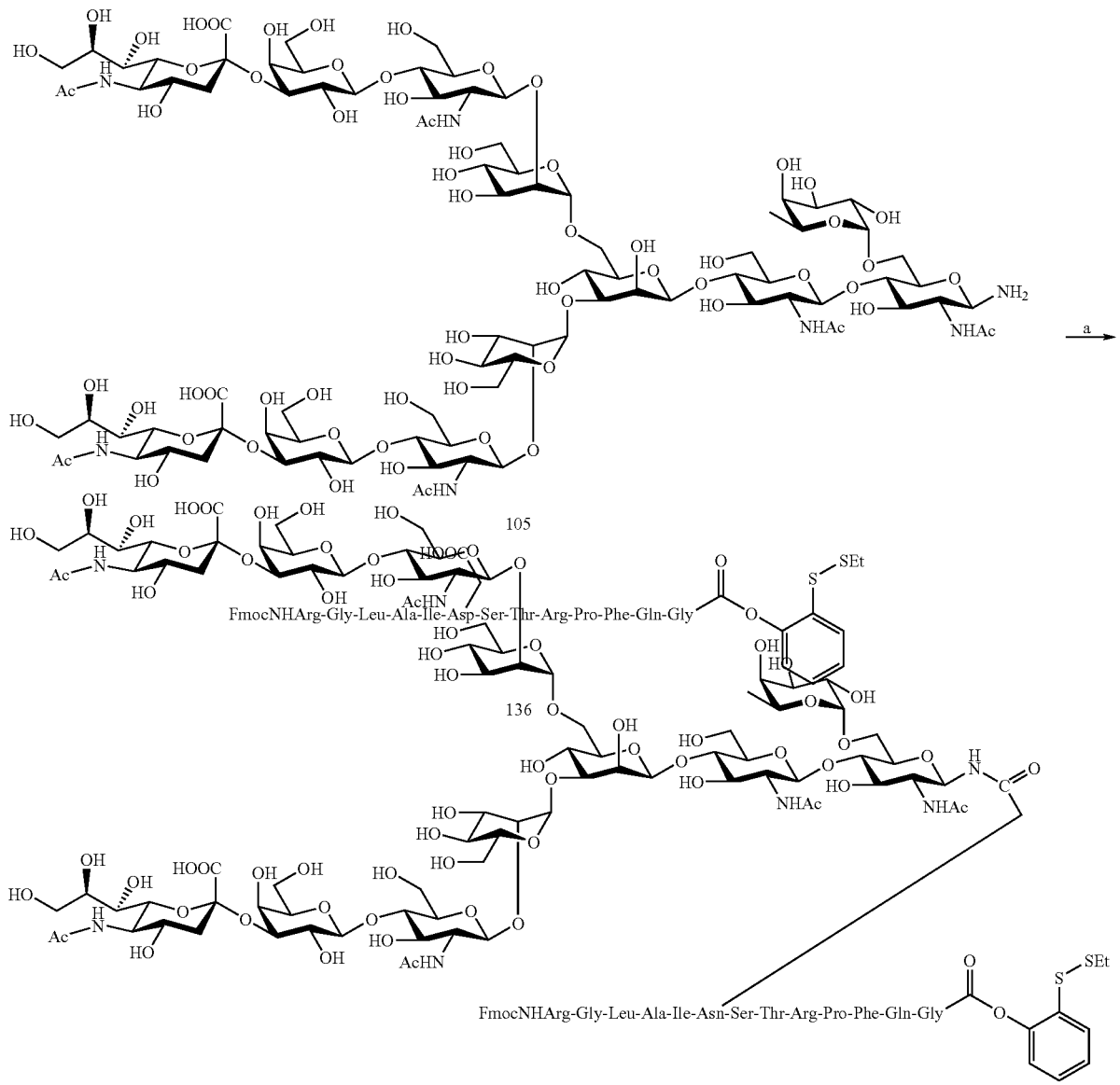

Synthesis of Compound 137:
  a) 105, 136, HATU, DIEA, DMSO, 2 h, ~35%.
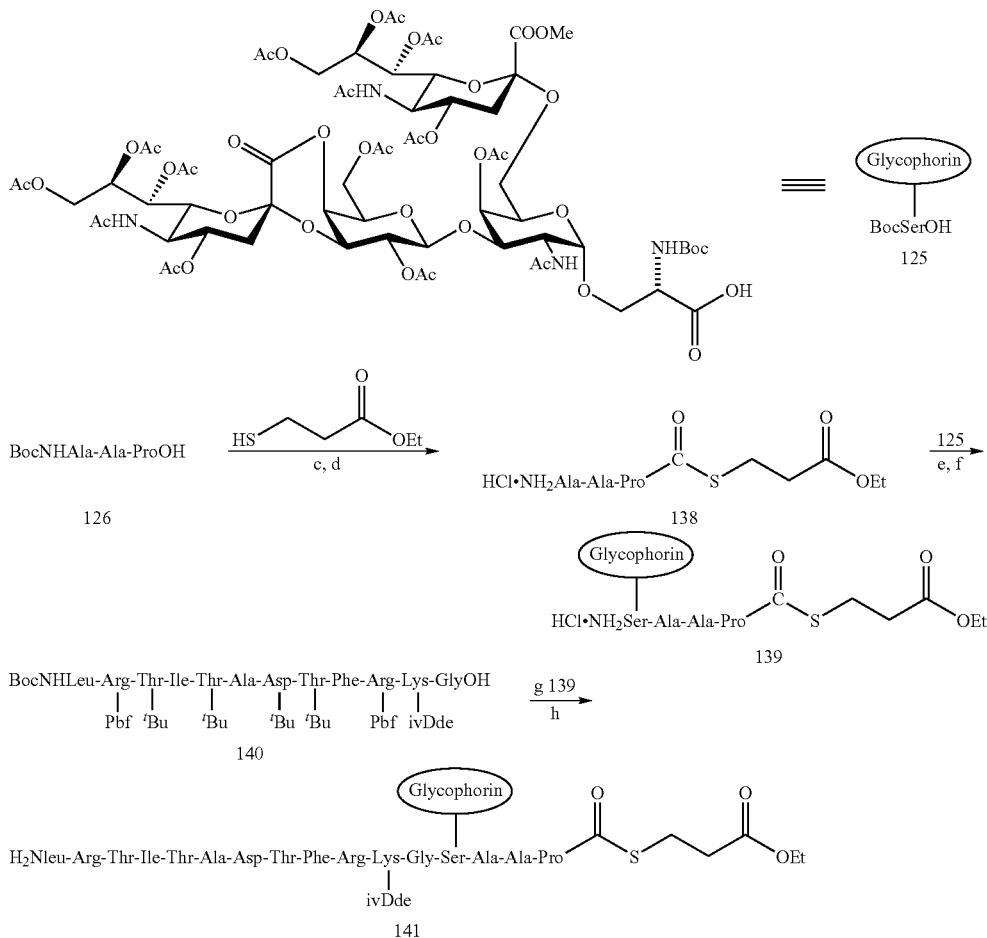
Synthesis of Compound 141:
  c) EDCI, HOBt, DIEA, DMF, RT, 12 h, 84%; d) 4M HCl in Dioxane, RT, 2 h, 95%; e) EDC, HOOBt, DMF/DCM, RT, 6 h, 76%; f) 4M HCl in Dioxane, RT, 2 h, 92%; g) EDC, HOOBt, DMF/DCM, RT, 8 h; h) TFA/PhOH/TIPS/H$_2$O/RT, 2 h, ~50% over 2 steps.

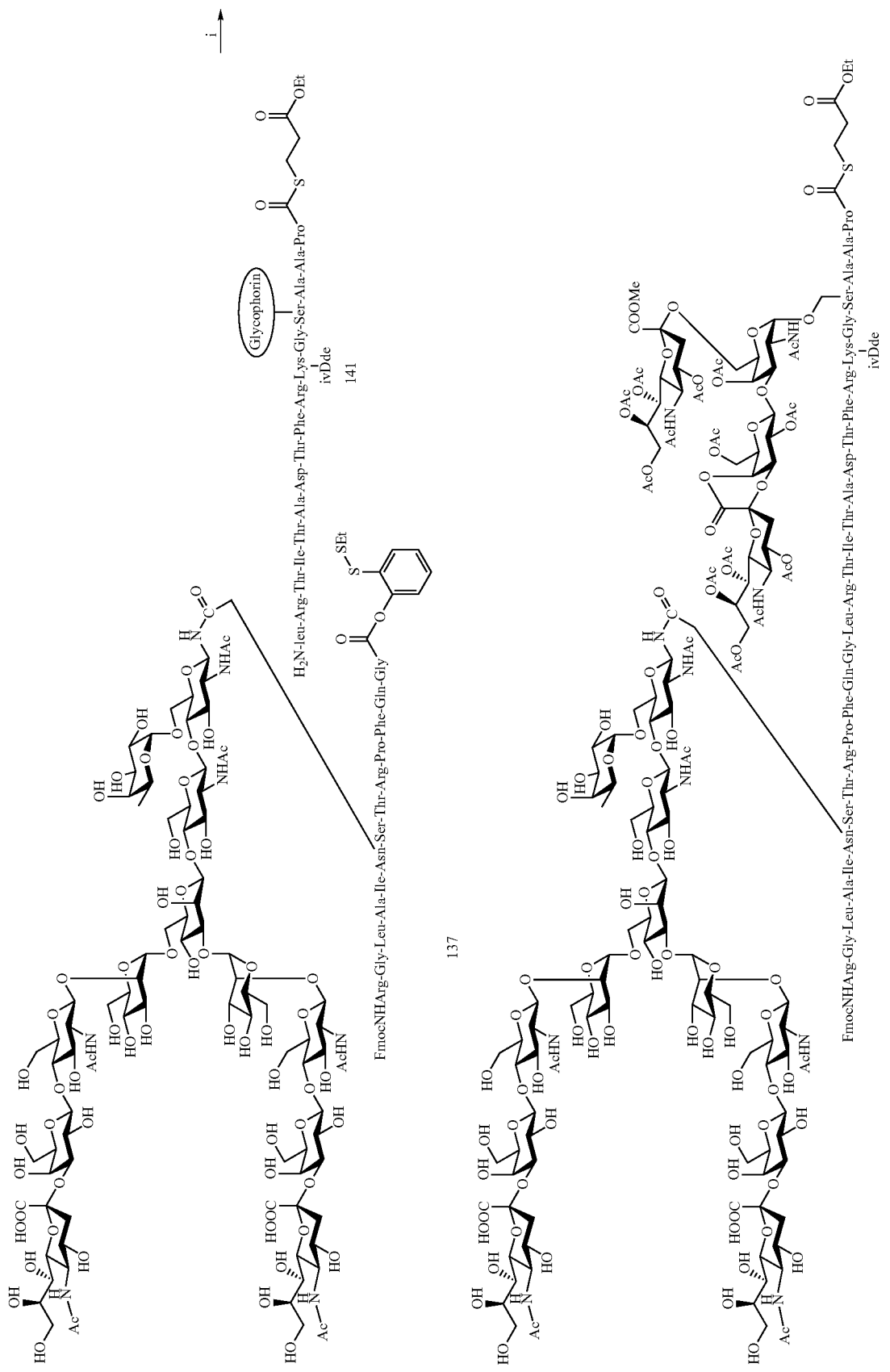

Synthesis of Complex Glycopeptide 142:
i) 137, 141, TCEP.HCl, HOOBt, DIEA, DMSO, RT, 10 h, 45%

Experimentals

To a solution of compound 141 (2.5 mg, 0.72 µmol), compound 137 (1.5 mg, 0.36 µmol), and HOOBt (1.2 mg, 7.2 µmol) in anhydrous DMSO (0.2 mL) was added TCEP.HCl (0.3 mg, 1.1 µmol) at rt. The resulting reaction mixture was stirred for 15 min. DIEA (1.3 µl, 7.2 µmol) was then added and the reaction mixture was stirred at rt for 10 hours before it was diluted with 2 mL of $CH_3CN/H_2O$ (1/1). The solution was filtered and subjected to reverse phase HPLC purification. (C18 column, Rt: 26 min, 35-55% $CH_3CN$ in $H_2O$ over 30 min) to give the final product 142 (1.8 mg): MS (ESI): $C_{317}H_{485}N_{53}O_{146}S$ Calc. 7402.19, Observed 1851.3 ($M+4H^+$), 1481.8 ($M+5H^+$), 1234.9 ($M+6H^+$).

Example 9

Chemical Synthesis of Cyclic Peptide and Glycopeptide Building Block by Phenolic Ester-Directed Amide Coupling The unique feature of the slow activation of phenolic ester by AgCl was exploited for the synthesis of cyclic peptides. Precursors to cyclic peptides can be easily prepared using standard SPPS, ester formation, TFA deprotection, and single HPLC purification. Excellent cyclization yield were achieved with cyclicpeptide 144 and cyclicglycopeptide 146 upon exposure to standard condition without dramatic dilution.

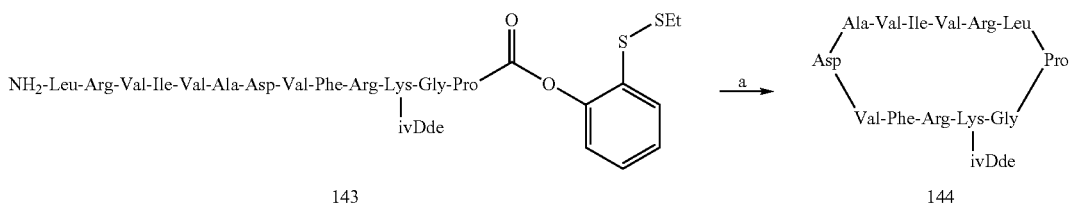

143 → 144

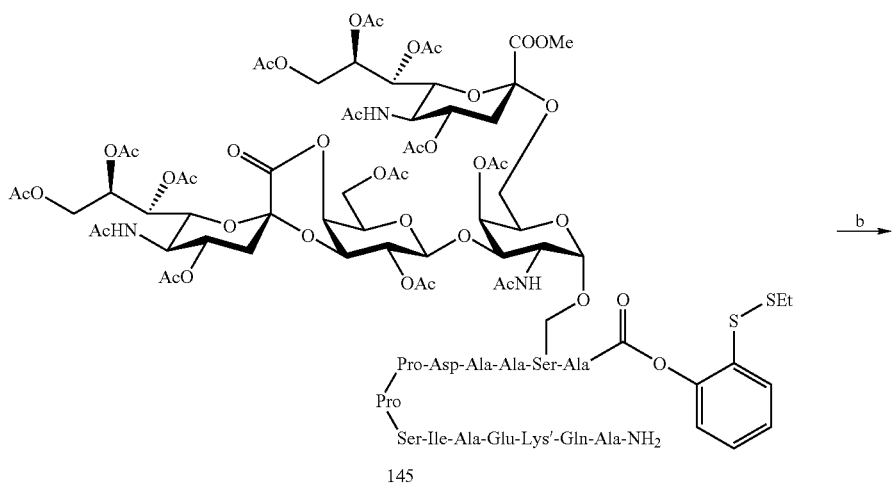

145

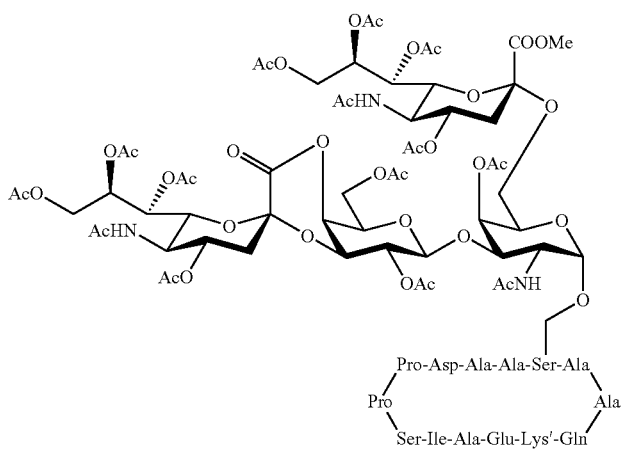

146

Synthesis of Cyclic Peptide and Glycopeptide:

a) AgCl, HOOBt, DIEA, DMSO, RT, 2 d, 68%; b) AgCl, HOOBt, DIEA, DMSO, RT, 18 h, 70%.

Experimentals

To a solution of compound 145 (6.2 mg, 2.0 μmol) and HOOBt (6.5 mg, 40 μmol) in anhydrous DMSO (0.5 mL) was added AgCl (1.4 mg, 10.0 μmol) and DIEA (5.3 μl, 30 μmol) at rt. The resulting reaction mixture was stirred in dark at rt for 18 hours before it was diluted with 2 mL of CH$_3$CN/H$_2$O (1/1). The solution was filtered and subjected to reverse phase HPLC purification. (C18 column, Rt: 16 min, 25-50% CH$_3$CN in H$_2$O over 30 min) to give the final product 146 (4.3 mg): MS (ESI): C$_{129}$H$_{189}$N$_{19}$O$_{59}$ Calc. 2948.24, Observed 1475.7 (M+2H$^+$).

Example 10

Chemical Synthesis of Long Peptide by Phenolic Ester Directed Amide Coupling in Iterative Fashion The phenolic ester directed amide coupling method can be excersided in iterative fashion to generate large peptides. An 89-mer peptide 151 was successfully prepared iteratively in ~50% yield using Fmoc protection strategy. Because of the size of the substrates, the second coupling reaction takes up to 3 days for completion, but the yield is not comprimised.

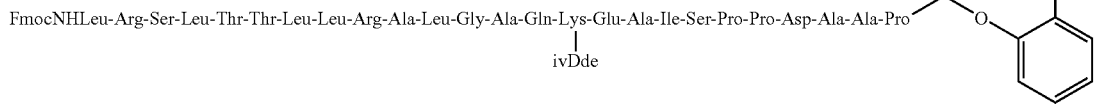
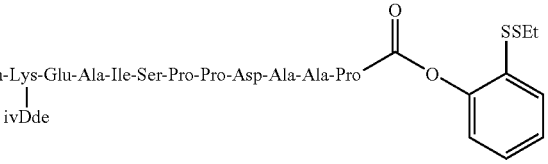

147

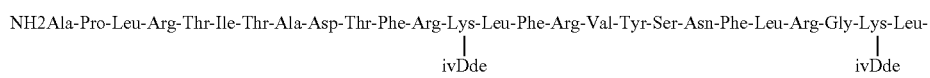
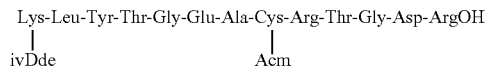

148

↓ a

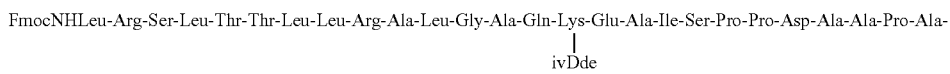
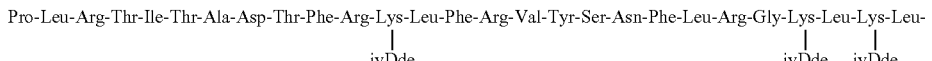
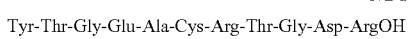

149

↓ b

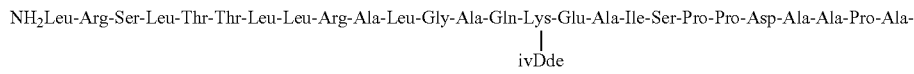
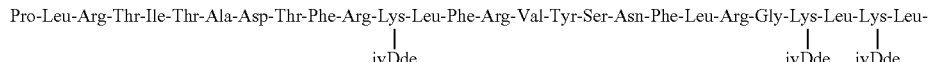
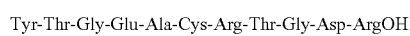

150

↓ c + 147

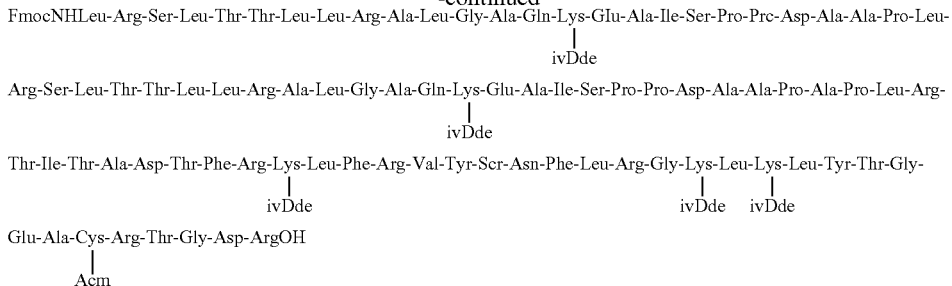

151

Iterative Synthesis of Large Peptide 151:

a) AgCl, HOOBt, DIEA, DMSO, RT, 2 d, 75%; b) 5% piperidine in DMF, RT, 92%; c) 147, AgCl, HOOBt, DIEA, DMSO, RT, 3d, 68%.

Experimentals

To a solution of compound 147 (6.2 mg, 2.0 μmol), compound 148 (7.3 mg, 1.4 μmol) and HOOBt (6.5 mg, 40 μmol) in anhydrous DMSO (1.0 mL) was added AgCl (1.4 mg, 10.0 μmol) and DIEA (5.3 μl, 30 μmol) at rt. The resulting reaction mixture was stirred in dark at rt for 2 days before it was diluted with 3 mL of $CH_3CN/H_2O$ (1/1). The solution was filtered and subjected to reverse phase HPLC purification. (C4 column, Rt: 24 min, 55-80% $CH_3CN$ in $H_2O$ over 30 min) to give the final product 149 (11.5 mg): MS (ESI): $C_{386}H_{609}N_{95}O_{100}S$ Calc. 8207.52, Observed 1642.3 $(M+5H^+)$, 1368.9 $(M+6H^+)$, 1173.1 $(M+7H^+)$, 1027.1 $(M+8H^+)$, 912.9 $(M+9H^+)$.

To a solution of compound 149 (8.2 mg, 1.0 μmol) in anhydrous DMF (0.5 mL) was added piperidine (25 μl) at rt. The resulting reaction mixture was stirred at rt for 2 hours and solvents removed under vacuum. The residue was then dissolved in 3 mL of $CH_3CN/H_2O$ (1/1). The solution was filtered and subjected to reverse phase HPLC purification. (C4 column, Rt: 14 min, 55-80% $CH_3CN$ in $H_2O$ over 30 min) to give the desired product 150 (7.3 mg): MS (ESI): $C_{371}H_{599}N_{95}O_{98}S$ Calc. 7985.45, Observed 1997.6 $(M+4H^+)$, 1599.3 $(M+5H^+)$, 1331.8 $(M+6H^+)$, 1141.5 $(M+7H^+)$, 999.2 $(M+8H^+)$.

To a solution of compound 150 (5.6 mg, 0.7 μmol), compound 147 (7.3 mg, 1.4 μmol) and HOOBt (4.5 mg, 28 μmol) in anhydrous DMSO (0.5 mL) was added AgCl (1.0 mg, 7.0 μmol) and DIEA (3.7 μl, 21 μmol) at rt. The resulting reaction mixture was stirred in dark at rt for 3 days before it was diluted with 3 mL of $CH_3CN/H_2O$ (1/1). The solution was filtered and subjected to reverse phase HPLC purification. (C4 column, Rt: 26-28 min, 65-80% $CH_3CN$ in $H_2O$ over 30 min) to give the final product 151 (5.2 mg): MS (ESI): $C_{512}H_{820}N_{128}O_{136}S$ Calc. 10970.09, Observed 2195.5 $(M+5H^+)$, 1829.5 $(M+6H^+)$, 1567.9 $(M+7H^+)$, 1372.0 $(M+8H^+)$.

---

What is claimed is:

1. A composition of a homogenously glycosylated erythropoietin or fragment thereof, comprising:

a polypeptide whose amino acid sequence includes a sequence that:

a) is identical to that of SEQ ID NO:1, or b) contains 1, 2, 3, 4, 5, 6, 7, 8, 9, or 10 amino acid deletions, substitutions, additions or combinations thereof relative to such SEQ ID NO: 1, and stimulates erythrocyte production; or c) is a fragment of a) or b), wherein the fragment has an amino acid sequence corresponding to amino acid residues 1-28, 29-77, 78-113, or 114-166 of SEQ ID NO: 1;

the polypeptide having at least one amino acid residue site glycosylated;

wherein each glycosylated polypeptide in the composition has the same glycosylation pattern in that:

it is glycosylated on at least one amino acid residue site;

it is glycosylated at the same at least one site;

it is glycosylated at a site selected from the group consisting of Asn$^{24}$, Asn$^{38}$, Asn$^{83}$, Ser$^{126}$ in SEQ ID NO: 1, and combinations thereof; and for a given glycosylation site, it has the same glycan.

2. The composition of claim 1, wherein the polypeptide's amino acid sequence is SEQ ID NO: 1, or is SEQ ID NO: 1 having 1-10 amino acid substitutions, additions, and/or deletions.

3. The composition of claim 1, wherein the fragment has an amino acid sequence as follows: SEQ ID NO: 3, SEQ ID NO: 4, SEQ ID NO: 5, or SEQ ID NO: 6.

4. The composition of claim 1, wherein the structure of the homogenously glycosylated erythropoietin is of formula:

(SEQ ID NO: 2)

Ala-Pro-Pro-Arg-Leu-Ile-Cys-Asp-Ser-Arg-Val-Leu-Glu-Arg-Tyr-Leu-Leu-Glu-Ala-Lys-

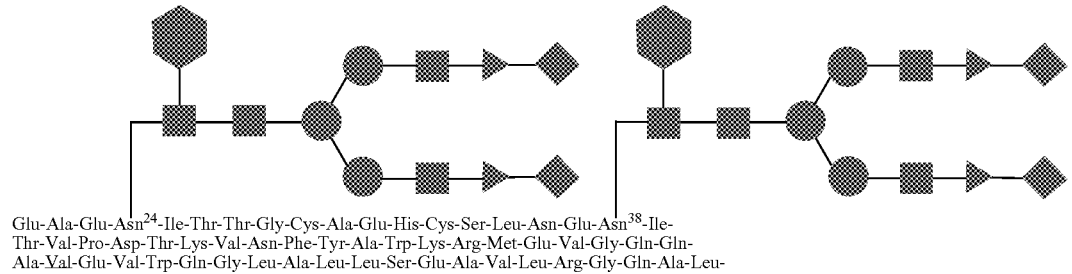

Glu-Ala-Glu-Asn$^{24}$-Ile-Thr-Thr-Gly-Cys-Ala-Glu-His-Cys-Ser-Leu-Asn-Glu-Asn$^{38}$-Ile-
Thr-Val-Pro-Asp-Thr-Lys-Val-Asn-Phe-Tyr-Ala-Trp-Lys-Arg-Met-Glu-Val-Gly-Gln-Gln-
Ala-Val-Glu-Val-Trp-Gln-Gly-Leu-Ala-Leu-Leu-Ser-Glu-Ala-Val-Leu-Arg-Gly-Gln-Ala-Leu-

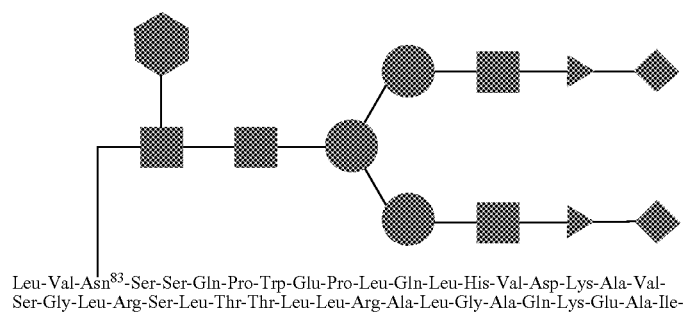

Leu-Val-Asn$^{83}$-Ser-Ser-Gln-Pro-Trp-Glu-Pro-Leu-Gln-Leu-His-Val-Asp-Lys-Ala-Val-
Ser-Gly-Leu-Arg-Ser-Leu-Thr-Thr-Leu-Leu-Arg-Ala-Leu-Gly-Ala-Gln-Lys-Glu-Ala-Ile-

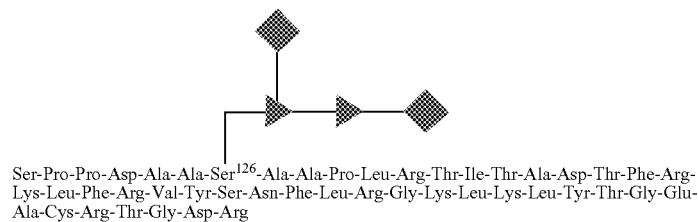

Ser-Pro-Pro-Asp-Ala-Ala-Ser$^{126}$-Ala-Ala-Pro-Leu-Arg-Thr-Ile-Thr-Ala-Asp-Thr-Phe-Arg-
Lys-Leu-Phe-Arg-Val-Tyr-Ser-Asn-Phe-Leu-Arg-Gly-Lys-Leu-Lys-Leu-Tyr-Thr-Gly-Glu-
Ala-Cys-Arg-Thr-Gly-Asp-Arg

◆ Sialic acid

▷ Galactose  ⬡ Fucose

● Mannose  ▨ Glucosamine.

5. The composition of claim 1, wherein the structure of the fragment of erythropoietin is as follows:
(SEQ ID NO: 7)
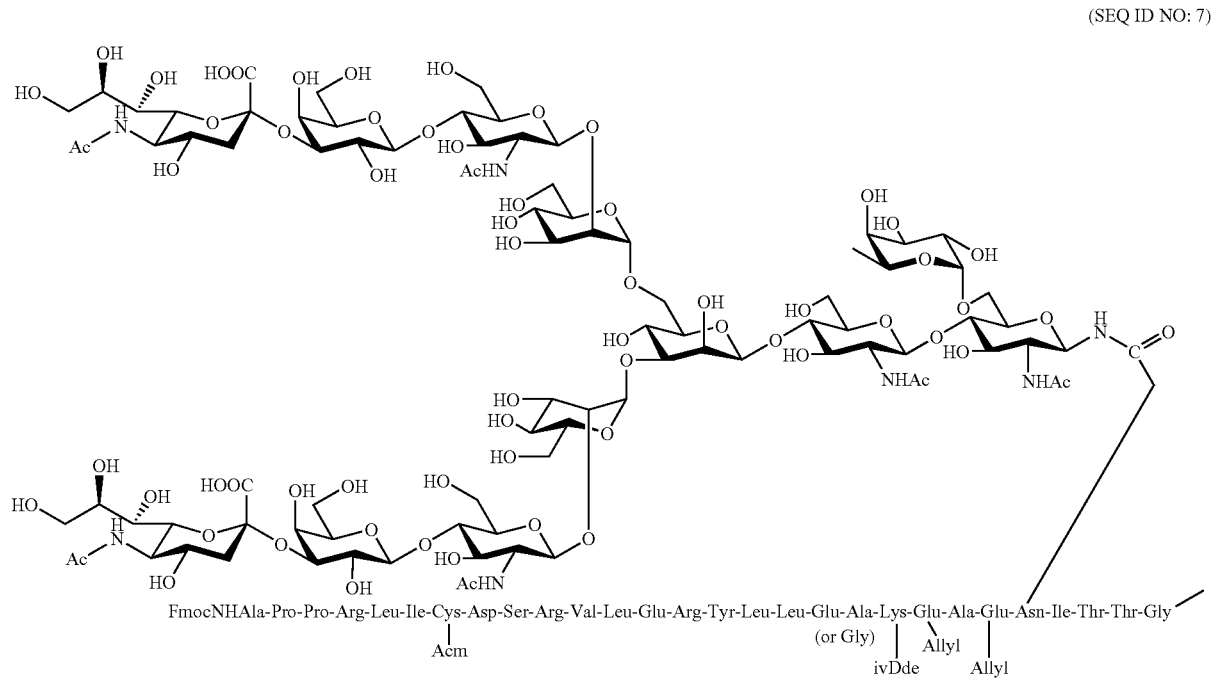
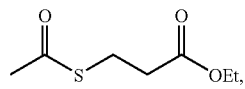
(SEQ ID NO: 8)
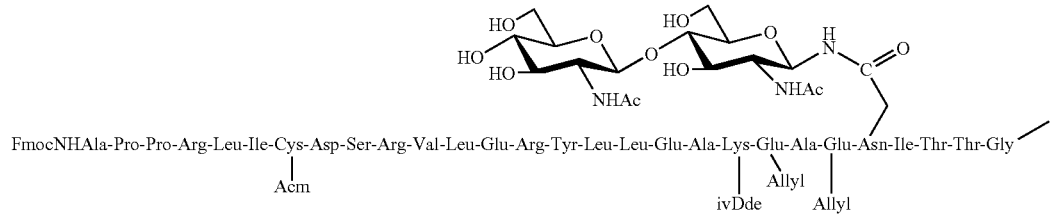
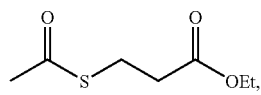

(SEQ ID NO: 9)
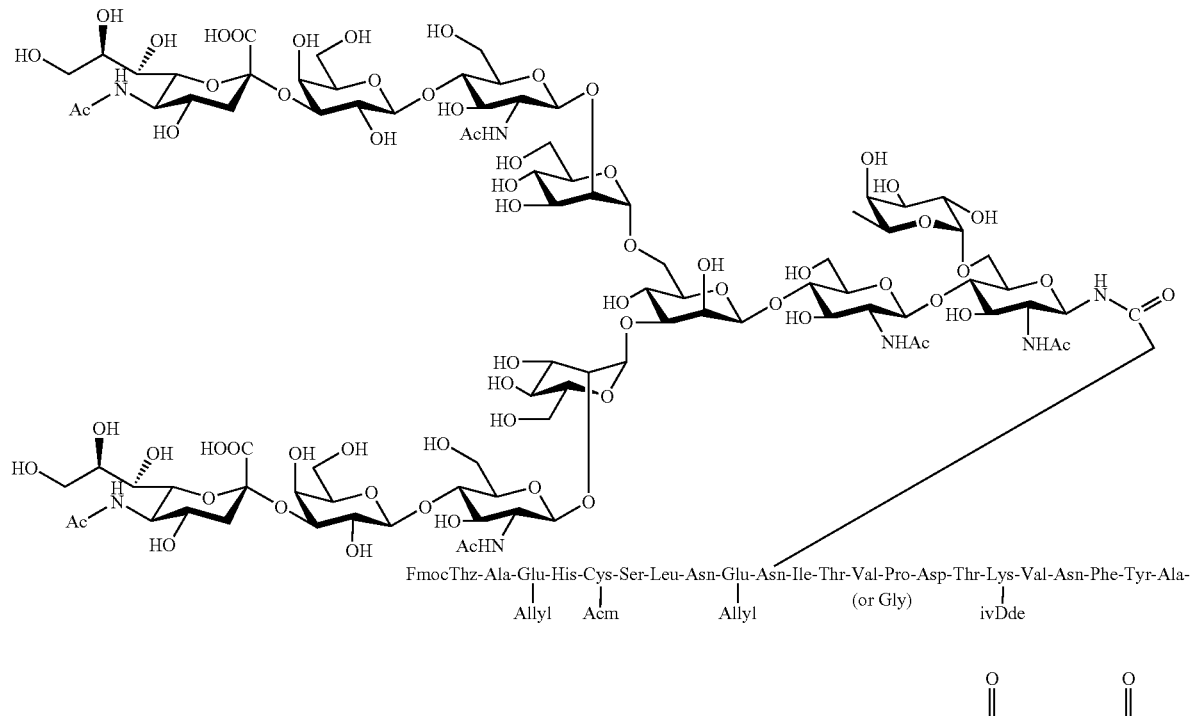
(SEQ ID NO: 10)
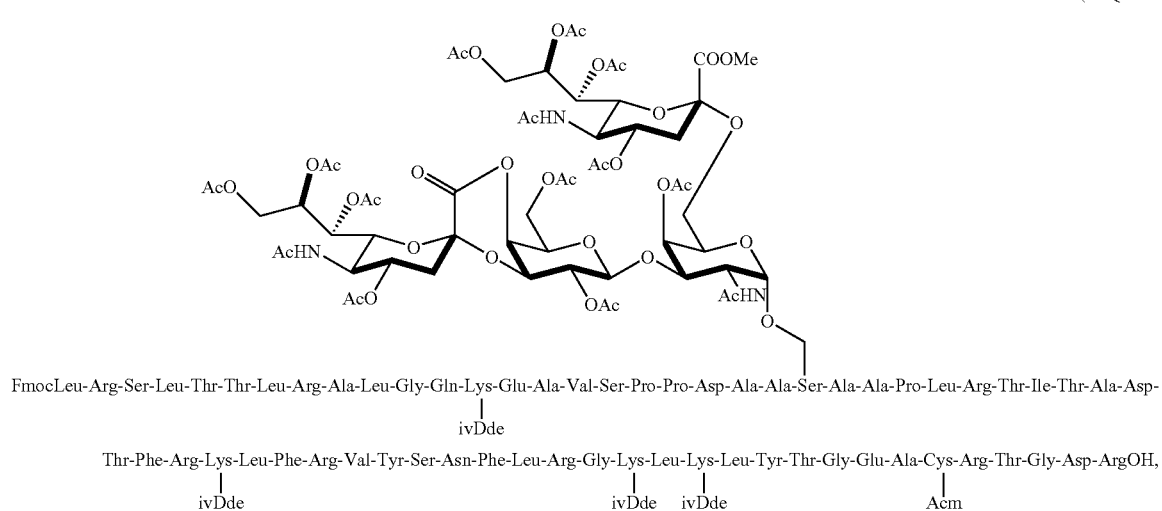
(SEQ ID NO: 8)
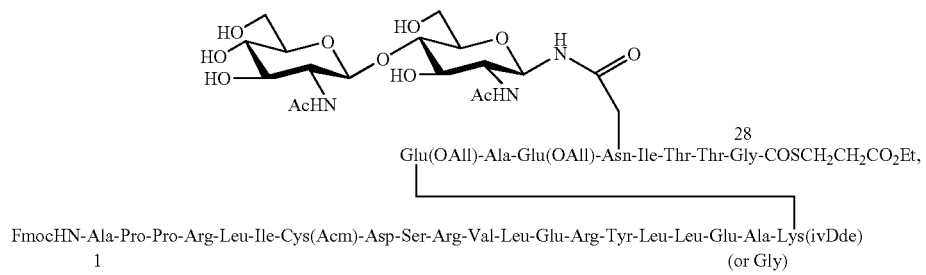

-continued
(SEQ ID NO: 8)
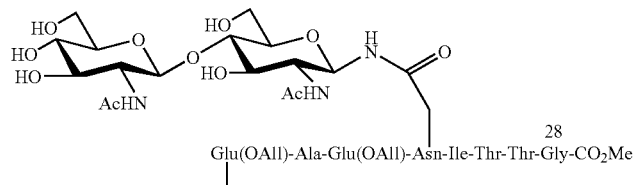
Glu(OAll)-Ala-Glu(OAll)-Asn-Ile-Thr-Thr-Gly-CO₂Me
FmocHN-Ala-Pro-Pro-Arg-Leu-Ile-Cys(Acm)-Asp-Ser-Arg-Val-Leu-Glu-Arg-Tyr-Leu-Leu-Glu-Ala-Lys(ivDde),
1                                                                                             (or Gly)
(SEQ ID NO: 7)
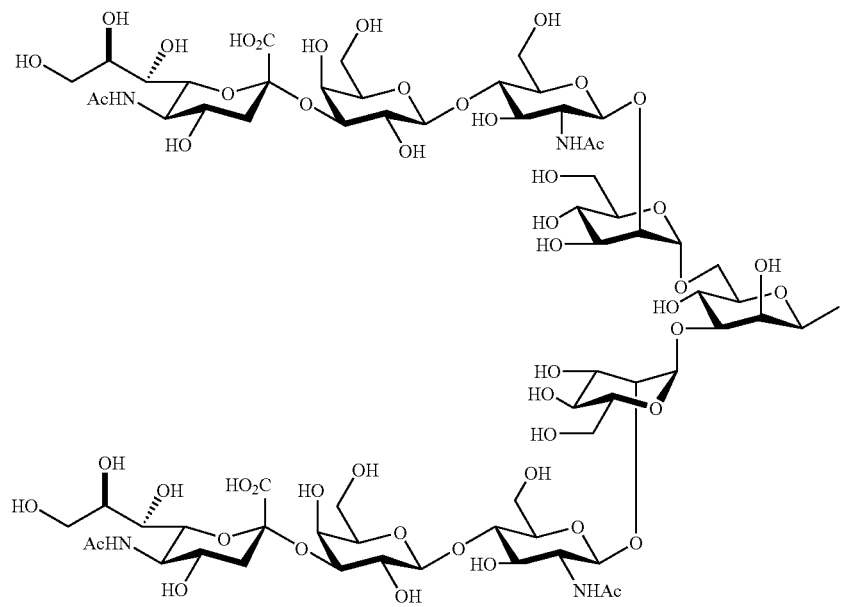
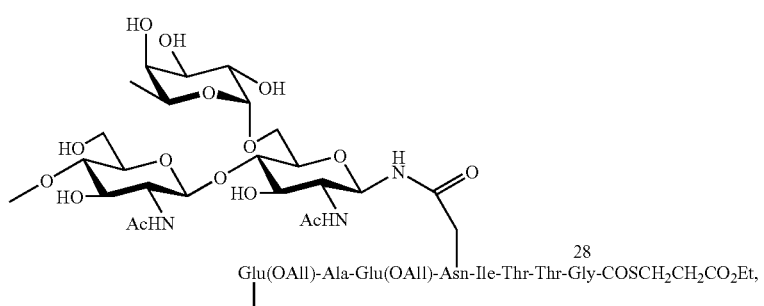
Glu(OAll)-Ala-Glu(OAll)-Asn-Ile-Thr-Thr-Gly-COSCH₂CH₂CO₂Et,
FmocHN-Ala-Pro-Pro-Arg-Leu-Ile-Cys(Acm)-Asp-Ser-Arg-Val-Leu-Glu-Arg-Tyr-Leu-Leu-Glu-Ala-Lys(ivDde)
1                                                                        (or Gly)

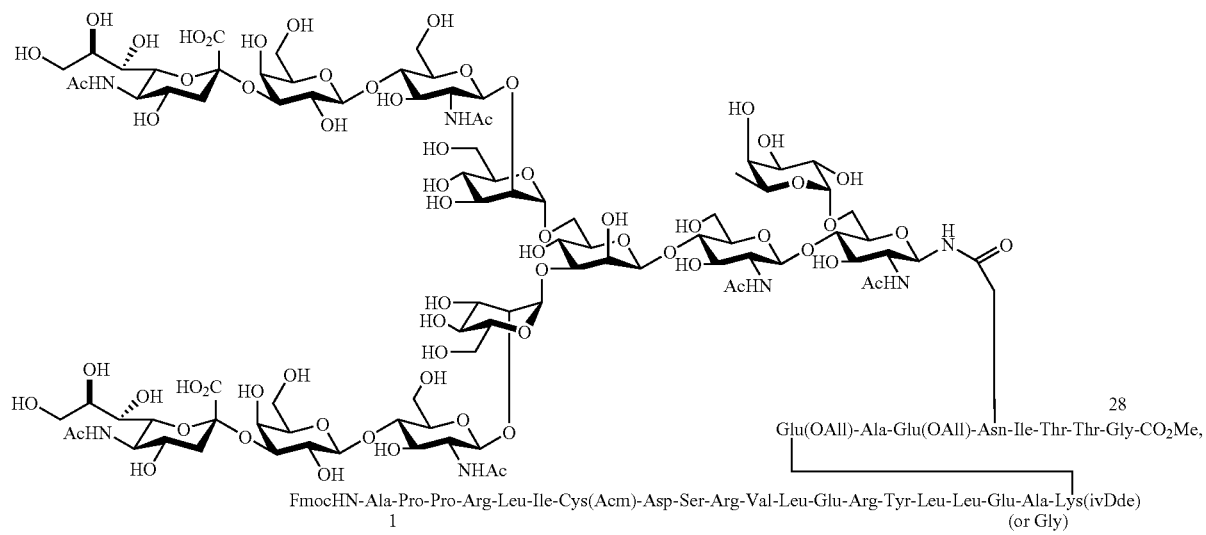
(SEQ ID NO: 7)
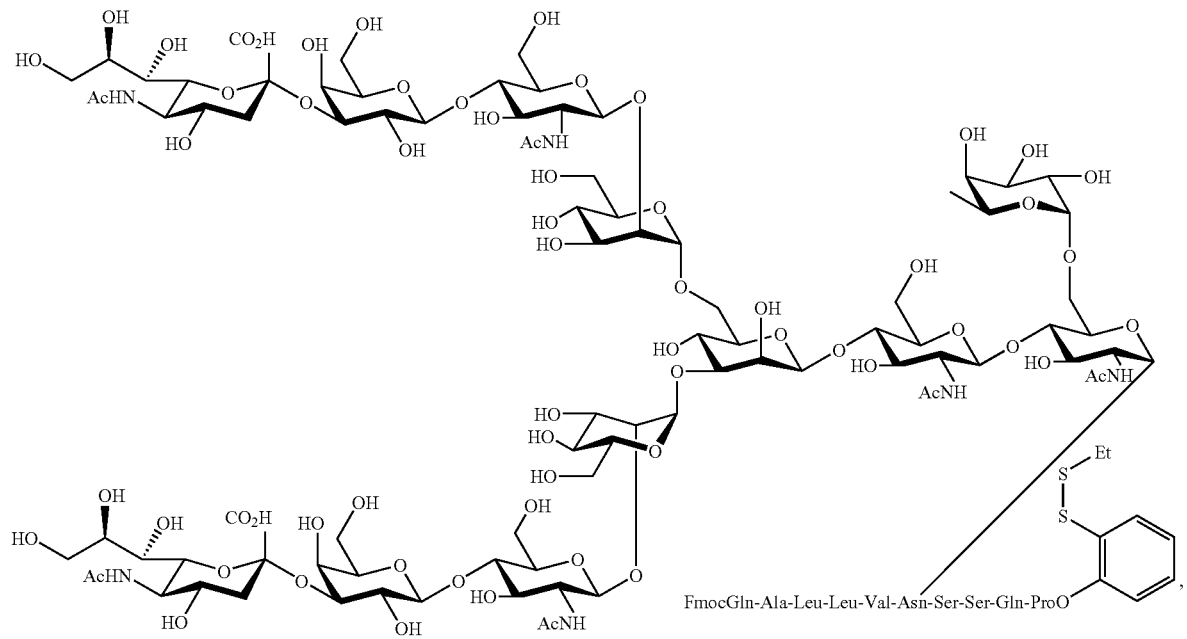
(SEQ ID NO: 11)

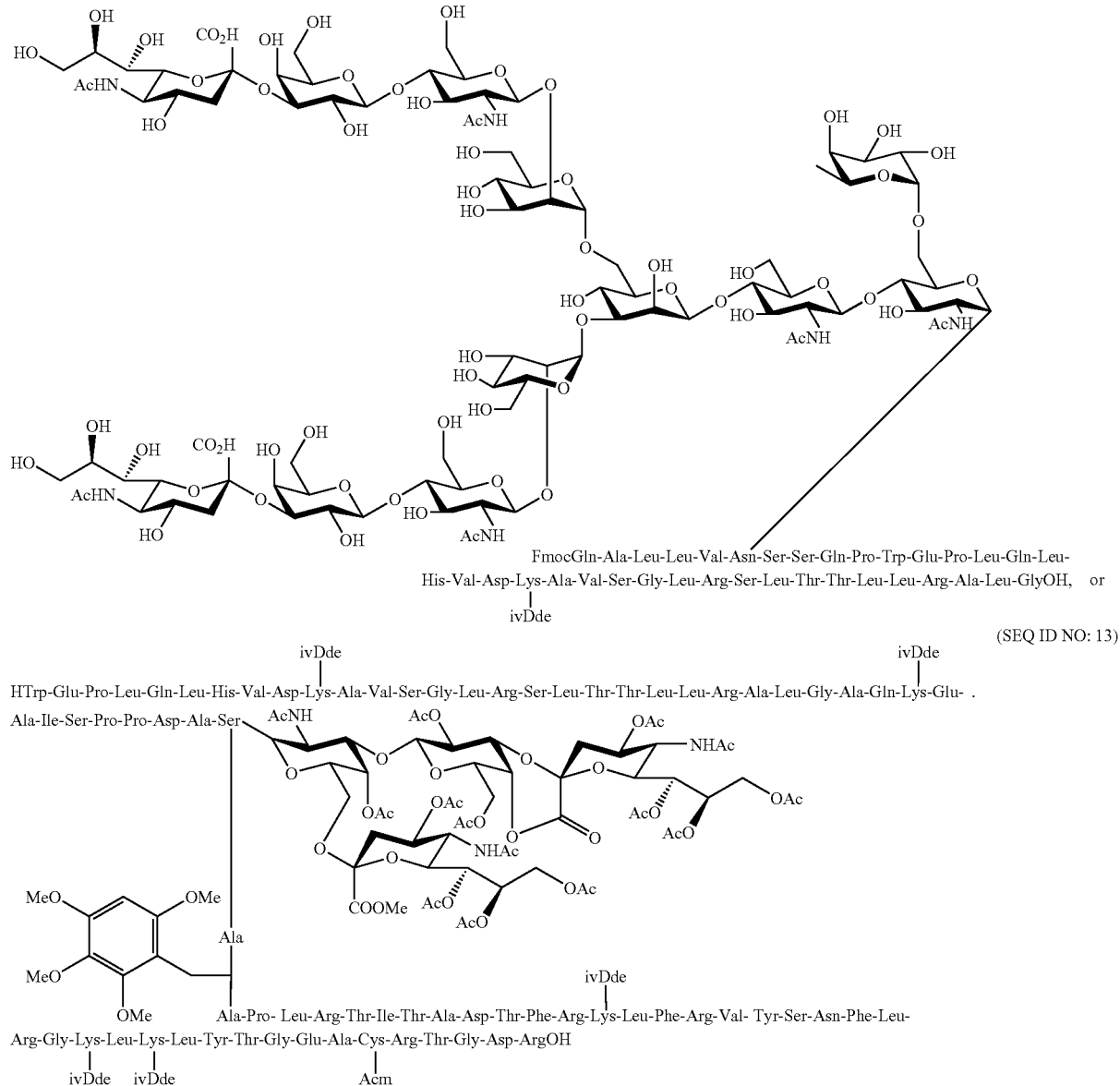

6. A method of preparing homogeneously glycosylated erythropoietin, the method comprising steps of:
ligating to one another a set of fragments of a polypeptide whose amino acid sequence includes a sequence that:
  a) is identical to that of SEQ ID NO: 1, or
  b) contains 1, 2, 3, 4, 5, 6, 7, 8, 9, or 10 amino acid deletions, substitutions, additions or combinations thereof relative to such SEQ ID NO: 1, and stimulates erythrocyte production:
the polypeptide having at least one amino acid residue site glycosylated;
wherein each glycosylated polypeptide in the composition has the same glycosylation pattern in that:
  it is glycosylated on at least one amino acid residue site;
  it is glycosylated at the same at least one site;
  it is glycosylated at a site selected from the group consisting of Asn$^{24}$, Asn$^{38}$, Asn$^{83}$, Ser$^{126}$ in SEQ ID NO: 1, and combinations thereof; and
  for a given glycosylation site, it has the same glycan;

which set of fragments includes fragments whose amino acid sequence corresponds to amino acid residues 1-28, 29-77, 78-113, and 114-166 of SEQ ID NO: 1, so that a homogenously glycosylated erythropoietin polypeptide is generated.

7. The composition of claim 1, wherein at least one glycosylated residue is glycosylated with an O-linked glycans selected from the group consisting of:

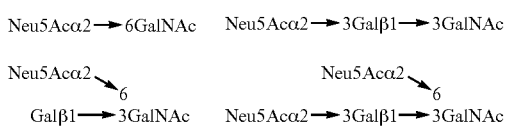

or wherein at least one glycosylated residue is glycosylated with an N-linked glycans selected from the group consisting of:
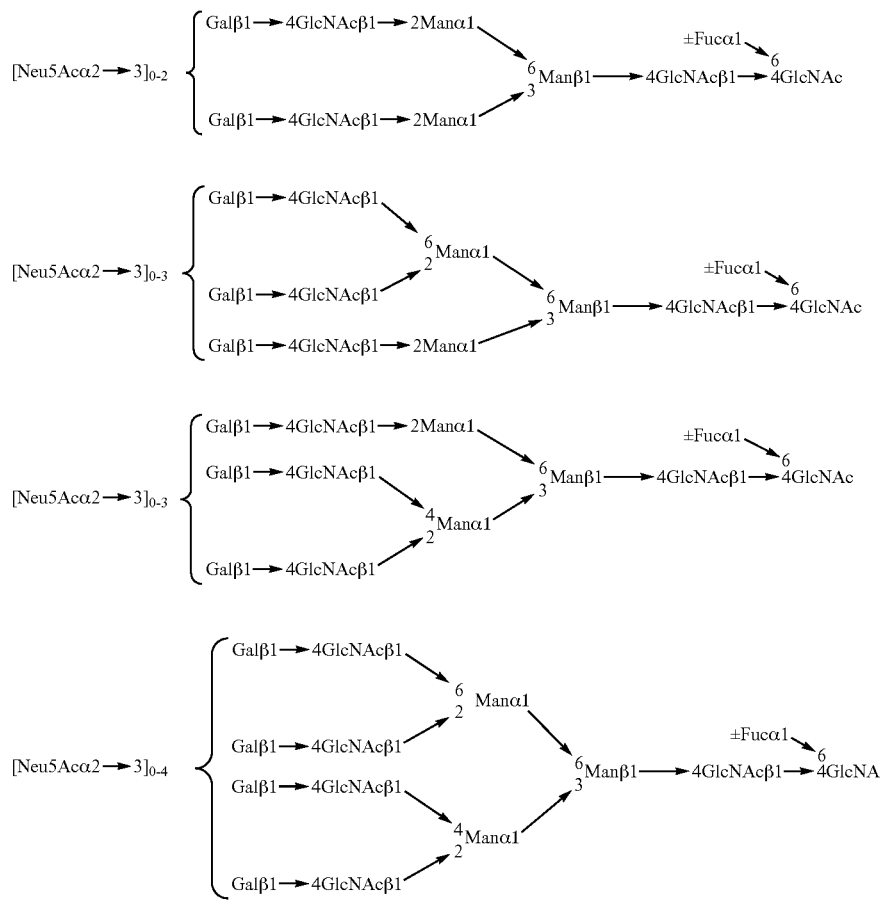
8. The composition of claim 4, wherein $Asn^{24}$, $Asn^{38}$, and $Asn^{83}$ are glycosylated with a glycan of formula:
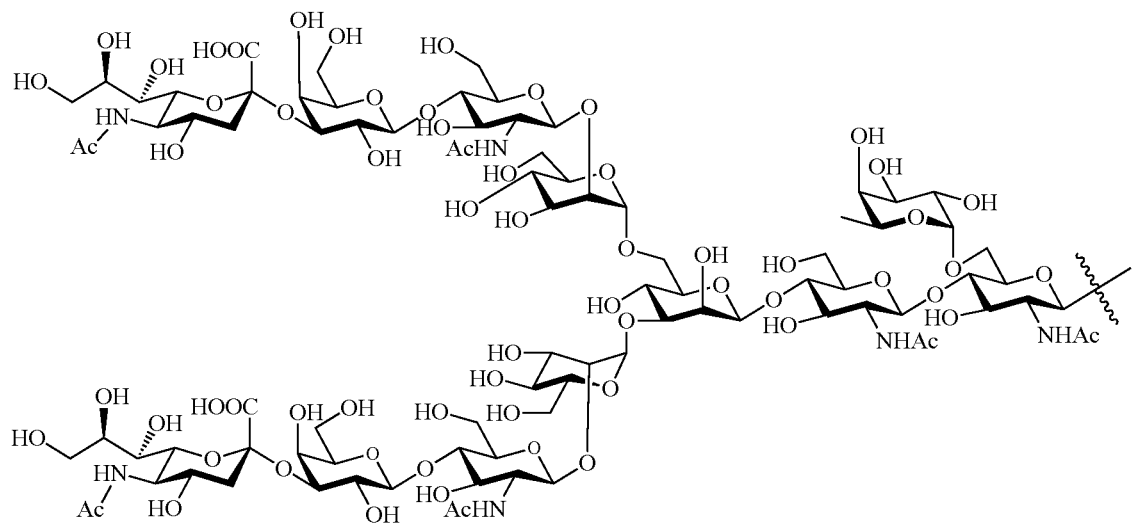

and $Ser^{126}$ is glycosylated with a glycan of formula:
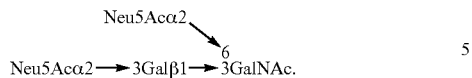
9. The composition of claim 1, wherein $Ser^{126}$ is glycosylated with glycophorin, and wherein at least one other glycosylated residue is glycosylated with chitobiose.
* * * * *